(12) United States Patent
Naylor et al.

(10) Patent No.: US 9,234,019 B2
(45) Date of Patent: Jan. 12, 2016

(54) MODIFIED CPN10 AND PRR SIGNALLING

(75) Inventors: Dean Jason Naylor, East Brisbane (AU); Richard James Brown, St. Lucia (AU); Christopher Bruce Howard, Rochedale South (AU); Christopher John De Bakker, Margate (AU); Linda Alisson Ward, Coopers Plains (AU); Jeanette Elizabeth Stok, Greenslopes (AU); Andrew Leigh James, Barellan Point (AU); Daniel Scott Lambert, Waterford (AU); Kylie Jane Ralston, Kahibah (AU); Walter Rene Antonius Van Heumen, Bellbowrie (AU)

(73) Assignee: CBio Limited, Queensland (AU)

( * ) Notice: Subject to any disclaimer, the term of this patent is extended or adjusted under 35 U.S.C. 154(b) by 200 days.

(21) Appl. No.: 12/934,980

(22) PCT Filed: Apr. 9, 2009

(86) PCT No.: PCT/AU2009/000444
§ 371 (c)(1),
(2), (4) Date: Nov. 19, 2010

(87) PCT Pub. No.: WO2009/124353
PCT Pub. Date: Oct. 15, 2009

(65) Prior Publication Data
US 2011/0082073 A1    Apr. 7, 2011

(30) Foreign Application Priority Data

Apr. 11, 2008 (AU) .................. PCT/AU2008/000520
Feb. 13, 2009 (AU) ................................ 2009900613

(51) Int. Cl.
| | |
|---|---|
| *A61K 38/16* | (2006.01) |
| *C07K 1/00* | (2006.01) |
| *C07K 14/47* | (2006.01) |
| *A61K 38/00* | (2006.01) |

(52) U.S. Cl.
CPC ............. *C07K 14/4715* (2013.01); *A61K 38/00* (2013.01)

(58) Field of Classification Search
None
See application file for complete search history.

(56) References Cited

U.S. PATENT DOCUMENTS 7,618,935 B2 * 11/2009 Hill et al. ....................... 514/1.1

FOREIGN PATENT DOCUMENTS

| WO | 2007/006095 A1 | 1/2007 |
|---|---|---|
| WO | 2007/025343 A1 | 3/2007 |
| WO | 2007/045046 A1 | 4/2007 |

OTHER PUBLICATIONS

Gearing 2007. Immunology and Cell Biology 85:490-494.*
Williams et al 2008. Arch Dermatol. 144:683-684.*
Vanags et al. 2006. Lancet 368:855-63.*
Van Eden 2008. Curr Opin in Invest Drugs. 9:523-533.*
Vanags et al., "Therapeutic Efficacy and Saftey of Chaperonin 10 in Patients With Rheumatoid Arthritis: A Double-Blind Randomised Trial," Lancet, 2006, vol. 368, pp. 855-863.
Bramhall et al., "Identification of Amino Acid Residues At Nucleotide-Binging Sites of Chaperonin GroEL/GroES and CPN 10 by Photoaffinity Labeling With 2-Azido-Adenosine 5'-Triphosphate," Eur. J. Biochem, 1997, vol. 244, pp. 627-634.
Numato et al., "Crystal Structure of the Co-Chaperonin CPN10 From *Thermus thermophilus* HB8," Proteins: Structure, Function, and Bioiaformatics, 2005, vol. 58, pp. 498-500.
Bonshtien et al., "Significance of the N-Terminal Domain for the Function of Chloroplast CPN20 Chaperonin," Journal of Biological Chemistry, 2007, vol. 282, No. 7, pp. 4463-4469.
Guidry et al., "Probing the Interface in a Human Co-Chaperonin Heptamer: Residues Disrupting Oligomeric Unfolded State Identified," BMC Biochemistry, 2003, vol. 4, 13 pages.

* cited by examiner

*Primary Examiner* — Shulamith H Shafer
(74) *Attorney, Agent, or Firm* — Ditthavong & Steiner, P.C.

(57) ABSTRACT

The present invention relates to isolated Cpn10 polypeptides possessing an increased affinity for a PRR ligand compared to Ala Cpn10 polypeptide. In a further embodiment, the present invention also relates to modified chaperonin 10 polypeptides, and to nucleic acids encoding the same and to compositions comprising such polypeptides and uses thereof.

7 Claims, 61 Drawing Sheets

A, Controls

B, Positive to Positive

C, Positive Substitution

FIGURE 3 - CONTINUED
D, Negative to Neutral substitution
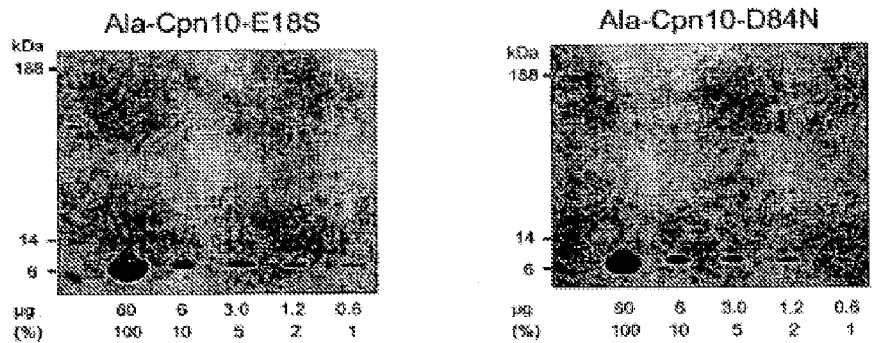
E, Positive Insertion (lengthening)
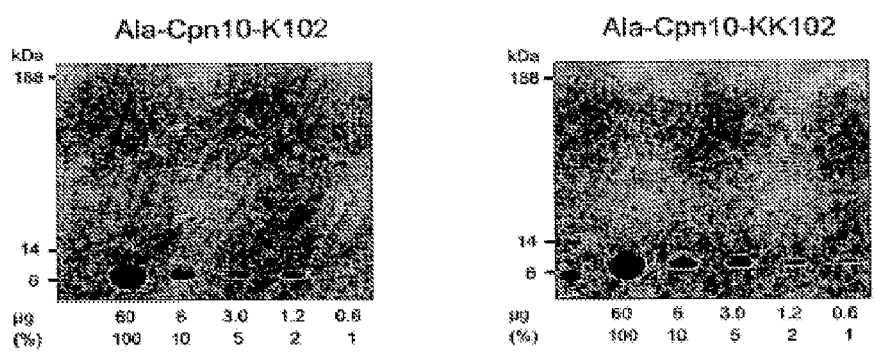
F, Negative Deletions (removal)
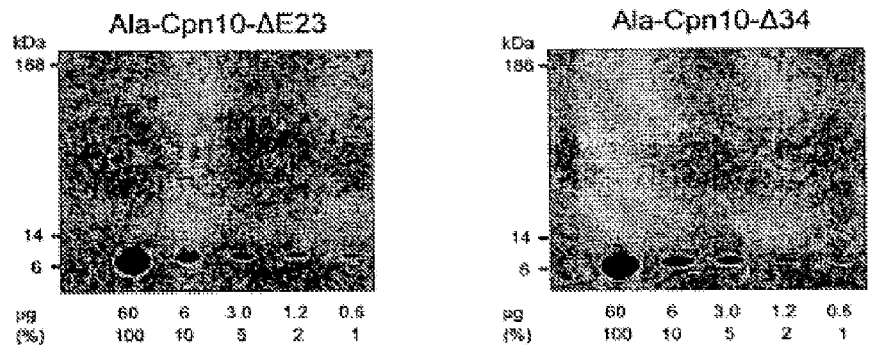

FIGUDE 3 - CONTINUED
G, Multiple Positive
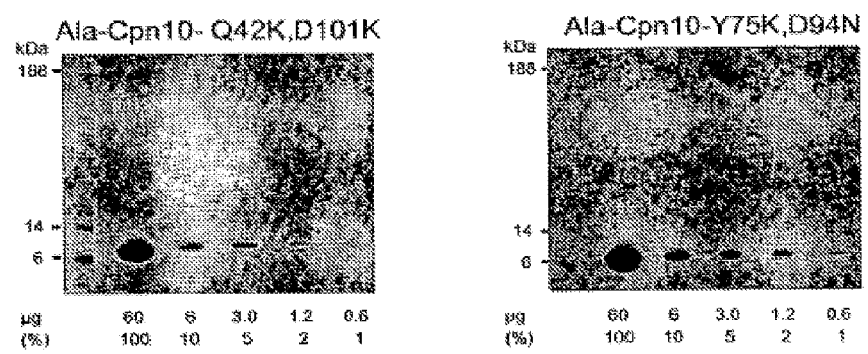

Figure 4a. Controls
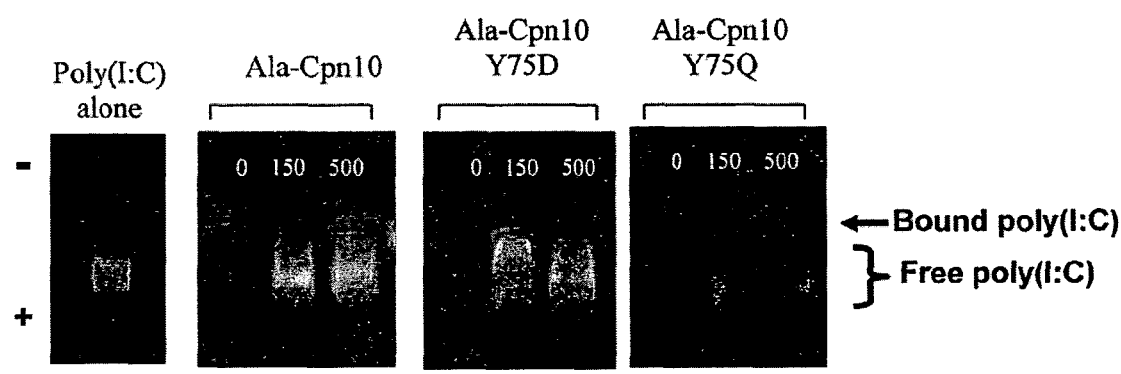
Figure 4b. Positive to positive substitution
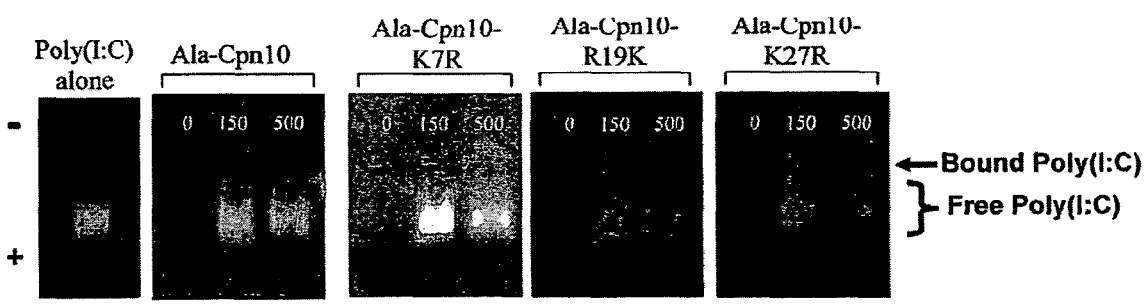

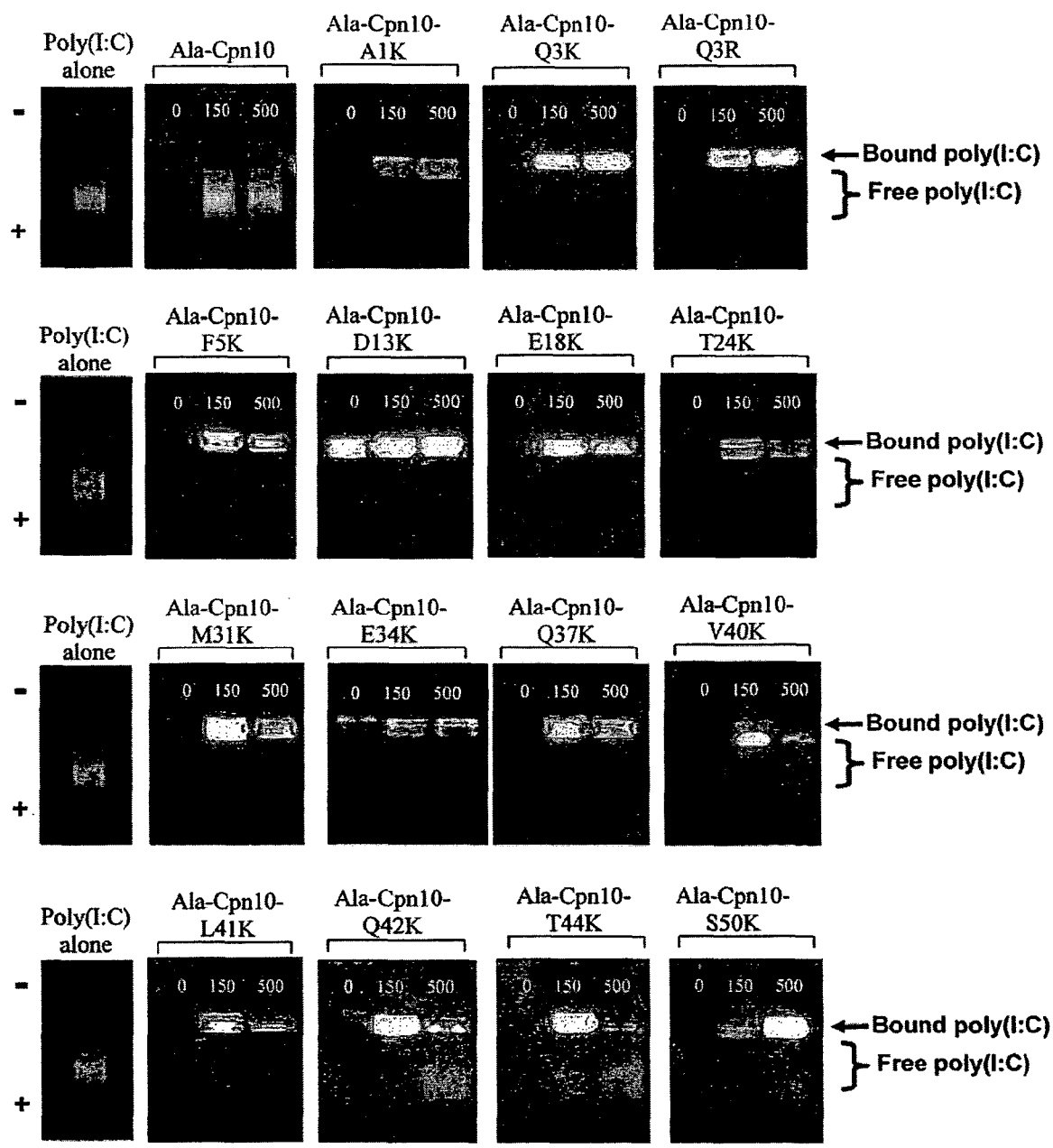
Figure 4c. Positive Substitution

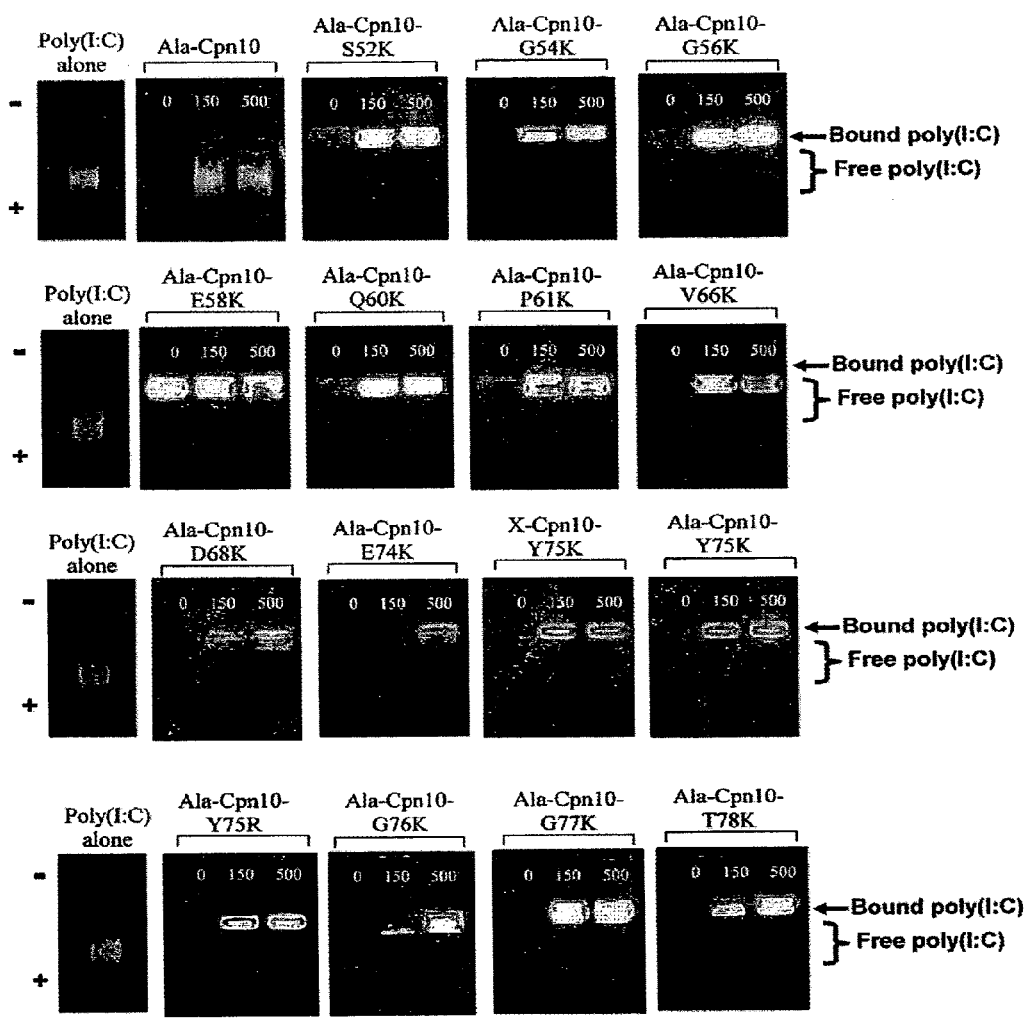
Figure 4c. Positive Substitution - CONTINUED

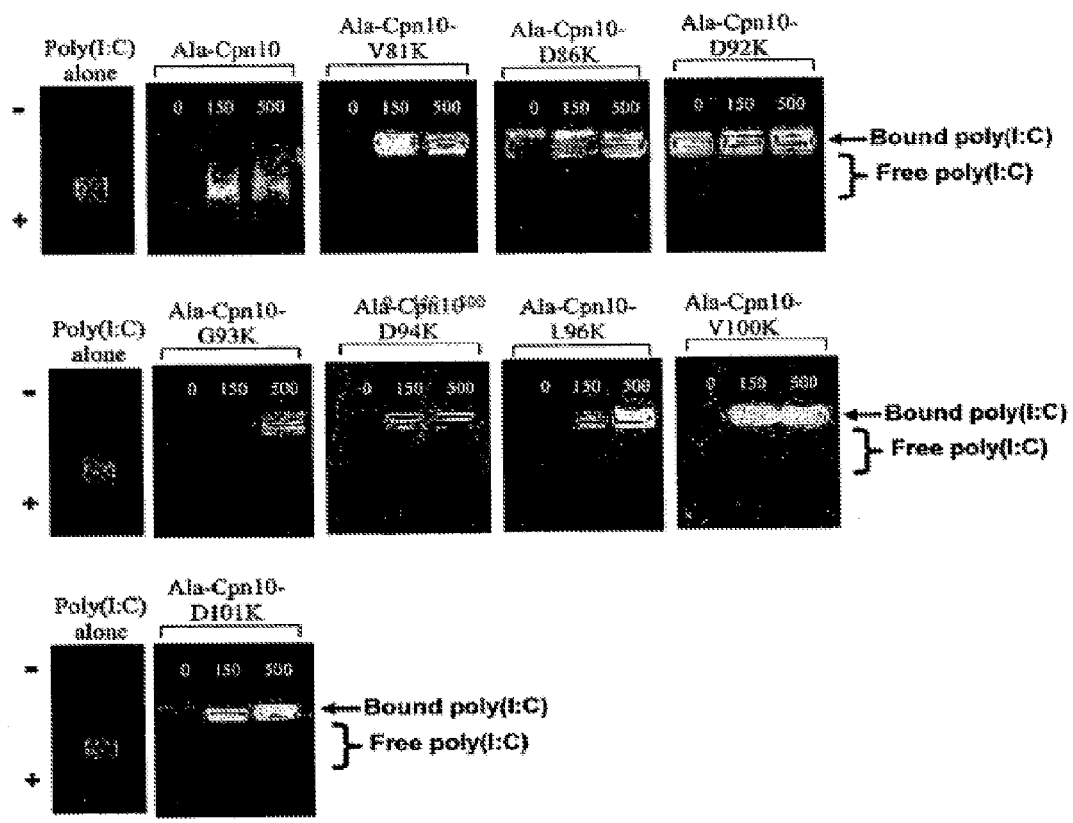

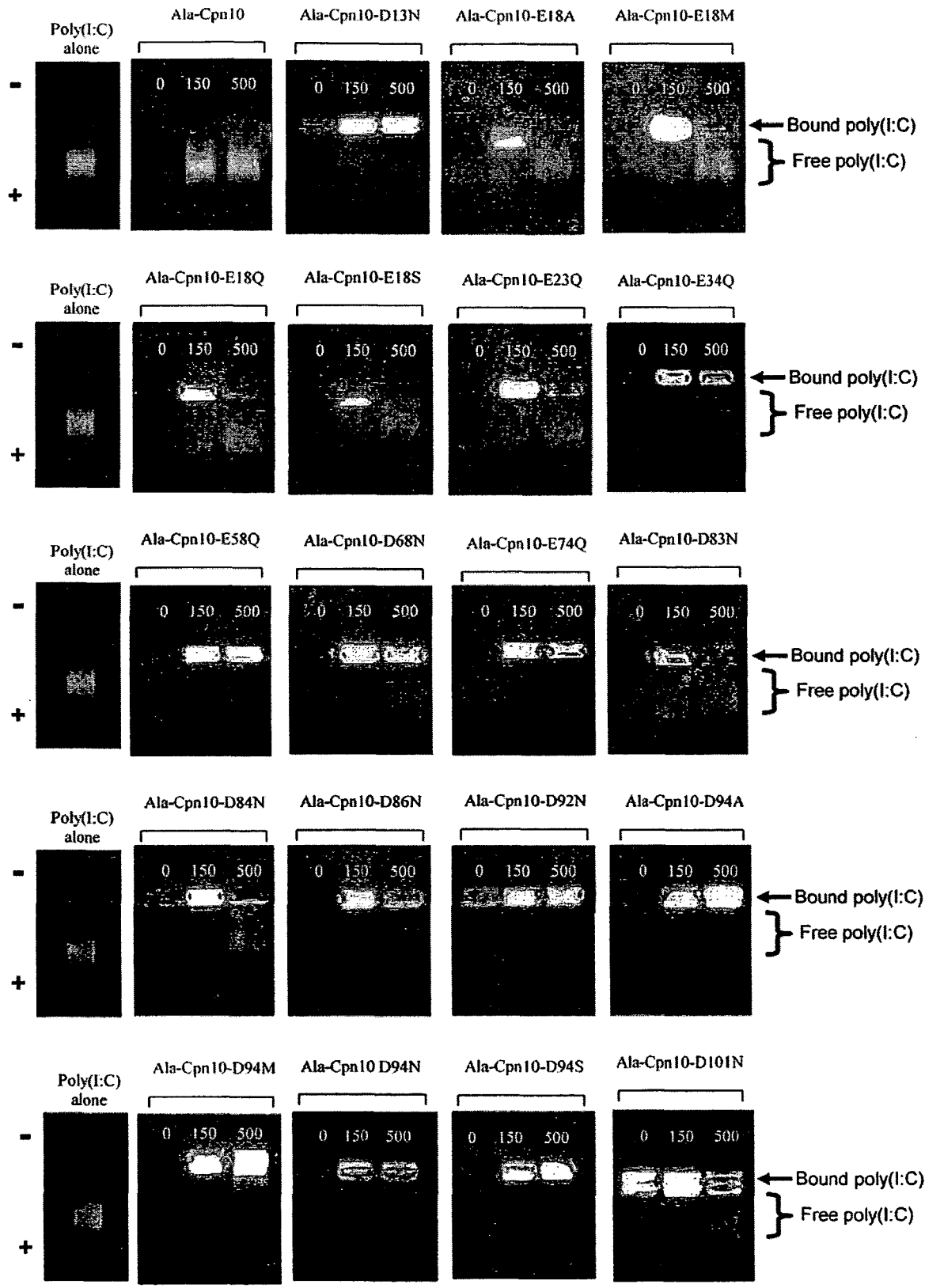
Figure 4d. Negative to Neutral Substitutions

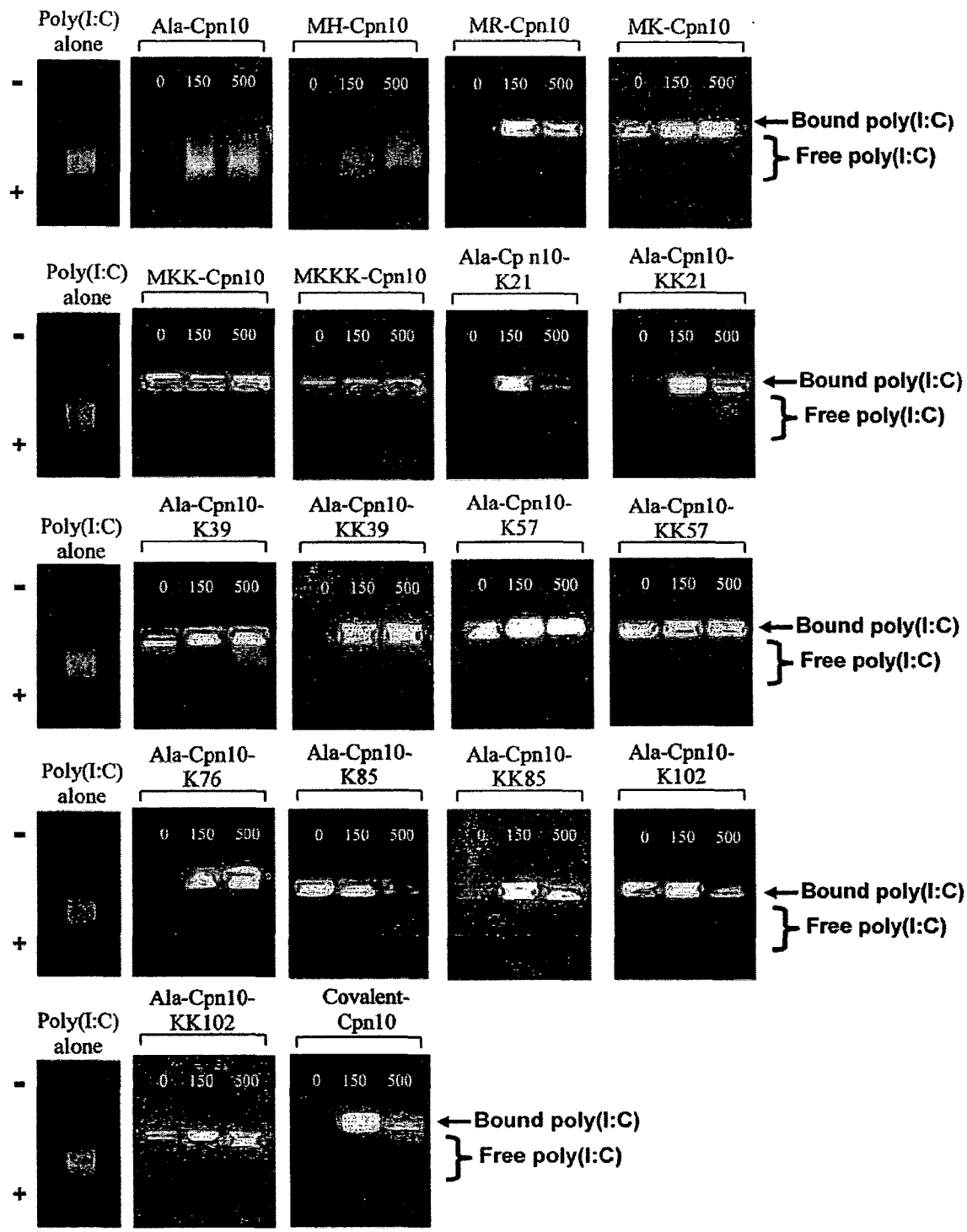
Figure 4e. Positive insertions

Figure 4f. Negative Deletions
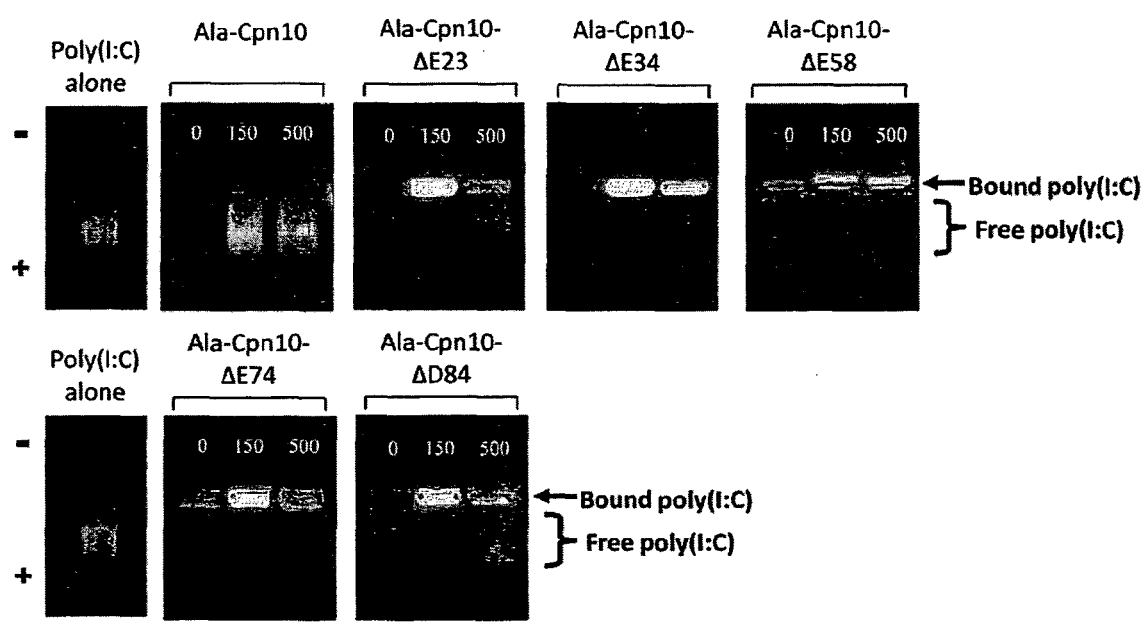

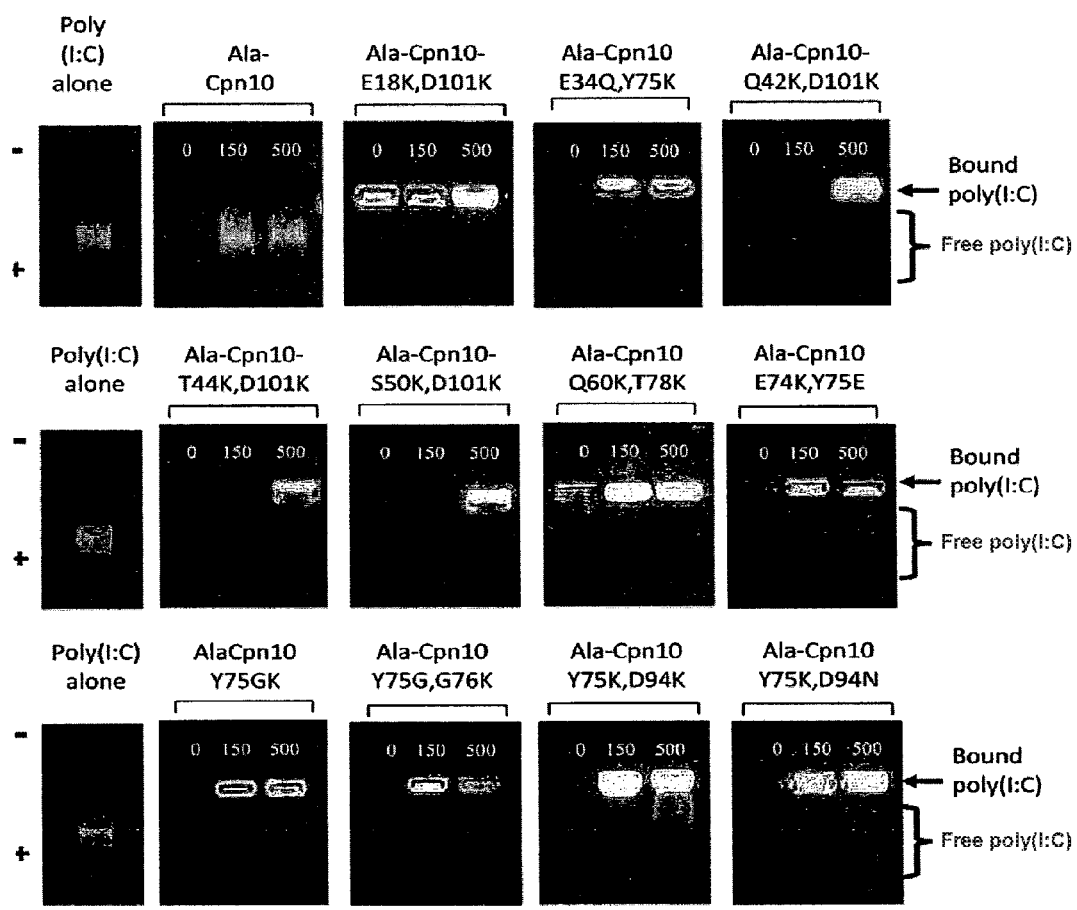
Figure 4g. Multiple Mutations

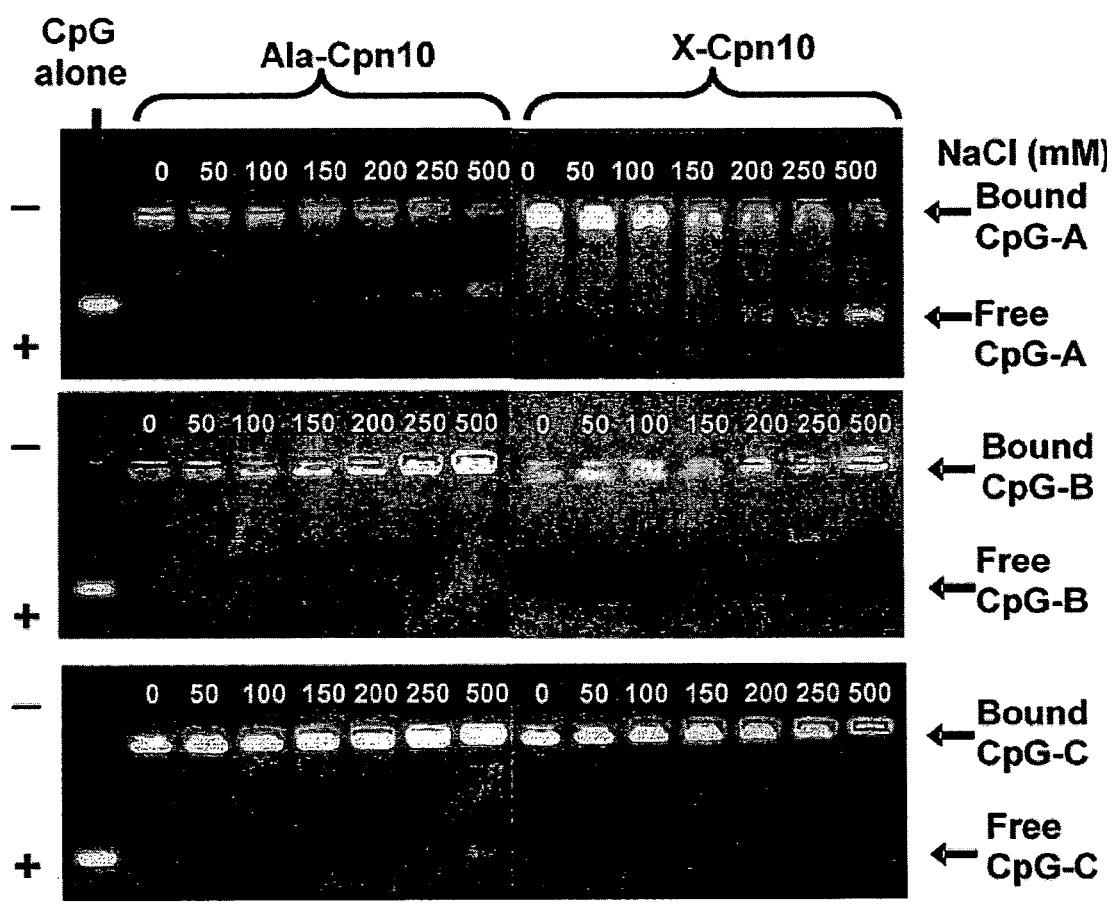
Figure 5a. Controls

Figure 5b. Positive to Positive Substitutions
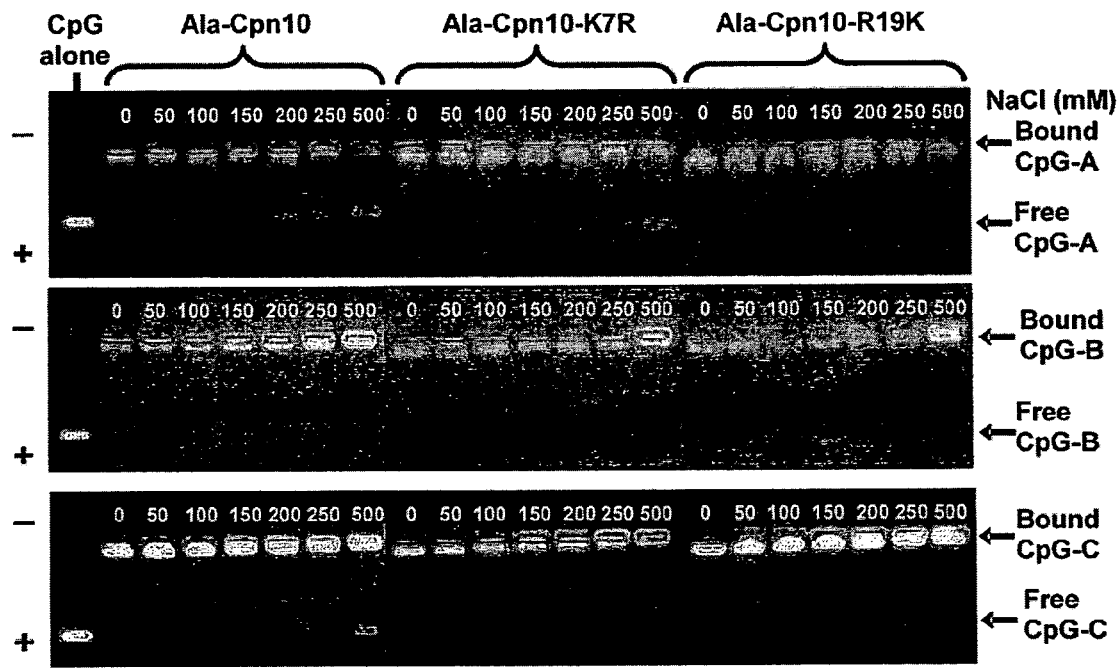
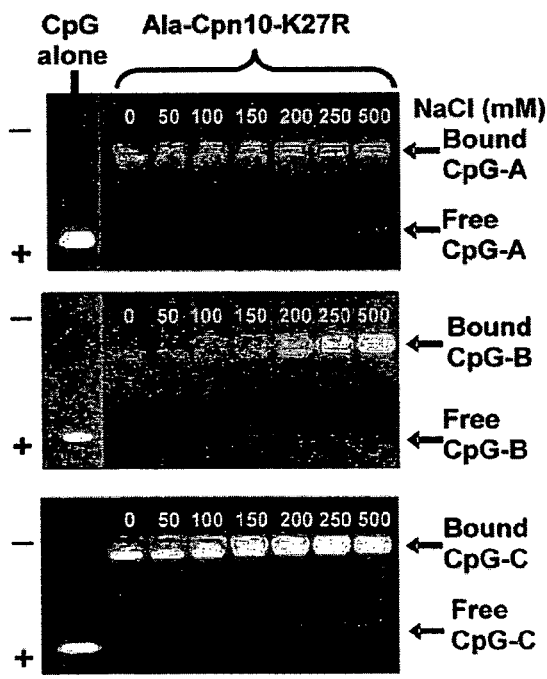

Figure 5c. Positive Substitutions
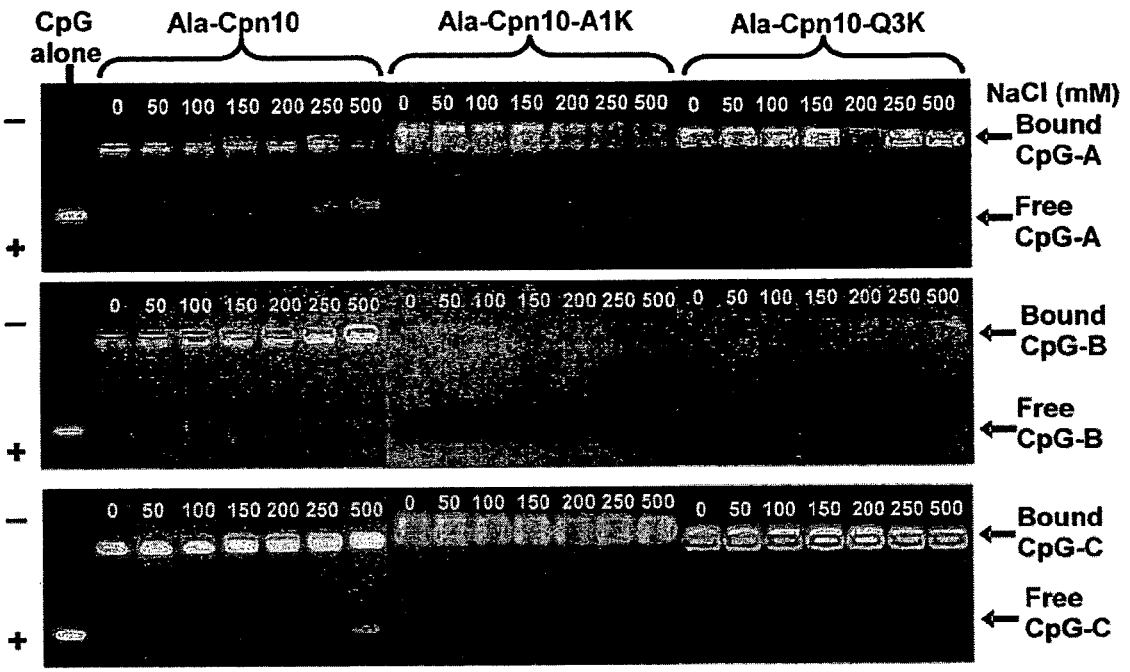
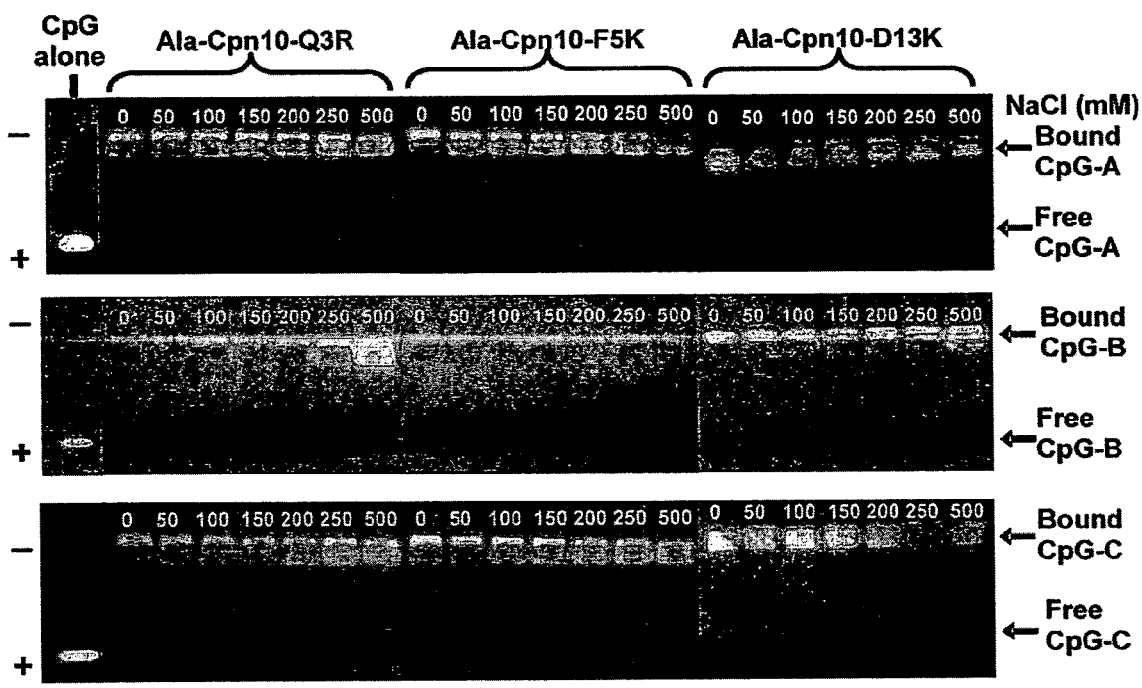

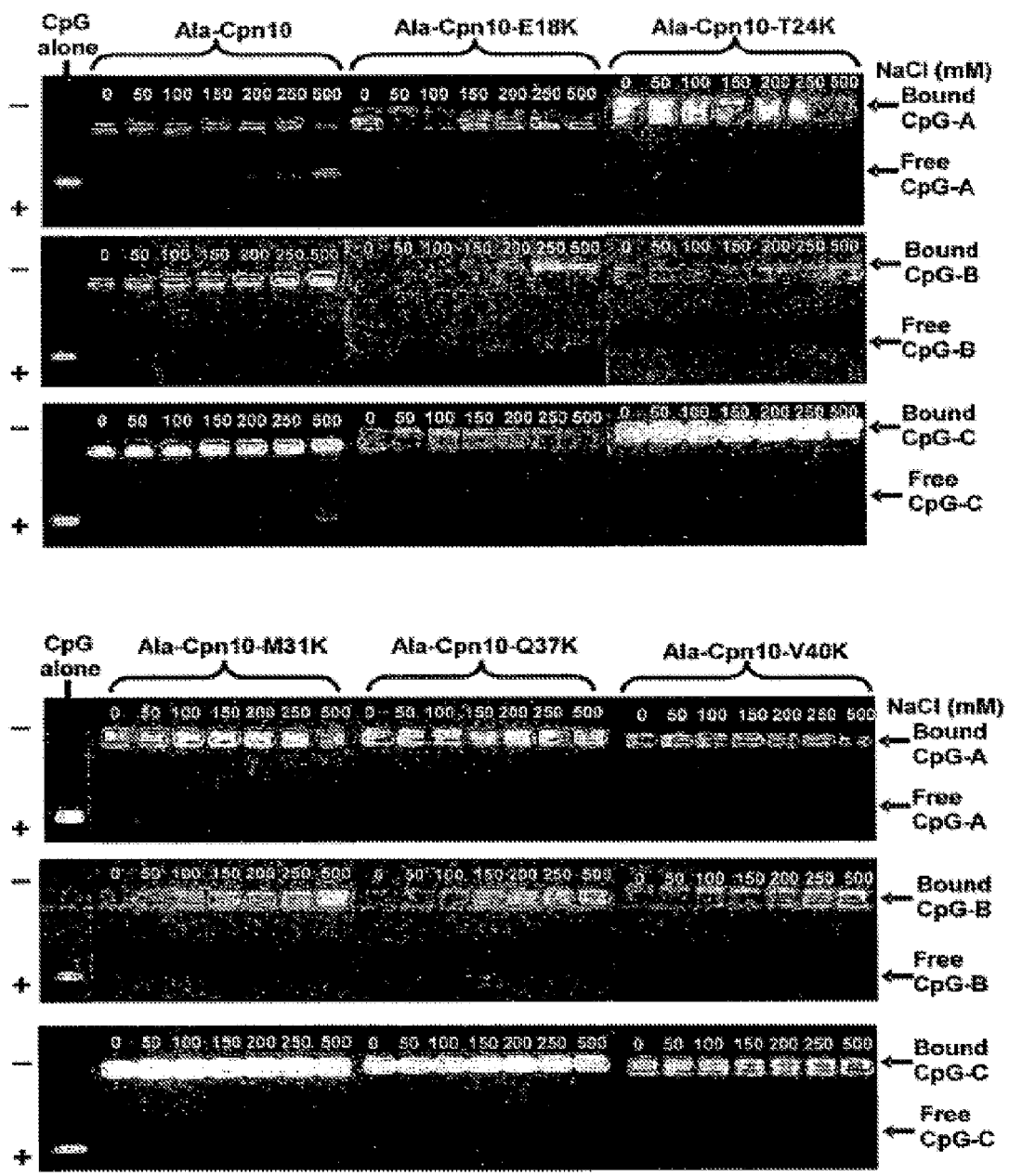

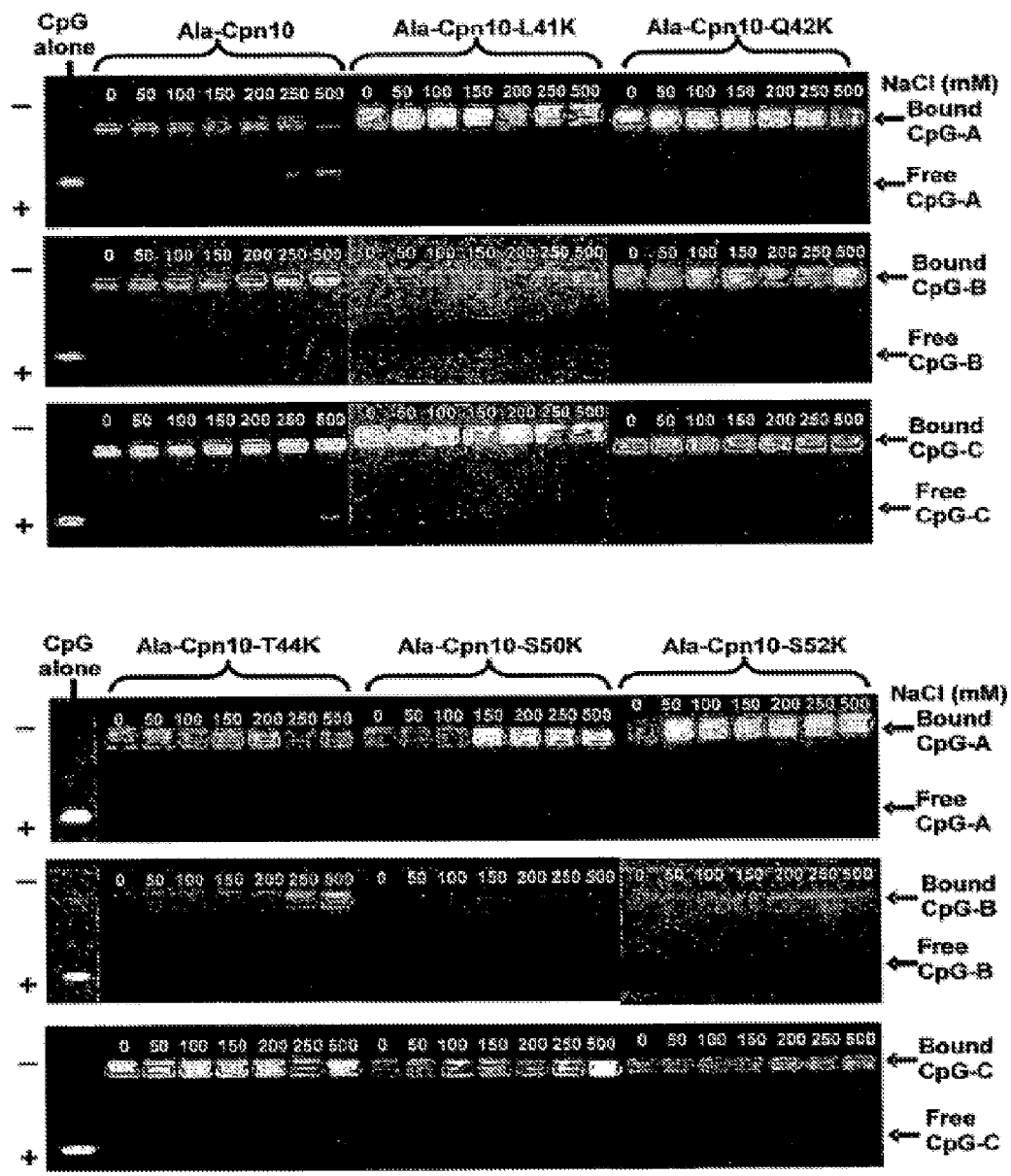
Figure 5c. Positive Substitutions - CONTINUED

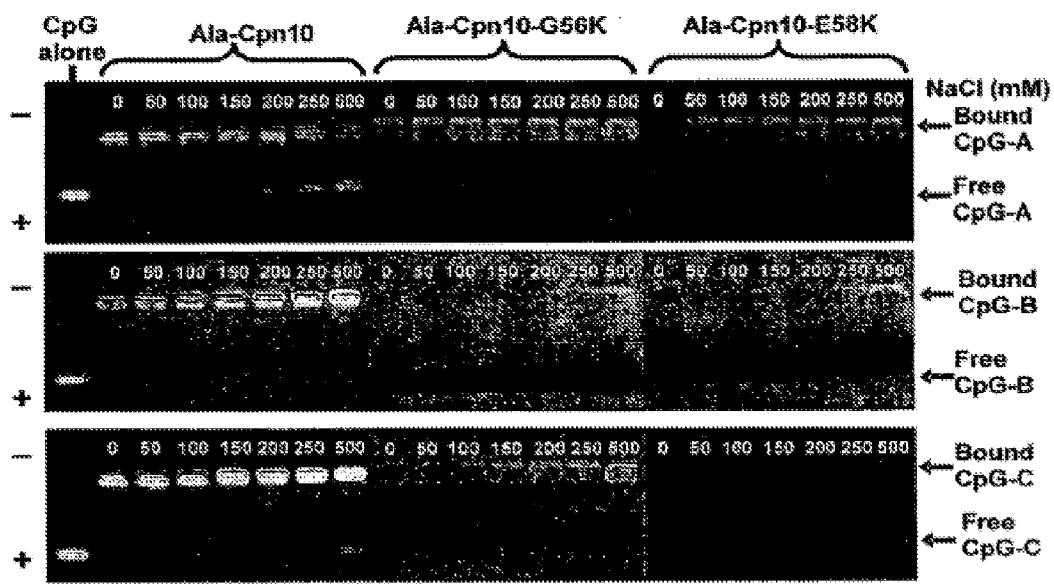
Figure 5c. Positive Substitutions - CONTINUED
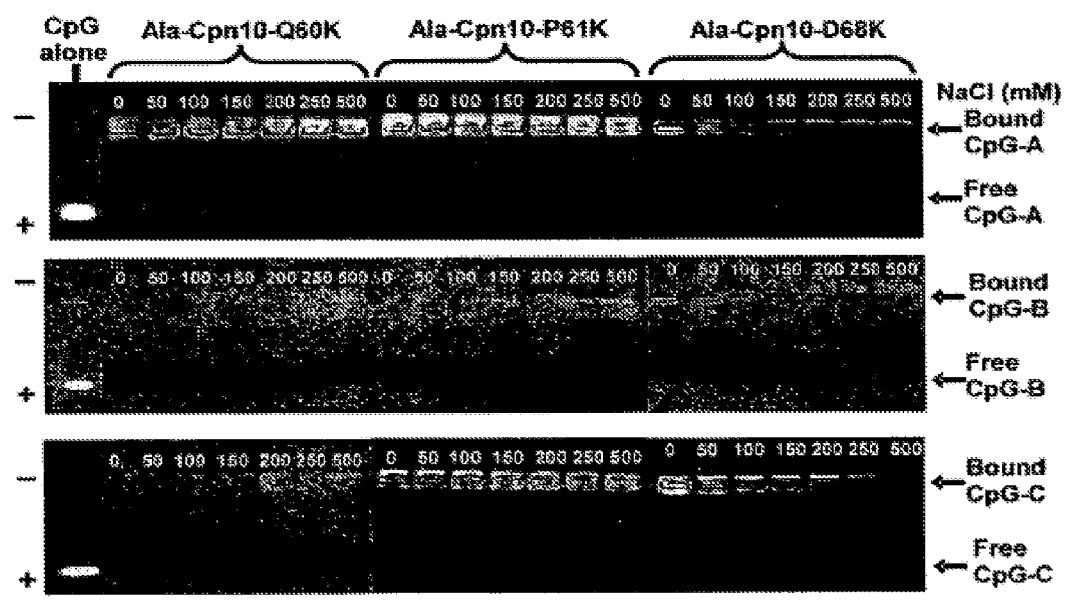

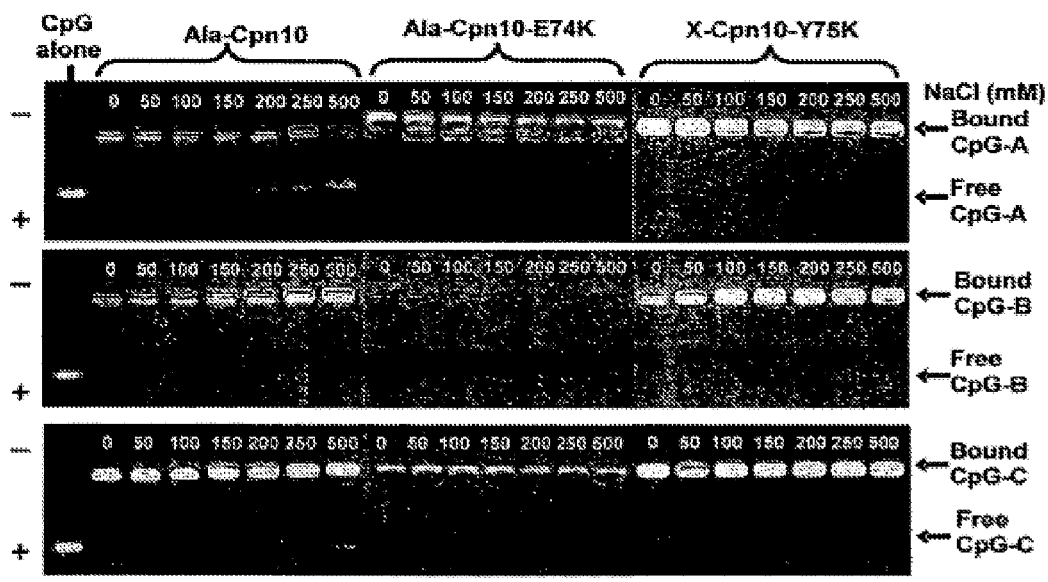
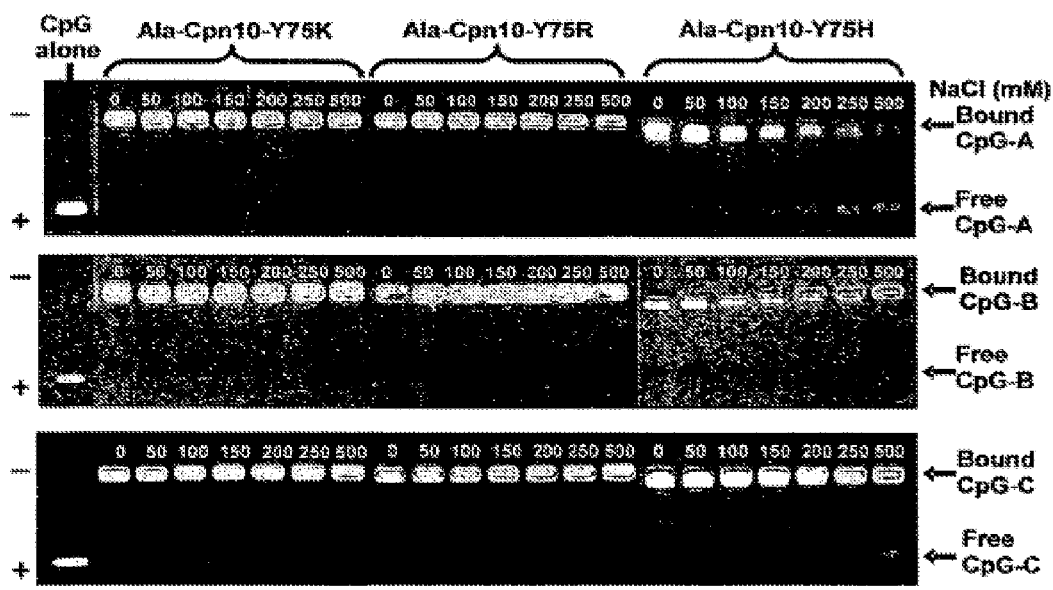
Figure 5c. Positive Substitutions - CONTINUED

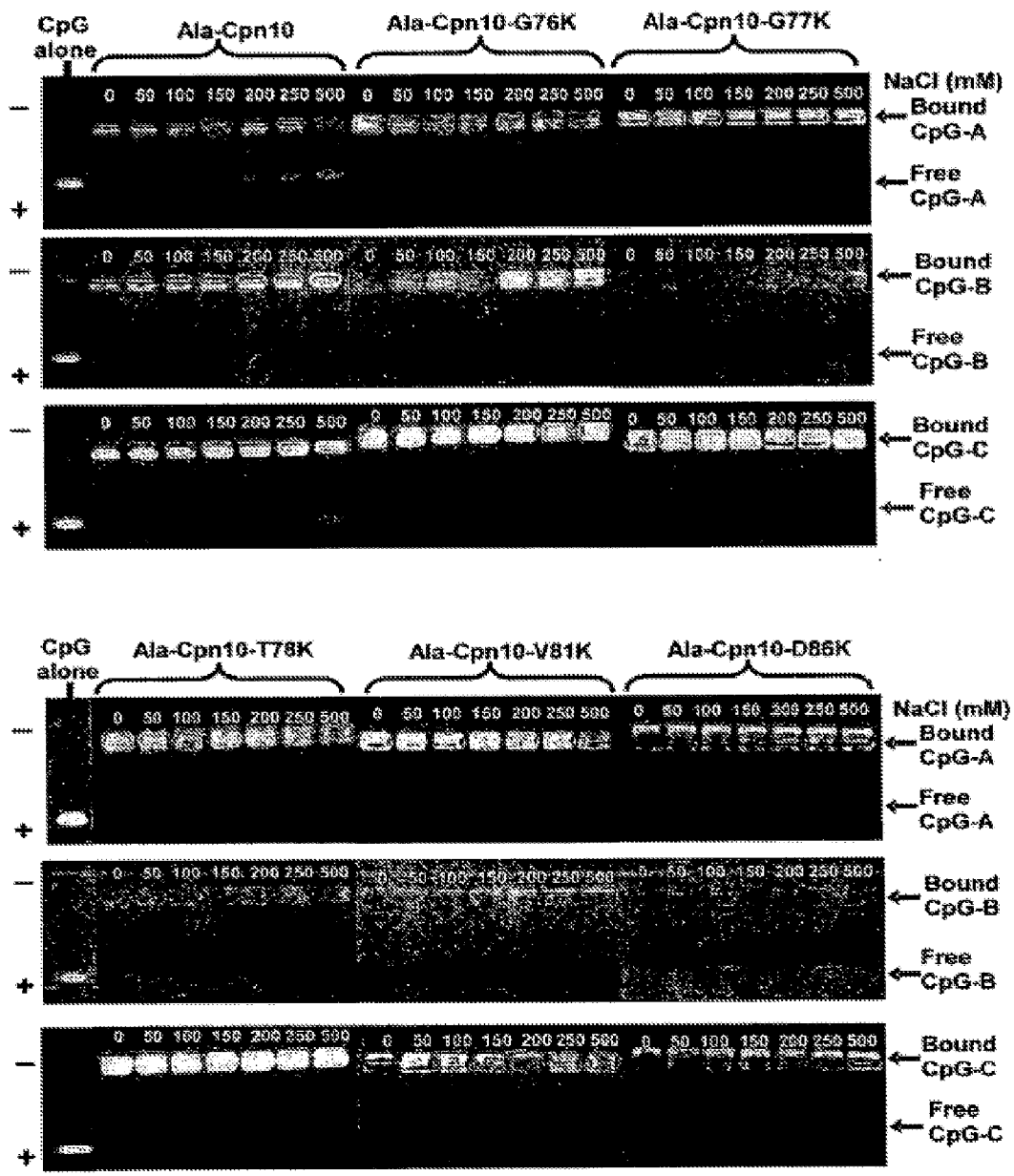
Figure 5c. Positive Substitutions - CONTINUED

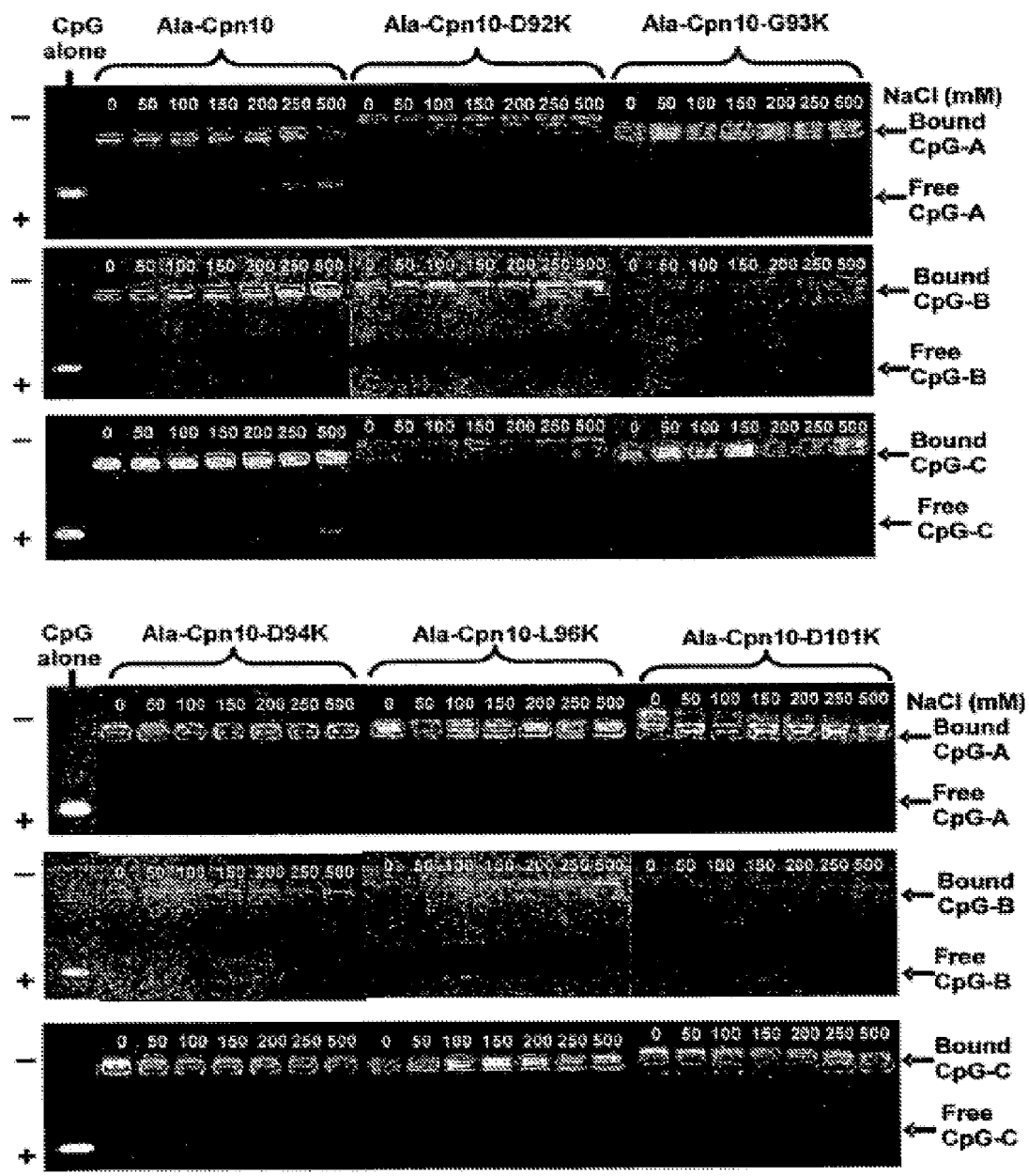
Figure 5c. Positive Substitutions - CONTINUED

Figure 5d. Negative to Neutral Substitutions
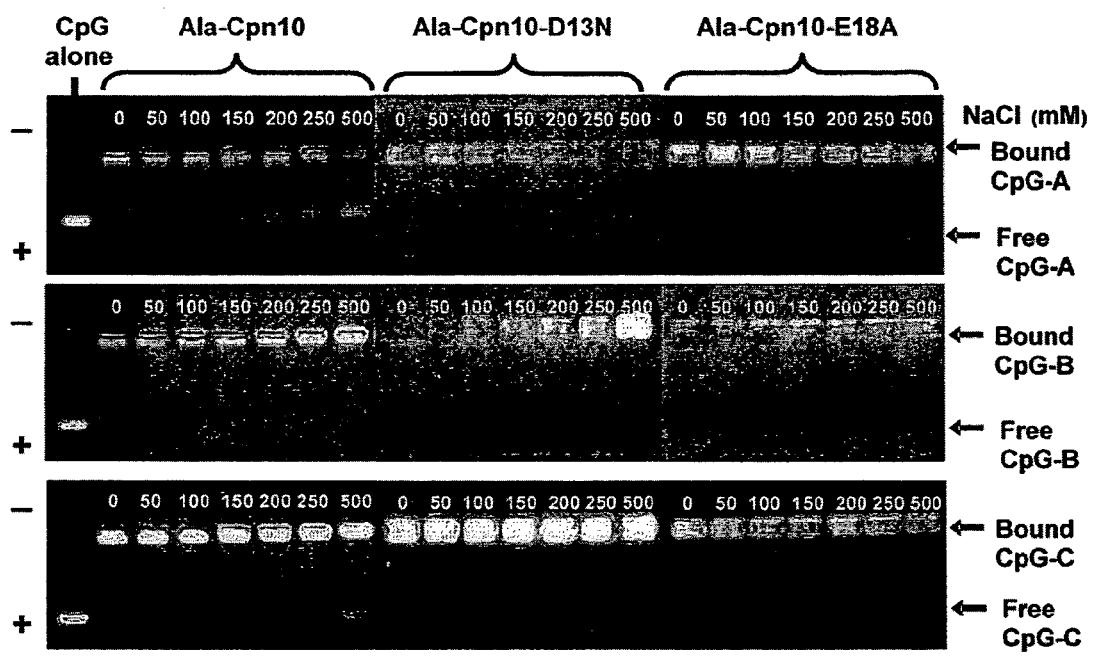
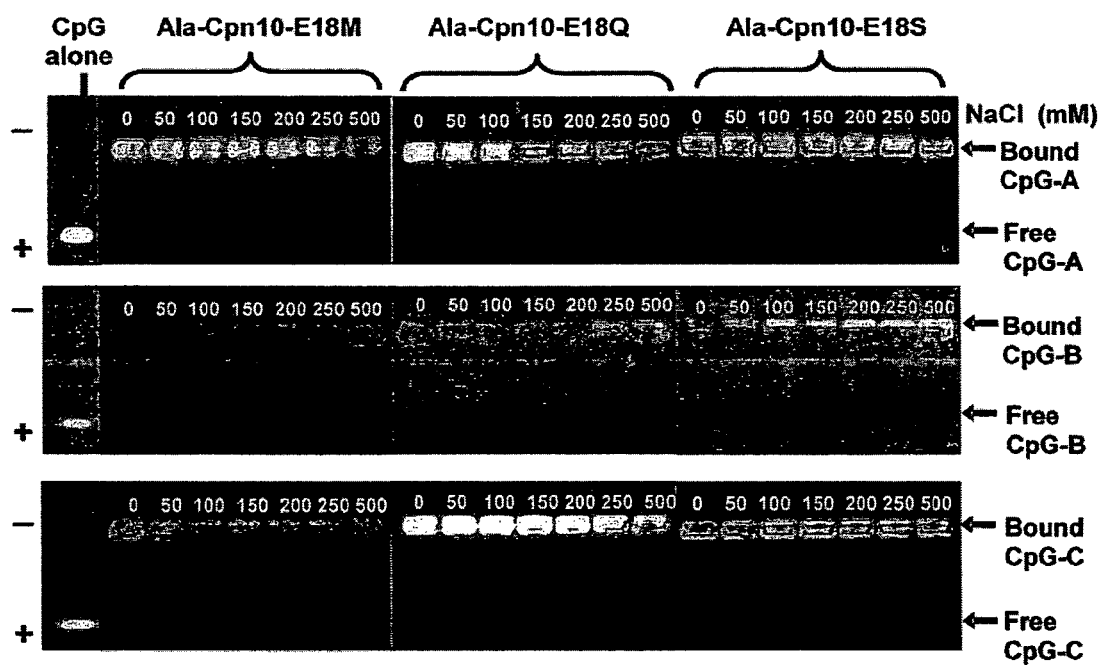

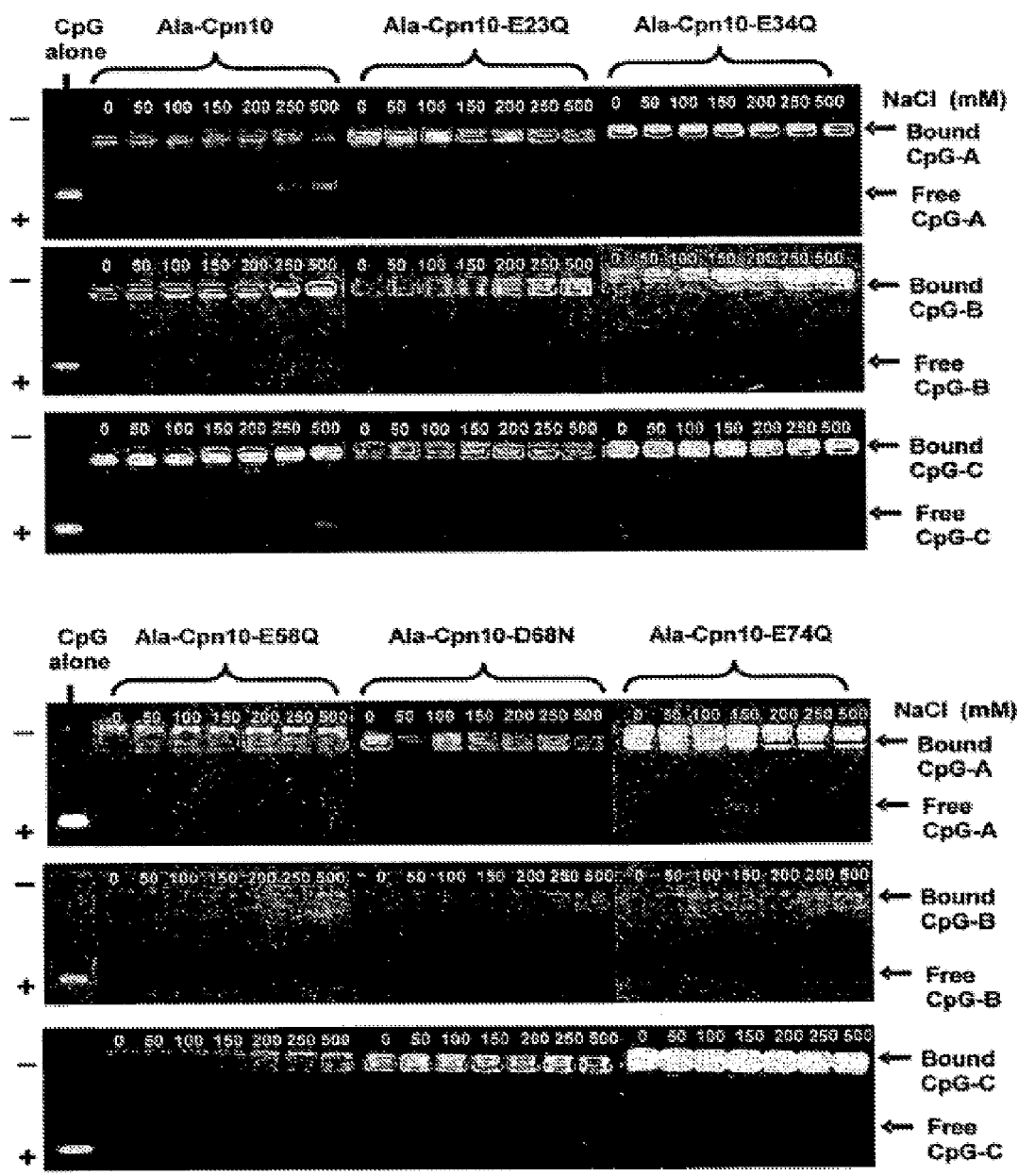
Figure 5d. Negative to Neutral Substitutions - CONTINUED

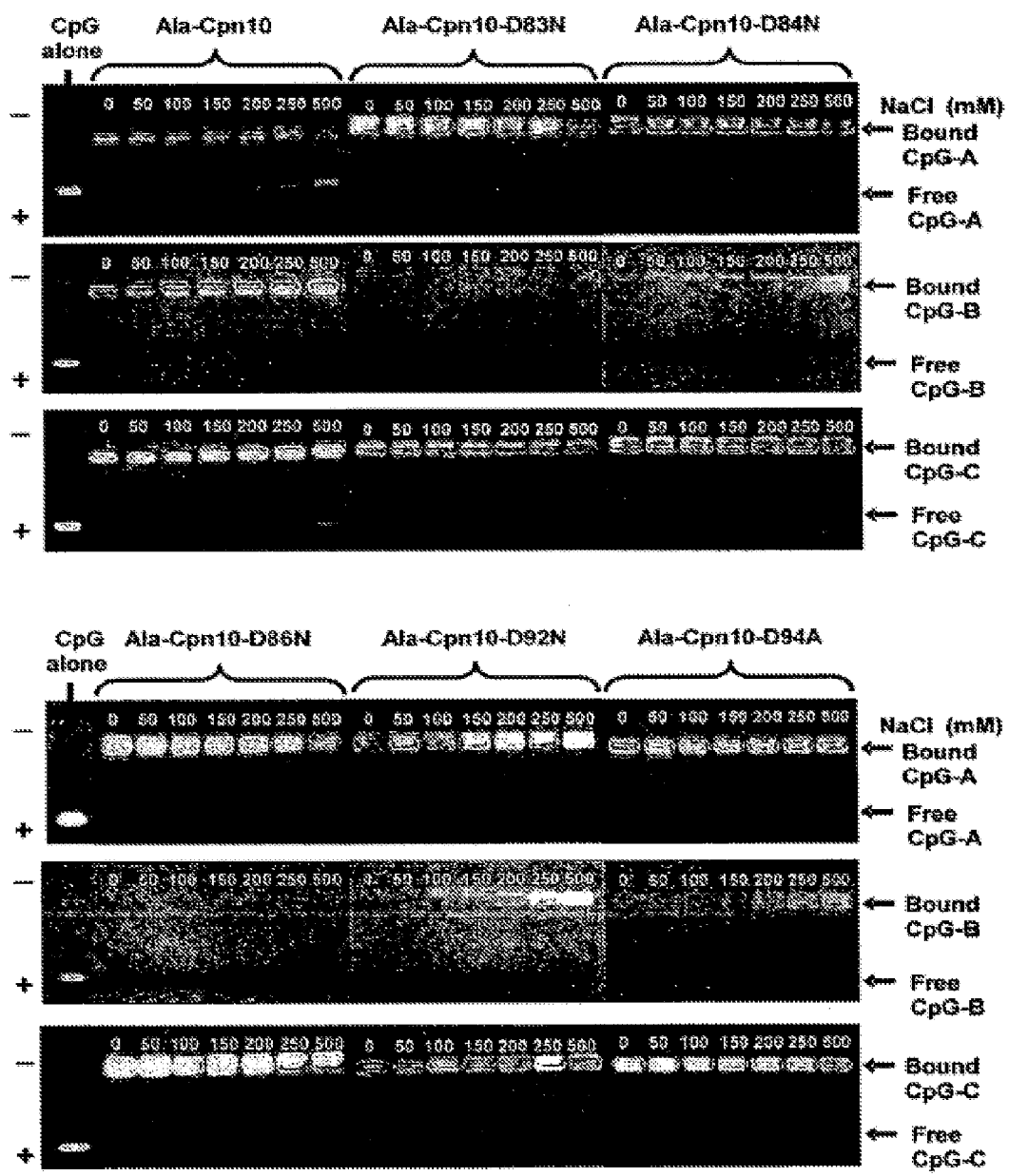
Figure 5d. Negative to Neutral Substitutions - CONTINUED

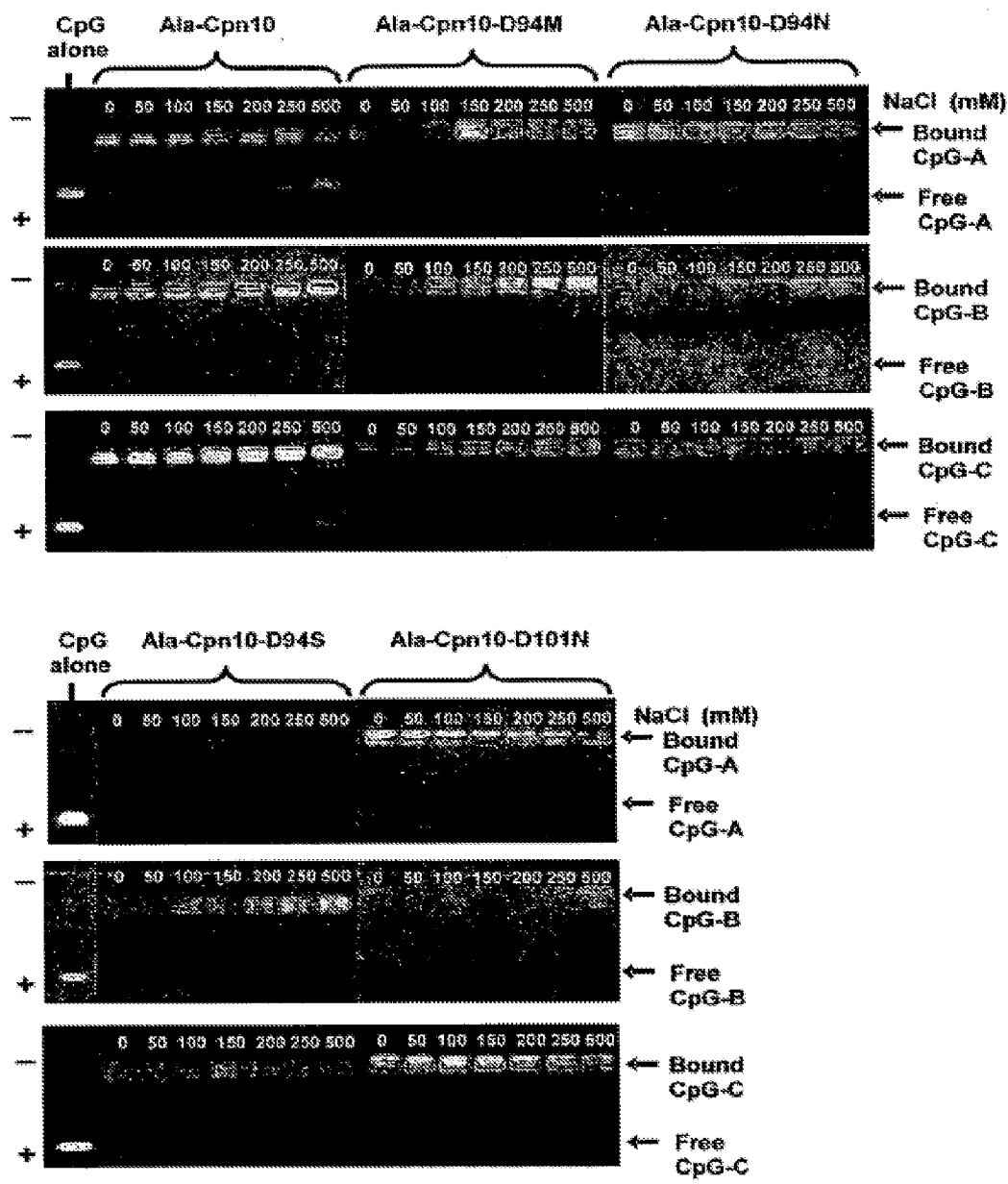
Figure 5d. Negative to Neutral Substitutions - CONTINUED

Figure 5e. Positive insertions
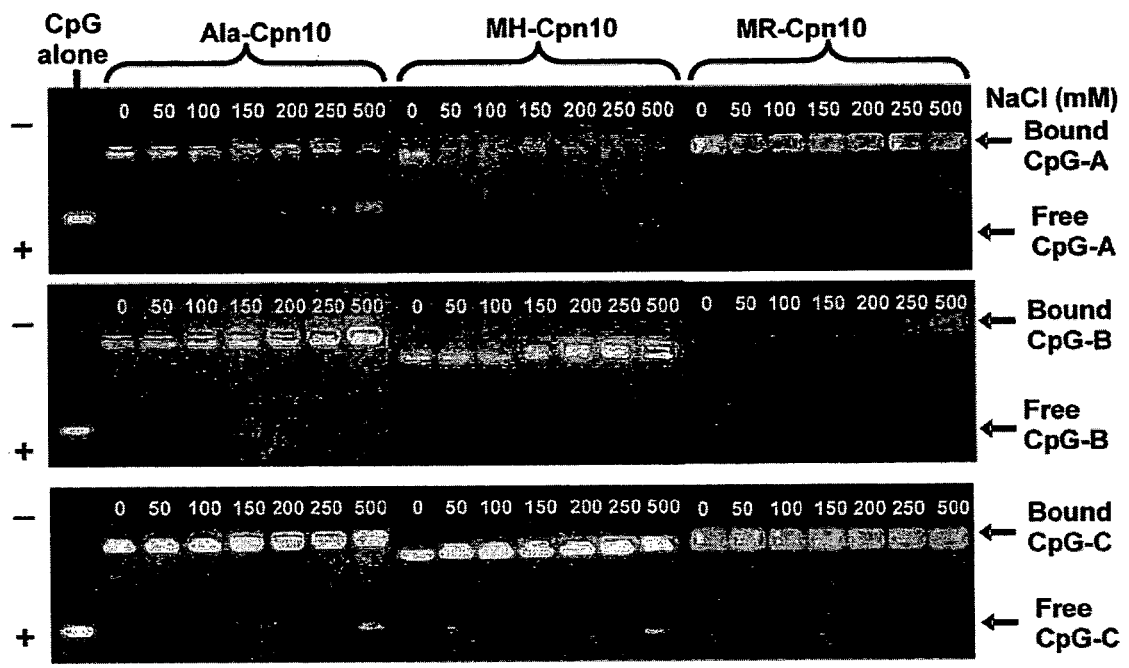
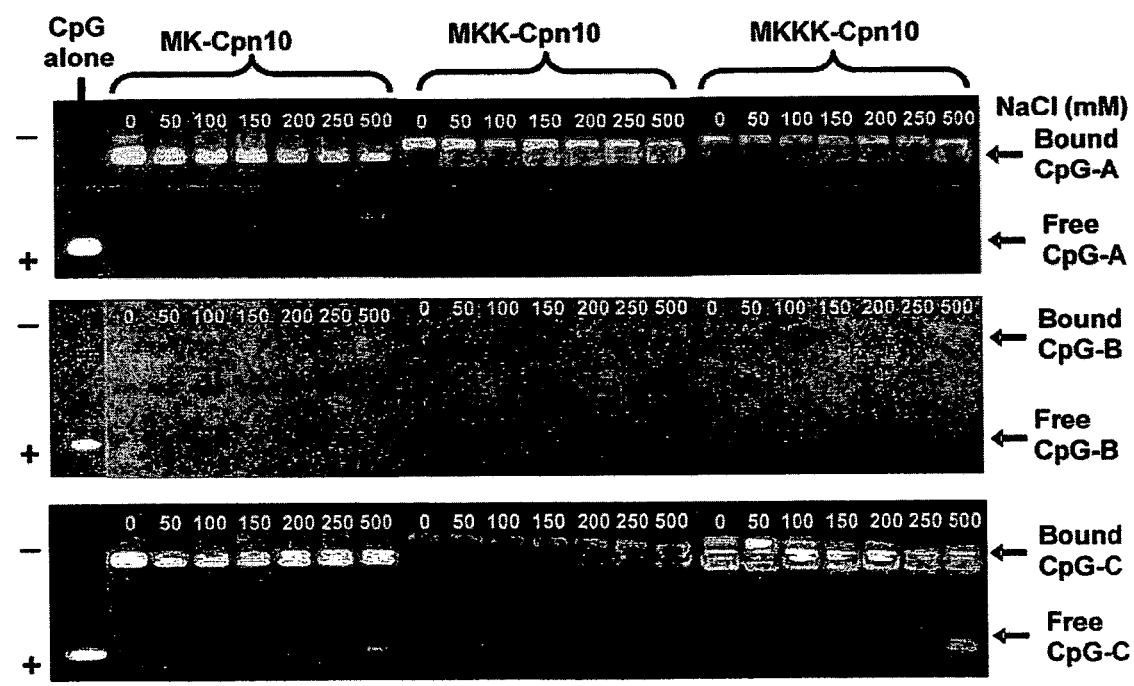

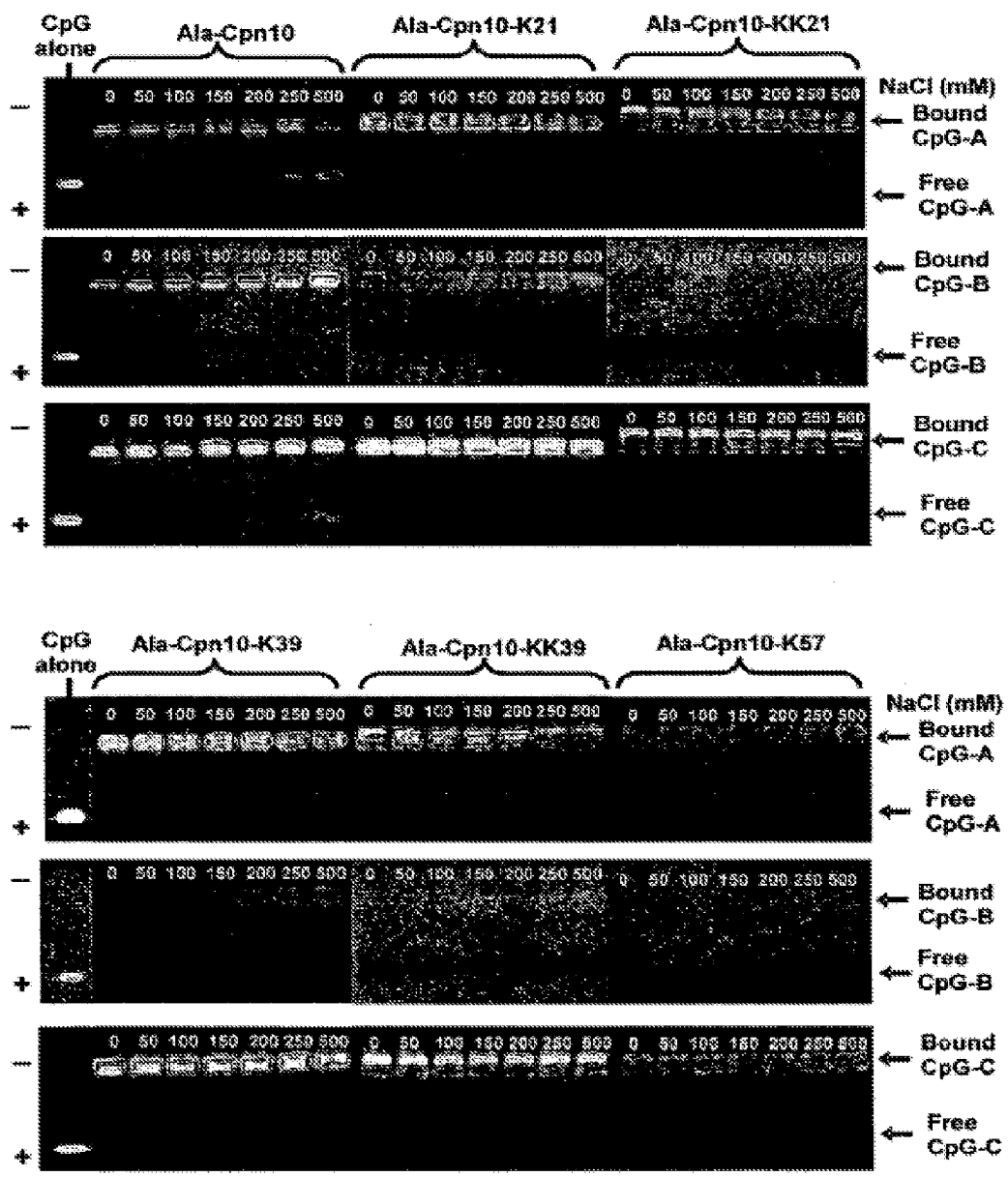
Figure 5e. Positive insertions - CONTINUED

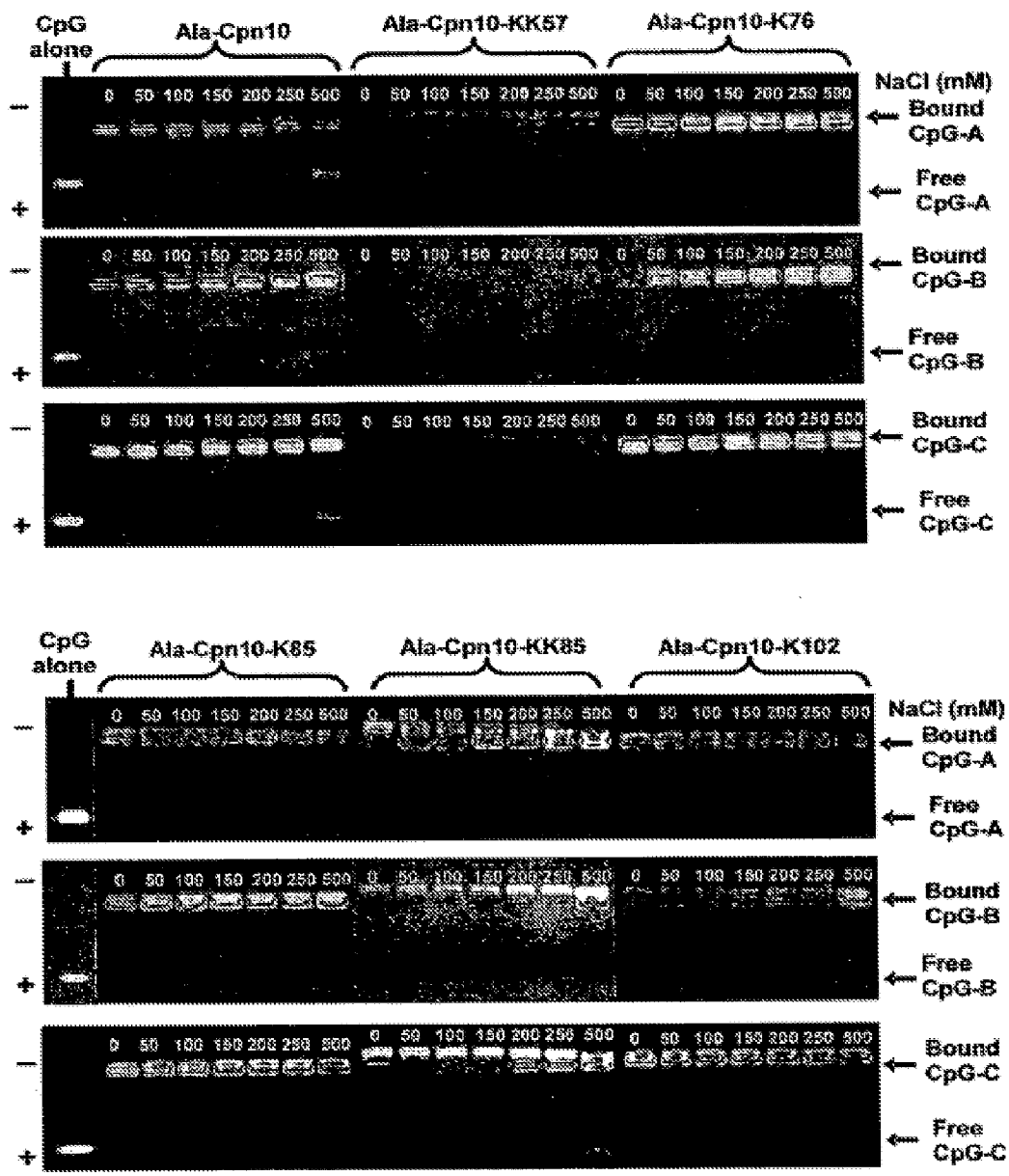
Figure 5e. Positive insertions - CONTINUED

Figure 5e. Positive insertions - CONTINUED

Figure 5f. Negative Deletions
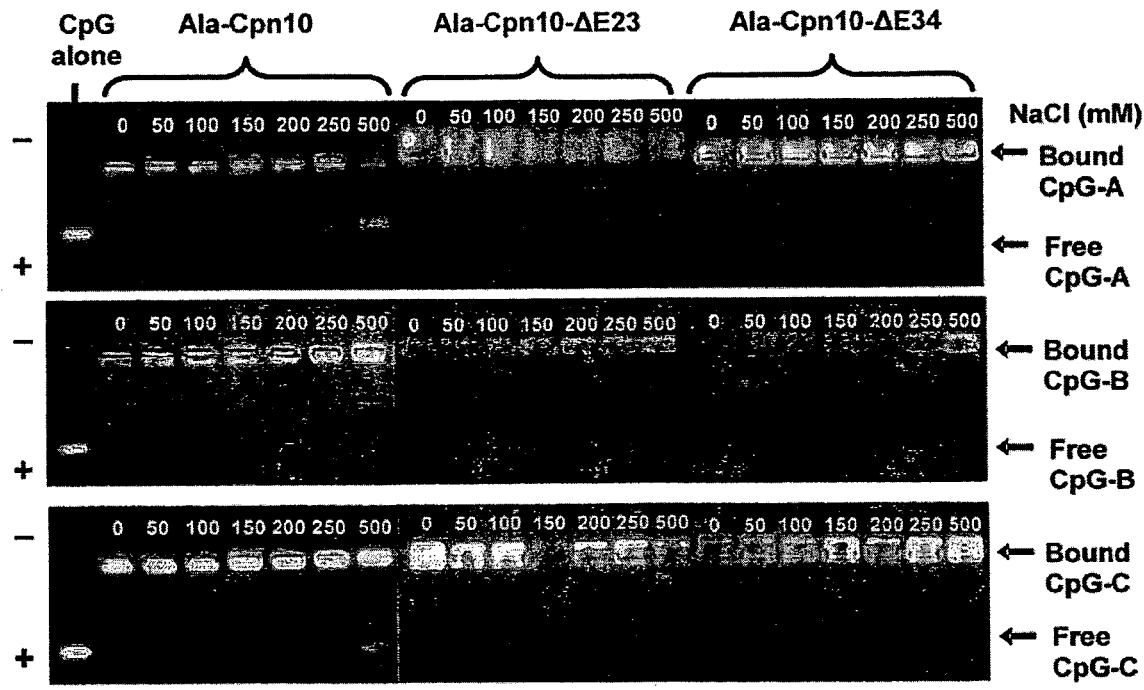
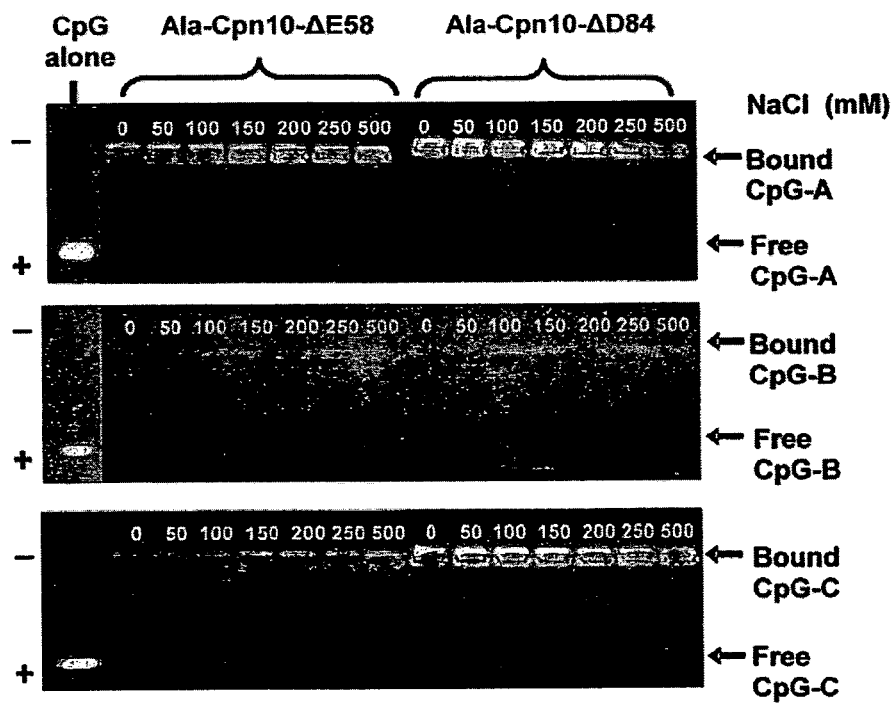

Figure 5g. Multiple Mutations
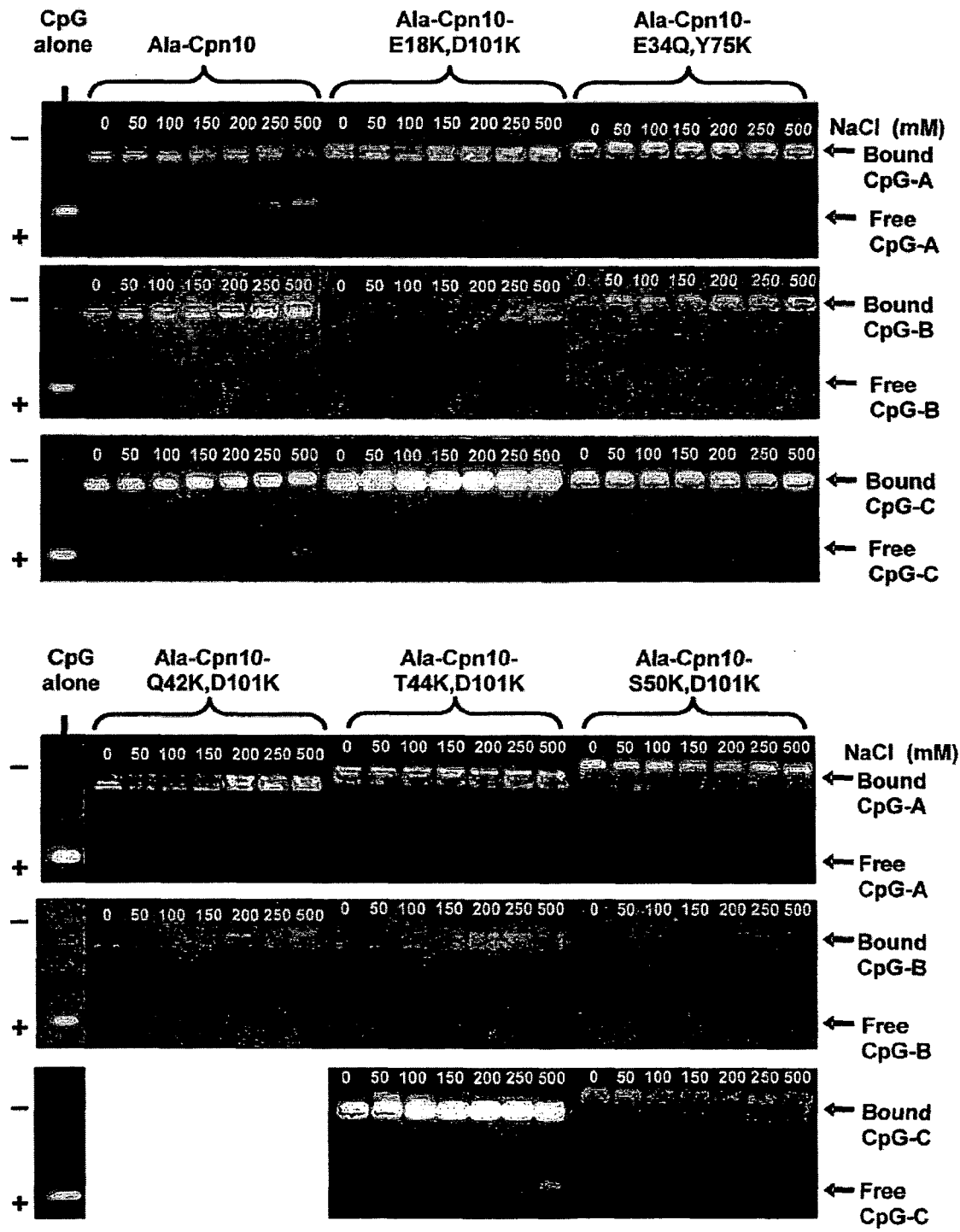

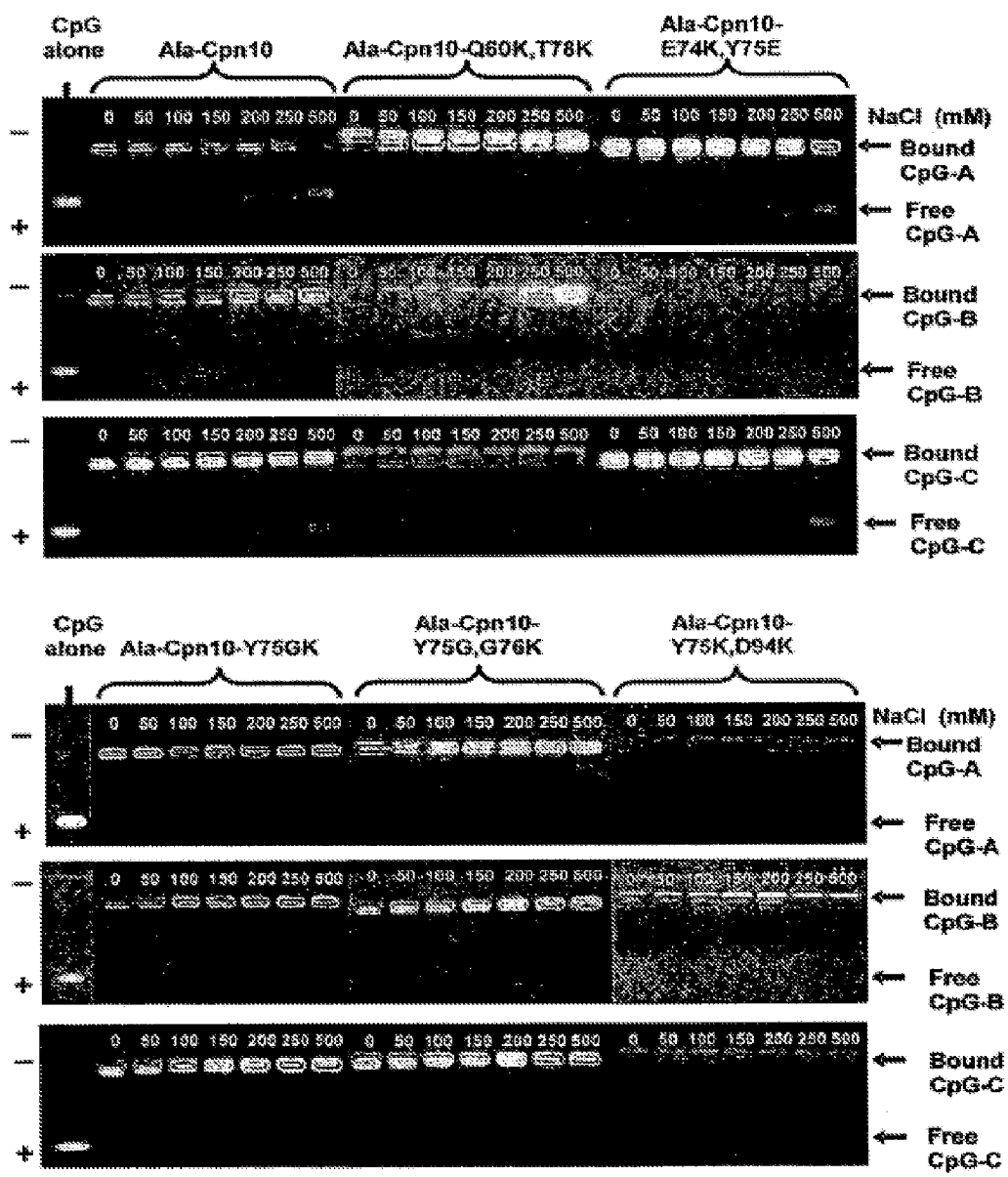
Figure 5g. Multiple Mutations - CONTINUED

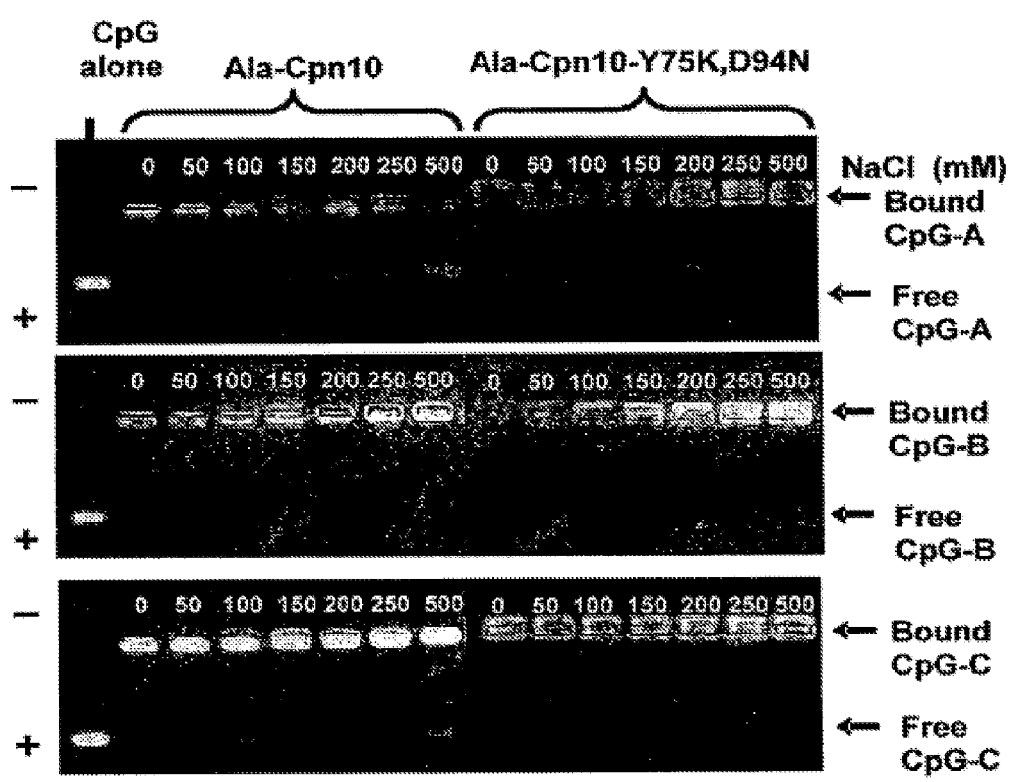
Figure 5g. Multiple Mutations - CONTINUED

Figure 6a. Controls
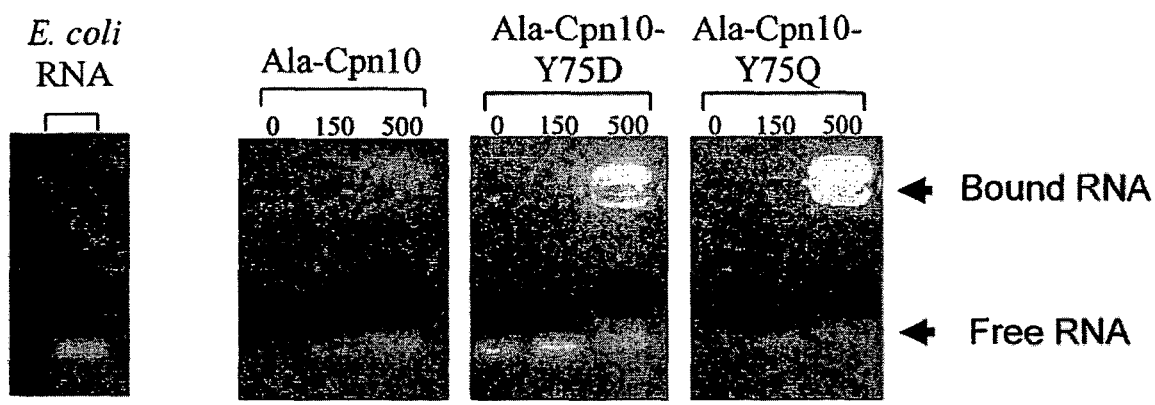
Figure 6b. Positive to Positive Substitution
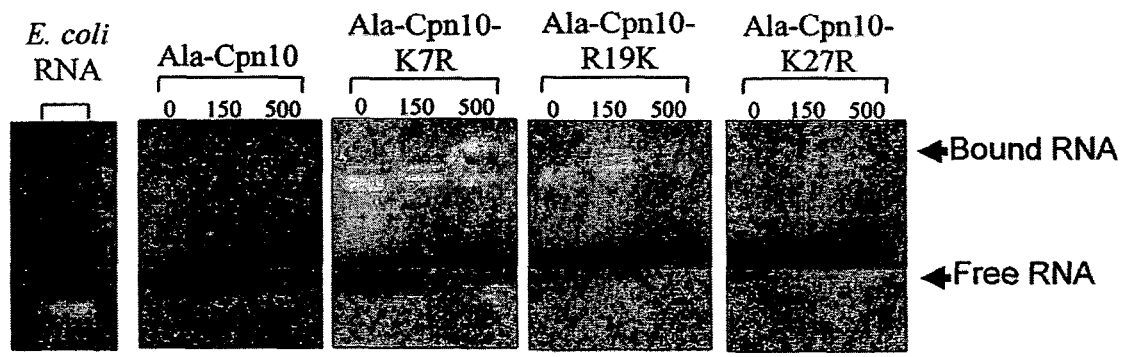

Figure 6c. Positive Substitution
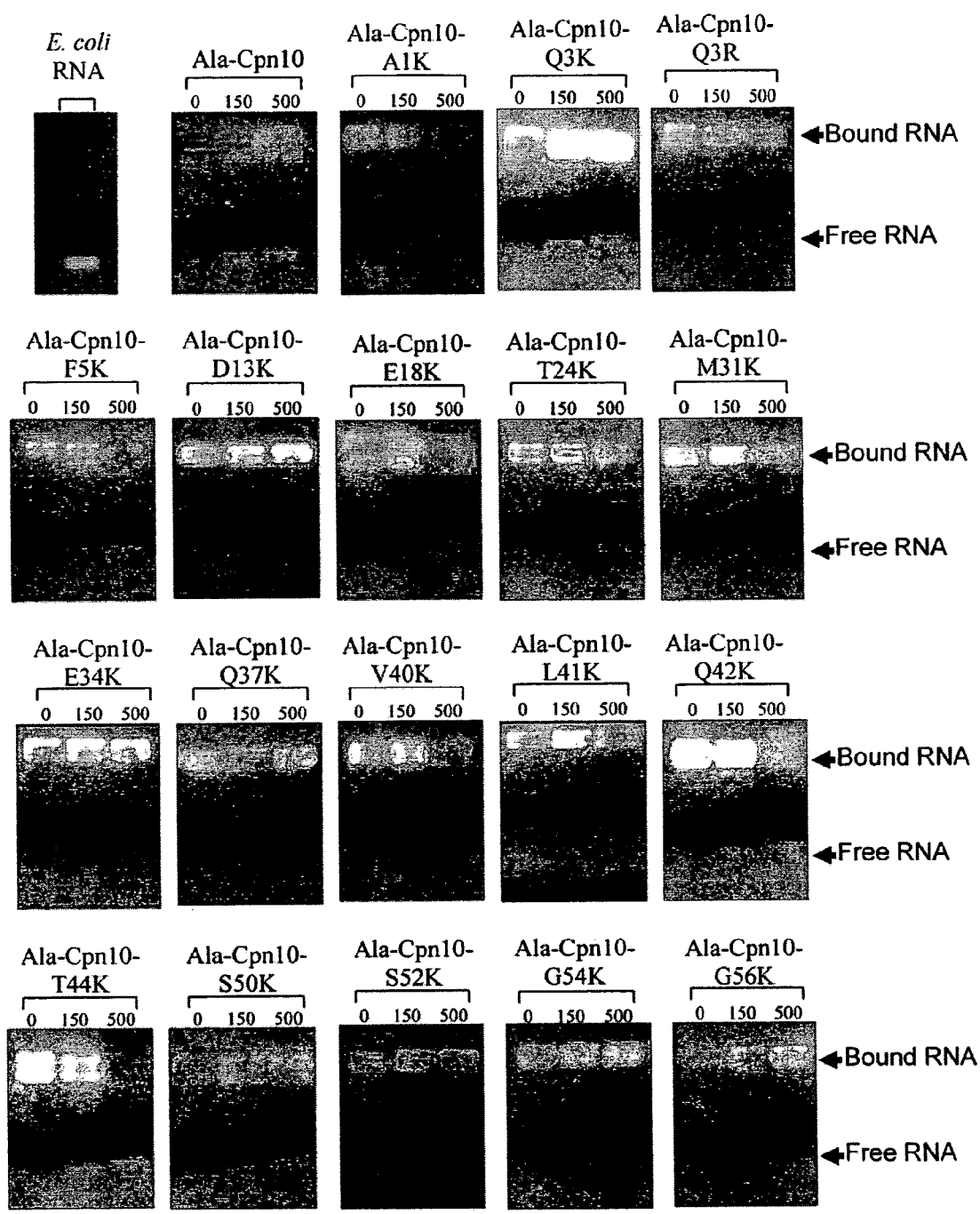

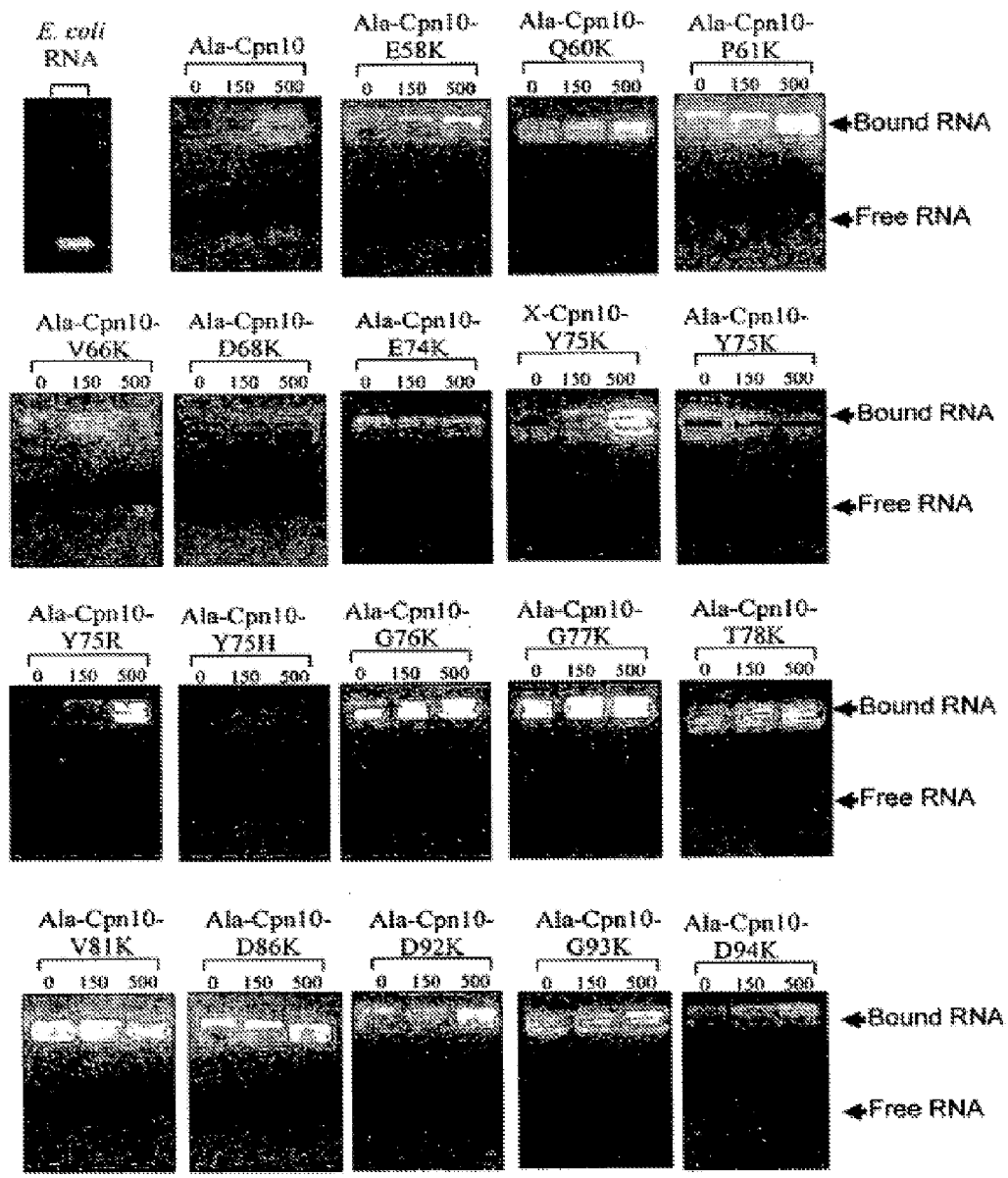
Figure 6c. Positive Substitution - CONTINUED

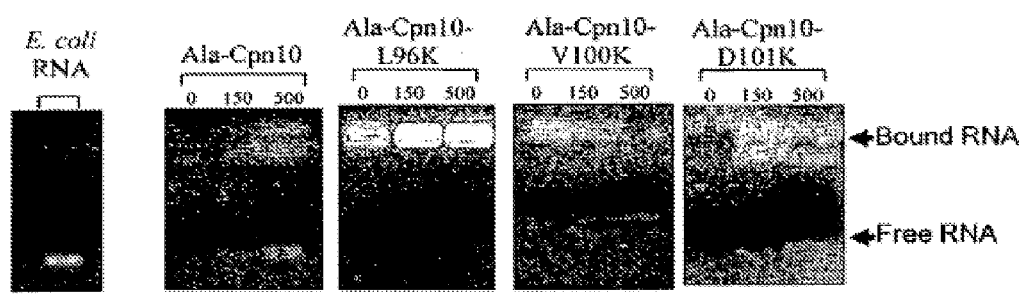
Figure 6c. Positive Substitution - CONTINUED

Figure 6d. Negative to Neutral Substitutions
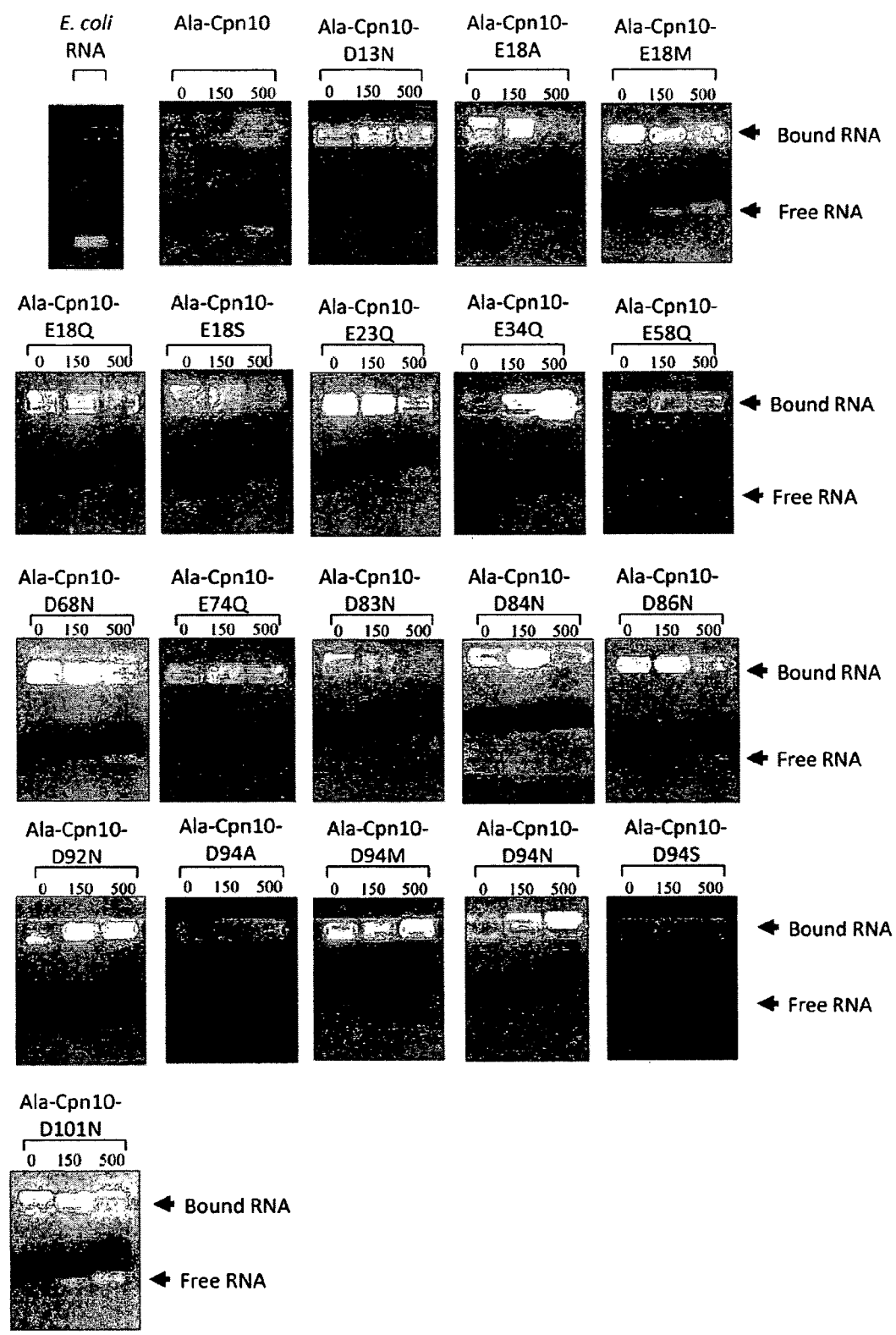

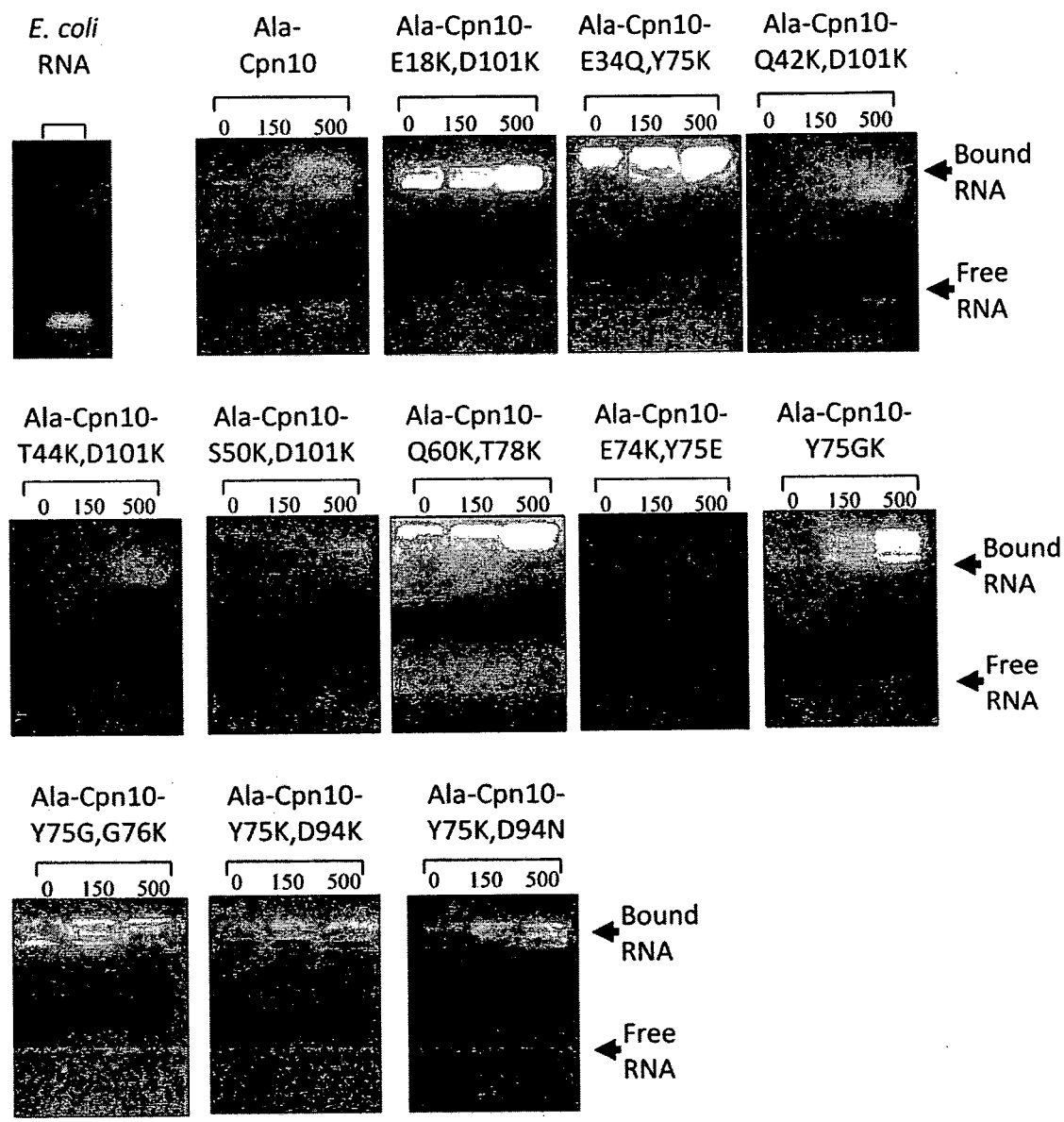
Figure 6e. Positive Insertions

Figure 6f. Negative Deletions
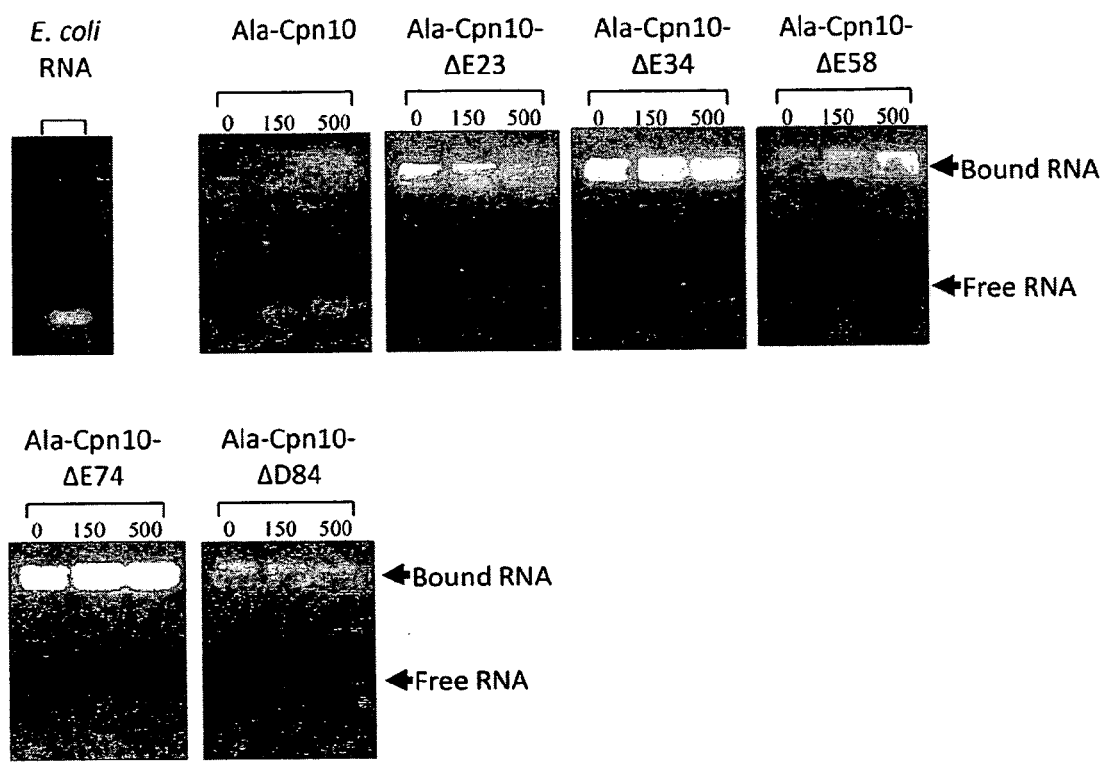

Figure 6g. Multiple Mutations
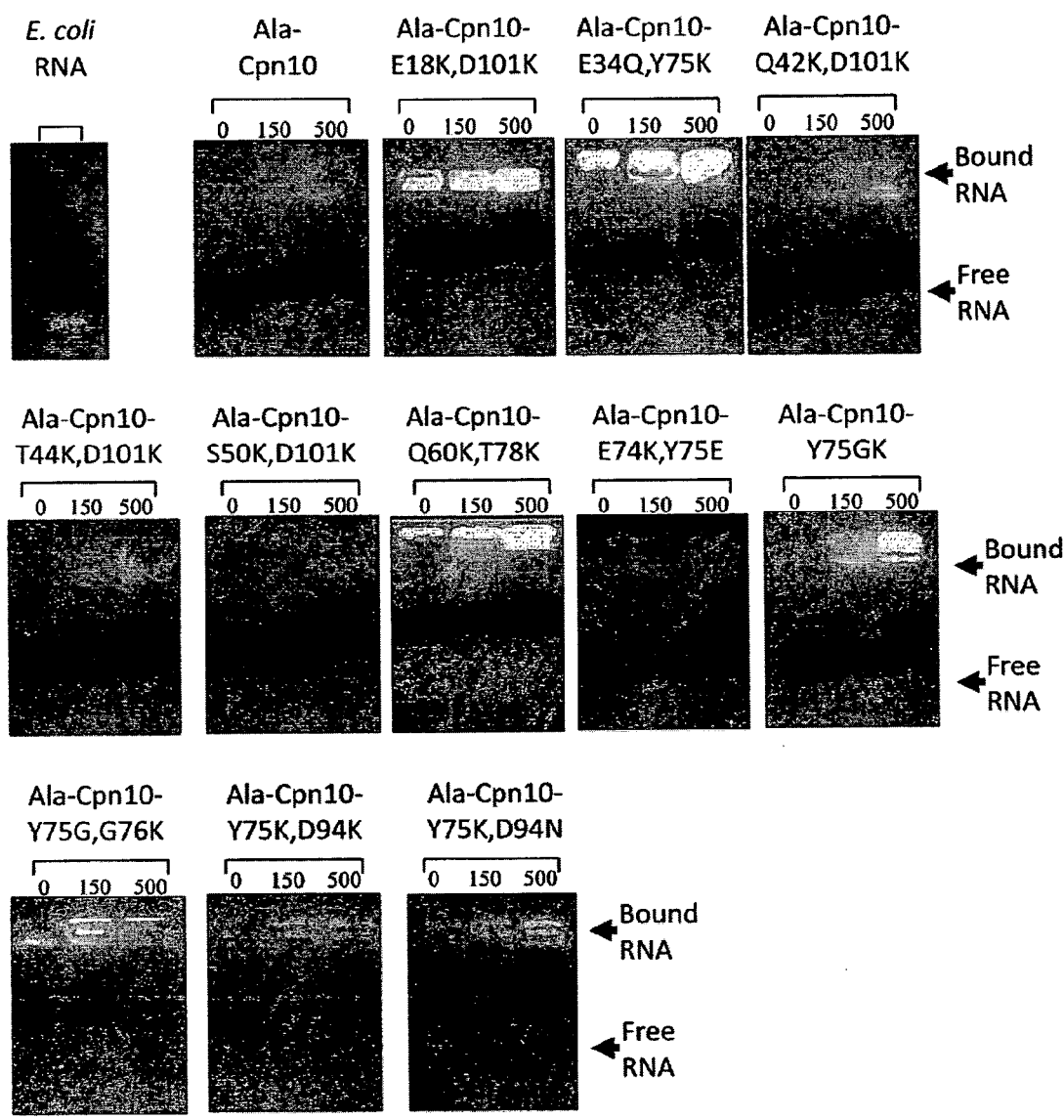

Figure 7a. Binding of CpG ODN to Cpn10 Controls
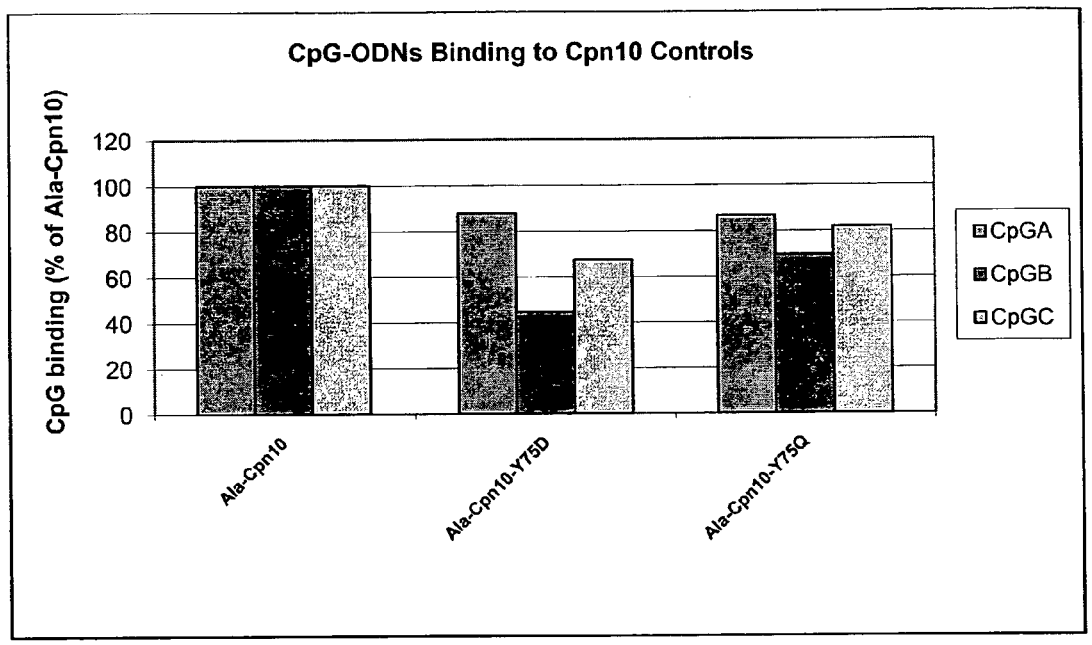
Figure 7b. Binding of CpG ODN to Cpn10 Mutants with Positive to Positive Substitutions
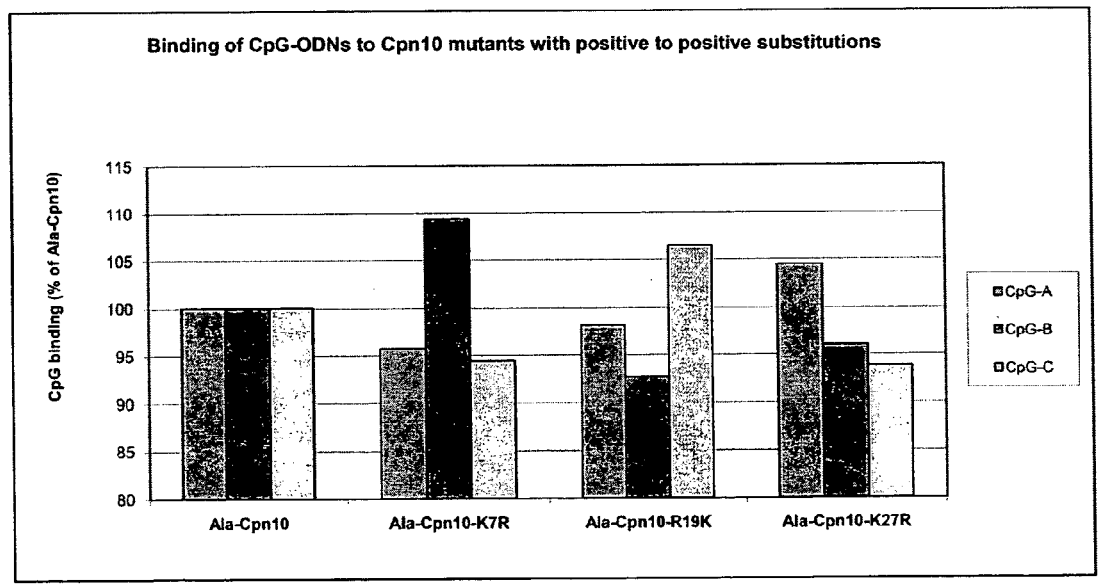

Figure 7c. Binding of CpG ODN to Cpn10 Mutants with Positive Substitutions

Figure 7d. Binding of CpG ODN to Cpn10 Mutants with Negative to Neutral Substitutions Figure 7e. Binding of CpG ODN to Cpn10 Mutants with Positive Insertions Figure 7f. Binding of CpG ODN to Cpn10 Mutants with Negative Deletions Figure 7g. Binding of CpG ODN to Cpn10 Mutants with Multiple Mutations

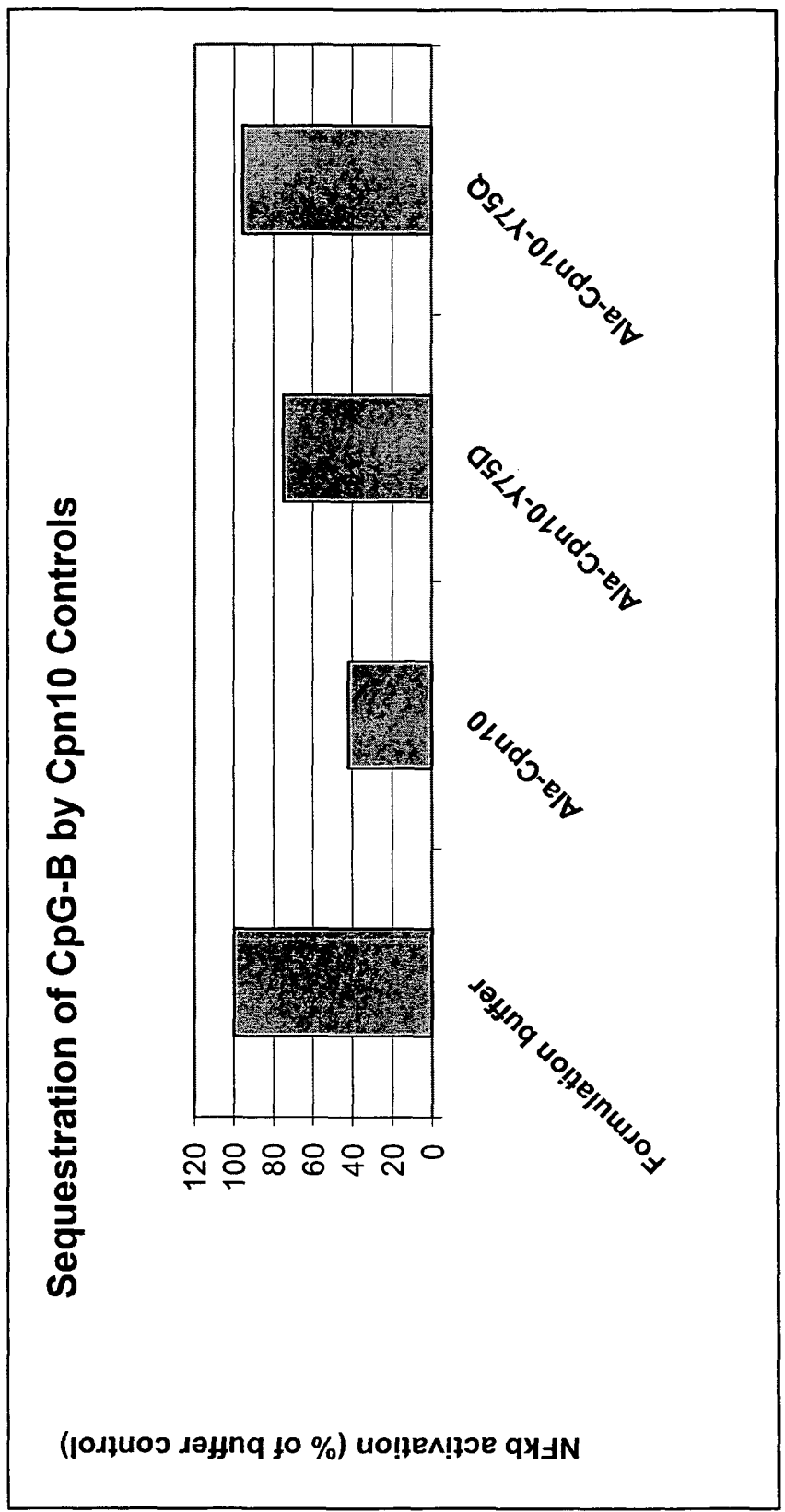
Figure 8a. Sequestration of CpGB ODN by Cpn10 Controls

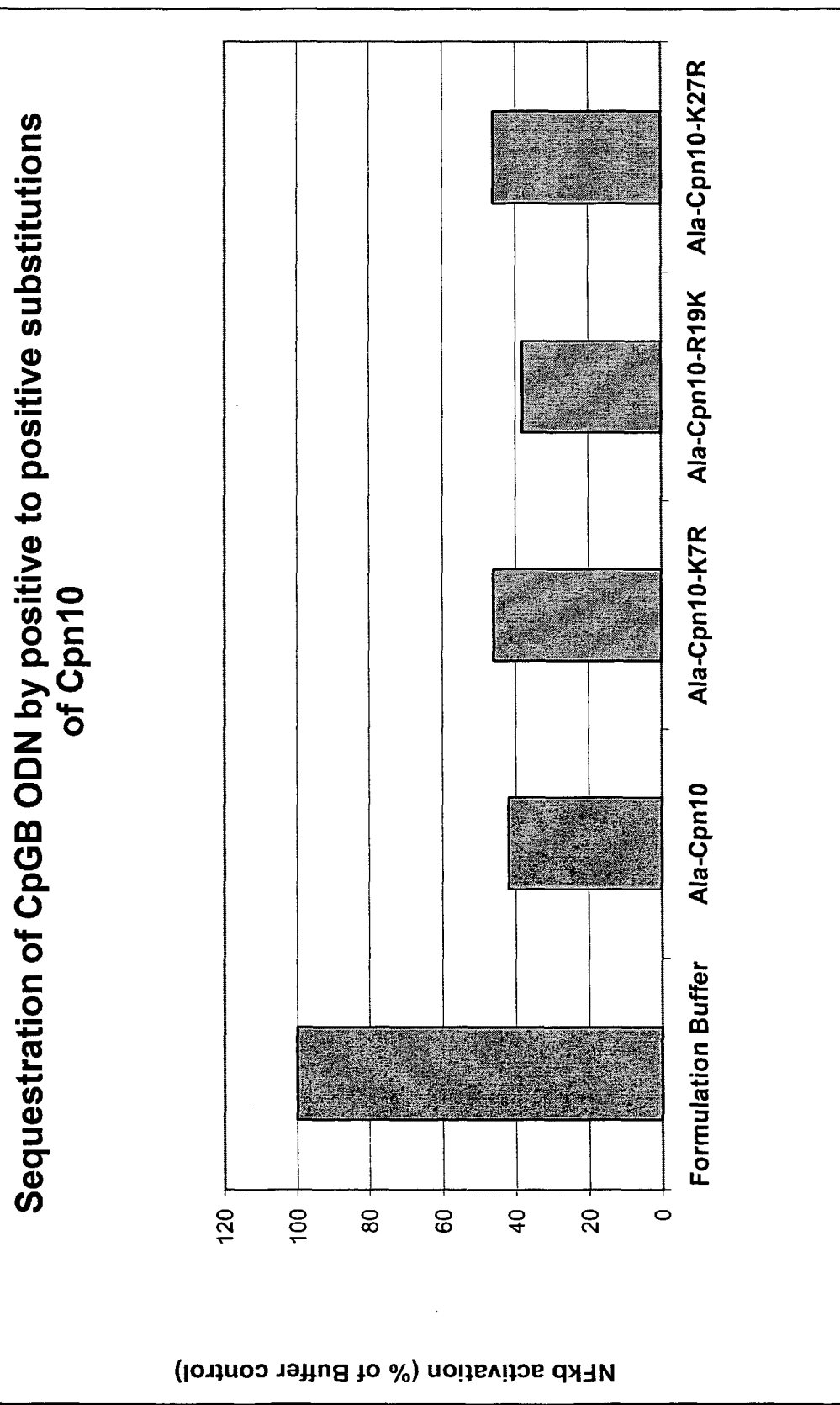
Figure 8b. Sequestration of CpGB ODN by Positive to Positive Substitutions of Cpn10

Figure 8c. Sequestration of CpGB ODN by Positive Substitutions of Cpn10

Figure 8d. Sequestration of CpGB ODN by Negative to Neutral Substitutions of Cpn10

Figure 8e. Sequestration of CpGB ODN by Positive Insertions of Cpn10

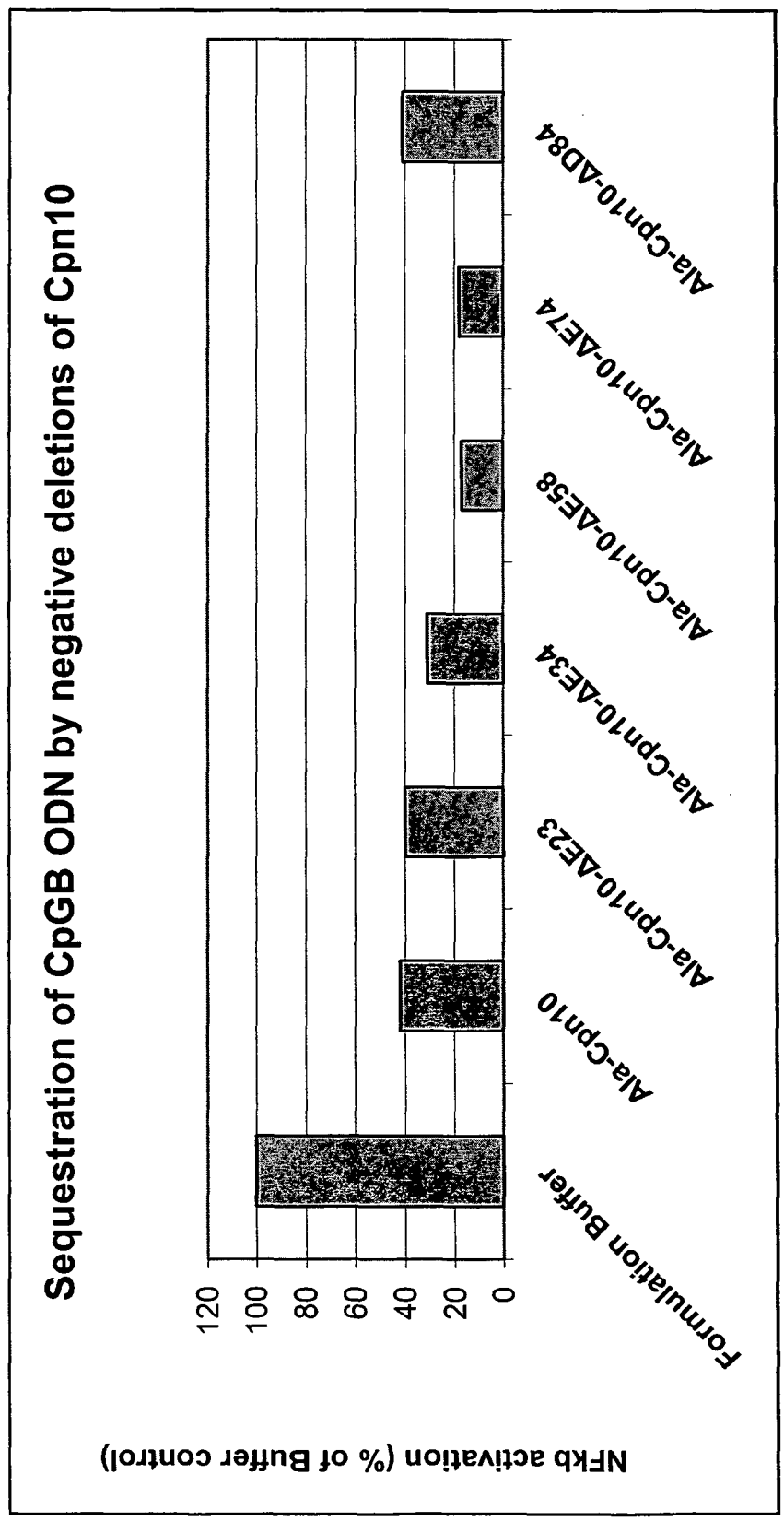
Figure 8f. Sequestration of CpGB ODN by Negative Deletions of Cpn10

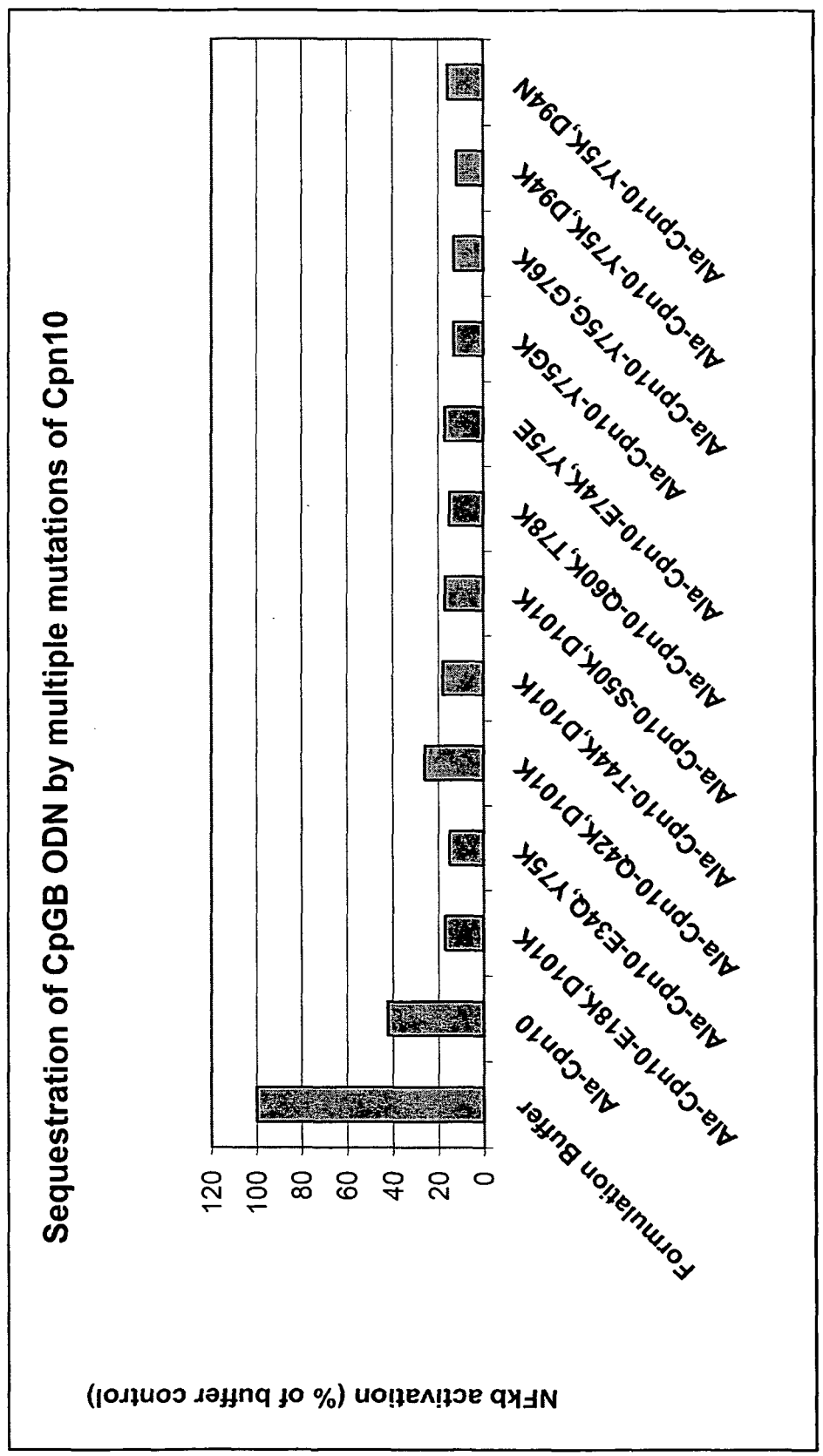
Figure 8g. Sequestration of CpGB ODN by Multiple Mutations of Cpn10

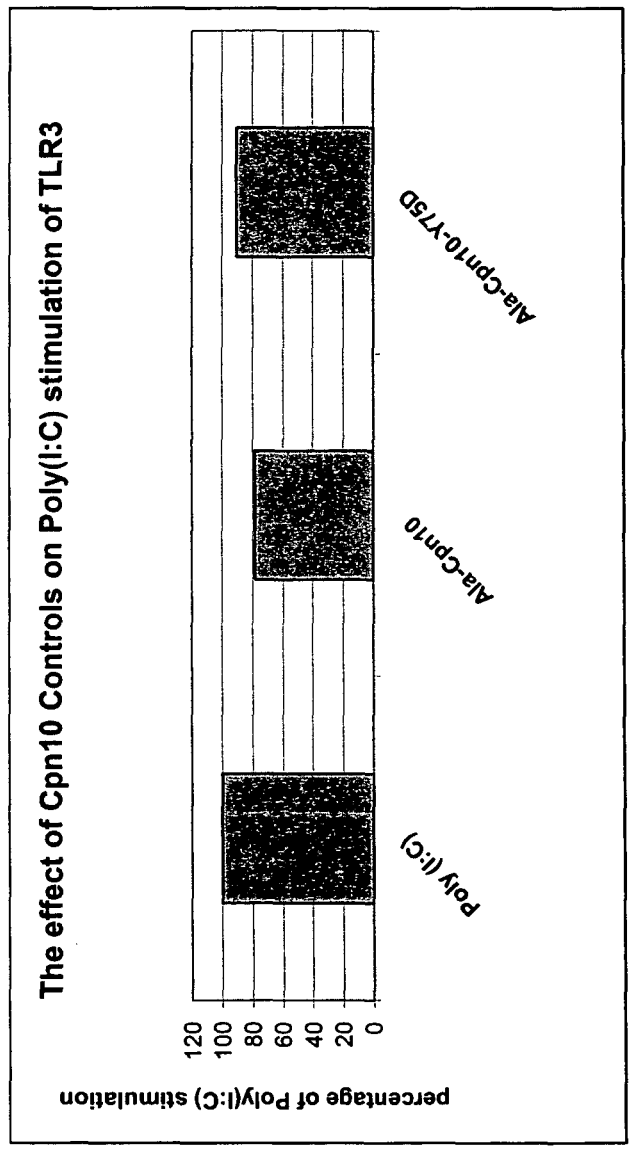
Figure 9a. Activation of TL3 by Cpn10 Controls

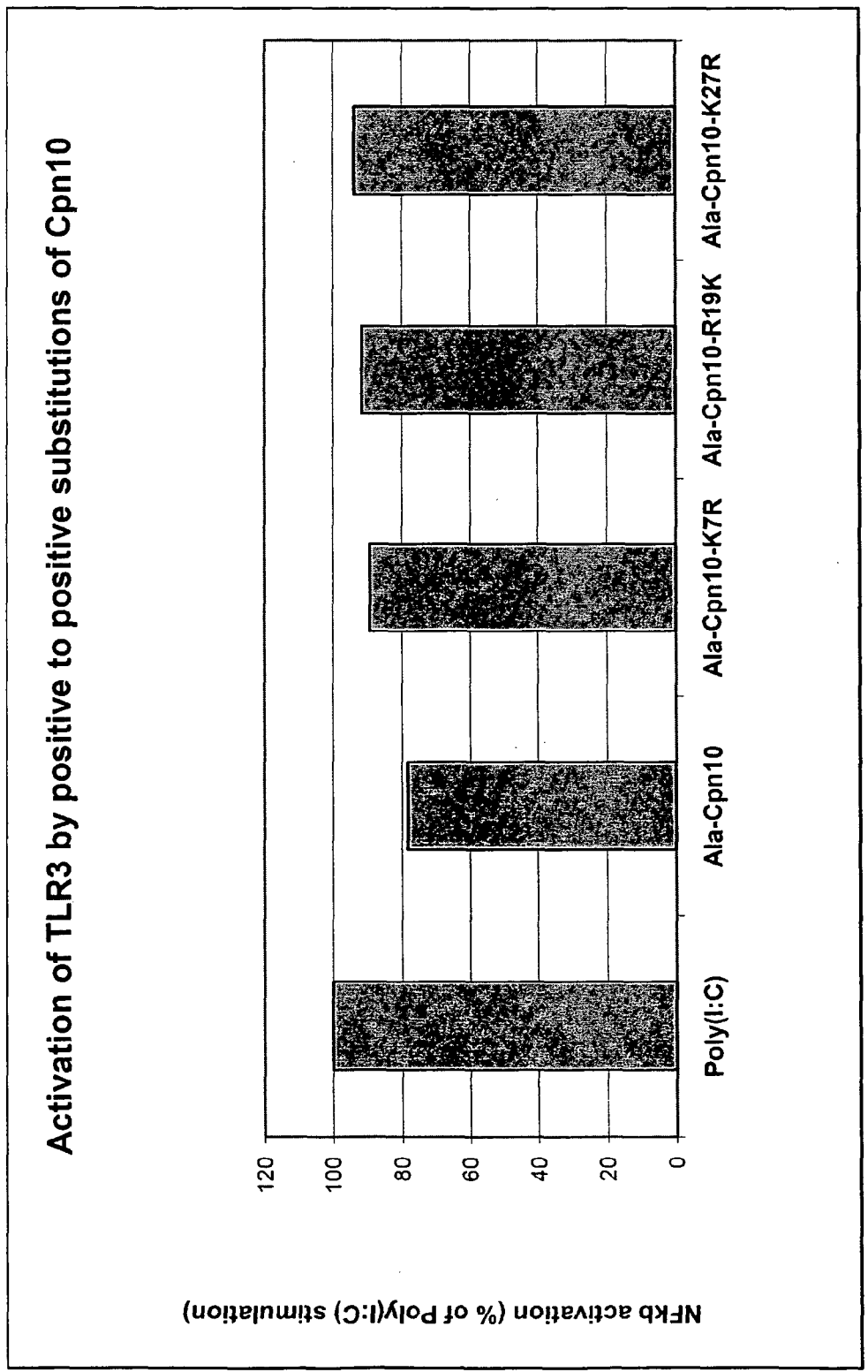
Figure 9b. Activation of TL3 by Positive to Positive Substitutions of Cpn10

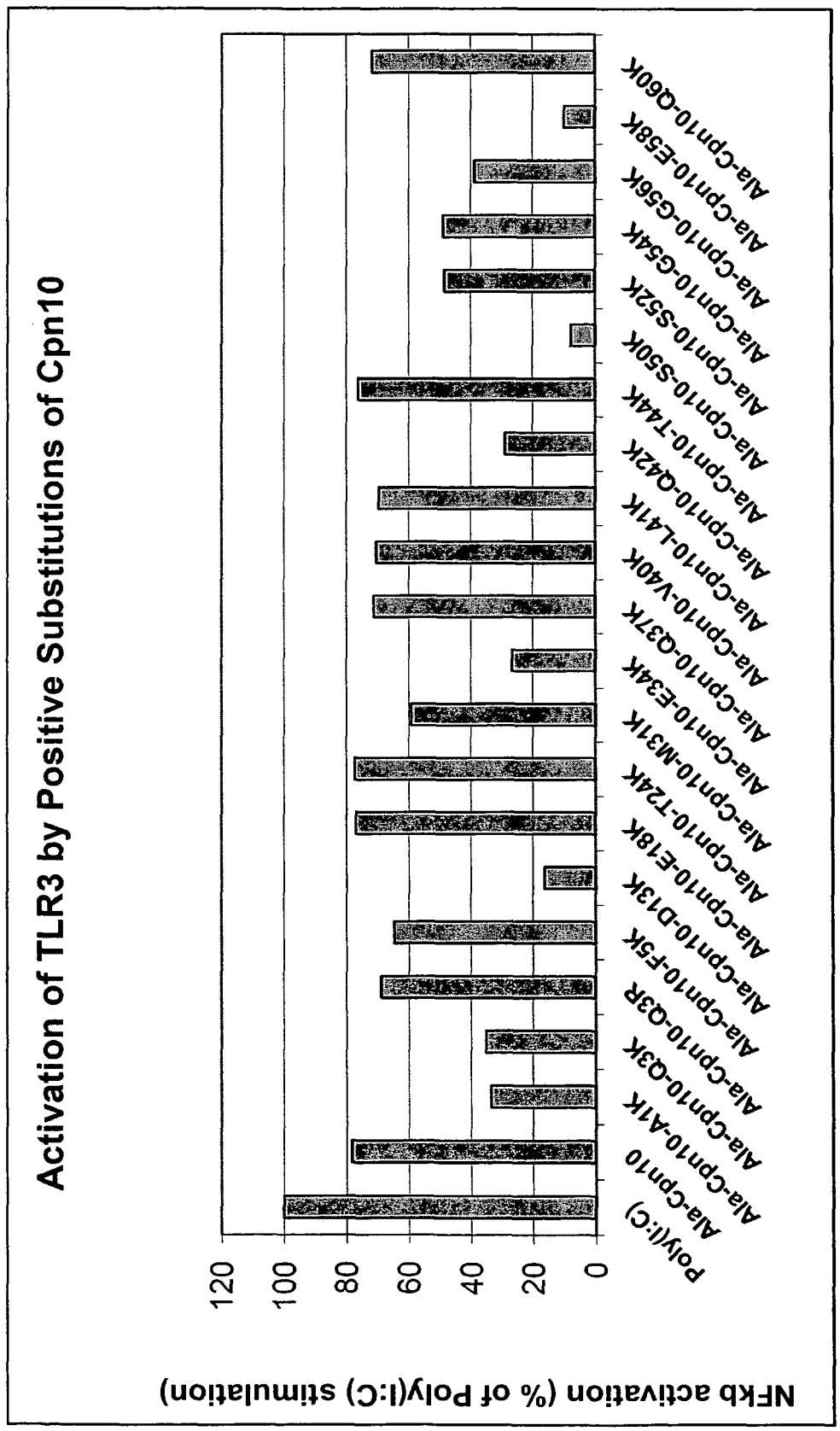
Figure 9c. Activation of TL3 by Positive Substitutions of Cpn10

Figure 9e. Activation of TL3 by Positive Insertions of Cpn10

Activation of TLR3 by Positive Insertions of Cpn10

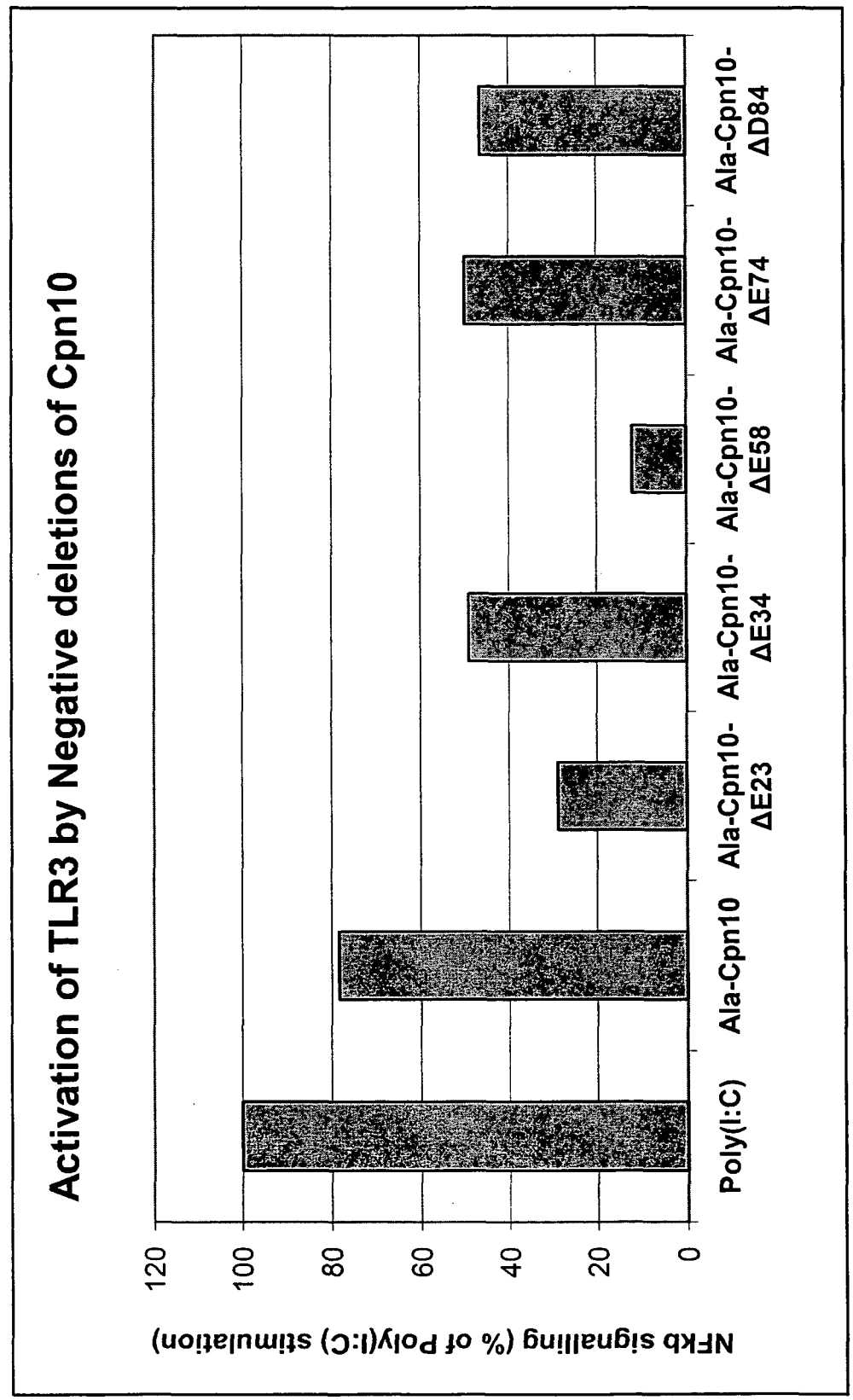
Figure 9f. Activation of TL3 by Negative Deletions of Cpn10

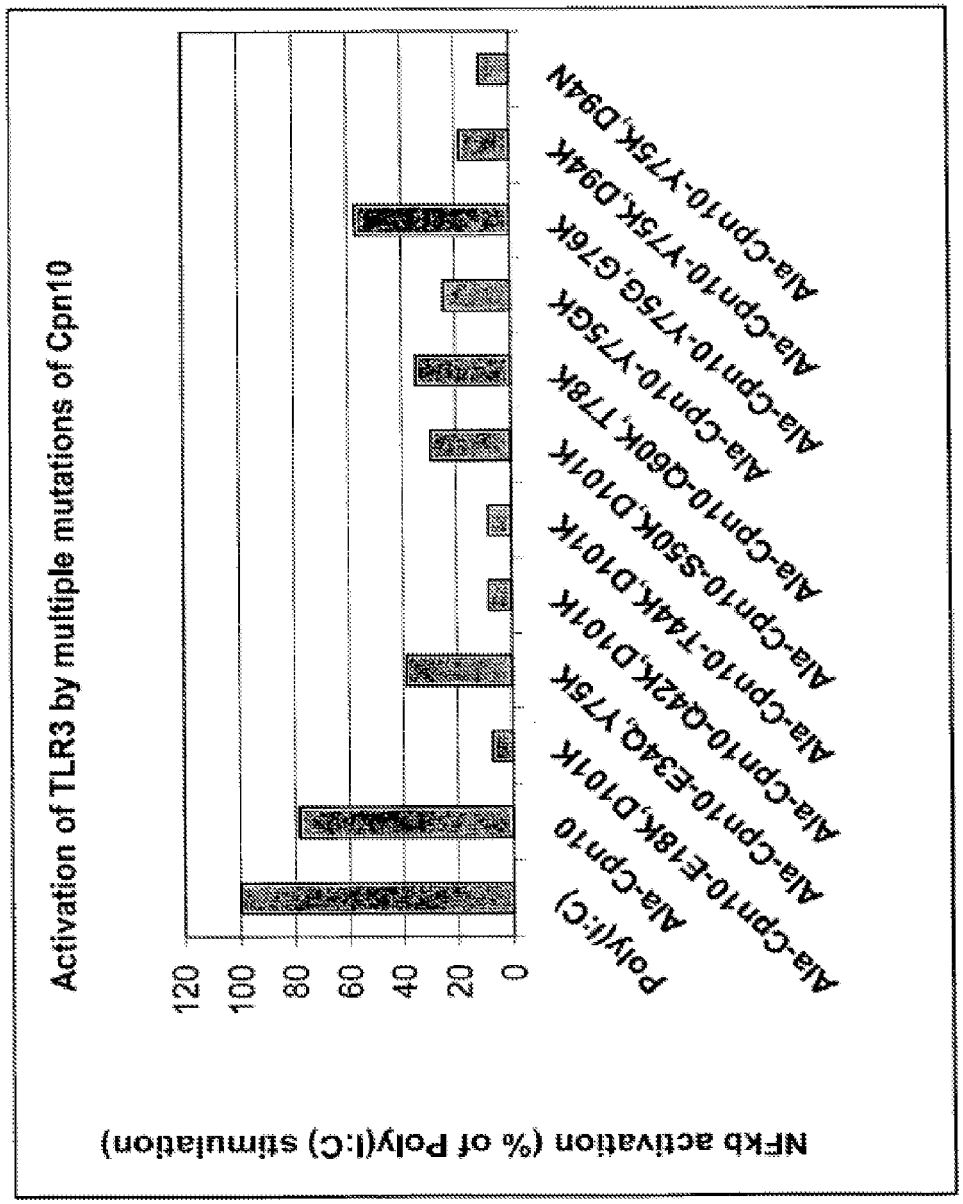
Figure 9f. Activation of TL3 by Multiple Mutations of Cpn10 - CONTINUED

MODIFIED CPN10 AND PRR SIGNALLING

This application is a section 371 national phase application of PCT/AU2009/000444, which claims priority to PCT application PCT/AU2008/000520, filed Apr. 11, 2008, and Australian patent application 2009900613, filed Feb. 13, 2009; all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jan. 16, 2013, is named P691US00.txt and is 346,108 bytes in size.

FIELD OF THE INVENTION

The present invention relates to modified chaperonin 10 polypeptides, and to nucleic acids encoding the same. The present invention further relates to mutants of chaperonin 10 and to compositions comprising such polypeptides.

BACKGROUND

Mammalian chaperonin 10 (Cpn10), also known as heat shock protein 10 (Hsp10) and early pregnancy factor (EPF), is typically characterised as a mitochondrial 'molecular chaperone' protein involved in protein folding together with chaperonin 60 (Cpn60), also known as heat shock protein 60 (Hsp60). Cpn10 and Cpn60 are homologues of the bacterial proteins GroES and GroEL respectively. GroES and Cpn10 each oligomerise into seven member rings that bind as a lid onto a barrel-like structure comprising fourteen GroEL or seven Cpn60 molecules respectively, which tether denatured proteins to the complex (Bukau and Horwich, 1998, *Cell* 92:351-366; Hartl and is Hayer-Hartl, 2002, *Science* 295:1852-1858).

Cpn10 proteins are highly conserved across species. Human Cpn10 is 100% identical to bovine, canine, ovine and porcine Cpn10 and differs from rat Cpn10 at only a single amino acid position. Human Cpn10 shares 38% sequence identity (60% similarity) with GroES from *Escherichia coli*. Cpn10/GroES proteins are dome shaped heptameric rings wherein each monomer is comprised of essentially three different structural regions, a core anti-parallel β-barrel region flanked by a "roof" β-hairpin loop region and a "mobile loop" region. The anti-parallel β-barrel region of each monomer forms the core of a dome and when assembled in the heptamer the β-hairpin loops of each monomer form the roof of the dome. In each monomer, the mobile loop region is at the opposite end of the β-barrel to the roof loops. A section of the anti-parallel β-barrel region forms an inward facing lower rim region of the cavity. This lower rim region contains a number of phylogenetically conserved amino acids including a Tyrosine at position 75 (Y75).

In addition to its intracellular role as a molecular chaperone, Cpn10 is also frequently found at the cell surface (see Belles et al., 1999, *Infect Immun* 67:4191-4200) and in the extracellular fluid (see Shin et al., 2003, *J Biol Chem* 278: 7607-7616) and is increasingly being recognised as a regulator of the immune response with potential in the treatment of inflammatory disorders. Accordingly, the efficacy and safety of Cpn10 has recently been established in the treatment of human patients with rheumatoid arthritis (Vanags et al. *Lancet* 2006, 368: 855-863) and psoriasis (Williams et al. Arch. Dermatol. 2008, 144: 683-685).

However the sites within the Cpn10 molecule responsible for mediating this immunomodulatory activity have remained elusive. The present invention relates to the discovery that modification of Cpn10 affects the immunomodulatory activity of Cpn10, in particular its role in binding ligands of pattern recognition receptors (PRRs) such as Toll-like Receptors (TLR), Nucleotide-binding domain LRR-containing family (NLR), RIG-I-like receptors (RLR), DNA-dependent activators of IRF (DAI), C-type Lectin receptors (CLR) or a member of the IFI20X/IFI16 family (e.g. Ifi16, Aim2, MNDA and IFIX).

SUMMARY

According to a first aspect of the present invention there is provided an isolated Cpn10 polypeptide possessing an increased affinity for a nucleic acid-based PRR ligand compared to Ala-Cpn10 polypeptide (SEQ ID No: 3).

The PRR may be a Toll-like Receptor (TLR), Nucleotide-binding domain LRR-containing family (NLR), RIG-I-like receptor (RLR), DNA-dependent activator of IRF (DAI), C-type Lectin receptor (CLR) or a member of the IFI20X/IFI16 family (e.g. Ifi16, Aim2, MNDA and IFIX)

The TLR may be selected from the group comprising of at least one of TLR3, TLR7, TLR8 or TLR9. In one embodiment the TLR may be TLR9.

The ligand may be an agonist or antagonist. In one embodiment, said polypeptide possesses a greater net positive charge compared to the Ala-Cpn10 polypeptide.

The isolated polypeptide may further comprise an amino acid insertion of glycine (G) at the N terminus compared to wild-type Cpn10 polypeptide. The polypeptide may be naturally-derived, recombinantly produced or synthetically produced. The Cpn10 may be of eukaryotic origin. The polypeptide may be of mammalian origin. The polypeptide may be human Cpn10.

In another embodiment, the isolated polypeptide possesses at least one mutation of the Ala-Cpn10 molecule. The mutation may be an amino acid substitution, addition or deletion or a combination thereof. The substitution may be the replacement of one or more amino acid residues with one or more positively charged residues. In another embodiment, one or more negatively charged residues may be replaced with a neutral or positively charged residue. The mutational addition may be the inclusion of one or more positively charges residues. The mutational deletion may be the removal of one or more negatively charged residues.

In another embodiment, a neutral residue may be replaced with a positively charged residue. The positively charged residue may be arginine (R), lysine (K) or histidine (H). The neutral residue may be asparagine (N), glutamine (Q), serine (S), threonine (T), glycine (G), alanine (A), valine (V), leucine (L), isoleucine (I), proline (P), phenylalanine (F), tyrosine (Y), tryptophan (W), cysteine (C), methionine (M) or H. Note, Histidine has a pKa ~6.5, therefore it will be ~11% ionised at pH7.4 (eg extracellular milieu) and ~76% ionised at pH6.0 (eg endo-lysosomal compartments containing TLR3, TLR7, TLR8 and TLR9).

In another embodiment, the at least one mutation is located in the N-terminus, β-barrel, mobile loop, roof loop, C-terminus, or any of the three connective loops of the wild-type Cpn10 molecule or any combination thereof.

In yet another embodiment, the polypeptide comprises a mutation at an amino acid position selected from the group consisting of position 1 to 7, 9, 12 to 14, 16, 18 to 42, 44, 46, 50, 52 to 63, 65 to 69, 73 to 79, 81, 83 to 89, 91 to 94, 96, 98, 100 and 101 of the wild-type Cpn10 molecule or any combination thereof.

In a further embodiment, said polypeptide comprises a mutation selected from the group consisting of A1(K, R or H), G2(K, R or H), Q3(K, R or H), A4(K, R or H), F5(K, R or H), R6(K or H), K7(R or H), L9(K, R or H), F12(K, R or H), D13(K, R, H, N, Q, G, A, V, L, I, P, F, Y, W, C, M, S or T), R14 (K or H), L16(K, R or H), E18(K, R, H, N, Q, G, A, V, L, I, P, F, Y, W, C, M, S or T), R19(K or H), S20(K, R or H), A21(K, R or H), A22 (K, R or H), E23(K, R, H, N, Q, G, A, V, L, I, P, F, Y, W, C, M, S or T), T24(K, R or H), V25(K, R or H), T26(K, R or H), R27(K or H), G28(K, R or H), G29(K, R or H), I30(K, R or H), M31(K, R or H), L32(K, R or H), P33(K, R or H), E34(K, R, H, N, Q, G, A, V, L, I, P, F, Y, W, C, M, S or T), K35(R or H), S36(K, R or H), Q37(K, R or H), G38(K, R or H), K39(K, R or H), V40(K, R or H), L41(K, R or H), Q42(K, R or H), T44(K, R or H), V46(K, R or H), S50(K, R or H), S52(K, R or H), K53(R or H), G54(K, R or H), K55(R or H), G56(K, R or H), G57(K, R or H), E58(K, R, H, N, Q, G, A, V, L, I, P, F, Y, W, C, M, S or T), I59(K, R or H), Q60(K, R or H), P61(K, R or H), V62(K, R or H), S63(K, R or H), K65(R or H), V66(K, R or H), G67(K, R or H), D68(K, R, H, N, Q, G, A, V, L, I, P, F, Y, W, C, M, S or T), K69(R or H), P73(K, R or H), E74(K, R, H, N, Q, G, A, V, L, I, P, F, Y, W, C, M, S or T), Y75(E, GK, K, R or H), G76(K, R or H), G77(K, R or H), T78(K, R or H), K79(R or H), V81(K, R or H), D83(K, R, H, N, Q, G, A, V, L, I, P, F, Y, W, C, M, S or T), D84(K, R, H, N, Q, G, A, V, L, I, P, F, Y, W, C, M, S or T), K85(K, R or H), D86(K, R, H, N, Q, G, A, V, L, I, P, F, Y, W, C, M, S or T), Y87(K, R or H), F88(K, R or H), L89(K, R or H), R91(K or H), D92(K, R, H, N, Q, G, A, V, L, 1, P, F, Y, W, C, M, S or T), G93(K, R or H), D94(K, R, H, N, Q, G, A, V, L, I, P, F, Y, W, C, M, S or T), L96(K, R or H), K98(R or H), V100(K, R or H), D101(K, R, H, N, Q, G, A, V, L, I, P, F, Y, W, C, M, S or T), MH-Cpn10, MR-Cpn10, MK-Cpn10, MKK-Cpn10, MKKK-Cpn10 SEQ ID NO: 319), Ala-Cpn10-K21, Ala-Cpn10-KK21, Ala-Cpn10-K39, Ala-Cpn10-KK39, Ala-Cpn10-K57, Ala-Cpn10-KK57, Ala-Cpn10-K76, Ala-Cpn10-KK76, Ala-Cpn10-K85, Ala-Cpn10-KK85, Ala-Cpn10-K102, Ala-Cpn10-KK102, deltaD13, deltaE18, deltaE23, deltaE34, deltaE58, deltaE68, deltaE74, deltaD83, deltaD84, deltaD86, deltaD92, deltaD94 and deltaD101 or a combination thereof.

In another embodiment, the mutation is located in the N-terminus as defined in Table 2. The mutation may be an insertion. For example, the insertion at the N-terminus is selected from the group consisting of MH, MK, MKK, MKKK (SEQ ID NO: 358) and MR as set forth in SEQ ID Nos:307, 313, 316, 319 and 310 respectively.

In addition, the Cpn10 polypeptide may comprise the substitution Q3K or K7R as set forth in SEQ ID Nos.37 or 10 respectively.

In yet another embodiment, the mutation is located in the mobile loop as defined in Table 2. The mutation may be a deletion. The deletion may be E23 or E34 as set forth in SEQ ID Nos: 199 and 202. The mutation may be an insertion. The insertion may be K21 or KK21 as set forth in SEQ ID Nos:322 and 325. The mutation may be a substitution. For example, the substitution is selected from the group consisting of A22K, E23Q, T24K, K27R, G29K, M31K, E34K, E34Q, Q37K as set forth in SEQ ID Nos: 16, 64, 67, 70, 73, 76, 79, 265 and 268.

There is also provided herein an isolated Cpn10 oligomer comprising seven Cpn10 monomers wherein two or more monomers are covalently linked to each other. The covalent bond is formed between the C-terminus of one monomer and the N-terminus of an adjacent monomer within the Cpn10 heptamer. The C- and N-termini, used to form a covalent bond, may be lengthed by the addition of one or more amino acids (eg Ala-Cpn10 or Gly-Cpn10), or shortened by the removal of one or more amino acids. For example, the isolated Cpn10 polypeptide is Covalent Cpn10 set forth in SEQ ID NO: 355.

In a further embodiment, each monomer within the covalently bound heptamer may contain one or more mutations selected from the group consisting of A1(K, R or H), G2(K, R or H), Q3(K, R or H), A4(K, R or H), F5(K, R or H), R6(K or H), K7(R or H), L9(K, R or H), F12(K, R or H), D13(K, R, H, N, Q, G, A, V, L, I, P, F, Y, W, C, M, S or T), R14 (K or H), L16(K, R or H), E18(K, R, H, N, Q, G, A, V, L, I, P, F, Y, W, C, M, S or T), R19(K or H), S20(K, R or H), A21(K, R or H), A22 (K, R or H), E23(K, R, H, N, Q, G, A, V, L, I, P, F, Y, W, C, M, S or T), T24(K, R or H), V25(K, R or H), T26(K, R or H), R27(K or H), G28(K, R or H), G29(K, R or H), I30(K, R or H), M31(K, R or H), L32(K, R or H), P33(K, R or H), E34(K, R, H, N, Q, G, A, V, L, I, P, F, Y, W, C, M, S or T), K35(R or H), S36(K, R or H), Q37(K, R or H), G38(K, R or H), K39(K, R or H), V40(K, R or H), L41(K, R or H), Q42(K, R or H), T44(K, R or H), V46(K, R or H), S50(K, R or H), S52(K, R or H), K53(R or H), G54(K, R or H), K55(R or H), G56(K, R or H), G57(K, R or H), E58(K, R, H, N, Q, G, A, V, L, I, P, F, Y, W, C, M, S or T), I59(K, R or H), Q60(K, R or H), P61(K, R or H), V62(K, R or H), S63(K, R or H), K65(R or H), V66(K, R or H), G67(K, R or H), D68(K, R, H, N, Q, G, A, V, L, I, P, F, Y, W, C, M, S or T), K69(R or H), P73(K, R or H), E74(K, R, H, N, Q, G, A, V, L, I, P, F, Y, W, C, M, S or T), Y75(E, GK, K, R or H), G76(K, R or H), G77(K, R or H), T78(K, R or H), K79(R or H), V81(K, R or H), D83(K, R, H, N, Q, G, A, V, L, I, P, F, Y, W, C, M, S or T), D84(K, R, H, N, Q, G, A, V, L, I, P, F, Y, W, C, M, S or T), K85(K, R or H), D86(K, R, H, N, Q, G, A, V, L, I, P, F, Y, W, C, M, S or T), Y87(K, R or H), F88(K, R or H), L89(K, R or H), R91(K or H), D92(K, R, H, N, Q, G, A, V, L, I, P, F, Y, W, C, M, S or T), G93(K, R or H), D94(K, R, H, N, Q, G, A, V, L, I, P, F, Y, W, C, M, S or T), L96(K, R or H), K98(R or H), V100(K, R or H), D101(K, R, H, N, Q, G, A, V, L, I, P, F, Y, W, C, M, S or T), MH-Cpn10, MR-Cpn10, MK-Cpn10, MKK-Cpn10, MKKK-Cpn10 (SEQ ID NO: 319), Ala-Cpn10-K21, Ala-Cpn10-KK21, Ala-Cpn10-K39, Ala-Cpn10-KK39, Ala-Cpn10-K57, Ala-Cpn10-KK57, Ala-Cpn10-K76, Ala-Cpn10-KK76, Ala-Cpn10-K85, Ala-Cpn10-KK85, Ala-Cpn10-K102, Ala-Cpn10-KK102, deltaD13, deltaE18, deltaE23, deltaE34, deltaE58, deltaE68, deltaE74, deltaD83, deltaD84, deltaD86, deltaD92, deltaD94 and deltaD101 or a combination thereof. In another embodiment, the mutation is located in the β-barrel as defined in Table 2. At least one mutation may be a substitution. The substitution may be L9K, F12K, D13K, D13N, E18A, E18K, E18M, E18Q, E18S, E18R, R19K, 520K, L41K, Q42K, T44K, S50K, S50R, V66K, D68K, D68N, K69R, P73K, G77K, T78K, K85R, D86K, D86N, D86R, Y87K, F88K, L89K, D92K, D92N, G93K, D94A, D94K, D94M, D94N, D94R, D94S, L96K, K98R or V100K as set forth in SEQ ID Nos 13, 25, 28, 31, 46, 49, 52, 55, 58, 61, 58, 61, 85, 88, 91, 94, 97, 118, 121, 124, 145, 148, 160, 163, 166, 169, 172, 175, 178, 181, 184, 187, 190, 217, 244, 250, 253, 256, 259, 262, 274, 286, 289, 292, 295, 298, 301.

In another embodiment, the mutation is located in the roof loop as defined in Table 2. The mutation may be an insertion. The insertion may be K57 or KK57 as set forth in SEQ ID Nos:334 or 337 The mutation may be a deletion. The deletion may be E58 as set forth in SEQ ID Nos:205. The mutation may be a substitution, for example, the isolated Cpn10 polypeptide is X-Cpn10-K53E, Ala-Cpn10-S52K, G54K, K55R, G56K, E58K, E58Q, Q60K, P61K as set forth in SEQ. ID Nos: 6, 22, 100, 103, 106, 109, 112, 115, 271. In another embodiment, the isolated Cpn10 polypeptide comprises one or more amino acid substitutions in the roof loop at amino acid residue positions 53 and/or 55 of the amino acid sequence of the wild-type Cpn10 polypeptide. For example, the isolated Cpn10 polypeptide may be Ala-Cpn10-K53M, K55M as encoded by the sequence set forth in SEQ. ID No: 8.

In another embodiment, the mutation is located in the connective loop L1 as defined in Table 2. The mutation may be an insertion. The insertion may be K39 or KK39 as set forth in SEQ ID Nos:328 or 331. The mutation may be a substitution. For example, the substitution is selected from the group consisting of K39R or V40K as set forth in SEQ ID Nos: 19 or 82. In yet another embodiment, the mutation is located in connective loop 2 (lower rim region) as defined in Table 2. The mutation may be an insertion. The insertion may be K76 as set forth in SEQ ID Nos:340. The mutation may be a substitution. The substitution may be X-Cpn10-Y75K as set forth in SEQ ID No: 130 or Ala-Cpn10-E74K, Y75H, Y75K, Y75R, Y75GK or G76K as set forth in SEQ ID Nos:127, 133, 136, 139, 142, 238 or 277. The mutation may be a deletion. The deletion may be E74 as set forth in SEQ ID Nos:208.

In a further embodiment, the mutation is located in connective loop 3 as defined in Table 2. The mutation may be an insertion. The insertion may be K85 or KK85 as set forth in SEQ ID Nos:343 or 346. The mutation may be a substitution. The substitution may be V81K, D83K, D83N, D84K or D84N as set forth in SEQ ID Nos:151, 154, 157, 280 or 283. The mutation may be a deletion. The deletion may be D84 as set forth in SEQ ID No:211.

In another embodiment, the mutation is located in the C-terminus as defined in Table 2. The mutation may be an insertion. The insertion may be K102 or KK102 as set forth in SEQ ID Nos:349 or 352. The mutation may be a substitution. The substitution may D101K, D101N or D101R as set forth in SEQ ID Nos:193, 196 or 304.

In another embodiment, the polypeptide may comprise at least two mutations at any position within one or more regions of Cpn10, wherein the regions consist of the N-terminus, β-barrel, mobile loop, roof loop, C-terminus, or any of the three connective loops of the wild-type Cpn10 molecule as defined in Table 2. For example, the Cpn10 polypeptide may comprise Ala-Cpn10-F12K, D92K,E18K,D101K; E34Q, Y75K; Q42K,D101K; T44K,D101K; S50K,D101K; Q60K, T78K; E74K,Y75E; Y75GK; Y75G,G76K; Y75K,D94K; Y75K,D94N. The polypeptides may comprise amino acid sequences as set forth in SEQ ID Nos. 214, 217, 220, 223, 226, 229, 232, 235, 238, 241, 244, 247.

According to a second aspect of the present invention there is provided an isolated nucleic acid encoding a polypeptide according to the first aspect.

In one embodiment, the isolated nucleic acid may comprise a nucleotide sequence selected from the group consisting of SEQ ID Nos. 7, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 75, 77, 78, 80, 81, 83, 84, 86, 87, 89, 90, 92, 93, 95, 96, 98, 99, 101, 102, 104, 105, 107, 108, 110, 111, 113, 114, 116, 117, 119, 120, 122, 123, 125, 126, 128, 129, 131, 132, 134, 135, 137, 138, 140, 141, 143, 144, 146, 147, 149, 150, 152, 153, 155, 156, 158, 159, 161, 162, 164, 165, 167, 168, 170, 171, 173, 174, 176, 177, 179, 180, 182, 183, 185, 186, 188, 189, 191, 192, 194, 195, 197, 198, 200, 201, 203, 204, 206, 207, 209, 210, 212, 213, 215, 216, 218, 219, 221, 222, 224, 225, 227, 228, 230, 231, 233, 234, 236, 237, 239, 240, 242, 243, 245, 246, 248, 249, 251, 252, 254, 255, 257, 258, 260, 261, 263, 264, 266, 267, 269, 270, 272, 273, 275, 276, 278, 279, 281, 282, 284, 285 287, 288, 290, 291, 293, 294, 296, 297, 299, 300, 302, 303, 305, 306, 308, 309, 311, 312, 314, 315, 317, 318, 320, 321, 323, 324, 326, 327, 329, 330, 332, 333, 335, 336, 338, 339, 341, 342, 344, 345, 347, 348, 350, 351, 353, 354 or 356.

According to a third aspect of the present invention there is provided an expression construct comprising a nucleic acid according to the second aspect operably-linked to one or more regulatory sequences.

The nucleic acid may be a codon optimised Cpn10 nucleic acid.

The codon optimised nucleic acid sequence may have one or more nucleotide substitutions that increase the utilisation of transfer RNA pools, exploit more efficient stop codons, remove RNA secondary structures and/or destabilising elements.

According to a fourth aspect of the present invention there is provided a host cell expressing a polypeptide of the first aspect, or comprising a nucleic acid of the second aspect or an expression construct of the third aspect.

According to a fifth aspect of the present invention there is provided an antibody that selectively binds to a polypeptide of the first aspect.

According to a sixth aspect of the present invention there is provided a proinflammatory nucleic acid or immunosuppressive nucleic acid in complex with a polypeptide of the first aspect.

According to a seventh aspect of the present invention there is provided a pharmaceutical composition comprising a polypeptide of the first aspect, a nucleic acid of the second aspect or an expression construct of the third aspect or an antibody of the fifth aspect.

According to an eighth aspect of the present invention there is provided a method of treating a subject, including the step of administering to said subject a therapeutically effective amount of a Cpn10 polypeptide of the first aspect or a nucleic acid of the second aspect.

The treatment may modulate the immune response in the subject. The immune response may be modulated via regulation of PRR signalling.

According to a ninth aspect of the present invention there is provided a method for treating or preventing a disease, disorder or condition in a subject, the method comprising administering to the subject an effective amount of a Cpn10 polypeptide of the first aspect or a nucleic acid of the second aspect.

The disease, disorder or condition may be selected from acute or chronic inflammatory diseases such as, insulin dependent diabetes mellitus, systemic lupus erythematosis, Sjorgren's disease, Graves disease, multiple sclerosis, rheumatoid arthritis, chronic fatigue syndrome, Alzheimer's disease, asthma, allergy, GVHD, artherosclerosis, inflammatory pain, psoriasis, HIV, Chronic immune activation, chronic myositis, scleroderma; or cancers such as, non-small cell lung carcinoma, renal cell carcinoma, melanoma, non-Hodgkin's lymphoma, colorectal cancer, basal cell carcinoma; or an infectious disease. The infectious disease may be the result of a bacterial, viral or fungal infection.

In one embodiment, chronic immune activation is associated with leakage of bacterial and/or viral products from the gastrointestinal tract into the circulatory system. For example, leakage can occur from the oral cavity, gut or small intestine. Leakage of bacterial or viral products can be caused by an infection or disease such as bacterial infections, viral infections, inflammatory bowel disease and gum disease. An example of viral infection is a HIV or Hepatitis C infection. The bacterial products can comprise LPS or nucleic acids. The viral products can comprise nucleic acids.

In a further embodiment, chronic immune activation involves immunomodulation of TLR signalling through LPS or nucleic acid binding to TLRs. LPS binds to TLR4 whilst nucleic acids can bind to TLR3, 7, 8 or 9.

According to a tenth aspect of the present invention there is provided a method for modulating PRR signalling in a subject, or in at least one cell, tissue or organ thereof, the method comprising administering a therapeutically effective amount of a Cpn10 polypeptide of the first aspect or a nucleic acid of the second aspect.

According to an eleventh aspect of the present invention there is provided a method for modulating the production and/or secretion of one or more immunomodulators in a subject, or at least one cell, tissue or organ thereof, the method comprising administering a therapeutically effective amount of a Cpn10 polypeptide of the first aspect or a nucleic acid of the second aspect.

The polypeptide may modulate signalling from a PRR by binding a PRR ligand. The immunomodulator may be a pro-inflammatory cytokine or chemokine or an anti-inflammatory cytokine or chemokine. The cytokine or chemokine may be selected from TNF-α, IL-1, IL-6, RANTES, IL-10, IL-17, IL-23, TGF-β or a type I interferon. The type I interferon may be IFNα, IFNβ or IFNγ.

According to a twelfth aspect of the present invention there is provided a method for inhibiting the production and/or secretion of one or more immunomodulators in a subject, or at least one cell, tissue or organ thereof, the method comprising administering an effective amount of a Cpn10 polypeptide of the first aspect or a nucleic acid of the second aspect.

The polypeptide may modulate signalling from a PRR by binding a PRR ligand. Binding of the polypeptide to a PRR ligand may have an immunomodulatory affect on the cell that possesses the PRR. The cell may be an antigen presenting cell or a T-cell or a B-cell. The antigen presenting cell may be a dendritic cell, macrophage or monocyte.

The immunomodulator may be a pro-inflammatory cytokine or chemokine or an anti-inflammatory cytokine or chemokine. The cytokine or chemokine may be selected from TNF-α, IL-1, IL-6, RANTES, IL-10, IL-17, IL-23, TGF-β or a type I interferon. The type I interferon may be IFNα, IFNβ or IFNγ.

According to a thirteenth aspect of the present invention there is provided a method of identifying a compound that binds to a polypeptide of the first aspect, the method comprising the steps of:

(a) contacting a candidate compound with said polypeptide; and (b) assaying for the formation of a complex between the candidate compound and said polypeptide.

The assay for the formation of a complex may be a competitive binding assay, a two-hybrid assay, gel filtration chromatography, AlphaScreen® High Throughput Screening, an electrophoretic mobility shift (gel-shift) assay and/or a plate capture assay.

The assay may be qualitative or quantitative.

According to a fourteenth aspect of the present invention there is provided a method of screening for a compound that modulates the activity of a polypeptide of the first aspect, the method comprising the steps of:

(a) contacting said polypeptide with a candidate compound under conditions suitable to enable interaction of said candidate compound to said polypeptide; and (b) assaying for activity of said polypeptide.

Assaying for activity of the polypeptide may comprise a step of adding a labelled substrate and measuring a change in the labelled substrate.

According to a fifteenth aspect of the present invention there is provided a method of screening for a PRR ligand, the method comprising the steps of:

(a) contacting a polypeptide of the first aspect with a candidate PRR ligand compound under conditions suitable to enable interaction of said candidate compound to said polypeptide; and (b) assaying for increased affinity of said compound with said polypeptide compared to Ala-Cpn10; and/or (c) assaying for decreased or increased PRR activation in the presence of the candidate PRR ligand compound and the polypeptide of the first aspect.

The invention also contemplates variants, derivatives, homologues, analogues and fragments of the isolated Cpn10 polypeptides and polynucleotides according to the above aspects and embodiments.

According to the above aspects and embodiments, the Cpn10 polypeptides and polynucleotides may be derived from any animal, may be generated using recombinant DNA technologies or may be synthetically produced. Cpn10 may be a eukaryotic Cpn10. For example, Cpn10 is human Cpn10.

The wild-type Cpn10 molecule or polypeptide may be acetyl-Cpn10 or X-Cpn10 (SEQ ID No. 1).

According to the above aspects and embodiments the immunomodulatory activity of a Cpn10 polypeptide may involve generation of heptamers of the polypeptide. The heptamers may comprise a mutant or non-mutant polypeptides in any combination.

DEFINITIONS

In the context of this specification, the term "comprising" means "including principally, but not necessarily solely". Furthermore, variations of the word "comprising", such as "comprise" and "comprises", have correspondingly varied meanings.

The term "wild-type" as used herein in relation to Cpn10 molecules or polypeptides includes native or non-native forms. For example, native human Cpn10 is acetylated at its N-terminus. The present invention contemplates, within the scope of the term wild-type Cpn10, acetylated or non-acetylated (X-Cpn10) molecules as represented by SEQ ID No. 1.

The term "Ala-Cpn10" refers to human Cpn10 produced in *E. coli* wherein it is produced with an extra N-terminal Alanine residue. The sequence of Ala-Cpn10 is presented as SEQ ID No. 3.

The term "immunomodulator" means a molecular mediator which interacts with the immune system and that plays a role in the activation, inhibition, modulation, maintenance, maturation, suppression or augmentation of an immune response. The immunomodulator may be a pro-inflammatory cytokine or chemokine or an anti-inflammatory cytokine or chemokine. The cytokine or chemokine may be selected from TNF-α, IL-1, IL-6, RANTES, IL-10, IL-17, IL-23, TGF-β or a type I interferon. The type I interferon may be IFNα, IFNβ or IFNγ.

The term "Pattern recognition receptors" or PRRs as used herein means several classes of germline-encoded proteins including Toll-like receptors (TLRs), Nucleotide-binding domain LRR-containing family (NLRs), RIG-I-like receptors (RLRs), DNA-dependent activators of IRF (DAIs), C-type Lectin receptors (CLRs) or a member of the IFI20X/ IFI16 family (e.g. Ifi16, Aim2, MNDA and IFIX) (see for example Akira et al., Cell 2006, 124: 783-801; Latz, E. and Fitzgerald, K. A. (2008) Nat. Rev. Immunol. Vol. 8, No. 4, Poster). In general, PRRs can be divided into two groups, nucleic acid-based PRRs (that generally reside intracellularly) and cell surface PRRs (that generally recognise hydrophobic ligands). PRRs are located on various cell types including but not limited to antigen presenting cells (e.g. dendritic cells, monocytes and macrophages), Tcells and B-cells.

The term "Toll-like receptors" or TLRs means receptors which interact with pathogens and initiate the host immune response to infection. In mammals, activation of TLRs by pathogens sets in motion an innate immune inflammatory process that prevents pathogen dissemination and, through TLRs on dendritic cells, directs the development of acquired immunity. The TLRs are encoded by a limited number of genes in the germline, 10 known in humans. These 10 receptors recognize a wide variety of pathogen-derived molecular signatures, including glycolipids such as lipopolysaccharide, proteins such as flagellin, and nucleic acids such as dsRNA. TLRs can be divided into two groups, cell surface TLRs which generally recognize hydrophobic ligands and intracellular TLRs (i.e. TLR-3, TLR-7, TLR-8 and TLR-9) which generally recognize nucleic acid based ligands.

As used herein the terms "modulating", "modulates" and variations thereof refer to increasing or decreasing the level of activity, production, secretion or functioning of a molecule in the presence of a particular modulatory molecule or agent of the invention compared to the level of activity, production, secretion or other functioning thereof in the absence of the modulatory molecule or agent. These terms do not imply quantification of the increase or decrease. The modulation may be of any magnitude sufficient to produce the desired result and may be direct or indirect.

The term "net charge" as used herein refers to the charge of a molecule. Molecules that comprise an amino acid sequence such as proteins, peptides, and polypeptides (e.g. Cpn10 polypeptide) can either be positively or negatively charged. The net charge of a polypeptide at a given pH can be calculated on the basis of the Henderson-Hasselbalch equation (Hasselbalch, K. A., 1917 Biochemische Zeitschrift 78: 112-144) and known pKa values of ionisable amino acid side chains and the N- and C-termini of a polypeptide.

The term "greater net positive charge" as used herein is the increase in positive charge of the molecule over Ala-Cpn10.

The term "mobile loop" is a flexible region of the Cpn10 molecule that comprises 18 amino acid residues. The mobile loop comprises residues A21 to G38 (see FIG. 1; residue numbering is based on either acetylated or non-acetylated X-Cpn10 (SEQ ID No. 1) as described herein).

The term "roof loop" is a flexible region of the Cpn10 molecule that comprises 14 amino acid residues. The roof loop comprises residues S52 to V62 (see FIG. 1; residue numbering is based on either acetylated or non-acetylated X-Cpn10 (SEQ ID No. 1 as described herein).

"Beta barrel" as described herein is a region of the Cpn10 molecule that comprises five segments, namely 1st, 2nd, 3rd, 4th and 5th segments. 1st segment comprises residues F8 to S20, 2nd segment comprises L41 to G51, 3rd segment comprises S63 to P73, 4th segment comprises G77 to V80 and 5th segment comprises residues K85 to V100 (see FIG. 1). Residue numbering is based X-Cpn10 (SEQ ID No. 1) as described herein.

The term "Connective loops" refer to flexible regions of the Cpn10 molecule that connect various loops of the Cpn10 molecule to the Beta barrel, such as the mobile loop and the roof loop. There are three connective loops, 1st, 2nd and 3rd. 1st connective loop comprises residues K39 to V40. 2nd connective loop comprises E74 to G76 and 3rd loop comprises residues V81 to D84 (see FIG. 1). Residue numbering is based on X-Cpn10 (SEQ ID No. 1) as described herein.

The term "N-terminus" is a flexible region at the N-terminal of the Cpn10 molecule that comprises residues A1 to K7 (see FIG. 1). Residue numbering is based on X-Cpn10 (SEQ ID No. 1) as described herein.

The term "C-terminus" comprises D101 of the Cpn10 molecule (see FIG. 1; residue numbering is based on X-Cpn10 (SEQ ID No. 1) as described herein).

The term "amino acid" as used herein means any molecule that contains both amine and carboxyl functional groups.

The term "charged residue" as used herein means any amino acid residue with a side-chain that has the potential to carry a positive or negative charge.

The term "polypeptide" means a polymer made up of amino acids linked together by peptide bonds. The term "polypeptide" may constitute a portion of a full length protein. Further, the term "polypeptide" refers to a polypeptide that may exhibit at least one modification of its amino acid sequence, compared to a wild type Cpn10 molecule. The modification may include chemical modifications such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which are naturally occurring in human proteins.

The term "polynucleotide" as used herein refers to a single- or double-stranded polymer of deoxyribonucleotide, ribonucleotide bases or known analogues of natural nucleotides, or mixtures thereof. The term includes reference to the specified sequence as well as to the sequence complimentary thereto, unless otherwise indicated. The terms "polynucleotide" and "nucleic acid" are used interchangeably herein.

The term "CpG" as used herein refers to unmethylated sites within regions of DNA where a cytosine nucleotide occurs next to a guanine nucleotide in linear sequence of bases along its length and is separated by a phosphate, which links the two nucleosides together in DNA. "CpG" is used to distinguish the above meaning from a cytosine base paired to a guanine. Three distinct types of CpG oligodeoxynucleotides have been identified that differ in their capacity to stimulate antigen-presenting cells: CpG-A (human ODN-2216) induces high amounts of interferon-$\alpha$ (IFN-$\alpha$) and IFN-$\beta$ in plasmacytoid dendritic cells (PDCs); CpG-B (human ODN-2006 and mouse ODN-1826) induces PDC maturation and is a potent activator of B cells but stimulates only small amounts of IFN-$\alpha$ and IFN-$\beta$ whereas CpG-C (human ODN-M362) induces B and NK cells and inducing IFN-$\alpha$ production of human peripheral blood mononuclear cells.

The term "isolated" means that the molecule in question has been removed from its natural environment or host, and associated impurities reduced or eliminated such that the molecule in question is the predominant species present (e.g., on a molar basis it is more abundant than any other individual species in the composition/sample). Typically a substantially purified fraction is a composition wherein the object species comprises at least about 30 percent of all macromolecular species present. Generally, a substantially pure composition will comprise more than about 80 to 90 percent of all macromolecular species present in the composition. Most typically, the object species is purified to essential homogeneity (contaminant species cannot be detected in the composition by conventional detection methods) wherein the composition consists essentially of a single macromolecular species.

As used herein the term "substantially" means the majority but not necessarily all, and thus in relation to a modified polypeptide "substantially" lacking a component region of a corresponding wild-type polypeptide, the modified polypeptide may retain a portion of that component region. For example, a modified polypeptide "substantially" lacking a component region of a corresponding wild-type polypeptide may retain approximately 50 percent or less of the sequence of the component region, although typically the component region is rendered structurally and/or functionally inactive by virtue of the proportion of the sequences of the region omitted.

The term "conservative amino acid substitution" as used herein refers to the replacement of one amino acid with another amino acid having similar structural and/or chemical properties. Conservative amino acid substitutions may be made on the basis of similarity in one or more of the following: polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tyrosine, tryptophan, cysteine and methionine; polar uncharged amino acids include glycine, serine, threonine, asparagine, and glutamine; polar positively charged (basic) amino acids include arginine, lysine, and histidine; and negatively charged (acidic) amino acids include aspartic acid and glutamic acid. Amino acid "Insertions" or "deletions" are preferably in the range of about 1 to 20 amino acids, more preferably 1 to 10 amino acids. The variation may be experimentally determined by systematically making insertions, deletions, or substitutions of amino acids in a polypeptide molecule using recombinant DNA techniques and assaying the resulting recombinant variants for activity.

As used herein the terms "treatment", "treating" and variations thereof, refer to any and all uses which remedy a disease state or symptoms, prevent the establishment of disease, or otherwise prevent, hinder, retard, or reverse the progression of disease or other undesirable symptoms in any way whatsoever.

As used herein the term "effective amount" includes within its meaning a non-toxic but sufficient amount of an agent or compound to provide the desired therapeutic or prophylactic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

BRIEF DESCRIPTION OF THE DRAWINGS

FIG. 4. 1 µg of TLR3 agonist Poly(I:C) (a synthetic dsRNA analog) was incubated with 50 µg of a Cpn10 variant and the indicated salt concentration in 10 mM Tris-HCl (pH7.6) for 1 hr at 23° C. Samples were resolved in a 1% TAE agarose gel and stained with Ethidium Bromide. Free Cpn10 migrates towards the negative electrode (top of the gel) while free poly(I:C) migrates towards the positive electrode (bottom of the gel), complexes of Cpn10-poly(I:C) retard the movement of both molecules. FIG. 4e discloses "MKKK-Cpn10" as SEQ ID NO: 319.

FIG. 5. 1 µg of human ODN-2216 class A (TLR9 agonist; Invivogen) was incubated with 50 µg of Cpn10 in 10 mM Tris-HCl (pH7.6) and the indicated salt concentration for 15 min at 23° C. Samples were resolved in a 1% TAE agarose gel and stained with ethidium bromide. Free Cpn10 migrates towards the negative electrode (top of the gel) while free CpG-ODNs migrate towards the positive electrode (bottom of the gel), complexes of Cpn10-CpG-ODNs retard the movement of both molecules. FIG. 5e discloses "MKKK-Cpn10" as SEQ ID NO: 319.

FIG. 6. 0.5 µg of *E. coli* K12 ssRNA (Invivogen Cat# tlrl-ecma) (TLR7/8 agonist) was incubated with 50 µg of a Cpn10 variant, in 10 mM Tris-HCl (pH 7.6) and the indicated salt concentrations (0, 150 and 500 mM NaCl) for 30 mins at 23° C. Samples were resolved in a 1% TAE agarose gel and stained with Ethidium Bromide. Free Cpn10 migrates towards the negative electrode (top of the gel) while free ssRNA migrate towards the positive electrode (bottom of the gel), complexes of Cpn10-ssRNA retard the movement of both molecules.

FIG. 7. Quantitative analysis of Cpn10 binding to CpG oligonucleotides (ODNs). Ala-Cpn10 and Cpn10 mutants were formulated at 1 µg/µl in formulation buffer pH7.2 (Invitrogen) and 50 µg was adsorbed to triplicate wells of a 96 well plate 16 hr at 4° C. Following the decanting of non-bound protein, the plate was blocked with 1% BSA and 5% sucrose in PBS pH7.2 for 2 hr at 23° C. 50 µl of 3'-biotin labeled human ODN-2216 class-A, human ODN-2006 class-B, or human ODN-M362 class-C (TLR9 agonists) (Proligo/Sigma) formulated at 0.02 µg/µl in PBS pH 7.2 was added to each well and incubated for 2 hr at 23° C. Unbound ligand was removed with five PBS (pH7.2)+0.05% Tween 20 washes. Bound CpG-ODNs were analysed with a Streptavidin-HRP and TMB detection system at A450 nm. The results are the average of three replicates and are normalized to the level of binding of Ala-Cpn10 to each CpG. FIG. 7e discloses "MKKK-Cpn10" as SEQ ID NO: 319.

FIG. 8. Cpn10 modulates CpG-B ODN-induced NFκB activity. RAW264.7 (mouse macrophage) cells were transfected with pNifty NFκB-luciferase reporter plasmid (InvivoGen) using Genejuice according to the manufacturers instructions (Novogen). 24 hours later cells were trypsinised, counted and $2.5 \times 10^5$ cells were plated in 1 ml of media into each well of a 24 well plate and left to adhere overnight. 100 µg of a Cpn10 construct or Formulation buffer control was mixed with 4 µg of CpG-B ODN-1826 (Invivogen) and passed through a centrifugal filter device YM10 (Amicon). The entire flow through volume was added to the RAW264-pNIFty-LUC cells and incubated at 37° C. for 5 hours. Cells were washed and subsequently lysed with 100 µl per well of CCLR 1× solution (Promega luciferase lysis buffer), mixed with luciferase substrate following the manufactures instructions and the luciferase counts measured. Figure show NFκB activation levels normalized to Ala-Cpn10 at 100%. FIG. 8e discloses "MKKK-Cpn10" as SEQ ID NO: 319.

FIG. 9. Effect of Cpn10 mutants on Poly (I:C) stimulation. HEK293 cells were transiently transfected with plasmids encoding for TLR3 and pNifty NFκB-luciferase (InvivoGen) using GeneJuice according to the manufacturers instructions (Novogen). 24 hours later the transfected cells were trypsinised, counted and 1×10$^5$ cells were plated in 1 ml of media into each well of a 24 well plate and allowed to adhere for 24 hrs. Then 100 µg of Cpn10, 0.1 µg Poly (I:C) (InvivoGen) and 10 µl of SUPERase RNAse inhibitor (Ambion) were added to each well for 24 hrs. The supernatants were then removed, the cells washed in PBS and lysed with 1× Lysis Buffer (Promega), and assayed for luciferase. Levels of luciferase were normalized to Poly (I:C) alone at 100%. Values represent the mean of triplicate wells. FIG. 9a shows activation of TLR3 by Cpn10 controls. FIG. 9b shows activation of TLR3 by positive to positive substitutions of Cpn10. FIG. 9c shows activation of TLR3 by positive substitutions of Cpn10. FIG. 9e shows activation of TLR3 by positive insertions of Cpn10. FIG. 9f shows activation of TLR3 by negative deletions of Cpn10 and activation of TLR3 by multiple mutations of Cpn10.

DETAILED DESCRIPTION

Figure 1:
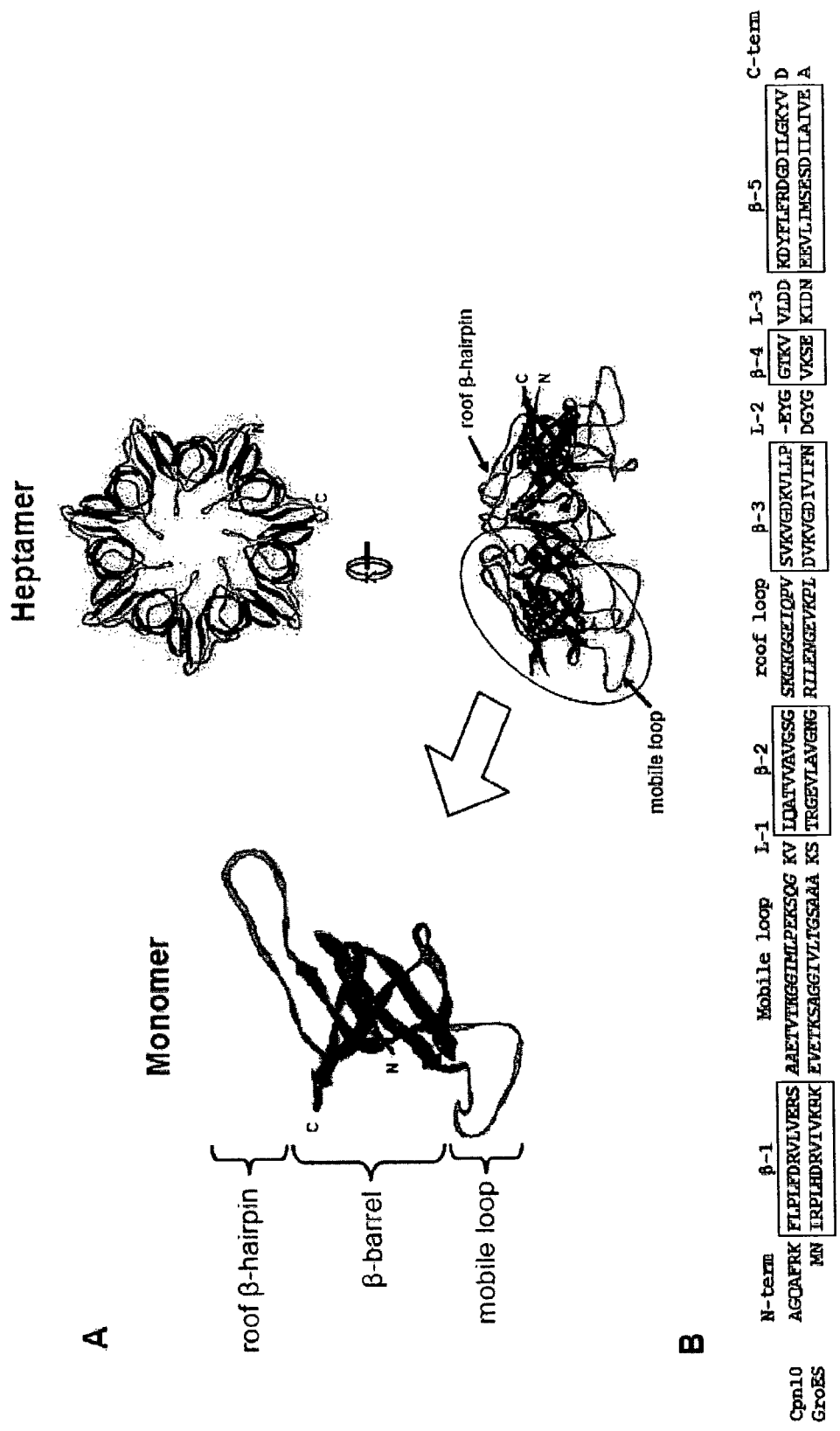
FIG. 1. A. Crystal structure of *E. coli* Cpn10 (GroES) showing various regions of Cpn10. Cpn10 is comprised of seven identical 10 kDa subunits. B. Amino acid sequences of Cpn10 (SEQ ID NO: 1) and GroES (SEQ ID NO: 370) are shown. The GroES ribbon structure was created from the X-ray crystal coordinates published by Xu et al. (Nature 1997, 388: 741-750), in this structure the usually disordered mobile loops are perfectly aligned through interaction with GroEL (GroEL was omitted in the diagram).

Cpn10 is a dome-shaped, heptameric ring of identical 10 kDa subunits (FIG. 1). The surface of the dome is hydrophilic and highly charged. Each Cpn10 subunit forms an irregular β-barrel topology with five segments that are joined by several loop structures. Three small connective loops are present and two large loop extensions that protrude from the barrel. The first extension is a β-hairpin loop ("roof loop") that extends towards the centre of the heptamer and forms the roof of the dome-like structure. Intriguingly, whereas the roof of GroES (E. coli Cpn10) contains a cluster of negatively charged residues at the tips of the roof loops under physiological conditions, the roof of mammalian Cpn10 contains a positively charged cluster of amino acids at the tips of the roof loops; while a large portion of the roof is missing completely from the bacteriophage Cpn10 (Gp31). The molecule also has another extension that is a flexible 18 amino acid mobile loop that extends from the base of the dome and mediates an interaction with Cpn60. One of the small connection loops, comprised of residues Glu-74, Tyr-75 and Gly-76, extends from the base of the dome and protrudes inwards to form a lower rim region. The amino acid residues in the lower rim region are phylogenetically conserved amongst most eukaryotes.

Without being bound to any mechanism or pathway, the inventors have generated a series of mutations through primarily amino acid substitutions, deletions, additions or combinations thereof which modify the charge of a Cpn10 polypeptide and demonstrated herein that these mutations are effective in modifying the interaction of Cpn10 with one or more PRR ligands, specifically increasing the binding affinity of Cpn10 with the PRR ligand, which indicates an ability to modulate the immune system/response through PRR signalling. Binding of the Cpn10 polypeptide to a PRR ligand may have an immunomodulatory affect on the particular immune cell that possesses the PRR. The cell may be an antigen presenting cell, T-cell or B-cell. The antigen presenting cell may be a dendritic cell, macrophage or monocyte.

Pattern Recognition Receptors (PRRs), including Toll-like receptors (TLRs), Nucleotide-binding domain LRR-containing family (NLR), RIG-I-like receptor (RLR), DNA-dependent activator of IRF (DAI), C-type Lectin receptor (CLR) and the IFI20X/IFI16 family (Ifi16, Aim2, MNDA and IFIX), are the sentinels of the immune system, they act as the first line of defense against invading pathogens, recognising specific pathogenic associated molecular patterns (PAMPS) and initiating an immune response. It appears that PRRs also play a role in many inflammatory syndromes, including sepsis, autoimmune or chronic inflammatory diseases where altered self molecules hyperactivate PRRs leading to the development of a pathological state.

Cpn10 Polypeptide Mutants

The addition of extra positive charge, through adding positive or removing negative residues generates a Cpn10 molecule which binds significantly stronger (compared to Ala-Cpn10 and X-Cpn10) to nucleic acid-based PRR ligands. Extra positive charge could be added by (1) substituting an existing surface/solution exposed neutral or negative residue for a positive residue, (2) substituting an existing surface/solution exposed negative residue for a neutral residue, (3) introducing an additional surface/solution exposed positive residues (eg lengthen a loop structure or the N-terminus and C-terminus) or (4) deleting an existing surface/solution exposed negative residue (eg shortening a loop structure or the N-terminus and C-terminus). Our results also show that introducing multiple positive charges (eg Ala-Cpn10-Y75K, D94K) may increase the binding potential significantly greater than the individual mutations.

Calculation of Protein Net Charge

The net charge of a polypeptide at a given pH is calculated on the basis of the Henderson-Hasselbalch equation (Hasselbalch, K. A., 1917 *Biochemische Zeitschrift* 78: 112-144) and known pKa values of ionisable amino acid side chains and the N- and C-termini of a polypeptide. The Henderson-Hasselbalch equation states that the pH of a solution containing a weak acid/base and its conjugate base/acid is dependent only upon the ratio between the molar concentrations of these two solutes and remains independent of dilution, as shown in the following equations:

Henderson-Hasselbalch equation the acid equation: $pH=pK_a+\log [A^-]/[HA]$(used for C-terminus,Asp,Glu,Cys,Tyr)

the base equation: $pH=pK_a+\log [B]/[BH^+]$(used for N-terminus,Lys,Arg,His)

where $[A^-]$ denotes the molar concentration of the conjugate base of a relevant acid (C-terminus, Asp, Glu, Cys, Tyr) and $[BH^+]$ is the molar concentration of the conjugate acid of a relevant base (N-terminus, Lys, Arg, His). The pKa values of ionisable groups within a polypeptide are well known in the art and can be found in numerous journals and textbooks. Depending on the set of pKa values used, the calculated net charge of a protein will vary slightly, but this does not change the conclusions obtained in this study. The pKa values utilised in Table 3 are N-terminus 8.0, C-terminus 3.1, Lys 10.0, Arg 12.0, His 6.5, Glu 4.4, Asp 4.4, Tyr 10.0 and Cys 8.5 (Stryer, L., 1988 "Biochemistry" textbook 3rd Edition, New York, W.H. Freeman, ISBN 0716719207).

So for a polypeptide with multiple ionisable groups the net charge of that polypeptide may be calculated at a given pH as follows:
1. List all ionizable residues (Cys, Asp, Glu, His, Lys, Arg, Tyr, carboxyl terminus, amino terminus)
2. If the pKa of an ionisable group is 2 units away from the pH value, the charge can be assigned as 1, 0, −1 without calculation. For example, at pH 7.3 Lysine (pKa 10.0) is going to be 100% protonated and will have an average charge of +1. On the other hand, at pH 7.3 Glutamate (pKa 4.4) and Aspartate (pKa 4.4) will both be 100% deprotonated giving an average charge of −1.
3. Use the Henderson-Hasselbalch equation to calculate the percent ionisation of each ionisable group at the given pH. In Table 3 calculations were made at pH 7.3 and pH7.4 (taken as physiological pH).
4. Multiply the percent ionisation of each ionisable group ($z_i$) by the total number of individual ionisable groups occurring within a given polypeptide ($n_i$) to get the total charge contributed by each ionisable group. The net charge (Z) of a polypeptide at a given pH is then provided by the sum of all charges contributed by each ionisable group $Z=\Sigma n_i z_i$ to arrive at the net charge of that polypeptide at a given pH.

A number of freely available resources exist where this approach to calculating the net charge on a polypeptide has been automated for ease of use. For example Protein Calculator V3.3 (http://www.scripps.edu/~cdputnam/protcal-c.html) is a freely available tool to calculate the net charge on a protein based on the amino acid sequence. This tool was used to calculate the net charge of a number of Cpn10 polypeptides at physiological pH (taken as 7.3 to 7.4) as in table 3.

Types of Mutations

Cpn10 variants with high affinity for proinflammatory nucleic acids can be generated by adding positive or removing negative residues. The mutations utilised to create Cpn10 variants with high affinity for proinflammatory nucleic acids may be amino acid residue insertion, deletion substitution or addition or a combinations thereof, provided that the mutation results in a Cpn10 variant with higher positive charge at pH 7.4 than Ala-Cpn10.

In one embodiment an existing residue may be substituted for a positively charged residue, a negatively charged residue may be replaced by a neutral residue, an additional positively charged residue may be added, or negatively charged residue may be deleted, for example to any of the regions of the Cpn10 polypeptide defined in FIG. 1b. The mutation may be made by any means known in the art for example site-directed mutagenesis, homologous recombination, transposon mutagenesis or sequence tag mutagenesis. Typically site directed mutagenesis will be used.

One skilled in the art will recognize that any number and type of mutations that result in a Cpn10 variant with a higher positive charge at pH 7.4 and a higher affinity for proinflammatory nucleic acids than Ala-Cpn10 falls within the scope of the invention.

Polypeptides

As disclosed herein the present invention contemplates isolated Cpn10 polypeptides and its increased affinity for a nucleic acid-based PRR ligand, comprising one or more amino acid deletions, additions or substitutions in comparison with Ala-Cpn10.

Figure 2:
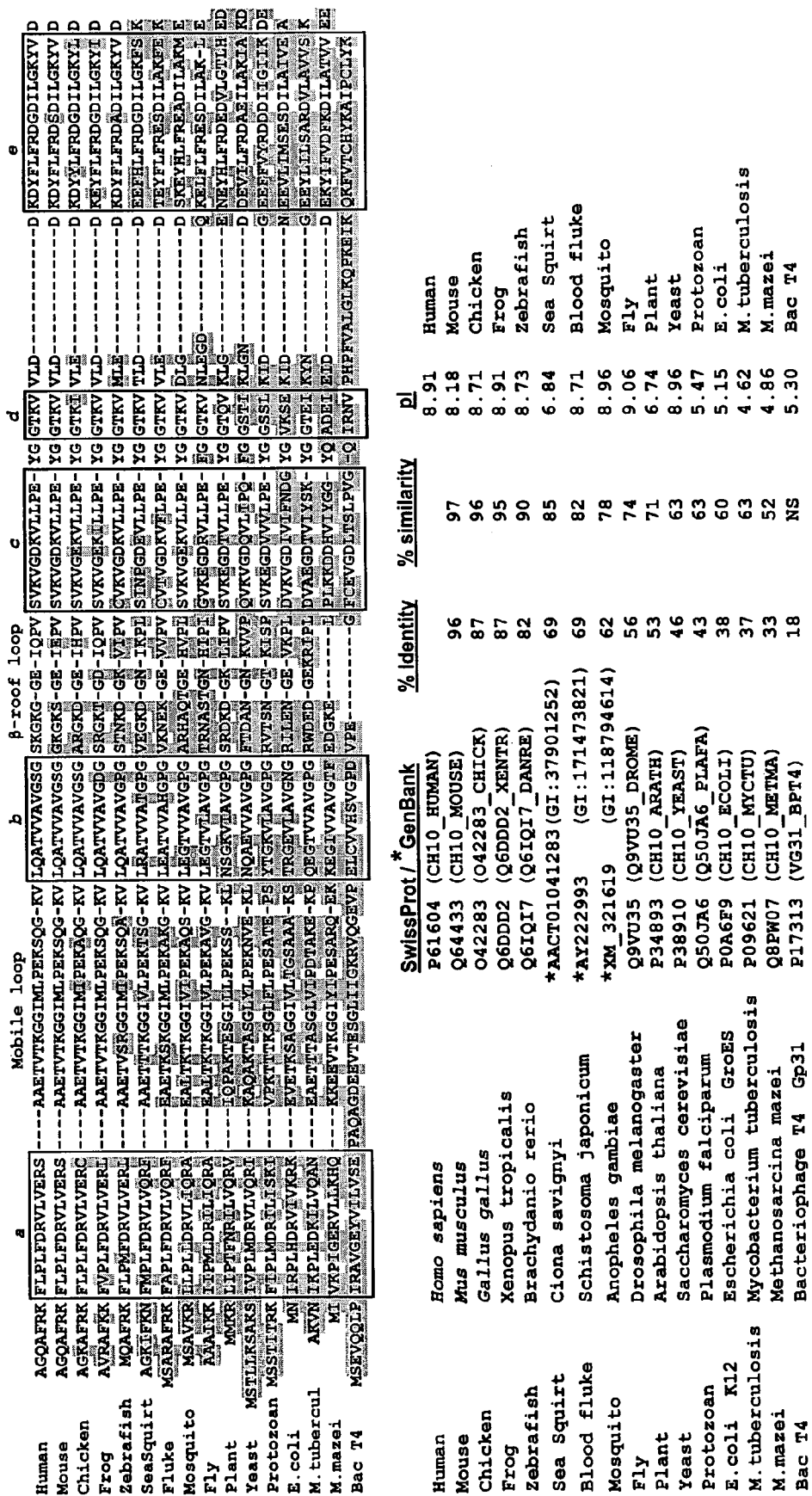
FIG. 2. Sequence alignment of human Cpn10 (SEQ ID NO: 1) with Cpn10 homologs from numerous biological kingdoms (SEQ ID NOS 371-381, 370, and 382-384, respectively, in order of appearance). Amino acids that are different to human Cpn10 are shaded. The location of the mobile loop and the β-hairpin roof loop are indicated. Boxes (marked a to e) indicate the predicted boundaries of the 55 residue β-barrel core (Hunt et al., 1997 Cell 90: 361-371). The percentage identity and similarity of the various homologs relative to human Cpn10 are shown. The SwissProt accession number of each protein is given. Calculation of sequence % identity and % similarity to human Cpn10 was performed with NCBI blast (Altschul et al., 1997 Nucleic Acids Res. 25:3389-3402), NS=no significant similarity found. Isoelectric points (pI) were calculated using the ExPASy proteomics server ProtParam Tool (www.expasy.org/tools/protparam.html).

Cpn10 may be native, naturally-derived, recombinant or synthetic Cpn10. The Cpn10 molecule may be any Cpn10 polypeptide from a eukaryotic organism. By way of example as shown in FIG. 2, the Cpn10 may be derived from yeast (e.g. *Saccharomyces cerevisiae*), nematode (e.g. *Caenorhabditis elegans*), frog (e.g. *Xenopus tropicalis*), chicken (e.g. *Gallus gallus*), zebrafish (e.g. *Danio rerio*), fly (e.g. fruit fly such as *Drosphila melanogaster*), plant (e.g. *Arabidopsis thaliana*) or a mammal. The mammalian Cpn10 may be primate, murine, ovine, bovine, canine, feline, porcine or equine. Alternatively the Cpn10 may be archaeal in origin. In particular embodiments the Cpn10 is human Cpn10.

The present invention also relates to modifications of human Cpn10 polypeptides homologues as disclosed above and encompasses these molecules modified by the addition, deletion, or substitution of one or more amino acid residues herein, and how these modifications can increase the affinity of these Cpn10 polypeptides to a nucleic acid-based PRR ligand. Furthermore, amino acid additions may involve the fusion of a Cpn10 polypeptide or fragment thereof with a second polypeptide or peptide, such as a polyhistidine tag, maltose binding protein fusion, glutathione S transferase fusion, green fluorescent protein fusion, or the addition of an epitope tag such as FLAG, c-myc or hexahistidine tag (SEQ ID NO: 359). The Cpn10 polypeptide may or may not include the initiating methionine at the N-terminus. For example, human Cpn10 may comprise at the N-terminus an additional GSM tripeptide, see for example WO 95/15338, the disclosure of which is incorporated herein by reference, or an additional alanine (A; SEQ ID Nos.3-5) or an additional glycine. The present invention also contemplates the use of polynucleotides encoding such modified forms of Cpn10. In the case of Cpn10 polypeptides of the invention based on, or substantially derived from human Cpn10, such polypeptides may comprise the N-terminal sequence AGQAFRKFL (SEQ ID NO: 360), MAGQ (SEQ ID NO: 361), AGQ or AAGQ (SEQ ID NO: 362) and optionally including one or more modifications as described above.

The term "variant" as used herein refers to substantially similar sequences. Generally, polypeptide sequence variants possess qualitative biological activity in common. Further, these polypeptide sequence variants may share at least 50%, 55%, 60%, 65%, 70%, 75%, 80%, 85%, 90%, 95%, 96%, 97%, 98% or 99% sequence identity. Also included within the meaning of the term "variant" are homologues of polypeptides of the invention. A homologue is typically a polypeptide from a different species but sharing substantially the same biological function or activity as the corresponding polypeptide disclosed herein.

Further, the term "variant" also includes analogues of the polypeptides of the invention, wherein the term "analogue" means a polypeptide which is a derivative of a polypeptide of the invention, which derivative comprises addition, deletion, substitution of one or more amino acids, such that the polypeptide retains substantially the same function.

The present invention also contemplates fragments of the polypeptides disclosed herein. The term "fragment" refers to a polypeptide molecule that encodes a constituent or is a constituent of a polypeptide of the invention or variant thereof. Typically the fragment possesses qualitative biological activity in common with the polypeptide of which it is a constituent. The peptide fragment may be between about 5 to about 150 amino acids in length, between about 5 to about 100 amino acids in length, between about 5 to about 50 amino acids in length, or between about 5 to about 25 amino acids in length. Alternatively, the peptide fragment may be between about 5 to about 15 amino acids in length.

Cpn10 polypeptides modified at the N- and/or C-terminus by the addition, deletion or substitution of one or more amino acid residues as described above also fall within the scope of the present invention.

Optimisation of Cpn10 cDNA Sequence

The present invention utilises optimised Cpn10 cDNA sequences to increase the use of abundant transfer RNA (tRNA) pools for the production of Cpn10 polypeptide. It is known that tRNA pools provide specific codons encoding specific amino acids for the translation of a protein from a messenger RNA. Furthermore, it is also known that some tRNA pools are more abundant than others. This can result in lower abundance tRNA pools being depleted resulting lower yields and/or tRNA substitution generating mutations when a large amount of protein is produced from certain expression systems.

In relation to this invention specific Cpn10 variants were found that were susceptible to this. For example, during overexpression of Cpn10 in *E. coli*, the rare glycine (Gly) GGA tRNA, used for Gly39, is depleted and may be substituted by the very common glutamate/glutamic acid (Glu) GM tRNA.

Accordingly, an optimised sequence using optimised codons at any number of positions may be constructed. In particular, the specific optimization of glycine and arginine residues G3, G29, G39, G50, G55, G58, G68, G77, G98, R8, R16, R21 and R93 resulted in wild-type cDNA expression levels but a significant decrease of variant levels while maintaining overall yield of Cpn10.

In addition, Cpn10 variants may be generated due to ribosomes reading through the cellular TGA stop codon. In that regard the TGA stop codon may be optimised by changing it to a TAA stop codon to eliminate this problem.

Production of Cpn10

In accordance with the present invention Cpn10 polypeptides may be produced using standard techniques of recombinant DNA and molecular biology that are well known to those skilled in the art. Guidance may be obtained, for example, from standard texts such as Sambrook et al., *Molecular Cloning: A Laboratory Manual*, Cold Spring Harbor, N.Y., 1989 and Ausubel et al., *Current Protocols in Molecular Biology*, Greene Publ. Assoc. and Wiley-Intersciences, 1992. Methods described in Morton et al., 2000 (*Immunol Cell Biol* 78:603-607), Ryan et al., 1995 (*J Biol Chem* 270:22037-22043) and Johnson et al., 2005 (*J Biol Chem* 280:4037-4047) are examples of suitable purification methods for Cpn10 polypeptides, although the skilled addressee will appreciate that the present invention is not limited by the method of purification or production used and any other method may be used to produce Cpn10 for use in accordance with the methods and compositions of the present invention.

Cpn10 polypeptides and peptide fragments for use in accordance with the present invention may be obtained using standard recombinant nucleic acid techniques or may be synthesized, for example using conventional liquid or solid phase synthesis techniques. Cpn10 peptides may be produced by digestion of a polypeptide with one or more proteinases such as endoLys-C, endoArg-C, endoGlu-C and staphylococcus V8-protease. The digested peptide fragments can be purified by, for example, high performance liquid chromatographic (HPLC) techniques.

The purification of Cpn10 polypeptides of the invention may be scaled-up for large-scale production purposes. For example, as described herein the present inventors have developed a bioprocess for the production of large (gram) quantities of highly pure, clinical grade Cpn10 polypeptides.

Cpn10 polypeptides of the present invention, as well as fragments and variants thereof, may also be synthesised by standard methods of liquid or solid phase chemistry well known to those of ordinary skill in the art. For example such molecules may be synthesised following the solid phase chemistry procedures of Steward and Young (Steward, J. M. & Young, J. D., Solid Phase Peptide Synthesis. (2nd Edn.) Pierce Chemical Co., Ill., USA (1984).

In general, such a synthesis method comprises the sequential addition of one or more amino acids or suitably protected amino acids to a growing peptide chain. Typically, either the amino or carboxyl group of the first amino acid is protected by a suitable protecting group. The protected amino acid is then either attached to an inert solid support or utilised in solution by adding the next amino acid in the sequence having the complimentary (amino or carboxyl) group suitably protected and under conditions suitable for forming the amide linkage. The protecting group is then removed from this newly added amino acid residue and the next (protected) amino acid is added, and so forth. After all the desired amino acids have been linked, any remaining protecting groups, and if necessary any solid support, is removed sequentially or concurrently to produce the final polypeptide.

Amino acid changes in Cpn10 polypeptides may be effected by techniques well known to those persons skilled in the relevant art. For example, amino acid changes may be effected by nucleotide replacement techniques which include the addition, deletion or substitution of nucleotides (conservative and/or non-conservative), under the proviso that the proper reading frame is maintained. Exemplary techniques include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction.

The generation of immunomodulatory activity by the Cpn10 polypeptides of the invention may involve the formation of heptamers of the Cpn10 polypeptides. Testing of immunomodulatory activity for the purposes of the present invention may be via any one of a number of techniques known to those of skill in the art. As exemplified herein immunomodulatory activity of Cpn10 polypeptides may be determined by measuring the ability of the polypeptide to modulate signalling from the Toll-like receptor TLR-3, for example using an NF-κB-luciferase reporter cell line, and typically in the presence of a TLR-3 agonist such as poly(I:C). Other TLRs such as TLR-7, 8 and 9 are also tested as described herein. Alternatively or in addition, immunomodulatory activity may be determined using other assays in vitro, ex vivo or in vivo, for example via measurement of the production of cytokines in cells such as peripheral blood mononuclear cells, competitive binding assay, a two-hybrid assay, a filter assay, an electrophoretic mobility shift (gel-shift) assay, a plate capture assay or any combination of assays that enables one to measure immunomodulatory activity.

Polynucleotides

Embodiments of the present invention provide isolated polynucleotides encoding Cpn10 polypeptides as described above, and variants and fragments of such polynucleotides. Non-limiting examples of polynucleotides that are contemplated within the scope of the invention are represented herein as SEQ ID No's 7, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 75, 77, 78, 80, 81, 83, 84, 86, 87, 89, 90, 92, 93, 95, 96, 98, 99, 101, 102, 104, 105, 107, 108, 110, 111, 113, 114, 116, 117, 119, 120, 122, 123, 125, 126, 128, 129, 131, 132, 134, 135, 137, 138, 140, 141, 143, 144, 146, 147, 149, 150, 152, 153, 155, 156, 158, 159, 161, 162, 164, 165, 167, 168, 170, 171, 173, 174, 176, 177, 179, 180, 182, 183, 185, 186, 188, 189, 191, 192, 194, 195, 197, 198, 200, 201, 203, 204, 206, 207, 209, 210, 212, 213, 215, 216, 218, 219, 221, 222, 224, 225, 227, 228, 230, 231, 233, 234, 236, 237, 239, 240, 242, 243, 245, 246, 248, 249, 251, 252, 254, 255, 257, 258, 260, 261, 263, 264, 266, 267, 269, 270, 272, 273, 275, 276, 278, 279, 281, 282, 284, 285 287, 288, 290, 291, 293, 294, 296, 297, 299, 300, 302, 303, 305, 306, 308, 309, 311, 312, 314, 315, 317, 318, 320, 321, 323, 324, 326, 327, 329, 330, 332, 333, 335, 336, 338, 339, 341, 342, 344, 345, 347, 348, 350, 351, 353, 354 or 356.

As for polypeptides discussed above, the term "variant" as used herein refers to substantially similar sequences. Generally, polynucleotide sequence variants encode polypeptides which possess qualitative biological activity in common. Further, these polynucleotide sequence variants may share at least 50%, 55%, 60%, 65%, 70%, 75%, 80%, 85%, 90%, 95%, 96%, 97%, 98% or 99% sequence identity. Also included within the meaning of the term "variant" are homologues of polynucleotides of the invention. A homologue is typically a polynucleotide from a different species but sharing substantially the same activity.

Fragments of polynucleotides of the invention are also contemplated. The term "fragment" refers to a nucleic acid molecule that encodes a constituent or is a constituent of a polynucleotide of the invention. Fragments of a polynucleotide, do not necessarily need to encode polypeptides which retain biological activity. Rather the fragment may, for example, be useful as a hybridization probe or PCR primer. The fragment may be derived from a polynucleotide of the invention or alternatively may be synthesized by some other means, for example chemical synthesis. Polynucleotides of the invention and fragments thereof may also be used in the production of antisense molecules using techniques known to those skilled in the art.

Accordingly, the present invention contemplates oligonucleotides and fragments based on the sequences of the polynucleotides of the invention for use as primers and probes. Oligonucleotides are short stretches of nucleotide residues suitable for use in nucleic acid amplification reactions such as PCR, typically being at least about 10 nucleotides to about 50 nucleotides in length, more typically about 15 to about 30 nucleotides in length. Probes are nucleotide sequences of variable length, for example between about 10 nucleotides and several thousand nucleotides, for use in detection of homologous sequences, typically by hybridization. The level of homology (sequence identity) between sequences will largely be determined by the stringency of hybridization conditions. In particular the nucleotide sequence used as a probe may hybridize to a homologue or other variant of a polynucleotide disclosed herein under conditions of low stringency, medium stringency or high stringency. Low stringency hybridization conditions may correspond to hybridization performed at 50° C. in 2×SSC. There are numerous conditions and factors, well known to those skilled in the art, which may be employed to alter the stringency of hybridization. For instance, the length and nature (DNA, RNA, base composition) of the nucleic acid to be hybridized to a specified nucleic acid; concentration of salts and other components, such as the presence or absence of formamide, dextran sulfate, polyethylene glycol etc; and altering the temperature of the hybridization and/or washing steps. For example, a hybridization filter may be washed twice for 30 minutes in 2×SSC, 0.5% SDS and at least 55° C. (low stringency), at least 60° C. (medium stringency), at least 65° C. (medium/high stringency), at least 70° C. (high stringency) or at least 75° C. (very high stringency).

In particular embodiments, polynucleotides of the invention may be cloned into a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences.

Antibodies

The present invention provides antibodies that selectively bind to the Cpn10 polypeptides of the present invention, as well as fragments and analogues thereof. Suitable antibodies include, but are not limited to polyclonal, monoclonal, chimeric, humanised, single chain, Fab fragments, and an Fab expression library. Antibodies of the present invention may act as agonists or antagonists of Cpn10 polypeptides, or fragments or analogues thereof.

Antibodies may be prepared from discrete regions or fragments of the Cpn10 polypeptides of the invention, in particular those involved in conferring immunomodulatory activity and/or partner or substrate binding. An antigenic Cpn10 polypeptide contains at least about 5, and preferably at least about 10, amino acids.

Methods for the generation of suitable antibodies will be readily appreciated by those skilled in the art. For example, an anti-Cpn10 monoclonal antibody, typically containing Fab portions, may be prepared using the hybridoma technology described in Antibodies—A Laboratory Manual, Harlow and Lane, eds., Cold Spring Harbor Laboratory, N.Y. (1988).

In the preparation of monoclonal antibodies directed toward Cpn10 polypeptides of the invention, fragments or analogues thereof, any technique that provides for the production of antibody molecules by continuous cell lines in culture may be used. These include the hybridoma technique originally developed by Kohler et al., Nature, 256:495-497 (1975), as well as the trioma technique, the human B-cell hybridoma technique [Kozbor et al., Immunology Today, 4:72 (1983)], and the EBV-hybridoma technique to produce human monoclonal antibodies [Cole et al., in Monoclonal Antibodies and Cancer Therapy, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

In summary, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies to Cpn10 polypeptides of the invention, or fragments or analogues thereof. For the production of Cpn10 polyclonal antibody, various host animals can be immunized by injection with a Cpn10 polypeptide, or a fragment or analogue thereof, including but not limited to rabbits, mice, rats, sheep, goats, etc. Further, the Cpn10 polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary anti-Cpn10 antibody. Alternatively, the anti-Cpn10 antibody may be detected by virtue of its binding with a secondary antibody or reagent which is appropriately labelled. A variety of methods are known in the art for detecting binding in an immunoassay and are within the scope of the present invention.

Antibodies of the present invention can be used in diagnostic methods and kits that are well known to those of ordinary skill in the art to detect qualitatively or quantify Cpn10 in a body fluid or tissue, or alternatively antibodies may be used in methods and compositions for the treatment of various diseases, disorders and conditions.

The antibody (or fragment thereof) raised against a Cpn10 polypeptide of the invention or a fragment or analogue thereof has binding affinity for Cpn10. Preferably, the antibody (or fragment thereof) has binding affinity or avidity greater than about $10^5$ M$^{-1}$, more preferably greater than about $10^6$ M$^{-1}$, more preferably still greater than about $10^7$ M$^{-1}$ and most preferably greater than about $10^8$ M$^{-1}$.

In terms of obtaining a suitable amount of an antibody according to the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Agonists and Antagonists

Using the methods described above, an agent may be identified that is an agonist of a polypeptide of the invention or a variant or fragment thereof. Agents which are agonists enhance one or more of the biological activities of the polypeptide. Alternatively, the methods described above may identify an agent that is an antagonist of a polypeptide of the invention or a variant or fragment thereof. Agents which are antagonists retard one or more of the biological activities of the polypeptide. Agonists enhance one or more of the biological activities of a molecule, such as Cpn10 polypeptides as described herein, whilst antagonists retard one or more of the biological activities of the polypeptides. In one example, an agonist of a polypeptide of the invention may be an immunosuppressive nucleic acid. This nucleic acid may bind a polypeptide of the present invention in a complex. In another example, an antagonist of a polypeptide of the invention may be a proinflammatory nucleic acid. This nucleic acid may also bind a polypeptide of the present invention in a complex. Such potential modulators of the activity of the polypeptides of the invention may be generated for screening by the above methods by a number of techniques known to those skilled in the art. For example, methods such as X-ray crystallography and nuclear magnetic resonance spectroscopy may be used to model the structure of polypeptide of the invention or a variant or fragment thereof, thus facilitating the design of potential modulating agents using computer-based modeling. Various forms of combinatorial chemistry may also be used to generate putative modulators. Using the screening methods as described below, an agent may be identified that is an agonist or antagonist of a polypeptide of the invention or a variant or fragment thereof. Antibodies, low molecular weight peptides, nucleic acids and non-proteinaceous organic molecules are examples of such agents that may act as agonists or antagonists of a polypeptide of the invention or a variant or fragment thereof.

Screening

Compounds which bind, or otherwise interact with the polypeptides and polynucleotides of the invention, and specifically compounds which modulate their activity, may be identified by a variety of suitable methods. Non limiting methods include the two-hybrid method, co-immunoprecipitation, affinity purification, mass spectroscopy, tandem affinity purification, phage display, label transfer, DNA microarrays/gene coexpression and protein microarrays.

Cpn10 polypeptides of the invention and appropriate fragments and variants can be used in high-throughput screens to assay candidate compounds for the ability to bind to, or otherwise interact with Cpn10. Such candidate compounds could be proinflammatory nucleic acids or immunosuppressive nucleic acids which form a complex with a polypeptide, fragment or variants of the polypeptide as described herein. Candidate compounds can be proteins.

These candidate compounds can be further screened against functional Cpn10 to determine the effect of the compound on Cpn10 activity. The polypeptides and polynucleotides of the present invention, and fragments and analogues thereof are useful for the screening and identification of compounds and agents that interact with these molecules. In particular, desirable compounds are those that modulate the activity of these polypeptides and polynucleotides. Such compounds may exert a modulatory effect by activating, stimulating, increasing, inhibiting or preventing expression or activity of the polypeptides and/or polynucleotides. Suitable compounds may exert their effect by virtue of either a direct (for example binding) or indirect interaction. As described herein, there are methods of screening for a compound that may modulate the activity of, or otherwise interact with, Cpn10 polypeptides of the invention. These compounds may be identified by a variety of suitable methods. Interaction and/or binding may be determined using standard competitive binding assays, such as gel-shift assays and plate bound assays described within, or two-hybrid assay systems.

For example, the two-hybrid assay is a yeast-based genetic assay system (Fields and Song, 1989) typically used for detecting protein-protein interactions. Briefly, this assay takes advantage of the multi-domain nature of transcriptional activators. For example, the DNA-binding domain of a known transcriptional activator may be fused to a Cpn10 polypeptide of the invention, or fragment or variant thereof, and the activation domain of the transcriptional activator fused to a candidate protein. Interaction between the candidate protein and the Cpn10 polypeptide, or fragment or variant thereof, will bring the DNA-binding and activation domains of the transcriptional activator into close proximity. Interaction can thus be detected by virtue of transcription of a specific reporter gene activated by the transcriptional activator.

Alternatively, affinity chromatography may be used to identify binding partners of Cpn10. For example, a Cpn10 polypeptide of the invention, or fragment or variant thereof, may be immobilised on a support (such as sepharose) and cell lysates passed over the column. Proteins binding to the immobilised Cpn10 polypeptide, fragment or variant can then be eluted from the column and identified. Initially such proteins may be identified by N-terminal amino acid sequencing for example.

In a modification of the above technique, a fusion protein may be generated by fusing a Cpn10 polypeptide, fragment or variant to a detectable tag, such as alkaline phosphatase, and using a modified form of immunoprecipitation as described by Flanagan and Leder (1990).

Methods for detecting compounds that modulate Cpn10 activity may involve combining a Cpn10 polypeptide with a candidate compound and a suitable labelled substrate and monitoring the effect of the compound on Cpn10 by changes in the substrate (may be determined as a function of time). Suitable labelled substrates include those labelled for colourimetric, radiometric, fluorimetric or fluorescent resonance energy transfer (FRET) based methods, for example.

For example, co-immunoprecipation may be used to determine whether a candidate agent or plurality of candidate agents interacts or binds with polypeptide of the invention or a variant or fragment thereof. Using this technique, cyanotoxic organisms, cyanobacteria and/or dinoflagellates may be lysed under nondenaturing conditions suitable for the preservation of protein-protein interactions. The resulting solution can then be incubated with an antibody specific for a polypeptide of the invention or a variant or fragment thereof and immunoprecipitated from the bulk solution, for example by capture with an antibody-binding protein attached to a solid support. Immunoprecipitation of the polypeptide of the invention or a variant or fragment thereof by this method facilitates the co-immunoprecipitation of an agent associated with that protein. The identification an associated agent can be established using a number of methods known in the art, including but not limited to SDS-PAGE, western blotting, and mass spectrometry.

Alternatively, the phage display method may be used to determine whether a candidate agent or plurality of candidate agents interacts or binds with a polypeptide of the invention or a variant or fragment thereof. Phage display is a test to screen for protein interactions by integrating multiple genes from a gene bank into phage. Under this method, recombinant DNA techniques are used to express numerous genes as fusions with the coat protein of a bacteriophage such the peptide or protein product of each gene is displayed on the surface of the viral particle. A whole library of phage-displayed peptides or protein products of interest can be produced in this way. The resulting libraries of phage-displayed peptides or protein products may then be screened for the ability to bind a polypeptide of the invention or a variant or fragment thereof. DNA extracted from interacting phage contains the sequences of interacting proteins.

Alternatively, affinity chromatography may be used to determine whether a candidate agent or plurality of candidate agents interacts or binds with a polypeptide of the invention or a variant or fragment thereof. For example, a polypeptide of the invention or a variant or fragment thereof, may be immobilised on a support (such as sepharose) and cell lysates passed over the column. Proteins binding to the immobilised polypeptide of the invention or a variant or fragment thereof, may then be eluted from the column and identified, for example by N-terminal amino acid sequencing.

The present invention also contemplates compounds which may exert their modulatory effect on polypeptides of the invention by altering expression of the polypeptide. In this case, such compounds may be identified by comparing the level of expression of the polypeptide in the presence of a candidate compound with the level of expression in the absence of the candidate compound.

In the context of antibodies, screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., Current Protocols in Molecular Biology, Vol. 1, John Wiley & Sons, Inc., New York (1994)). Antibody binding may be detected by virtue of a detectable label on the primary antibody. Alternatively, the antibody may be detected by virtue of its binding with a secondary antibody or reagent which is appropriately labelled. A variety of methods are known in the art for detecting binding in an immunoassay and are included in the scope of the present invention.

It will be appreciated that the methods described above are merely examples of the types of methods that may be utilised to identify agents that are capable of interacting with, or modulating the activity of polypeptides of the invention or variants or fragments thereof. Other suitable methods will be known by persons skilled in the art and are within the scope of this invention.

Compositions and Routes of Administration

Cpn10 polypeptides and polynucleotides of the invention may be useful as therapeutic agents. These molecules find use, for example, in treating or preventing a disease or condition in a subject, by administering a therapeutically effective amount of such a molecule to the subject. Typically such diseases and conditions are amenable to treatment by modulation of the immune response in the subject. By way of example, such diseases and conditions may include acute or chronic inflammatory diseases such as insulin dependent diabetes mellitus, systemic lupus erythematosis, Sjorgren's disease, Graves disease, multiple sclerosis, rheumatoid arthritis, chronic fatigue syndrome, Alzheimer's disease, asthma, allergy, multiple sclerosis, GVHD, artherosclerosis, inflammatory pain, psoriasis, HIV, chronic immune activation, chronic myositis, scleroderma. The disease may also be a cancer such as, non-small cell lung carcinoma, renal cell carcinoma, melanoma, non-Hodgkin's lymphoma, colorectal cancer, basal cell carcinoma. The disease may be an infectious disease.

The infectious disease may result from a bacterial, viral, or fungal infection. Chronic immune activation is associated with leakage of bacterial (e.g. LPS) and/or viral products (e.g. nucleic acids) from the gastrointestinal tract into the circulatory system. For example, leakage can occur from the oral cavity, gut or small intestine. Leakage of bacterial or viral products can be caused by an infection or disease such as bacterial infections, viral infections, inflammatory bowel disease and gum disease. An example of viral infection is a HIV or Hepatitis C infection.

Chronic immune activation involves immunomodulation of TLR signalling through LPS or nucleic acid binding to TLRs. LPS can bind to TLR2 or TLR4 whilst nucleic acids can bind to TLR3, 7, 8 or 9.

Accordingly, pharmaceutically useful compositions comprising Cpn10 polypeptides and polynucleotides for use in treating or preventing diseases and conditions are contemplated herein.

Agonists and antagonists of Cpn10 polypeptides of the invention, including anti-Cpn10 antibodies, may also be useful as therapeutic agents. Accordingly, the present invention also contemplates methods of treatment using such agonists and antagonists and pharmaceutical compositions comprising the same.

In general, suitable compositions for use in accordance with the methods of the present invention may be prepared according to methods and procedures that are known to those of ordinary skill in the art and accordingly may include a pharmaceutically acceptable carrier, diluent and/or adjuvant.

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringers solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The compositions may be conjugated to an array of polyethylene glycol (PEG) derivatives. The addition of PEG to proteins (PEGylation) is a well established method for decreasing the plasma clearance rates of proteins, thereby increasing their efficacy (Nucci et al., 1991, *Adv. Drug Del. Rev.* 6:133). Additional benefits of PEGylation may include, greater stability of proteins, decreased immunogenicity, enhanced solubility and decreased susceptibility to proteolysis (Sheffield W. 2001, *Curr Drug Targets Cardiovasc Haematol Disord.* 1:1-22). PEG molecules contain the basic repeating structure of —$(OCH_3CH_2)$n-OH and are classified into groups according to their molecular weight. PEG derivatives are conjugated to proteins to increase their hydrodynamic radius and in general, their increase in half-life is directly related to the size of the PEG chain attached (Sheffield W. 2001, *Curr Drug Targets Cardiovasc Haematol Disord.* 1:1-22).

The compositions may also be administered in the form of microparticles. Biodegradable microparticles formed from polylactide (PLA), polylactide-co-glycolide (PLGA), and epsilon-caprolactone (ε-caprolactone) have been extensively used as drug carriers to increase plasma half life and thereby prolong efficacy (R. Kumar, M., 2000, *J Pharm Pharmaceut Sci.* 3 (2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallize but exists as a clear viscous liquid. Mixing SAIB with a pharmaceutically accepted organic solvent such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent diffuses from the matrix allowing the SAIB-drug or SAIB-drug-polymer mixtures to set up as an in situ forming depot.

For the purposes of the present invention molecules and agents may be administered to subjects as compositions either therapeutically or preventively. In a therapeutic application, compositions are administered to a patient already suffering from a disease, in an amount sufficient to cure or at least partially arrest the disease and its complications. The composition should provide a quantity of the molecule or agent sufficient to effectively treat the patient.

Embodiments of the invention also contemplate the administration of a polynucleotide encoding Cpn10. In such situations the polynucleotide is typically operably linked to a promoter such that the appropriate polypeptide sequence is produced following administration of the polynucleotide to the subject. The polynucleotide may be administered to subjects in a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

Those skilled in the art will appreciate that in accordance with the methods of the present invention Cpn10 polypeptides of the invention may be administered alone or in conjunction with one or more additional agents. For example, a Cpn10 polypeptide of the invention may be administered together with one or more agonists capable of stimulating a TLR receptor such as TLR-3. Additionally, the present invention contemplates combination therapy using Cpn10 polypeptides of the invention in conjunction with other therapeutic approaches to the treatment of diseases and disorders. For example, Cpn10 polypeptides may be useful in the treatment of viral diseases which are responsive to therapy with Type I interferons such as IFNβ or IFN1β and Cpn10 polypeptides of the invention may be used in conjunction with IFNβ in the treatment of autoimmune diseases such as multiple sclerosis.

For such combination therapies, each component of the combination therapy may be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

Dosages

The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases and conditions.

Generally, an effective dosage is expected to be in the range of about 0.0001 mg to about 100 mg per kg body weight bi weekly; typically, about 0.001 mg to about 75 mg per kg body weight bi weekly; about 0.01 mg to about 50 mg per kg body weight bi weekly; about 0.05 mg to about 50 mg per kg body weight bi weekly; about 0.1 mg to about 10 mg per kg body weight per bi weekly; approximately 0.1 mg per kg body weight bi weekly. Also contemplated herein is administration of the dosage on a weekly or tri weekly basis.

Alternatively, an effective dosage may be about 25 to 150 mg per patient bi weekly. Generally, an effective dosage is expected to be in the range of about 2.5 to about 750 mg per patient bi weekly, preferably about 10 to about 350 mg per patient bi weekly, more preferably about 25 to 150 mg per patient bi weekly, even more preferably about 25 to 200 mg weekly.

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

The present invention will now be described with reference to specific examples, which should not be construed, in any way, as limiting the scope of the invention.

EXAMPLES

Example 1

Production of Cpn10 Polypeptides

To further define the production process of Cpn10 polypeptides of the invention, the following non-limiting example is provided.

Firstly, a heat-inducible expression plasmid encoding human Cpn10 with or without modification was transformed into the *E. coli* strain XL1-Blue (Stratagene), and a master cell bank was established from a single selected clone.

Figure 3:
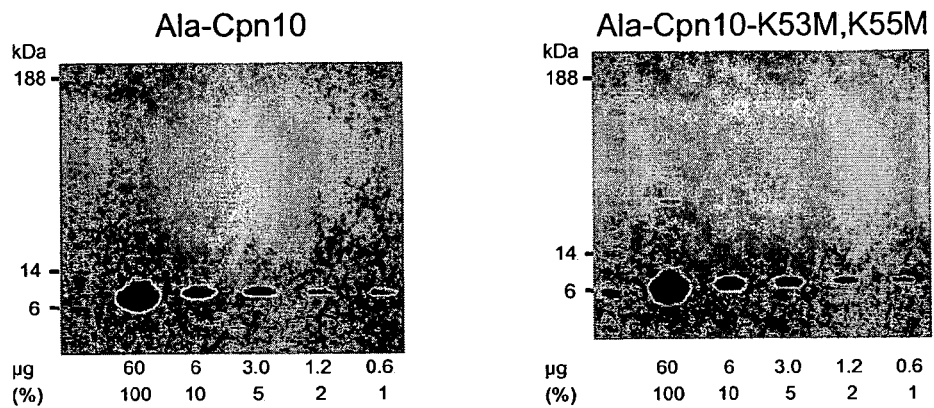
FIG. 3. SDS-PAGE stained with Coomassie brilliant blue reveals that recombinant Cpn10 proteins are >99% pure.
Figure 3:
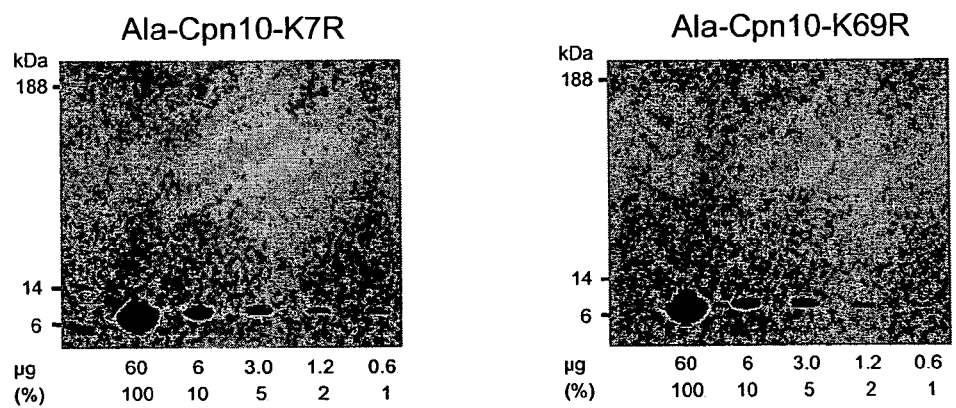
Figure 3:
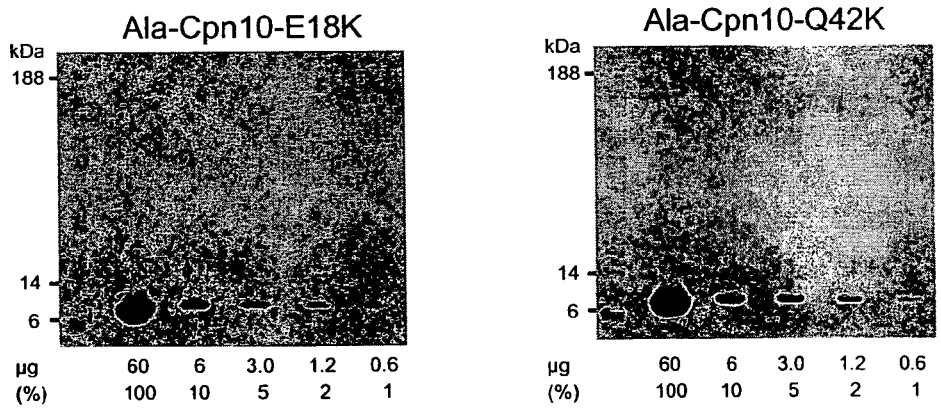

Cpn10 was then produced in *E. coli* essentially as described by Ryan et al. (1995, *J Biol Chem* 270: 22037-22043). In addition, the material that did not bind Macro-Prep High Q (BioRad) was further purified by S-Sepharose and then Gel-Filtration (Superdex 200, Amersham Biosciences). Purified Cpn10 in a 50 mM Tris-HCl (pH 7.6) and 150 mM NaCl buffer, was filtered through an Acrodisc with a 0.2 mm Mustang E membrane according to the manufacturer's instructions (Pall Corporation, Ann Arbor, Mich. Cat No. MSTG5E3) to remove residual endotoxins and was stored at −70° C. The purity of Cpn10, such as various Cpn10 mutant polypeptides as shown in FIG. 3, for example, was determined to be >99% by Coomassie brilliant staining on SDS-PAGE. Aliquots were thawed once prior to use.

Example 2

Molecular Chaperone Activities of Cpn10 Proteins

To examine the importance of the various amino acid residues, their potential charge, and the location of these residues in relation to chaperone activity, the inventors tested the Cpn10 polypeptides (see Table 1) that contain one or more mutations and with or without an extra N-terminal Alanine (Ala) residue for their ability to act as a molecular chaperones and fold proteins in conjunction with *E. coli* GroEL. This was determined by assaying for rhodanese refolding in vitro utilising a method adapted from Weber F. and Hayer-Hartl M. K. (Chaperonin Protocols, Ed Schneider C., Humana Press Inc., 2000, p 117-126).

Native bovine rhodanese (30 μM, SIGMA) was denatured in 20 mM MOPS-KOH (pH7.5), 100 mM KCl and 20 mM MgCl$_2$ (buffer A) containing 5M Guanidine HCl and 8 mM DTT then subsequently diluted (75-fold) from denaturant into buffer A containing GroEL (400 nM), such that the final concentration of rhodanese was 400 nM. GroEL rapidly and stably binds denatured rhodanese (D-Rho) whereas in buffer alone, D-Rho mis-folds and aggregates (ie inefficient spontaneous refolding). The addition of Cpn10 and ATP (20.1 mM) to preformed, stable complexes of GroEL-bound rhodanese permits efficient refolding to proceed. In the absence of Cpn10, the addition of ATP causes D-Rho to cycle on and off GroEL in a folding incompetent manner leading eventually to misfolding and aggregation (this reaction serves as a suitable assay blank). Each folding reaction has a total volume of 290 μL, at specific time points (ie 0, 15, 30, 45, 60, 75, 90 mins) 304 aliquots are removed and combined with 70 μL rhodanese activity assay mixture (57.1 mM KH$_2$PO$_4$ (pH7.5), 71.4 mM EDTA, 71.4 mM Na thiosulfate and 71.4 mM KCN) for 6 min. Prior to the initiation of refolding reactions with ATP, a 30 μL aliquot is taken as a T=0 min of refolding time point. EDTA within the rhodanese activity assay mixture chelates Mg$^{2+}$ ions, which prevents GroEL binding ATP, the result is an immediate stopping of the folding reaction. Subsequently, rhodanese activity is stopped after 6 min by the addition of 50 μL of 15% (v/v) formaldehyde (final concentration 5% v/v).

Rhodanese catalyses the formation of thiocyanide ("Rhodanid") from thiosulfate and cyanide. Thiocyanide is easily detected colourimetrically (Absorbance 450 nm) by the formation of its red iron complex in the presence of Ferric Nitrate. Rhodanese activity measurements (150 μL) are developed by the addition of 150 μL of Ferric Nitrate reagent (164.5 mM ferric nitrate and 9.2% v/v nitric acid). Rhodanese activity measurements are read at A450 nm in 96 well microplates.

A typical rhodanese folding reaction follow an exponential incline in rhodanese activity (ie folded rhodanese) with time to a maximum yield of folded rhodanese. At constant amounts of GroEL (400 nM) and rhodanese (400 nM), a linear relationship is observed (between rhodanese activity and time) with increasing amounts of Cpn10 until an equal molar concentration of Cpn10 (7mer) to GroEL (14mer) is reached (ie 400 nM). At concentrations of Cpn10 above 400 nM, the increase in rhodanese activity rapidly reaches a maximum. The assay consists of five standards (in duplicate) and test samples (in duplicate). The concentrations of Cpn10 standards are 0 nM, 140 nM, 250 nM, 280 nM and 350 nM. Rhodanese activity (ie Cpn10 activity) measurements from the 30, 45, 60, 75 and 90 min time points are averaged. The 0 nM Cpn10 standard serves as a suitable measurement of the assays' background activity; therefore the absorbance value for the 0 nM Cpn10 standard is subtracted from all other calculated absorbance values (or activity values). Following background correction, the absorbance value for the 280 nM Cpn10 standard is nominated as 100% activity and all other absorbance values are converted to a relative % activity based on the 100% standard. Outlier data points are removed by comparison of duplicate measurements, >30% deviation between duplicates is considered unacceptable. Utilizing the acceptable data, a linear calibration curve is generated with five standard concentrations 0 nM Cpn10 (0% Activity), 140 nM Cpn10 (50% Activity), 250 nM Cpn10 (89.3% Activity), 280 nM Cpn10 (100% Activity) and 350 nM Cpn10 (125% Activity). Rhodanese activity (e,g, Ala-Cpn10 activity) is plotted against Ala-Cpn10 concentration. For correction of assay bias, the percentage activity values from the test samples are recalculated using the equation generated from the linear calibration curve.

Concentrations of chaperonins (GroEL and Cpn10) are calculated using the oligomeric molecular weights (MW) of the proteins while rhodanese is calculated using the monomeric MW; e.g. *E. coli* GroEL 14 mer (SwissProt P0A6F5) =800,766.4 g/mol, Human Ala-Cpn10 7 mer (SwissProt P61604)=76,100.5 g/mol, Human X-Cpn10-Y75K 7 mer=75,358.5 g/mol, Human Ala-Cpn10-Y75K 7 mer=75,855.5 g/mol and Bovine rhodanese 1 mer (SwissProt P00586)= 33,164.6 g/mol.

As shown in the table 1 below, the activities of the numerous Cpn10 proteins were determined from a Ala-Cpn10 standard curve linear equation. All reactions were done in duplicate.

TABLE 1

Chaperonin 10 activity

| SEQ ID | Cpn10 Protein | Chaperone Activity (% of Ala-Cpn10) |
|---|---|---|
| 1 | X-Cpn10 | 89.7 |
| 3 | Ala-Cpn10 | 100 |
| 6 | X-Cpn10-K53E | 96.7 |
| 8 | Ala-Cpn10-K53M, K55M | 102.3 |
| 10 | Ala-Cpn10-K7R | 113.5 |
| 25 | Ala-Cpn10-K69R | 105.8 |
| 37 | Ala-Cpn10-Q3K | 97.6 |
| 58 | Ala-Cpn10-E18R | 100.5 |
| 88 | Ala-Cpn10-Q42K | 109.7 |
| 91 | Ala-Cpn10-T44K | 106.3 |
| 94 | Ala-Cpn10-S50K | 108.6 |
| 121 | Ala-Cpn10-D68K | 6.2 |
| 130 | X-Cpn10-Y75K | 90.9 |
| 133 | Ala-Cpn10-Y75H | 81.1 |
| 136 | Ala-Cpn10-Y75K | 81.3 |
| 139 | Ala-Cpn10-Y75R | 92.3 |
| 181 | Ala-Cpn10-D94K | 97.4 |
| 193 | Ala-Cpn10-D101K | 103.3 |
| 217 | Ala-Cpn10-E18K, D101K | 97.2 |
| 220 | Ala-Cpn10-E34Q, Y75K | 91.5 |
| 223 | Ala-Cpn10-Q42K, D101K | 97.6 |
| 226 | Ala-Cpn10-T44K, D101K | 92.6 |
| 229 | Ala-Cpn10-S50K, D101K | 101.1 |
| 238 | Ala-Cpn10-Y75GK | 63.0 |
| 241 | Ala-Cpn10-Y75G, G76K | 62.0 |
| 244 | Ala-Cpn10-Y75K, D94K | 69.6 |
| 253 | Ala-Cpn10-E18A | 97.9 |
| 256 | Ala-Cpn10-E18M | 99.0 |
| 259 | Ala-Cpn10-E18Q | 99.0 |
| 262 | Ala-Cpn10-E18S | 93.5 |
| 274 | Ala-Cpn10-D68N | 81.8 |
| 280 | Ala-Cpn10-D83N | 98.1 |
| 283 | Ala-Cpn10-D84N | 95.8 |
| 298 | Ala-Cpn10-D94N | 88.2 |
| 304 | Ala-Cpn10-D101N | 104.3 |
| 307 | MH-Cpn10 | 96.7 |
| 310 | MR-Cpn10 | 103.6 |
| 313 | MK-Cpn10 | 88.6 |
| 316 | MKK-Cpn10 | 95.9 |
| 319 | MKKK-Cpn10 | 98.8 |
| 328 | Ala-Cpn10-K39 | 113.4 |
| 331 | Ala-Cpn10-KK39 | 90.1 |
| 343 | Ala-Cpn10-K85 | 63.1 |
| 346 | Ala-Cpn10-KK85 | 35.7 |
| 349 | Ala-Cpn10-K102 | 115.5 |
| 352 | Ala-Cpn10-KK102 | 95.9 |
| 355 | Covalent Cpn10 | 81.6 |

Example 3

Cpn10 Mutants Bind to Poly(I:C), CpG-ODNs and RNA

TLRs are expressed both extra- and intracellularly, those on the cell surface (TLR1, TLR2, TLR4, TLR5, TLR6, TLR10 and TLR11) generally recognize hydrophobic ligands while those in intracellular compartments (TLR3, TLR7, TLR8 and TLR9) generally recognize negatively charged nucleic acid based ligands (Akira et al. 2006, 124: 783-801).

As described herein, the inventors have shown that Ala-Cpn10 binds negatively charged nucleic acid based TLR ligands, these include poly(I:C) (TLR3 agonists) as shown in FIG. 4, several classes of unmethylated single-stranded CpG-oligonucleotides (ODN) as shown in FIGS. 5 and 7 (human ODN-2216 class A, human ODN-2006 class B, human ODN-M362 class C; all TLR9 agonists) and *E. coli* K12 ssRNA (TLR7/8 ligand) as shown in FIG. 6.

As described below, the inventors have additionally shown that a number of mutants bind more tightly to poly(I:C) (FIG. 4), CpG-ODNs (FIG. 5) and ssRNA (FIG. 6) than Ala-Cpn10.

In relation to FIG. 4, mutants such as Ala-Cpn10-E18A, Ala-Cpn10-E34Q, Ala-Cpn10-D68N, Ala-Cpn10-D83N, Ala-Cpn10-D94N, Ala-Cpn10-Y75R, Ala-Cpn10-E18K, D101K, Ala-Cpn10-E34Q,Y75K, Ala-Cpn10-Q42,D101K, Ala-Cpn10-T44K,D101K, Ala-Cpn10-S50K,D101K, Ala-Cpn10-E74K,Y75E, Ala-Cpn10-Y75G,G76K, Ala-Cpn10-Y75GK, Ala-Cpn10-Y75K,D94K, Ala-Cpn10-Q3K, Ala-Cpn10-550K, Ala-Cpn10-D68K, Ala-Cpn10-D94K, Ala-Cpn10-D101K, Covalent-Cpn10, MR-Cpn10 and MKKK-Cpn10 (SEQ ID NO: 319) bind poly I:C more tightly than Ala-Cpn10. Furthermore, several mutants such as X-Cpn10-Y75K and Ala-Cpn10-Y75K bind so tightly to TLR3 agonist poly(I:C) that it cannot be fully released with 500 mM NaCl, unlike Ala-Cpn10 which is dissociated at 150 mM NaCl (FIG. 4). Intriguingly, at low NaCl concentrations many Cpn10 variants bind the long polymers of poly(I:C) in manner that sequesters them from ethidium bromide intercalation (FIG. 4), possibly indicating that several Cpn10 heptamers bind a single poly(I:C) chain. Several mutants including Ala-Cpn10-Y75K, Ala-Cpn10-KK21, Ala-Cpn10-D94N and Ala-Cpn10-Y75K,D94K also sequester bound poly(I:C) from ethidium bromide intercalation at low salt concentrations but at ≥150 mM the binding site is opened enough for ethidium bromide intercalation without escape of the bound poly(I:C).

Like the interaction with poly(I:C), an unstable complex of X-Cpn10 and Ala-Cpn10 with the TLR9 agonist CpG-class A was observed at physiological salt concentrations (~150 mM) (FIG. 5). In contrast, the inventors observed that like the interaction with poly(I:C) a significantly stronger association was formed between several Cpn10 variants and CpG-class A (FIGS. 4 and 5). In fact, the complexes with CpG-class A were mostly resistant to dissociation at 500 mM NaCl (FIG. 5). In regards to the TLR7 and TLR8 agonist *E. coli* K12 ssRNA, experiments also show a stronger association was formed with many Cpn10 variants such as Ala-Cpn10-Y75K, Ala-Cpn10-KK21, Ala-Cpn10-D94N and Ala-Cpn10-Y75K, D94K compared with Ala-Cpn10 (FIG. 6). At 150 mM NaCl Ala-Cpn10 and X-Cpn10 are completely dissociated from ssRNA. However, several mutants remain firmly bound in the presence of 500 mM NaCl.

Example 4

Quantitative Analysis of Cpn10 Binding to CpG Oligonucleotides (ODNs)

To determine the amount of binding of the Cpn10 mutants to ODNs, the mutants were formulated at 10 µg/µl in PBS pH7.2 (Invitrogen) and 50 µg was adsorbed to triplicate wells of a 96 well plate 16 hr at 4° C. Following the decanting of non-bound protein, the plate was blocked with 1% BSA and 5% sucrose in PBS pH7.2 for 2 hr at 23° C. 50 µl of 3'-biotin labeled human ODN-2216 class-A, human ODN-2006 class-B, or human ODN-M362 class-C (TLR9 agonists) (Proligo/Sigma) formulated at 0.01 µg/µl in PBS pH 7.2 was added to each well and incubated for 2 hr at 23° C. Unbound ligand was removed with five PBS (pH7.2)+0.05% Tween 20 washes. Bound CpG-ODNs were analysed with a Streptavidin-HRP and TMB detection system at A450 nm.

In FIG. 7 a quantitative analysis at physiological salt concentrations (~150 mM) highlights the significantly stronger interaction of CpG-classes A, B and C with a number of mutants compared to Ala-Cpn10.

Cpn10 mutants containing positive substitutions (Q3K, E18K, Q42K, T44K, S50K, D86K and D101K) were made and tested had significantly improved affinities for CpG-ODN classess-A\B\C compared to Ala-Cpn10.

All of the negative to neutral substitutions studied (E18Q, E18A, E18S, E18M, D68N, D83N and D101N) had significantly improved affinities for CpG-ODN classess-A\B\C compared to Ala-Cpn10.

With regard to the multiple positive substitution Cpn10 mutants, quantitative analysis of binding to CpG-ODN classess-A\B\C confirmed that all have significantly improved affinity, such as Ala-Cpn10-Y75K,D94K and Ala-Cpn10-E34Q,Y75K compared to Ala-Cpn10 (FIG. 7).

All of the positive insertions (lengthening) Cpn10 mutants studied, for example MK-Cpn10 and Ala-Cpn10-K85, had significantly improved affinities for \CpG-ODN classes-A/B/C compared to Ala-Cpn10.

Example 5

Cpn10 Modulates CpG-B ODN-Induced NFκB Activity

In order to establish whether high affinity binding of PRR ligands could be correlated with increased immunomodulatory activity, several cell based assays were developed to assess the abilities of various Cpn10 mutants to sequestor proinflammatory nucleic acids and thereby reduced the level of PRR signaling. Firstly, high affinity binders compared to Ala-Cpn10 and X-Cpn10 where incubated with CpG-ODN class B and the unbound PRR ligand was used to stimulate NFκB in mouse macrophages (RAW264 cells).

RAW264.7 (mouse macrophage) cells were stably transfected with an NFκB-luciferase reporter plasmid (pNIFty2-LUC; Invivogen). RAW264-pNIFty2-LUC cells were plated out and left to adhere overnight. 100 µg of a Cpn10 construct or Formulation buffer control was mixed with 4 µg of CpG-B ODN-1826 (Invivogen) and passed through a centrifugal filter device YM10 (Amicon). The entire flow through volume was added to the RAW264-pNIFty2-LUC cells and incubated at 37° C. for 5 hours. Cells were washed and subsequently lysed with 100 µl per well of CCLR 1× solution (Promega luciferase lysis buffer), mixed with luciferase substrate following the manufactures instructions and the luciferase counts measured. The level of activation of TLR9 for Ala-Cpn10 was assigned the value of 100%.

FIG. 8 shows a tight correlation between high affinity binders and reduced NFκB levels compared to Ala-Cpn10. It can be seen from FIG. 8 that isolated Cpn10 polypeptides comprising one or more amino acid substitutions, deletions and/or additions such as Ala-Cpn10-Y75K, Ala-Cpn10-E18A, Ala-Cpn10-Y75K, D94K, Ala-Cpn10-E34Q,Y75K, Ala-Cpn10-Q3K, Ala-Cpn10-E18K,D101K and MKK-Cpn10 result in lower levels of activation of TLR9 than for Ala-Cpn10.

Example 6

Cpn10 Mutants Inhibit Poly(I:C)-Induced NFκB Production Through TLR-3 in HEK293 Cells HEK293 cells were transiently transfected with TLR3 and the pNIFTY-NFκB luciferase reporter gene. 24 hours post transfection cells were plated out into 24 well plates at $1\times10^5$ and left to adhere overnight. Cells were then stimulated for 18 hours with 0.1 μg poly(I:C) in the presence or absence of 100 ug the Cpn10 mutants and 10 ul of SUPERase RNAse inhibitor (Ambion) as a competition assay (FIG. 9). Poly(I:C) and Cpn10 were mixed together at the required concentrations for 30 mins before being added to the cells. Three replicates of each condition were tested. 18 hours post stimulation cells were lysed and luciferase counts were measured.

Luciferase counts were normalized to poly(I:C) alone, which was given the value of 100%. When the cells were stimulated with poly(I:C), Ala-Cpn10 was able to reduce the level of luciferase (ie NFκB) by 22%. Several of the mutants, Ala-Cpn10-Y75K, X-Cpn10-Y75K, Ala-Cpn10-D94K,Ala-Cpn10-Y75GK, Ala-Cpn10-E18K,D101K and Ala-Cpn10-E34Q,Y75K show significant modulation of Poly(I:C) induced TLR3, with Ala-Cpn10-Y75K reducing signalling by 53%, X-Cpn10-Y75K reducing signalling by 71% and Ala-Cpn10-D94K reducing signalling by 82%, for example (FIG. 9). This indicates that most of the Cpn10 mutants have the ability to modulate the immune system, particularly, when involving TLR3 signalling.

Example 7

Panel of Mutants

In applying the above methods and tests, the inventors produced a number of Cpn10 polypeptides with various mutations to assess the importance of various amino acid residues (e.g. such as charge and positioning in the Cpn10 molecule) in their ability to have an increased binding to a PRR ligand, such as poly(I:C) and several classes of ODNs compared to such Cpn10 molecules as X-Cpn10 and Ala-Cpn10.

The inventors have substituted at least one of amino acid residue in each of the N-terminus, β-barrel, mobile loop, roof loop, C-terminus and connective loops of the Cpn10 molecule as shown in the Table 1. The inventors have either replaced a neutral amino acid residue with a positively charged residue, replaced a negatively charged amino acid residue with a neutral or positively charged residue, positively charged residue with another positively charged residue, inserted positively charged residues, or deleted negatively charged residues.

TABLE 2

Panel of Cpn10 Mutations (Table discloses residues 1-7, 18-42, 52-63, 65-69, 73-79, 83-89, and 91-94 as SEQ ID NOS 363-369, respectively.)

| Region of Mutation | Residue number (residues with surface exposed side-chains) | Amino acid | Mutation(s) |
|---|---|---|---|
| N-terminus | 1 | A | K, R, H |
| | 2 | G | K, R, H |
| | 3 | Q | K, R, H |
| | 4 | A | K, R, H |
| | 5 | F | K, R, H |
| | 6 | R | K, H |
| | 7 | K | R, H |
| β-barrel (β-1) | 9 | L | K, R, H |
| | 12 | F | K, R, H |
| | 13 | D | K, R, H, G, A, V, L, I, P, F, Y, W, C, M, S, T, N, Q |
| | 14 | R | K, H |
| | 16 | L | K, R, H |
| | 18 | E | K, R, H, G, A, V, L, I, P, F, Y, W, C, M, S, T, N, Q |
| | 19 | R | K, H |
| | 20 | S | K, R, H |
| Mobile loop | 21 | A | K, R, H |
| | 22 | A | K, R, H |
| | 23 | E | K, R, H, G, A, V, L, I, P, F, Y, W, C, M, S, T, N, Q |
| | 24 | T | K, R, H |
| | 25 | V | K, R, H |
| | 26 | T | K, R, H |
| | 27 | R | K, H |
| | 28 | G | K, R, H |
| | 29 | G | K, R, H |
| | 30 | I | K, R, H |
| | 31 | M | K, R, H |
| | 32 | L | K, R, H |
| | 33 | P | K, R, H |
| | 34 | E | K, R, H, G, A, V, L, I, P, F, Y, W, C, M, S, T, N, Q |
| | 35 | K | R, H |
| | 36 | S | K, R, H |
| | 37 | Q | K, R, H |
| | 38 | G | K, R, H |
| Connective loop 1 (L-1) | 39 | K | R, H |
| | 40 | V | K, R, H |
| β-barrel (β-2) | 41 | L | K, R, H |
| | 42 | Q | K, R, H |
| | 44 | T | K, R, H |
| | 46 | V | K, R, H |
| | 50 | S | K, R, H |
| Roof loop | 52 | S | K, R, H |
| | 53 | K | R, H |
| | 54 | G | K, R, H |
| | 55 | K | R, H |
| | 56 | G | K, R, H |
| | 57 | G | K, R, H |
| | 58 | E | K, R, H, G, A, V, L, I, P, F, Y, W, C, M, S, T, N, Q |
| | 59 | I | K, R, H |
| | 60 | Q | K, R, H |
| | 61 | P | K, R, H |
| | 62 | V | K, R, H |
| β-barrel (β-3) | 63 | S | K, R, H |
| | 65 | K | R, H |
| | 66 | V | K, R, H |
| | 67 | G | K, R, H |
| | 68 | D | K, R, H, G, A, V, L, I, P, F, Y, W, C, M, S, T, N, Q |
| | 69 | K | R, H |
| | 73 | P | K, R, H |
| Connective loop 2 (L-2) | 74 | E | K, R, H, G, A, V, L, I, P, F, Y, W, C, M, S, T, N, QG |
| | 75 | Y | G, GK, K, R, H, D, E, Q |
| | 76 | G | K, R, H, D, E, N ,Q, S, T |
| β-barrel (β-4) | 77 | G | K, R, H |
| | 78 | T | K, R, H |
| | 79 | K | R, H |

TABLE 2-continued

Panel of Cpn10 Mutations (Table discloses residues 1-7, 18-42, 52-63, 65-69, 73-79, 83-89, and 91-94 as SEQ ID NOS 363-369, respectively.)

| Region of Mutation | Residue number (residues with surface exposed side-chains) | Amino acid | Mutation(s) |
|---|---|---|---|
| Connective loop 3 (L-3) | 81 | V | K, R, H |
| | 83 | D | K, R, H, G, A, V, L, I, P, F, Y, W, C, M, S, T, N, Q |
| | 84 | D | K, R, H, G, A, V, L, I, P, F, Y, W, C, M, S, T, N, Q |
| β-barrel (β-5) | 85 | K | R, H |
| | 86 | D | K, R, H, G, A, V, L, I, P, F, Y, W, C, M, S, T, N, Q |
| | 87 | Y | K, R, H |
| | 88 | F | K, R, H |
| | 89 | L | K, R, H |
| | 91 | R | K, H |
| | 92 | D | K, R, H, G, A, V, L, I, P, F, Y, W, C, M, S, T, N, Q |
| | 93 | G | K, R, H |
| | 94 | D | K, R, H, G, A, V, L, I, P, F, Y, W, C, M, S, T, N, Q, |
| | 96 | L | K, R, H |
| | 98 | K | R, H |
| | 100 | V | K, R, H |
| C-terminus | 101 | D | K, R, H, G, A, V, L, I, P, F, Y, W, C, M, S, T, N, Q |

In addition to single substitution mutations, the inventors have produced Cpn10 polypeptides with any combination of two or more of the above mutations such as double mutants (e.g. Ala-Cpn10-F12K,D92K, Ala-Cpn10-E18K,D101K, Ala-Cpn10-E34Q,Y75K, Ala-Cpn10-Q42K,D101K, Ala-Cpn10-T44K,D101K, Ala-Cpn10-S50K,D101K, Ala-Cpn10-Q60K,T78K, Ala-Cpn10-E74K,Y75E, Ala-Cpn10-Y75GK, Ala-Cpn10-Y75G,G76K, Ala-Cpn10-Y75K,D94K and Ala-Cpn10-Y75K,D94N. Furthermore, the inventors have produced positive insertion (lengthening) and negative deletion (removal) Cpn10 variants (e.g. MH-Cpn10, MR-Cpn10, MK-Cpn10, MKK-Cpn10, MKKK-Cpn10 (SEQ ID NO: 319), Ala-Cpn10-K21, Ala-Cpn10-KK21, Ala-Cpn10-K39, Ala-Cpn10-KK39, Ala-Cpn10-K57, Ala-Cpn10-KK57, Ala-Cpn10-K76, Ala-Cpn10-KK76, Ala-Cpn10-K85, Ala-Cpn10-KK85, Ala-Cpn10-K102, Ala-Cpn10-KK102, deltaD13, deltaE18, deltaE23, deltaE34, deltaE58, deltaE68, deltaE74, deltaD83, deltaD84, deltaD86, deltaD92, deltaD94 and deltaD101).

It is contemplated herein that any combination of the above mutations that results in the creation of additional double mutants, triple mutants, and so on, are within the scope of the invention.

Example 8

Calculation of Net Charge of Cpn10 Polypeptides

Calculation of Protein Net Charge

As described above the net charge of a polypeptide at a given pH is calculated on the basis of the Henderson-Hasselbalch equation (Hasselbalch, K. A., 1917 *Biochemische Zeitschrift* 78: 112-144) and known pKa values of ionisable amino acid side chains and the N- and C-termini of a polypeptide. The pKa values utilised in Table 3 are N-terminus 8.0, C-terminus 3.1, Lys 10.0, Arg 12.0, His 6.5, Glu 4.4, Asp 4.4, Tyr 10.0 and Cys 8.5 (Stryer, L., 1988 "Biochemistry" textbook 3rd Edition, New York, W.H. Freeman, ISBN 0716719207). Using the method described above the net charge of Cpn10 variants was calculated at pH 7.3 and pH7.4 (taken as physiological pH) as shown in Table 3.

TABLE 3

Calculated Net Charge values of Cpn10 Variants.

| SEQ ID | Cpn10 Protein | Net Charge at pH7.3 | Net Charge at pH7.4 |
|---|---|---|---|
| 1 | X-Cpn10 | 1.8 | 1.8 |
| 3 | Ala-Cpn10 | 1.8 | 1.8 |
| 6 | X-Cpn10-K53E | −0.2 | −0.2 |
| 8 | Ala-Cpn10-K53M, K55M | −0.2 | −0.2 |
| 10 | Ala-Cpn10-K7R | 1.8 | 1.8 |
| 13 | Ala-Cpn10-R19K | 1.8 | 1.8 |
| 16 | Ala-Cpn10-K27R | 1.8 | 1.8 |
| 19 | Ala-Cpn10-K39R | 1.8 | 1.8 |
| 22 | Ala-Cpn10-K55R | 1.8 | 1.8 |
| 25 | Ala-Cpn10-K69R | 1.8 | 1.8 |
| 28 | Ala-Cpn10-K85R | 1.8 | 1.8 |
| 31 | Ala-Cpn10-K98R | 1.8 | 1.8 |
| 34 | Ala-Cpn10-A1K | 2.8 | 2.8 |
| 37 | Ala-Cpn10-Q3K | 2.8 | 2.8 |
| 40 | Ala-Cpn10-Q3R | 2.8 | 2.8 |
| 43 | Ala-Cpn10-F5K | 2.8 | 2.8 |
| 46 | Ala-Cpn10-L9K | 2.8 | 2.8 |
| 49 | Ala-Cpn10-F12K | 2.8 | 2.8 |
| 52 | Ala-Cpn10-D13K | 3.8 | 3.8 |
| 55 | Ala-Cpn10-E18K | 3.8 | 3.8 |
| 58 | Ala-Cpn10-E18R | 3.8 | 3.8 |
| 61 | Ala-Cpn10-S20K | 2.8 | 2.8 |
| 64 | Ala-Cpn10-A22K | 2.8 | 2.8 |
| 67 | Ala-Cpn10-T24K | 2.8 | 2.8 |
| 70 | Ala-Cpn10-G29K | 2.8 | 2.8 |
| 73 | Ala-Cpn10-M31K | 2.8 | 2.8 |
| 76 | Ala-Cpn10-E34K | 3.8 | 3.8 |
| 79 | Ala-Cpn10-Q37K | 2.8 | 2.8 |
| 82 | Ala-Cpn10-V40K | 2.8 | 2.8 |
| 85 | Ala-Cpn10-L41K | 2.8 | 2.8 |
| 88 | Ala-Cpn10-Q42K | 2.8 | 2.8 |
| 91 | Ala-Cpn10-T44K | 2.8 | 2.8 |
| 94 | Ala-Cpn10-S50K | 2.8 | 2.8 |
| 97 | Ala-Cpn10-S50R | 2.8 | 2.8 |
| 100 | Ala-Cpn10-S52K | 2.8 | 2.8 |
| 103 | Ala-Cpn10-G54K | 2.8 | 2.8 |
| 106 | Ala-Cpn10-G56K | 2.8 | 2.8 |
| 109 | Ala-Cpn10-E58K | 3.8 | 3.8 |
| 112 | Ala-Cpn10-Q60K | 2.8 | 2.8 |
| 115 | Ala-Cpn10-P61K | 2.8 | 2.8 |
| 118 | Ala-Cpn10-V66K | 2.8 | 2.8 |
| 121 | Ala-Cpn10-D68K | 3.8 | 3.8 |
| 124 | Ala-Cpn10-P73K | 2.8 | 2.8 |
| 127 | Ala-Cpn10-E74K | 3.8 | 3.8 |
| 130 | X-Cpn10-Y75K | 2.8 | 2.8 |
| 133 | Ala-Cpn10-Y75H | 2.0 | 1.9 |
| 136 | Ala-Cpn10-Y75K | 2.8 | 2.8 |
| 139 | Ala-Cpn10-Y75R | 2.8 | 2.8 |
| 142 | Ala-Cpn10-G76K | 2.8 | 2.8 |
| 145 | Ala-Cpn10-G77K | 2.8 | 2.8 |
| 148 | Ala-Cpn10-T78K | 2.8 | 2.8 |
| 151 | Ala-Cpn10-V81K | 2.8 | 2.8 |
| 154 | Ala-Cpn10-D83K | 3.8 | 3.8 |
| 157 | Ala-Cpn10-D84K | 3.8 | 3.8 |
| 160 | Ala-Cpn10-D86K | 3.8 | 3.8 |
| 163 | Ala-Cpn10-D86R | 3.8 | 3.8 |
| 166 | Ala-Cpn10-Y87K | 2.8 | 2.8 |
| 169 | Ala-Cpn10-F88K | 2.8 | 2.8 |
| 172 | Ala-Cpn10-L89K | 2.8 | 2.8 |
| 175 | Ala-Cpn10-D92K | 3.8 | 3.8 |
| 178 | Ala-Cpn10-G93K | 2.8 | 2.8 |
| 181 | Ala-Cpn10-D94K | 3.8 | 3.8 |
| 184 | Ala-Cpn10-D94R | 3.8 | 3.8 |
| 187 | Ala-Cpn10-L96K | 2.8 | 2.8 |
| 190 | Ala-Cpn10-V100K | 2.8 | 2.8 |
| 193 | Ala-Cpn10-D101K | 3.8 | 3.8 |
| 196 | Ala-Cpn10-D101R | 3.8 | 3.8 |
| 199 | Ala-Cpn10-ΔE23 | 2.8 | 2.8 |
| 202 | Ala-Cpn10-ΔE34 | 2.8 | 2.8 |
| 205 | Ala-Cpn10-ΔE58 | 2.8 | 2.8 |
| 208 | Ala-Cpn10-ΔE74 | 2.8 | 2.8 |

TABLE 3-continued

Calculated Net Charge values of Cpn10 Variants.

| SEQ ID | Cpn10 Protein | Net Charge at pH7.3 | Net Charge at pH7.4 |
|---|---|---|---|
| 211 | Ala-Cpn10-ΔD84 | 2.8 | 2.8 |
| 214 | Ala-Cpn10-F12K, D92K | 4.8 | 4.8 |
| 217 | Ala-Cpn10-E18K, D101K | 5.8 | 5.8 |
| 220 | Ala-Cpn10-E34Q, Y75K | 3.8 | 3.8 |
| 223 | Ala-Cpn10-Q42K, D101K | 4.8 | 4.8 |
| 226 | Ala-Cpn10-T44K, D101K | 4.8 | 4.8 |
| 229 | Ala-Cpn10-S50K, D101K | 4.8 | 4.8 |
| 232 | Ala-Cpn10-Q60K, T78K | 3.8 | 3.8 |
| 235 | Ala-Cpn10-E74K, Y75E | 2.8 | 2.8 |
| 238 | Ala-Cpn10-Y75GK | 2.8 | 2.8 |
| 241 | Ala-Cpn10-Y75G, G76K | 2.8 | 2.8 |
| 244 | Ala-Cpn10-Y75K, D94K | 4.8 | 4.8 |
| 247 | Ala-Cpn10-Y75K, D94N | 3.8 | 3.8 |
| 250 | Ala-Cpn10-D13N | 2.8 | 2.8 |
| 253 | Ala-Cpn10-E18A | 2.8 | 2.8 |
| 256 | Ala-Cpn10-E18M | 2.8 | 2.8 |
| 259 | Ala-Cpn10-E18Q | 2.8 | 2.8 |
| 262 | Ala-Cpn10-E18S | 2.8 | 2.8 |
| 265 | Ala-Cpn10-E23Q | 2.8 | 2.8 |

Net Charge values were calculated at physiological pH (pH 7.3 to 7.4) using the Protein Calculator V3.3 tool (http://www.scripps.edu/~cdputnam/protcalc.html).

Example 9

Summary

The inventors have previously discovered that Cpn10 modulates several Pathogen Recognition Receptors (PRRs) and have recently shown its efficacy and safety in the treatment of human patients with rheumatoid arthritis (Vanags et al. *Lancet* 2006; 368: 855-863) and psoriasis (Williams et al. *Arch. Dermatol.* 2008; 144: 683-685). The inventors now show that variants of Cpn10 binds specifically to several nucleic acid-based PRR ligands.

The addition of extra positive charge, through adding positive or removing negative residues generates a Cpn10 molecule which binds significantly stronger (compared to Ala-Cpn10 and X-Cpn10) to nucleic acid-based PRR ligands. Extra positive charge could be added by (1) substituting an existing surface/solution exposed neutral or negative residue for a positive residue, (2) substituting an existing surface/solution exposed negative residue for a neutral residue, (3) introducing an additional surface/solution exposed positive residues (eg lengthen a loop structure or the N-terminus and C-terminus) or (4) deleting an existing surface/solution exposed negative residue (eg shortening a loop structure or the N-terminus and C-terminus). Our results also show that introducing multiple positive charges (eg Ala-Cpn10-F12K, D92N; E18K,D101K; E34Q,Y75K; Q42K,D101K; T44K, D101K; S50K,D101K; Q60K,T78K; E74K,Y75E; Y75GK; Y75G,G76K; Y75K,D94K; Y75K,D94N) may increase the binding potential significantly greater than the individual mutations.

The effect of substituting pre-existing neutral and negative residues with either Lysine (K) or Arginine (R) residues was examined. All of the positive substitutions studied (A1K, Q3K, Q3R, F5K, D13K, E18K, E18R, S20K, A22K, T24K, G29K, M31K, E34K, Q37K, V40K, L41K, Q42K, T44K, S50K, S50R, S52K, G54K, G56K, E58K, Q60K, P61K, V66K, D68K, P73K, E74K, Y75K, Y75H, Y75R, G76K, G77K, T78K, V81K, D83K, D84L, D86K, D86R, Y87K, F88K, L89K, D92K, G93K, D94K, D94R, L96K, V101K, D101K and D101R; SEQ ID Nos: 34-45 and 52-198) had significantly improved affinities for poly(I:C), *E. coli* K12 ssRNA and several CpG-ODN classess-A\B\C compared to Ala-Cpn10 (FIGS. 4 to 9).

The effect of substituting pre-existing negative residues (ie E and D) with neutral residues (eg N, Q, G, A, V, L, I, P, F, Y, W, C, M, S, T, H) was also examined. Again, all of the negative to neutral substitutions studied (D13N, E18A, E18M, E18Q, E18S, E23Q, E34Q, E58Q, D68N, E74Q, D83N, D84N, D86N, D92N, D94A, D94M, D94N, D94S and D101N; SEQ ID Nos: 250-306) had significantly improved affinities for poly(I:C), *E. coli* K12 ssRNA and several CpG-ODN classess-A\B\C compared to Ala-Cpn10 (FIGS. 4 to 9).

To examine whether the addition of multiple positive charges would provide tighter binding, several variants were prepared (ieg E18K/D101K, Q42K/D101K, T44K/D101K and S50K/D101K, SEQ ID Nos: 217-231). As expected, high affinity binding was observed to all nucleic acid-based PRR ligands (FIGS. 4 to 9). As outlined above positive charge can be added to Cpn10 by replacement of existing neutral or negative residues with positive residues (K,R,H) and negative residues with neutral residues. Another way to add positive charge is to insert positive residue (K,R,H) at positions in Cpn10 that would tolerate such structural changes. Each Cpn10 subunit is formed from 101 amino acid which folds into a discontinuous β-barrel structure connected by 3 small loops and 2 larger β-hairpin turn loops (FIG. 1). The β-barrel structure provides all of the subunit-subunit interactions and the Cpn10 heptamer's stability. Lengthening segments of the β-barrel would probably lead to structural instability. In comparison lengthening the N-terminus, C-terminus or several connective loops would probably tolerate such structural changes better. In agreement with this prediction, several Cpn10 homologous have naturally extended segments (FIG. 2). For example, Bacteriophage T4 Cpn10 (Gp31) has a significantly lengthened mobile loop and L-3 loop. Mosquito, Fly and Mycobacterial Cpn10 have lengthened roof loops while numerous Cpn10s contain longer N- and C-termini. Positive residues were successfully inserted into each of the 5 connective loops (ie L-1, L-2, L-3, mobile loop and roof loop), the N-terminus and C-terminus as shown in Table 4.

TABLE 4

Positive insertion (lengthening) Cpn10 variants

| SEQ ID # | Mutant | Site of Lengthening |
|---|---|---|
| 307 | MH-Cpn10 | N-terminus |
| 310 | MR-Cpn10 | N-terminus |
| 313 | MK-Cpn10 | N-terminus |
| 316 | MKK-Cpn10 | N-terminus |
| 319 | MKKK-Cpn10 | N-terminus |
| 322 | Ala-Cpn10-K21 | mobile loop |
| 325 | Ala-Cpn10-KK21 | mobile loop |
| 328 | Ala-Cpn10-K39 | L1 connection loop |
| 331 | Ala-Cpn10-KK39 | L1 connection loop |
| 334 | Ala-Cpn10-K57 | roof loop |
| 337 | Ala-Cpn10-KK57 | roof loop |
| 340 | Ala-Cpn10-K76 | L2 connection loop |
| 343 | Ala-Cpn10-K85 | L3 connection loop |
| 346 | Ala-Cpn10-KK85 | L3 connection loop |
| 349 | Ala-Cpn10-K102 | C-terminus |
| 352 | Ala-Cpn10-KK102 | C-terminus |

All of the positive insertion (lengthening) Cpn10 variants studied had significantly improved affinities for poly(I:C) and several CpG-ODN classess-A\B\C compared to Ala-Cpn10 (FIGS. 4 to 9; SEQ ID Nos: 307-354).

All Cpn10 variants with a single positive addition interact with *E. coli* K12 ssRNA and display higher affinities compared to Ala-Cpn10. Similarly, Cpn10 variants with multiple positive additions (ie E18K/D101K, Q42K/D101K, T44K/D101K, S50K/D101K, MKK-Cpn10, MKKK-Cpn10 (SEQ ID NO: 319), Ala-Cpn10-KK39, Ala-Cpn10-KK85 and Ala-Cpn10-KK102) have an improved affinity for *E. coli* K12 ssRNA compared to Ala-Cpn10 (FIG. 6). Net positive charge can be increased by substituting negative residues with neutral or positive residues. Another possibility is to remove the negative residues completely. As discussed above, numerous Cpn10 homologous have naturally extended and also shortened connective loops (ie L-1, L-2, L-3, mobile loop and roof loop). Removal of negative residues at positions 23, 34, 58, 74 and 84 (SEQ ID Nos: 199-213) demonstrates that these Cpn10 variants have increased affinity for nucleic acid based PRR ligands. Negative residues D68, D84 and D101 could also be deleted without compromising the structural integrity of Cpn10 and that these variants are envisaged to also be high affinity binders.

In order to establish whether high affinity binding of PRR ligands could be correlated with increased immunomodulatory activity, several cell based assays were developed to assess the abilities of various Cpn10 mutants to sequestor proinflammatory nucleic acids and thereby reduced the level of PRR signaling. Firstly, high affinity binders compared to Ala-Cpn10 were incubated with CpG-ODN class B and the unbound PRR ligand was used to stimulate NFκB in mouse macrophages (RAW264 cells). FIG. 8 shows a tight correlation between high affinity binders and reduced NFκB levels compared to Ala-Cpn10. Likewise, mutants with compromised affinities for PRR ligands, such as X-Cpn10-K53E and Ala-Cpn10-K53M,K55M, had an increased level of NFκB activation compared to Ala-Cpn10. In order to test the biological activities of high affinity binders on cells, Cpn10 variants were next assessed for their abilities to reduce proinflammatory NFκB activation (from HEK cells expressing TLR3) when stimulated with poly(I:C). In this system the high affinity binders (eg Ala-Cpn10-D101K) generally showed significantly improved ability to inhibit NFκB activation compared to Ala-Cpn10 (FIGS. 7+9). Replacement of a positively charged residue with another positively charged residue (eg K7R, R19K, K27R, K39R, K55R, K69R, K85R and K98R; SEQ ID Nos: 10-33) has no significant effect on the ability of such Cpn10 variants to bind pro-inflammatory nucleic acids compared to Ala-Cpn10 (FIG. 8).

It is demonstrated herein that the isolated Cpn10 polypeptides with the mutations described above and throughout the specification possess an increased affinity for nucleic acid-based PRR ligands, in particular the TLR-3 agonist poly(I:C), TLR7 and TLR8 agonist *E. coli* ssRNA and TLR9 agonists unmethylated CpG-oligonucleotides (ODNs) (ODN-2216 class A, ODN-2006 class B and ODN-M362 class C). It is also demonstrated herein that these Cpn10 polypeptides inhibit poly(I:C) and CpG induced NFκB activation

CONCLUSIONS

The data contained herein reveals that the Cpn10 mutants as listed under Example 8 with an increased affinity for nucleic acid-based ligands of PRRs can be generated by adding positively charged or deleting negatively charged residues, by substituting negatively charged residues for neutral or positively charged residues or by substituting neutral residues for positively charged residues within the Cpn10 molecule. For example, the inventors have identified that Ala-Cpn10-Y75K, as well as many other Cpn10 mutants, had significantly improved affinity for poly(I:C), CpG-ODN classess-A\B\C and *E. coli* K12 ssRNA compared to Ala-Cpn10 (FIGS. 4 to 7) which can be attributed to increasing the net positive charge of the Cpn10 molecule through amino acid substitutions, deletions, and/or insertions.

Furthermore, the inventors have found that high affinity binding to nucleic acid-based ligands of PRRs can be achieved by introducing positive charge at several locations within the Cpn10 molecule. The increased affinity of the polypeptides of the invention to a nucleic acid-based PRR ligand is indicative of increased immunomodulatory activity.

The invention claimed is:

1. An isolated Cpn10 polypeptide possessing an increased affinity for a PRR ligand compared to Ala-Cpn10 polypeptide, the isolated Cpn10 polypeptide comprising the amino acid sequence selected from the group consisting of SEQ ID NO:58, SEQ ID NO:88, SEQ ID NO:91, SEQ ID NO:94, SEQ ID NO:181, SEQ ID NO:193, SEQ ID NO:229, SEQ ID NO:256, SEQ ID NO:259, SEQ ID NO:304, SEQ ID NO:310, SEQ ID NO:328 and SEQ ID NO:349.

2. The polypeptide of claim 1, wherein said PRR ligand modulates the signaling of PRRs selected from the group consisting of a Toll-like Receptor (TLR), Nucleotide-binding domain LRR-containing family (NLR), a RIG-I-like receptor (RLR), a DNA-dependent activator of IRF (DAI), a C-type Lectin receptor (CLR) or a member of the IFI20X/IFI16 family (e.g. 1fi16, Aim2, MNDA and IFIX).

3. The polypeptide of claim 1, wherein said TLR is selected from the group consisting of at least one of TLR3, TLR7, TLR8 or TLR9.

4. A method for treating a disease, disorder or condition in a subject in need of treatment thereof, the method comprising administering to the subject an effective amount of a polypeptide according to claim 1.

5. The method of claim 4, wherein said disease, disorder or condition is selected from: rheumatoid arthritis, GVHD, and psoriasis.

6. A pharmaceutical composition comprising a polypeptide according to claim 1.

7. A method for modulating PRR signaling in a subject in need thereof, or in at least one cell tissue or organ thereof, the method comprising administering a therapeutically effective amount of a polypeptide according to claim 1.

* * * * *

SEQUENCE LISTING

<160> NUMBER OF SEQ ID NOS: 384

<210> SEQ ID NO 1
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 produced in E. coli without
      N-terminal acetylation (X-Cpn10)

<400> SEQUENCE: 1

Ala Gly Gln Ala Phe Arg Lys Phe Leu Pro Leu Phe Asp Arg Val Leu
1               5                   10                  15

Val Glu Arg Ser Ala Ala Glu Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Ser Gly Ser Lys Gly Lys Gly Gly Glu Ile Gln Pro Val Ser Val
    50                  55                  60

Lys Val Gly Asp Lys Val Leu Leu Pro Glu Tyr Gly Gly Thr Lys Val

```
                65                  70                  75                  80
Val Leu Asp Asp Lys Asp Tyr Phe Leu Phe Arg Asp Gly Asp Ile Leu
                    85                  90                  95

Gly Lys Tyr Val Asp
            100

<210> SEQ ID NO 2
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA
<300> PUBLICATION INFORMATION:
<308> DATABASE ACCESSION NUMBER: GenBank X75821; GI:509780

<400> SEQUENCE: 2
atggcaggac aagcgtttag aaagtttctt ccactctttg accgagtatt ggttgaaagg    60
agtgctgctg aaactgtaac caaggaggc attatgcttc agaaaaatc tcaaggaaaa    120 gtattgcaag caacagtagt cgctgttgga tcgggttcta aaggaaaggg tggagagatt   180
caaccagtta gcgtgaaagt tggagataaa gttcttctcc agaatatgg aggcaccaaa   240 gtagttctag atgacaagga ttatttccta tttagagatg gtgacattct tggaaagtac   300
gtagactga                                                           309

<210> SEQ ID NO 3
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 produced in E.coli without the
      N-terminal acetylation. This protein contains an extra N-term
      Alanine (Ala-Cpn10)

<400> SEQUENCE: 3

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
                20                  25                  30

Leu Pro Glu Lys Ser Gln Gly Lys Val Leu Gln Ala Thr Val Val Ala
            35                  40                  45

Val Gly Ser Gly Ser Lys Gly Lys Gly Gly Glu Ile Gln Pro Val Ser
        50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 4
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: Native cDNA of Cpn10 variant Ala-Cpn10

<400> SEQUENCE: 4
atggcagcag acaagcgtt tagaaagttt cttccactct tgaccgagt attggttgaa        60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc cccagaata tggaggcacc      240 aaagtagttc tagatgacaa ggattatttc ctatttagag atggtgacat tcttggaaag    300
tacgtagact ga                                                         312

<210> SEQ ID NO 5
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10 (Gly,
      Arg and stop codons are optimized in the cDNA)

<400> SEQUENCE: 5
atggcagcag gccaagcgtt tcgcaagttt cttccactct tgaccgtgt attggttgaa       60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc cccagaata tggtggcacc     240 aaagtagttc tagatgacaa ggattatttc ctatttcgtg atggtgacat tcttggcaag    300
tacgtagact aa                                                         312

<210> SEQ ID NO 6
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant X-Cpn10-K53E with residue
      Lysine (K) 54 changed to Glutamic Acid (E) 54. This mutation
      changes a unique positive charge in the roof loops to a negative
      charge

<400> SEQUENCE: 6

Ala Gly Gln Ala Phe Arg Lys Phe Leu Pro Leu Phe Asp Arg Val Leu
1               5                   10                  15

Val Glu Arg Ser Ala Ala Glu Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Ser Gly Ser Glu Gly Lys Gly Gly Glu Ile Gln Pro Val Ser Val
    50                  55                  60

Lys Val Gly Asp Lys Val Leu Leu Pro Glu Tyr Gly Gly Thr Lys Val
65                  70                  75                  80

Val Leu Asp Asp Lys Asp Tyr Phe Leu Phe Arg Asp Gly Asp Ile Leu
                85                  90                  95

Gly Lys Tyr Val Asp
            100
```

<210> SEQ ID NO 7
<211> LENGTH: 309
<212> TYPE: DNA
<213> ORGANISM: Artificial Sequence
<220> FEATURE:
<223> OTHER INFORMATION: Description of Artificial Sequence: Synthetic
       polynucleotide
<220> FEATURE:
<223> OTHER INFORMATION: Native cDNA of Cpn10 variant X-Cpn10-K53E

<400> SEQUENCE: 7

```
atggcaggac aagcgtttag aaagtttctt ccactctttg accgagtatt ggttgaaagg      60
agtgctgctg aaactgtaac caaggaggc attatgcttc cagaaaaatc tcaaggaaaa     120
gtattgcaag caacagtagt cgctgttgga tcgggttctg aaggaaaggg tggagagatt     180
caaccagtta gcgtgaaagt tggagataaa gttcttctcc agaatatgg aggcaccaaa      240 gtagttctag atgacaagga ttatttccta tttagagatg gtgacattct tggaaagtac     300
gtagactga                                                             309
```

<210> SEQ ID NO 8
<211> LENGTH: 102
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<223> OTHER INFORMATION: Human Cpn10 mutant Ala-Cpn10-K53M,K55M with
       residue Lysine (K) 54 and Lysine (K) 56 changed to Methionine (M)
       54 and Methionine (M) 56 respectively. These mutations remove a
       unique cluster of positive charge at the top of the roof loops.
<220> FEATURE:
<223> OTHER INFORMATION: This construct contains an extra N-terminal
       Alanine residue

<400> SEQUENCE: 8

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Met Gly Met Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 9
<211> LENGTH: 312
<212> TYPE: DNA
<213> ORGANISM: Artificial Sequence
<220> FEATURE:
<223> OTHER INFORMATION: Description of Artificial Sequence: Synthetic
       polynucleotide
<220> FEATURE:
<223> OTHER INFORMATION: Native cDNA of Cpn10 variant Ala-Cpn10-K53M,
       K55M

<400> SEQUENCE: 9

```
atggcagcag gacaagcgtt tagaaagttt cttccactct ttgaccgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctatgggaat gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                      312
```

<210> SEQ ID NO 10
<211> LENGTH: 102
<212> TYPE: PRT
<213> ORGANISM: Homo sapiens
<220> FEATURE:
<223> OTHER INFORMATION: Human Cpn10 mutant Ala-Cpn10-K7R with residue
    Lysine (K) 8 changed to Arginine (R) 8

<400> SEQUENCE: 10

```
Ala Ala Gly Gln Ala Phe Arg Arg Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 11
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Native cDNA of Cpn10 variant Ala-Cpn10-K7R

<400> SEQUENCE: 11

```
atggcagcag gacaagcgtt tagacgcttt cttccactct ttgaccgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                      312
```

<210> SEQ ID NO 12
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:

<223> OTHER INFORMATION: Optimised cDNA of Cpn10 variant Ala-Cpn10-K7R
(Gly, Arg and stop codons are optimized in the cDNA)

<400> SEQUENCE: 12

```
atggcagcag gccaagcgtt tcgccgcttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc cccagaata tggtggcacc     240
aaagtagttc tagatgacaa ggattatttc ctatttcgtg atggtgacat tcttggcaag     300
tacgtagact aa                                                         312
```

<210> SEQ ID NO 13
<211> LENGTH: 102
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Human Cpn10 mutant Ala-Cpn10-R19K with residue
Arginine (R) 20 changed to Lysine (K) 20. This construct contains
an extra N-terminal Alanine residue.

<400> SEQUENCE: 13

```
Ala Ala Gly Gln Ala Phe Arg Lys Phe Leu Pro Leu Phe Asp Arg Val
 1               5                  10                  15
Leu Val Glu Lys Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Gly Glu Ile Gln Pro Val Ser
    50                  55                  60
Val Lys Val Gly Asp Lys Val Leu Leu Pro Glu Tyr Gly Gly Thr Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100
```

<210> SEQ ID NO 14
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Native cDNA of Cpn10 variant Ala-Cpn10-R19K

<400> SEQUENCE: 14

```
atggcagcag gacaagcgtt tagaaagttt cttccactct ttgaccgagt attggttgaa      60
aaagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc cccagaata tggaggcacc     240
aaagtagttc tagatgacaa ggattatttc ctatttagag atggtgacat tcttggaaag     300
tacgtagact ga                                                         312
```

<210> SEQ ID NO 15
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-R19K
      (Gly, Arg and stop codons are optimized in the cDNA)

<400> SEQUENCE: 15
atggcagcag gccaagcgtt tcgcaagttt cttccactct ttgaccgtgt attggttgaa    60
aaaagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc cccagaata tggtggcacc    240 aaagtagttc tagatgacaa ggattatttc ctatttcgtg atggtgacat tcttggcaag   300
tacgtagact aa                                                        312

<210> SEQ ID NO 16
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K27R with residue
      Lysine (K) 28 changed to Arginine (R) 28. This construct contains
      an extra N-terminal Alanine residue.

<400> SEQUENCE: 16

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Arg Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 17
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K27R

<400> SEQUENCE: 17
atggcagcag gacaagcgtt tagaaagttt cttccactct ttgaccgagt attggttgaa    60
aggagtgctg ctgaaactgt aacccgcgga ggcattatgc ttccagaaaa atctcaagga   120
aaagtattgc aagcaacagt agtcgctgtt ggatcgggtt ctaaaggaaa gggtggagag   180

-continued

```
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 18
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Optimised cDNA of Cpn10 variant Ala-Cpn10-K27R
    (Gly, Arg and stop codons are optimized in the cDNA)

<400> SEQUENCE: 18

```
atggcagcag gccaagcgtt tcgcaagttt cttccactct ttgaccgtgt attggttgaa     60
cgcagtgctg ctgaaactgt aacccgcggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

<210> SEQ ID NO 19
<211> LENGTH: 102
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Human Cpn10 mutant Ala-Cpn10-K39R with residue
    Lysine (K) 40 changed to Arginine (R) 40. This construct contains
    an extra N-terminal Alanine residue.

<400> SEQUENCE: 19

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Arg Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 20
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Native cDNA of Cpn10 variant Ala-Cpn10-K39R

<400> SEQUENCE: 20

```
atggcagcag gacaagcgtt tagaaagttt cttccactct tgaccgagt attggttgaa      60
aggagtgctg ctgaaactgt aaccaaagga ggcattatgc ttccagaaaa atctcaagga     120
cgtgtattgc aagcaacagt agtcgctgtt ggatcgggtt ctaaaggaaa gggtggagag     180
attcaaccag ttagcgtgaa agttggagat aaagttcttc tcccagaata tggaggcacc     240
aaagtagttc tagatgacaa ggattatttc ctatttagag atggtgacat tcttggaaag     300
tacgtagact ga                                                        312
```

<210> SEQ ID NO 21
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K39R
      (Gly, Arg and stop codons are optimized in the cDNA)

<400> SEQUENCE: 21

```
atggcagcag gccaagcgtt tcgcaagttt cttccactct tgaccgtgt attggttgaa      60
cgcagtgctg ctgaaactgt aaccaaaggt ggcattatgc ttccagaaaa atctcaaggc     120
cgtgtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggattatttc ctatttcgtg atggtgacat tcttggcaag     300
tacgtagact aa                                                        312
```

<210> SEQ ID NO 22
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K55R with residue
      Lysine (K) 56 changed to Arginine (R) 56. This construct contains
      an extra N-terminal Alanine residue.

<400> SEQUENCE: 22

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Arg Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 23

-continued

```
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K55R

<400> SEQUENCE: 23
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaggacg cggtggagag    180 attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 24
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K55R
      (Gly, Arg and stop codons are optimized in the cDNA)

<400> SEQUENCE: 24
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaggtcg cggtggcgag    180 attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 25
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K69R with residue
      Lysine (K) 70 changed to Arginine (R) 70. This construct contains
      an extra N-terminal Alanine residue.

<400> SEQUENCE: 25

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
                20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Arg Val Leu Leu Pro Glu Tyr Gly Gly Thr Lys
65                  70                  75                  80
```

Val Val Leu Asp Asp Lys Asp Tyr Phe Leu Phe Arg Asp Gly Asp Ile
            85                  90                  95

Leu Gly Lys Tyr Val Asp
            100

<210> SEQ ID NO 26
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K69R

<400> SEQUENCE: 26
atggcagcag acaagcgtt tagaaagttt cttccactct tgaccgagt attggttgaa        60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat cgcgttcttc tcccagaata tggaggcacc     240
aaagtagttc tagatgacaa ggattatttc ctatttagag atggtgacat tcttggaaag     300
tacgtagact ga                                                        312

<210> SEQ ID NO 27
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K69R
      (Gly, Arg and stop codons are optimized in the cDNA)

<400> SEQUENCE: 27
atggcagcag gccaagcgtt tcgcaagttt cttccactct tgaccgtgt attggttgaa        60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat cgcgttcttc tcccagaata tggtggcacc     240
aaagtagttc tagatgacaa ggattatttc ctatttcgtg atggtgacat tcttggcaag     300
tacgtagact aa                                                        312

<210> SEQ ID NO 28
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K85R with residue
      Lysine (K) 86 changed to Arginine (R) 86. This construct contains
      an extra N-terminal Alanine residue.

<400> SEQUENCE: 28

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala

```
                    35                  40                  45
Val Gly Ser Gly Ser Lys Gly Lys Gly Gly Glu Ile Gln Pro Val Ser
         50                  55                  60

Val Lys Val Gly Asp Lys Val Leu Leu Pro Glu Tyr Gly Gly Thr Lys
 65                  70                  75                  80

Val Val Leu Asp Asp Arg Asp Tyr Phe Leu Phe Arg Asp Gly Asp Ile
                 85                  90                  95

Leu Gly Lys Tyr Val Asp
            100

<210> SEQ ID NO 29
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K85R

<400> SEQUENCE: 29
atggcagcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgaccg cgattatttc ctatttagag atggtgacat tcttggaaag    300
tacgtagact ga                                                        312

<210> SEQ ID NO 30
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K85R
      (Gly, Arg and stop codons are optimized in the cDNA)

<400> SEQUENCE: 30
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgaccg cgattatttc ctatttcgtg atggtgacat tcttggcaag    300
tacgtagact aa                                                        312

<210> SEQ ID NO 31
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K98R with residue
      Lysine (K) 99 changed to Arginine (R) 99. This construct contains
      an extra N-terminal Alanine residue.

<400> SEQUENCE: 31
```

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Arg Tyr Val Asp
            100

<210> SEQ ID NO 32
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K98R

<400> SEQUENCE: 32
atggcagcag gacaagcgtt tagaaagttt cttccactct tgaccgagt attggttgaa       60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc     240
aaagtagttc tagatgacaa ggattatttc ctatttagag atggtgacat tcttggacgc     300
tacgtagact ga                                                         312

<210> SEQ ID NO 33
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K98R
      (Gly, Arg and stop codons are optimized in the cDNA)

<400> SEQUENCE: 33
atggcagcag gccaagcgtt tcgcaagttt cttccactct tgaccgtgt attggttgaa       60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggattatttc ctatttcgtg atggtgacat tcttggccgc     300
tacgtagact aa                                                         312

<210> SEQ ID NO 34
<211> LENGTH: 102
<212> TYPE: PRT
<213> ORGANISM: Homo sapiens
<220> FEATURE:

<223> OTHER INFORMATION: Human Cpn10 mutant Ala-Cpn10-A1K with residue
      Alanine (A) 2 changed to Lysine (K) 2. This construct contains an
      extra N-terminal Alanine residue.

<400> SEQUENCE: 34

Ala Lys Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 35
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-A1K

<400> SEQUENCE: 35
atggcaaaag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 36
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-A1K
      (Gly, Arg and stop codons are optimized in the cDNA)

<400> SEQUENCE: 36
atggcaaaag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 37
<211> LENGTH: 102
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Human Cpn10 mutant Ala-Cpn10-Q3K with residue
Glutamine (Q) 4 changed to Lysine (K) 4. This construct contains
an extra N-terminal Alanine residue.

<400> SEQUENCE: 37

Ala Ala Gly Lys Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
                20                  25                  30

Leu Pro Glu Lys Ser Gln Gly Lys Val Leu Gln Ala Thr Val Val Ala
            35                  40                  45

Val Gly Ser Gly Ser Lys Gly Lys Gly Gly Glu Ile Gln Pro Val Ser
        50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 38
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Native cDNA of Cpn10 variant Ala-Cpn10-Q3K

<400> SEQUENCE: 38
atggcagcag gaaaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 39
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Optimised cDNA of Cpn10 variant Ala-Cpn10-Q3K
(Gly, Arg and stop codons are optimized in the cDNA)

<400> SEQUENCE: 39
atggcagcag gcaaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180

```
attcaaccag ttagcgtgaa agttggcgat aaagttcttc tcccagaata tggtggcacc      240
aaagtagttc tagatgacaa ggattatttc ctatttcgtg atggtgacat tcttggcaag      300
tacgtagact aa                                                         312
```

```
<210> SEQ ID NO 40
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Q3R with residue
      Glutamine (Q) 4 changed to Arginine (R) 4. This construct contains
      an extra N-terminal Alanine residue.

<400> SEQUENCE: 40
```

```
Ala Ala Gly Arg Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

```
<210> SEQ ID NO 41
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Q3R

<400> SEQUENCE: 41
atggcagcag gacgcgcgtt tagaaagttt cttccactct tgaccgagt attggttgaa        60 aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagatgacaa ggattatttc ctatttagag atggtgacat tcttggaaag      300
tacgtagact ga                                                         312
```

```
<210> SEQ ID NO 42
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-Q3R
      (Gly, Arg and stop codons are optimized in the cDNA)
```

<400> SEQUENCE: 42

```
atggcagcag gccgcgcgtt tcgcaagttt cttccactct ttgaccgtgt attggttgaa    60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc cccagaata tggtggcacc    240
aaagtagttc tagatgacaa ggattatttc ctatttcgtg atggtgacat tcttggcaag   300
tacgtagact aa                                                       312
```

<210> SEQ ID NO 43
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-F5K with residue Phenylalanine (F) 6 changed to Lysine (K) 6. This construct contains an extra N-terminal Alanine residue.

<400> SEQUENCE: 43

```
Ala Ala Gly Gln Ala Lys Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Gly Glu Ile Gln Pro Val Ser
    50                  55                  60
Val Lys Val Gly Asp Lys Val Leu Leu Pro Glu Tyr Gly Gly Thr Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100
```

<210> SEQ ID NO 44
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-F5K

<400> SEQUENCE: 44

```
atggcagcag gacaagcgaa agaaagtttc cttccactct ttgaccgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc cccagaata tggaggcacc    240
aaagtagttc tagatgacaa ggattatttc ctatttgag atggtgacat tcttggaaag    300
tacgtagact ga                                                       312
```

<210> SEQ ID NO 45
<211> LENGTH: 312

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-F5K
      (Gly, Arg and stop codons are optimized in the cDNA)

<400> SEQUENCE: 45
atggcagcag gccaagcgaa acgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 46
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-L9K with residue
      Leucine (L) 10 changed to Lysine (K) 10. This construct contains
      an extra N-terminal Alanine residue.

<400> SEQUENCE: 46

Ala Ala Gly Gln Ala Phe Arg Lys Phe Lys Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 47
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-L9K

<400> SEQUENCE: 47
atggcagcag gacaagcgtt tagaaagttt aaaccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
```

```
aaagtagttc tagatgacaa ggattatttc ctatttagag atggtgacat tcttggaaag    300
tacgtagact ga                                                        312
```

<210> SEQ ID NO 48
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-L9K
      (Gly, Arg and stop codons are optimized in the cDNA)

<400> SEQUENCE: 48

```
atggcagcag gccaagcgtt tcgcaagttt aaaccactct tgaccgtgt  attggttgaa    60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                       312
```

<210> SEQ ID NO 49
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-F12K with residue
      Phenylalanine (F) 13 changed to Lysine (K) 13. This construct
      contains an extra N-terminal Alanine residue.

<400> SEQUENCE: 49

```
Ala Ala Gly Gln Ala Phe Arg Lys Phe Leu Pro Leu Lys Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 50
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-F12K

<400> SEQUENCE: 50

```
atggcagcag acaagcgtt tagaaagttt cttccactca aggaccgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                      312

<210> SEQ ID NO 51
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-F12K
      (Gly, Arg and stop codons are optimized in the cDNA)

<400> SEQUENCE: 51
atggcagcag ccaagcgtt tcgcaagttt cttccactca aggaccgtgt attggttgaa    60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                      312

<210> SEQ ID NO 52
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D13K with residue
      Aspartic Acid (D) 14 changed to Lysine (K) 14. This construct
      contains an extra N-terminal Alanine residue.

<400> SEQUENCE: 52

Ala Ala Gly Gln Ala Phe Arg Lys Phe Leu Pro Leu Phe Lys Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 53
<211> LENGTH: 312
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-D13K

<400> SEQUENCE: 53

```
atggcagcag acaagcgtt tagaaagttt cttccactct ttaaacgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc ccagaata tggaggcacc   240
aaagtagttc tagatgacaa ggattatttc ctatttagag atggtgacat tcttggaaag   300
tacgtagact ga                                                      312
```

<210> SEQ ID NO 54
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-D13K (Gly, Arg and stop codons are optimized in the cDNA)

<400> SEQUENCE: 54

```
atggcagcag gccaagcgtt tcgcaagttt cttccactct ttaaacgtgt attggttgaa    60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc ccagaata tggtggcacc   240
aaagtagttc tagatgacaa ggattatttc ctatttcgtg atggtgacat tcttggcaag   300
tacgtagact aa                                                      312
```

<210> SEQ ID NO 55
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-E18K with residue Glutamic Acid (E) 19 changed to Lysine (K) 19. This construct contains an extra N-terminal Alanine residue.

<400> SEQUENCE: 55

```
Ala Ala Gly Gln Ala Phe Arg Lys Phe Leu Pro Leu Phe Asp Arg Val
1               5                  10                  15

Leu Val Lys Arg Ser Ala Ala Glu Thr Val Thr Lys Gly Gly Ile Met
                20                  25                  30

Leu Pro Glu Lys Ser Gln Gly Lys Val Leu Gln Ala Thr Val Val Ala
            35                  40                  45

Val Gly Ser Gly Ser Lys Gly Lys Gly Gly Glu Ile Gln Pro Val Ser
        50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95
```

Leu Gly Lys Tyr Val Asp
            100

<210> SEQ ID NO 56
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E18K

<400> SEQUENCE: 56
atggcagcag gacaagcgtt tagaaagttt cttccactct tgaccgagt attggttaaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc ccagaata tggaggcacc    240 aaagtagttc tagatgacaa ggattatttc ctatttagag atggtgacat tcttggaaag   300
tacgtagact ga                                                        312

<210> SEQ ID NO 57
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E18K
      (Gly, Arg and stop codons are optimized in the cDNA)

<400> SEQUENCE: 57
atggcagcag gccaagcgtt tcgcaagttt cttccactct tgaccgtgt attggttaaa     60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc ccagaata tggtggcacc    240 aaagtagttc tagatgacaa ggattatttc ctatttcgtg atggtgacat tcttggcaag   300
tacgtagact aa                                                        312

<210> SEQ ID NO 58
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E18R with residue
      Glutamic Acid (E) 19 changed to Arginine (R) 19. This construct
      contains an extra N-terminal Alanine residue.

<400> SEQUENCE: 58

Ala Ala Gly Gln Ala Phe Arg Lys Phe Leu Pro Leu Phe Asp Arg Val
1               5                   10                  15

Leu Val Arg Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
        50                  55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                 85                  90                  95

Leu Gly Lys Tyr Val Asp
            100

<210> SEQ ID NO 59
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E18R

<400> SEQUENCE: 59
atggcagcag acaagcgtt tagaaagttt cttccactct ttgaccgagt attggttcgc      60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                      312

<210> SEQ ID NO 60
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E18R
      (Gly, Arg and stop codons are optimized in the cDNA)

<400> SEQUENCE: 60
atggcagcag gccaagcgtt tcgcaagttt cttccactct ttgaccgtgt attggttcgc      60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                      312

<210> SEQ ID NO 61
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-S20K with residue
      Serine (S) 21 changed to Lysine (K) 21. This construct contains an
      extra N-terminal Alanine residue.

<400> SEQUENCE: 61

Ala Ala Gly Gln Ala Phe Arg Lys Phe Leu Pro Leu Phe Asp Arg Val

```
                1               5                   10                  15
          Leu Val Glu Arg Lys Ala Ala Glu Thr Val Thr Lys Gly Gly Ile Met
                        20                  25                  30

Leu Pro Glu Lys Ser Gln Gly Lys Val Leu Gln Ala Thr Val Val Ala
                        35                  40                  45

Val Gly Ser Gly Ser Lys Lys Gly Gly Glu Ile Gln Pro Val Ser
                  50                  55                  60

Val Lys Val Gly Asp Lys Val Leu Leu Pro Glu Tyr Gly Gly Thr Lys
          65                  70                  75                  80

Val Val Leu Asp Asp Lys Asp Tyr Phe Leu Phe Arg Asp Gly Asp Ile
                              85                  90                  95

Leu Gly Lys Tyr Val Asp
                      100
```

<210> SEQ ID NO 62
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-S20K

<400> SEQUENCE: 62

```
atggcagcag gacaagcgtt tagaaagttt cttccactct tgaccgagt attggttgaa      60 aggaaagctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                          312
```

<210> SEQ ID NO 63
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-S20K
      (Gly, Arg and stop codons are optimized in the cDNA)

<400> SEQUENCE: 63

```
atggcagcag gccaagcgtt tcgcaagttt cttccactct tgaccgtgt attggttgaa      60 cgcaaagctg ctgaaactgt aaccaaaggt ggcattatgc ttccagaaaa atctcaaggc     120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                          312
```

<210> SEQ ID NO 64
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: Human Cpn10 mutant Ala-Cpn10-A22K with residue
      Alanine (A) 23 changed to Lysine (K) 23. This construct contains
      an extra N-terminal Alanine residue.

<400> SEQUENCE: 64

Ala Ala Gly Gln Ala Phe Arg Lys Phe Leu Pro Leu Phe Asp Arg Val
1               5                   10                  15

Leu Val Glu Arg Ser Ala Lys Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 65
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-A22K

<400> SEQUENCE: 65
atggcagcag gacaagcgtt tagaaagttt cttccactct tgaccgagt attggttgaa      60 aggagtgcta agaaactgt aaccaaagga ggcattatgc ttccagaaaa atctcaagga     120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 66
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-A22K
      (Gly, Arg and stop codons are optimized in the cDNA)

<400> SEQUENCE: 66
atggcagcag gccaagcgtt tcgcaagttt cttccactct tgaccgtgt attggttgaa      60 cgcagtgcta agaaactgt aaccaaaggt ggcattatgc ttccagaaaa atctcaaggc     120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 67
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-T24K with residue Threonine (T) 25 changed to Lysine (K) 25. This construct contains an extra N-terminal Alanine residue.

<400> SEQUENCE: 67

```
Ala Ala Gly Gln Ala Phe Arg Lys Phe Leu Pro Leu Phe Asp Arg Val
 1               5                  10                  15

Leu Val Glu Arg Ser Ala Ala Glu Lys Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 68
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-T24K

<400> SEQUENCE: 68

```
atggcagcag gacaagcgtt tagaaagttt cttccactct tgaccgagta attggttgaa      60
aggagtgctg ctgaaaaagt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc     240
aaagtagttc tagatgacaa ggattatttc ctatttagag atggtgacat tcttggaaag     300
tacgtagact ga                                                         312
```

<210> SEQ ID NO 69
<211> LENGTH: 311
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-T24K (Gly, Arg and stop codons are optimized in the cDNA)

<400> SEQUENCE: 69

```
atggcagcag gccaagcgtt tcgcaagttt cttccactct tgaccgtgt attggttgaa       60
cgcagtgctg ctgaaaaagt aaccaaaggt ggcattatgc ttccagaaaa atctcaaggc     120
```

```
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact a                                                         311
```

<210> SEQ ID NO 70
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-G29K with residue
      Glycine (G) 30 changed to Lysine (K) 30. This construct contains
      an extra N-terminal Alanine residue.

<400> SEQUENCE: 70

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Lys Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 71
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-G29K

<400> SEQUENCE: 71

```
atggcagcag gacaagcgtt tagaaagttt cttccactct tgaccgagt attggttgaa     60 aggagtgctg ctgaaactgt aaccaaagga aaaattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                        312
```

<210> SEQ ID NO 72
<211> LENGTH: 311
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-G29K (Gly, Arg and stop codons are optimized in the cDNA)

<400> SEQUENCE: 72

```
atggcagcag gccaagcgtt tcgcaagttt cttccactct ttgaccgtgt attggttgaa    60
cgcagtgctg ctgaaactgt aaccaaaggt aaaattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc cccagaata tggtggcacc    240 aaagtagttc tagatgacaa ggattatttc ctatttcgtg atggtgacat tcttggcaag   300
tacgtagact a                                                        311
```

<210> SEQ ID NO 73
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-M31K with residue
      Methionine (M) 32 changed to Lysine (K) 32. This construct
      contains an extra N-terminal Alanine residue.

<400> SEQUENCE: 73

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Lys
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 74
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-M31K

<400> SEQUENCE: 74

```
atggcagcag gacaagcgtt tagaaagttt cttccactct ttgaccgagt attggttgaa    60
aggagtgctg ctgaaactgt aaccaaagga ggcattaaac ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc cccagaata tggaggcacc    240 aaagtagttc tagatgacaa ggattatttc ctatttagag atggtgacat tcttggaaag   300
tacgtagact ga                                                       312
```

<210> SEQ ID NO 75

```
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-M31K
      (Gly, Arg and stop codons are optimized in the cDNA)

<400> SEQUENCE: 75
atggcagcag gccaagcgtt tcgcaagttt cttccactct ttgaccgtgt attggttgaa      60
cgcagtgctg ctgaaactgt aaccaaaggt ggcattaaac ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc cccagaata tggtggcacc      240 aaagtagttc tagatgacaa ggattatttc ctatttcgtg atggtgacat tcttggcaag     300
tacgtagact aa                                                        312

<210> SEQ ID NO 76
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E34K with residue
      Glutamic Acid (E) 35 changed to Lysine (K) 35. This construct
      contains an extra N-terminal Alanine residue.

<400> SEQUENCE: 76

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Lys Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 77
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E34K

<400> SEQUENCE: 77
atggcagcag gacaagcgtt tagaaagttt cttccactct ttgaccgagt attggttgaa      60
aggagtgctg ctgaaactgt aaccaaagga ggcattatgc ttccaaaaaa atctcaagga    120
aaagtattgc aagcaacagt agtcgctgtt ggatcgggtt ctaaaggaaa gggtggagag    180
```

```
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 78
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E34K
      (Gly, Arg and stop codons are optimized in the cDNA)

<400> SEQUENCE: 78

```
atggcagcag gccaagcgtt tcgcaagttt cttccactct ttgaccgtgt attggttgaa     60
cgcagtgctg ctgaaactgt aaccaaaggt ggcattatgc ttccaaaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

<210> SEQ ID NO 79
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Q37K with residue
      Glutamine (Q) 38 changed to Lysine (K) 38. This construct contains
      an extra N-terminal Alanine residue.

<400> SEQUENCE: 79

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Lys Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 80
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Q37K

<400> SEQUENCE: 80

```
atggcagcag acaagcgtt tagaaagttt cttccactct tgaccgagt attggttgaa      60
aggagtgctg ctgaaactgt aaccaaagga ggcattatgc ttccagaaaa atctaaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                        312
```

<210> SEQ ID NO 81
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-Q37K (Gly, Arg and stop codons are optimized in the cDNA)

<400> SEQUENCE: 81

```
atggcagcag gccaagcgtt tcgcaagttt cttccactct tgaccgtgt attggttgaa      60
cgcagtgctg ctgaaactgt aaccaaaggt ggcattatgc ttccagaaaa atctaaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                        312
```

<210> SEQ ID NO 82
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-V40K with residue Valine (V) 41 changed to Lysine (K) 41. This construct contains an extra N-terminal Alanine residue.

<400> SEQUENCE: 82

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Lys Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 83
<211> LENGTH: 312

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-V40K

<400> SEQUENCE: 83
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaaaaattgc aagcaacagt agtcgctgtt ggatcgggtt ctaaaggaaa gggtggagag    180
attcaaccag ttagcgtgaa agttggagat aaagttcttc ccagaata tggaggcacc     240 aaagtagttc tagatgacaa ggattatttc ctatttagag atggtgacat tcttggaaag    300
tacgtagact ga                                                         312

<210> SEQ ID NO 84
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-V40K
      (Gly, Arg and stop codons are optimized in the cDNA)

<400> SEQUENCE: 84
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaaaaattgc aagcaacagt agtcgctgtt ggctcgggtt ctaaaggtaa gggtggcgag    180
attcaaccag ttagcgtgaa agttggcgat aaagttcttc ccagaata tggtggcacc     240 aaagtagttc tagatgacaa ggattatttc ctatttcgtg atggtgacat tcttggcaag    300
tacgtagact aa                                                         312

<210> SEQ ID NO 85
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-L41K with residue
      Leucine (L) 42 changed to Lysine (K) 42. This construct contains
      an extra N-terminal Alanine residue.

<400> SEQUENCE: 85

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Lys Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
```

Leu Gly Lys Tyr Val Asp
            100

<210> SEQ ID NO 86
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-L41K

<400> SEQUENCE: 86
atggcagcag acaagcgtt tagaaagttt cttccactct tgaccgagt attggttgaa      60 aggagtgctg ctgaaactgt aaccaaagga ggcattatgc ttccagaaaa atctcaagga    120
aaagtaaaac aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 87
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-L41K
      (Gly, Arg and stop codons are optimized in the cDNA)

<400> SEQUENCE: 87
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtaaaac aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 88
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Q42K with residue
      Glutamine (Q) 43 changed to Lysine (K) 43. This construct contains
      an extra N-terminal Alanine residue.

<400> SEQUENCE: 88

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Lys Ala Thr Val Val Ala
        35                  40                  45

Val Gly Ser Gly Ser Lys Gly Lys Gly Gly Glu Ile Gln Pro Val Ser
            50                  55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 89
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Q42K

<400> SEQUENCE: 89
atggcagcag acaagcgtt tagaaagttt cttccactct ttgaccgagt attggttgaa      60
aggagtgctg ctgaaactgt aaccaaagga ggcattatgc ttccagaaaa atctcaagga    120
aaagtattga agcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                         312

<210> SEQ ID NO 90
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-Q42K
      (Gly, Arg and stop codons are optimized in the cDNA)

<400> SEQUENCE: 90
atggcagcag ccaagcgtt tcgcaagttt cttccactct ttgaccgtgt attggttgaa      60
cgcagtgctg ctgaaactgt aaccaaaggt ggcattatgc ttccagaaaa atctcaaggc    120
aaagtattga agcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                         312

<210> SEQ ID NO 91
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-T44K with residue
      Threonine (T) 45 changed to Lysine (K) 45. This construct contains
      an extra N-terminal Alanine residue.

<400> SEQUENCE: 91

```
Ala Ala Gly Gln Ala Phe Arg Lys Phe Leu Pro Leu Phe Asp Arg Val
1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Lys Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 92
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-T44K

<400> SEQUENCE: 92

```
atggcagcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaaaagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 93
<211> LENGTH: 311
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-T44K
      (Gly, Arg and stop codons are optimized in the cDNA)

<400> SEQUENCE: 93

```
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaaaagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact a                                                         311
```

<210> SEQ ID NO 94
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-S50K with residue
      Serine (S) 51 changed to Lysine (K) 51. This construct contains an
      extra N-terminal Alanine residue.

<400> SEQUENCE: 94

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Lys Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 95
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-S50K

<400> SEQUENCE: 95
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggaaaaggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 96
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-S50K
      (Gly, Arg and stop codons are optimized in the cDNA)

<400> SEQUENCE: 96
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggcaaaggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 97
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-S50R with residue
      Serine (S) 51 changed to Arginine (R) 51. This construct contains
      an extra N-terminal Alanine residue.

<400> SEQUENCE: 97

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Arg Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 98
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-S50R

<400> SEQUENCE: 98
atggcagcag gacaagcgtt tagaaagttt cttccactct tgaccgagt attggttgaa     60 aggagtgctg ctgaaactgt aaccaaagga ggcattatgc ttccagaaaa atctcaagga    120
aaagtattgc aagcaacagt agtcgctgtt ggacgcggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                       312

<210> SEQ ID NO 99
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-S50R
      (Gly, Arg and stop codons are optimized in the cDNA)

<400> SEQUENCE: 99
atggcagcag gccaagcgtt tcgcaagttt cttccactct tgaccgtgt attggttgaa     60 cgcagtgctg ctgaaactgt aaccaaaggt ggcattatgc ttccagaaaa atctcaaggc    120

```
aaagtattgc aagcaacagt agtcgctgtt ggccgcggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

<210> SEQ ID NO 100
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-S52K with residue
      Serine (S) 53 changed to Lysine (K) 53. This construct contains an
      extra N-terminal Alanine residue.

<400> SEQUENCE: 100

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Lys Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 101
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-S52K

<400> SEQUENCE: 101

```
atggcagcag gacaagcgtt tagaaagttt cttccactct tgaccgagt attggttgaa     60 aggagtgctg ctgaaactgt aaccaaagga ggcattatgc ttccagaaaa atctcaagga   120
aaagtattgc aagcaacagt agtcgctgtt ggatcgggta aaaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                        312
```

<210> SEQ ID NO 102
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: Optimised cDNA of Cpn10 variant Ala-Cpn10-S52K
(Gly, Arg and stop codons are optimized in the cDNA)

<400> SEQUENCE: 102

```
atggcagcag gccaagcgtt tcgcaagttt cttccactct tgaccgtgt attggttgaa      60
cgcagtgctg ctgaaactgt aaccaaaggt ggcattatgc ttccagaaaa atctcaaggc    120
aaagtattgc aagcaacagt agtcgctgtt ggctcgggta aaaaggtaa gggtggcgag     180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

<210> SEQ ID NO 103
<211> LENGTH: 102
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Human Cpn10 mutant Ala-Cpn10-G54K with residue
Glycine (G) 55 changed to Lysine (K) 55. This construct contains
an extra N-terminal Alanine residue.

<400> SEQUENCE: 103

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Lys Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 104
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Native cDNA of Cpn10 variant Ala-Cpn10-G54K

<400> SEQUENCE: 104

```
atggcagcag gacaagcgtt tagaaagttt cttccactct tgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaaagaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 105
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-G54K
      (Gly, Arg and stop codons are optimized in the cDNA)

<400> SEQUENCE: 105
atggcagcag gccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaaagaa gggtggcgag     180
attcaaccag ttagcgtgaa agttggcgat aaagttcttc tcccagaata tggtggcacc     240
aaagtagttc tagatgacaa ggattatttc ctatttcgtg atggtgacat tcttggcaag     300
tacgtagact aa                                                          312

<210> SEQ ID NO 106
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-G56K with residue
      Glycine (G) 57 changed to Lysine (K) 57. This construct contains
      an extra N-terminal Alanine residue.

<400> SEQUENCE: 106

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Lys Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 107
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-G56K

<400> SEQUENCE: 107
atggcagcag gacaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gaaaggagag     180

```
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 108
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-G56K
      (Gly, Arg and stop codons are optimized in the cDNA)

<400> SEQUENCE: 108

```
atggcagcag gccaagcgtt tcgcaagttt cttccactct ttgaccgtgt attggttgaa     60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gaaaggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

<210> SEQ ID NO 109
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E58K with residue
      Glutamic Acid (E) 59 changed to Lysine (K) 59. This construct
      contains an extra N-terminal Alanine residue.

<400> SEQUENCE: 109

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Lys Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 110
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E58K

<400> SEQUENCE: 110

```
atggcagcag gacaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggaaaa     180
attcaaccag ttagcgtgaa agttggagat aaagttcttc tcccagaata tggaggcacc     240
aaagtagttc tagatgacaa ggattatttc ctatttagag atggtgacat tcttggaaag     300
tacgtagact ga                                                         312
```

<210> SEQ ID NO 111
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-E58K (Gly, Arg and stop codons are optimized in the cDNA)

<400> SEQUENCE: 111

```
atggcagcag gccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcaaa     180
attcaaccag ttagcgtgaa agttggcgat aaagttcttc tcccagaata tggtggcacc     240
aaagtagttc tagatgacaa ggattatttc ctatttcgtg atggtgacat tcttggcaag     300
tacgtagact aa                                                         312
```

<210> SEQ ID NO 112
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-Q60K with residue Glutamine (Q) 61 changed to Lysine (K) 61. This construct contains an extra N-terminal Alanine residue.

<400> SEQUENCE: 112

```
Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Gly Glu Ile Lys Pro Val Ser
    50                  55                  60
Val Lys Val Gly Asp Lys Val Leu Leu Pro Glu Tyr Gly Gly Thr Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100
```

<210> SEQ ID NO 113

-continued

<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Q60K

<400> SEQUENCE: 113

```
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attaaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                       312
```

<210> SEQ ID NO 114
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-Q60K
      (Gly, Arg and stop codons are optimized in the cDNA)

<400> SEQUENCE: 114

```
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attaaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                       312
```

<210> SEQ ID NO 115
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-P61K with residue
      Proline (P) 62 changed to Lysine (K) 62. This construct contains
      an extra N-terminal Alanine residue.

<400> SEQUENCE: 115

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Lys Val Ser
    50                  55                  60

Val Lys Val Gly Asp Lys Val Leu Leu Pro Glu Tyr Gly Gly Thr Lys
65                  70                  75                  80
```

```
Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 116
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Q60K

<400> SEQUENCE: 116
atggcagcag acaagcgtt tagaaagttt cttccactct tgaccgagt attggttgaa        60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaaaag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 117
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-Q60K
      (Gly, Arg and stop codons are optimized in the cDNA)

<400> SEQUENCE: 117
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaaaag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 118
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-V66K with residue
      Valine (V) 67 changed to Lysine (K) 67. This construct contains an
      extra N-terminal Alanine residue.

<400> SEQUENCE: 118

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
```

Val Gly Ser Gly Ser Lys Gly Lys Gly Gly Glu Ile Gln Pro Val Ser
             35                  40                  45
         50                  55                  60

Val Lys Lys Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                 85                  90                  95

Leu Gly Lys Tyr Val Asp
            100

<210> SEQ ID NO 119
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-V66K

<400> SEQUENCE: 119
atggcagcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa aaaggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 120
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-V66K
      (Gly, Arg and stop codons are optimized in the cDNA)

<400> SEQUENCE: 120
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa aaaggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 121
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D68K with residue
      Aspartic Acid (D) 69 changed to Lysine (K) 69. This construct
      contains an extra N-terminal Alanine residue.

<400> SEQUENCE: 121

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60

Val Lys Val Gly Lys Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 122
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D68K

<400> SEQUENCE: 122
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggaaag aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 123
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D68K
      (Gly, Arg and stop codons are optimized in the cDNA)

<400> SEQUENCE: 123
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcaag aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 124
<211> LENGTH: 102
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Human Cpn10 mutant Ala-Cpn10-P73K with residue
Proline (P) 74 changed to Lysine (K) 74. This construct contains
an extra N-terminal Alanine residue.

<400> SEQUENCE: 124

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Lys Glu Tyr Gly Gly Thr Lys
65                  70                  75                  80

Val Val Leu Asp Asp Lys Asp Tyr Phe Leu Phe Arg Asp Gly Asp Ile
            85                  90                  95

Leu Gly Lys Tyr Val Asp
            100
```

<210> SEQ ID NO 125
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Native cDNA of Cpn10 variant Ala-Cpn10-P73K

<400> SEQUENCE: 125

```
atggcagcag gacaagcgtt tagaaagttt cttccactct tgaccgagt  attggttgaa      60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcaaagaata tggaggcacc     240
aaagtagttc tagatgacaa ggattatttc ctatttagag atggtgacat tcttggaaag     300
tacgtagact ga                                                          312
```

<210> SEQ ID NO 126
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Optimised cDNA of Cpn10 variant Ala-Cpn10-P73K
(Gly, Arg and stop codons are optimized in the cDNA)

<400> SEQUENCE: 126

```
atggcagcag gccaagcgtt tcgcaagttt cttccactct tgaccgtgt  attggttgaa      60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcaaagaata tggtggcacc     240
aaagtagttc tagatgacaa ggattatttc ctatttcgtg atggtgacat tcttggcaag     300
```
tacgtagact aa                                                          312

<210> SEQ ID NO 127
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E74K with residue
      Glutamic Acid (E) 75 changed to Lysine (K) 75. This construct
      contains an extra N-terminal Alanine residue.

<400> SEQUENCE: 127

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Lys Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 128
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E74K

<400> SEQUENCE: 128
atggcagcag gacaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccaaaata tggaggcacc     240
aaagtagttc tagatgacaa ggattatttc ctatttagag atggtgacat tcttggaaag     300
tacgtagact ga                                                         312

<210> SEQ ID NO 129
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E74K
      (Gly, Arg and stop codons are optimized in the cDNA)

<400> SEQUENCE: 129
atggcagcag gccaagcgtt tcgcaagttt cttccactct ttgaccgtgt attggttgaa      60

```
cgcagtgctg ctgaaactgt aaccaaaggt ggcattatgc ttccagaaaa atctcaaggc        120
aaagtattgc aagcaacagt agtcgctgtt ggctcgggtt ctaaaggtaa gggtggcgag        180
attcaaccag ttagcgtgaa agttggcgat aaagttcttc tcccaaaata tggtggcacc        240
aaagtagttc tagatgacaa ggattatttc ctatttcgtg atggtgacat tcttggcaag        300
tacgtagact aa                                                            312
```

<210> SEQ ID NO 130
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant X-Cpn10-Y75K with residue
      Tyrosine (Y) 75 changed to Lysine (K) 75

<400> SEQUENCE: 130

```
Ala Gly Gln Ala Phe Arg Lys Phe Leu Pro Leu Phe Asp Arg Val Leu
1               5                   10                  15

Val Glu Arg Ser Ala Ala Glu Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Ser Gly Ser Lys Gly Lys Gly Gly Glu Ile Gln Pro Val Ser Val
    50                  55                  60

Lys Val Gly Asp Lys Val Leu Leu Pro Glu Lys Gly Gly Thr Lys Val
65                  70                  75                  80

Val Leu Asp Asp Lys Asp Tyr Phe Leu Phe Arg Asp Gly Asp Ile Leu
                85                  90                  95

Gly Lys Tyr Val Asp
            100
```

<210> SEQ ID NO 131
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant X-Cpn10-Y75K

<400> SEQUENCE: 131

```
atggcaggac aagcgtttag aaagtttctt ccactctttg accgagtatt ggttgaaagg        60
agtgctgctg aaactgtaac caaaggaggc attatgcttc cagaaaaatc tcaaggaaaa        120
gtattgcaag caacagtagt cgctgttgga tcgggttcta aggaaagggt ggagagatt         180 caaccagtta gcgtgaaagt tggagataaa gttcttctcc cagaaaaagg aggcaccaaa        240
gtagttctag atgacaagga ttatttccta tttagagatg gtgacattct tggaaagtac        300
gtagactga                                                                309
```

<210> SEQ ID NO 132
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: Optimised cDNA of Cpn10 variant X-Cpn10-Y75K
      (Gly, Arg and stop codons are optimized in the cDNA)

<400> SEQUENCE: 132
atggcaggcc aagcgtttcg caagtttctt ccactctttg accgtgtatt ggttgaacgc    60
agtgctgctg aaactgtaac caaaggtggc attatgcttc cagaaaaatc tcaaggcaaa   120
gtattgcaag caacagtagt cgctgttggc tcgggttcta aaggtaaggg tggcgagatt   180
caaccagtta gcgtgaaagt tggcgataaa gttcttctcc agaaaaagg tggcaccaaa   240 gtagttctag atgacaagga ttatttccta tttcgtgatg gtgacattct tggcaagtac   300
gtagactaa                                                           309

<210> SEQ ID NO 133
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y75H with residue
      Tyrosine (Y) 76 changed to Histidine (H) 76. This construct
      contains an extra N-terminal Alanine residue.

<400> SEQUENCE: 133

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu His Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 134
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E74K

<400> SEQUENCE: 134
atggcagcag gacaagcgtt tagaaagttt cttccactct tgaccgagt attggttgaa    60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaaca cggaggcacc   240
aaagtagttc tagatgacaa ggattatttc ctatttagag atggtgacat tcttggaaag   300
tacgtagact ga                                                       312

<210> SEQ ID NO 135
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E74K
      (Gly, Arg and stop codons are optimized in the cDNA)

<400> SEQUENCE: 135

```
atggcagcag gccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc cccagaaaca cggtggcacc     240
aaagtagttc tagatgacaa ggattatttc ctatttcgtg atggtgacat tcttggcaag     300
tacgtagact aa                                                         312
```

<210> SEQ ID NO 136
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y75K with residue
      Tyrosine (Y) 76 changed to Lysine (K) 76. This construct contains
      an extra N-terminal Alanine residue.

<400> SEQUENCE: 136

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Lys Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 137
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Y75K

<400> SEQUENCE: 137

```
atggcagcag gacaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
```

```
attcaaccag ttagcgtgaa agttggagat aaagttcttc tcccagaaaa aggaggcacc    240
aaagtagttc tagatgacaa ggattatttc ctatttagag atggtgacat tcttggaaag    300
tacgtagact ga                                                        312
```

<210> SEQ ID NO 138
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-Y75K
      (Gly, Arg and stop codons are optimized in the cDNA)

<400> SEQUENCE: 138

```
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaaaa aggtggcacc    240
aaagtagttc tagatgacaa ggattatttc ctatttcgtg atggtgacat tcttggcaag    300
tacgtagact aa                                                        312
```

<210> SEQ ID NO 139
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y75R with residue
      Tyrosine (Y) 76 changed to Arginine (R) 76. This construct
      contains an extra N-terminal Alanine residue.

<400> SEQUENCE: 139

```
Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
             20                  25                  30

Leu Pro Glu Lys Ser Gln Gly Lys Val Leu Gln Ala Thr Val Val Ala
         35                  40                  45

Val Gly Ser Gly Ser Lys Gly Lys Gly Gly Glu Ile Gln Pro Val Ser
     50                  55                  60

Val Lys Val Gly Asp Lys Val Leu Leu Pro Glu Arg Gly Gly Thr Lys
 65                  70                  75                  80

Val Val Leu Asp Asp Lys Asp Tyr Phe Leu Phe Arg Asp Gly Asp Ile
                 85                  90                  95

Leu Gly Lys Tyr Val Asp
            100
```

<210> SEQ ID NO 140
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Y75R

<400> SEQUENCE: 140

```
atggcagcag gacaagcgtt tagaaagttt cttccactct tgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc ccagaacg cggaggcacc     240
aaagtagttc tagatgacaa ggattatttc ctatttagag atggtgacat tcttggaaag    300
tacgtagact ga                                                        312
```

<210> SEQ ID NO 141
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-Y75R (Gly, Arg and stop codons are optimized in the cDNA)

<400> SEQUENCE: 141

```
atggcagcag gccaagcgtt tcgcaagttt cttccactct tgaccgtgt attggttgaa      60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc ccagaacg cggtggcacc     240
aaagtagttc tagatgacaa ggattatttc ctatttcgtg atggtgacat tcttggcaag    300
tacgtagact aa                                                        312
```

<210> SEQ ID NO 142
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-G76K with residue Glycine (G) 77 changed to Lysine (K) 77. This construct contains an extra N-terminal Alanine residue.

<400> SEQUENCE: 142

```
Ala Ala Gly Gln Ala Phe Arg Lys Phe Leu Pro Leu Phe Asp Arg Val
1               5                  10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Gly Glu Ile Gln Pro Val Ser
    50                  55                  60
Val Lys Val Gly Asp Lys Val Leu Leu Pro Glu Tyr Lys Gly Thr Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100
```

<210> SEQ ID NO 143

-continued

```
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-G76K

<400> SEQUENCE: 143
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata taaaggcacc    240
aaagtagttc tagatgacaa ggattatttc ctatttagag atggtgacat tcttggaaag    300
tacgtagact ga                                                        312

<210> SEQ ID NO 144
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-G76K
      (Gly, Arg and stop codons are optimized in the cDNA)

<400> SEQUENCE: 144
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata taaaggcacc    240
aaagtagttc tagatgacaa ggattatttc ctatttcgtg atggtgacat tcttggcaag    300
tacgtagact aa                                                        312

<210> SEQ ID NO 145
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-G77K with residue
      Glycine (G) 78 changed to Lysine (K) 78. This construct contains
      an extra N-terminal Alanine residue.

<400> SEQUENCE: 145

Ala Ala Gly Gln Ala Phe Arg Lys Phe Leu Pro Leu Phe Asp Arg Val
1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Lys Thr Lys
65                  70                  75                  80
```

```
Val Val Leu Asp Asp Lys Asp Tyr Phe Leu Phe Arg Asp Gly Asp Ile
            85                  90                  95

Leu Gly Lys Tyr Val Asp
            100

<210> SEQ ID NO 146
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-G77K

<400> SEQUENCE: 146
atggcagcag acaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaaaaacc   240
aaagtagttc tagatgacaa ggattatttc ctatttagag atggtgacat tcttggaaag   300
tacgtagact ga                                                        312

<210> SEQ ID NO 147
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-G77K
      (Gly, Arg and stop codons are optimized in the cDNA)

<400> SEQUENCE: 147
atggcagcag gccaagcgtt tcgcaagttt cttccactct tgaccgtgt attggttgaa     60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtaaaacc   240
aaagtagttc tagatgacaa ggattatttc ctatttcgtg atggtgacat tcttggcaag   300
tacgtagact aa                                                        312

<210> SEQ ID NO 148
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-T78K with residue
      Glycine (G) 79 changed to Lysine (K) 79. This construct contains
      an extra N-terminal Alanine residue.

<400> SEQUENCE: 148

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
```

```
                   35                  40                  45
Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Lys Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 149
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-T78K

<400> SEQUENCE: 149

```
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcaaa    240
aaagtagttc tagatgacaa ggattatttc ctatttagag atggtgacat tcttggaaag    300
tacgtagact ga                                                        312
```

<210> SEQ ID NO 150
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-T78K
      (Gly, Arg and stop codons are optimized in the cDNA)

<400> SEQUENCE: 150

```
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcaaa    240
aaagtagttc tagatgacaa ggattatttc ctatttcgtg atggtgacat tcttggcaag    300
tacgtagact aa                                                        312
```

<210> SEQ ID NO 151
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-V81K with residue
      Valine (V) 82 changed to Lysine (K) 82. This construct contains an
      extra N-terminal Alanine residue.

<400> SEQUENCE: 151

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Glu Tyr Gly Gly Thr Lys
65                  70                  75                  80

Val Lys Leu Asp Asp Lys Asp Tyr Phe Leu Phe Arg Asp Gly Asp Ile
                85                  90                  95

Leu Gly Lys Tyr Val Asp
            100

<210> SEQ ID NO 152
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-V81K

<400> SEQUENCE: 152
atggcagcag gacaagcgtt tagaaagttt cttccactct tgaccgagt attggttgaa    60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtaaaac tagatgacaa ggattatttc ctatttagag atggtgacat tcttggaaag   300
tacgtagact ga                                                      312

<210> SEQ ID NO 153
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-V81K
      (Gly, Arg and stop codons are optimized in the cDNA)

<400> SEQUENCE: 153
atggcagcag gccaagcgtt tcgcaagttt cttccactct tgaccgtgt attggttgaa    60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtaaaac tagatgacaa ggattatttc ctatttcgtg atggtgacat tcttggcaag   300
tacgtagact aa                                                      312

<210> SEQ ID NO 154
<211> LENGTH: 102
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Human Cpn10 mutant Ala-Cpn10-D83K with residue
Aspartate (D) 84 changed to Lysine (K) 84. This construct contains
an extra N-terminal Alanine residue.

<400> SEQUENCE: 154

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Lys Asp Lys Asp Tyr Phe Leu Phe Arg Asp Gly Asp Ile
                85                  90                  95

Leu Gly Lys Tyr Val Asp
                100
```

<210> SEQ ID NO 155
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Native cDNA of Cpn10 variant Ala-Cpn10-D83K

<400> SEQUENCE: 155

```
atggcagcag gacaagcgtt tagaaagttt cttccactct tgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc taaaagacaa ggattatttc ctatttagag atggtgacat tcttggaaag    300
tacgtagact ga                                                        312
```

<210> SEQ ID NO 156
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Optimised cDNA of Cpn10 variant Ala-Cpn10-D83K
(Gly, Arg and stop codons are optimized in the cDNA)

<400> SEQUENCE: 156

```
atggcagcag gccaagcgtt tcgcaagttt cttccactct tgaccgtgt attggttgaa      60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc taaaagacaa ggattatttc ctatttcgtg atggtgacat tcttggcaag    300
```
tacgtagact aa                                                                    312

<210> SEQ ID NO 157
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D84K with residue
      Aspartate (D) 85 changed to Lysine (K) 85. This construct contains
      an extra N-terminal Alanine residue.

<400> SEQUENCE: 157

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Lys Lys Asp Tyr Phe Leu Phe Arg Asp Gly Asp Ile
                85                  90                  95

Leu Gly Lys Tyr Val Asp
            100

<210> SEQ ID NO 158
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D84K

<400> SEQUENCE: 158
atggcagcag gacaagcgtt tagaaagttt cttccactct tgaccgagt attggttgaa        60 aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagataaaaa ggattatttc ctatttagag atggtgacat tcttggaaag      300
tacgtagact ga                                                          312

<210> SEQ ID NO 159
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D84K
      (Gly, Arg and stop codons are optimized in the cDNA)

<400> SEQUENCE: 159
atggcagcag gccaagcgtt tcgcaagttt cttccactct tgaccgtgt attggttgaa        60

```
cgcagtgctg ctgaaactgt aaccaaaggt ggcattatgc ttccagaaaa atctcaaggc      120
aaagtattgc aagcaacagt agtcgctgtt ggctcgggtt ctaaaggtaa gggtggcgag      180
attcaaccag ttagcgtgaa agttggcgat aaagttcttc tcccagaata tggtggcacc      240
aaagtagttc tagataaaaa ggattatttc ctatttcgtg atggtgacat tcttggcaag      300
tacgtagact aa                                                          312
```

<210> SEQ ID NO 160
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D86K with residue
      Aspartate (D) 87 changed to Lysine (K) 87. This construct contains
      an extra N-terminal Alanine residue.

<400> SEQUENCE: 160

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Lys Tyr Phe Leu Phe Arg Asp Gly Asp Ile
                85                  90                  95

Leu Gly Lys Tyr Val Asp
            100
```

<210> SEQ ID NO 161
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D86K

<400> SEQUENCE: 161

```
atggcagcag gacaagcgtt tagaaagttt cttccactct ttgaccgagt attggttgaa       60
aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagatgacaa gaaatatttc ctatttagag atggtgacat tcttggaaag      300
tacgtagact ga                                                          312
```

<210> SEQ ID NO 162
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<223> OTHER INFORMATION: Optimised cDNA of Cpn10 variant Ala-Cpn10-D86K
      (Gly, Arg and stop codons are optimized in the cDNA)

<400> SEQUENCE: 162
atggcagcag gccaagcgtt tcgcaagttt cttccactct tgaccgtgt attggttgaa        60 cgcagtgctg ctgaaactgt aaccaaaggt ggcattatgc ttccagaaaa atctcaaggc      120
aaagtattgc aagcaacagt agtcgctgtt ggctcgggtt ctaaaggtaa gggtggcgag      180
attcaaccag ttagcgtgaa agttggcgat aaagttcttc tcccagaata tggtggcacc      240
aaagtagttc tagatgacaa gaaatatttc ctatttcgtg atggtgacat tcttggcaag      300
tacgtagact aa                                                          312

<210> SEQ ID NO 163
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D86R with residue
      Aspartate (D) 87 changed to Arginine (R) 87. This construct
      contains an extra N-terminal Alanine residue.

<400> SEQUENCE: 163

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Arg Tyr Phe Leu Phe Arg Asp Gly Asp Ile
                85                  90                  95

Leu Gly Lys Tyr Val Asp
            100

<210> SEQ ID NO 164
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D86R

<400> SEQUENCE: 164
atggcagcag gacaagcgtt tagaaagttt cttccactct tgaccgagt attggttgaa         60 aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagatgacaa gcgctatttc ctatttagag atggtgacat tcttggaaag      300
tacgtagact ga                                                          312
```

<210> SEQ ID NO 165
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D86R
      (Gly, Arg and stop codons are optimized in the cDNA)

<400> SEQUENCE: 165
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa gcgctatttc ctatttcgtg atggtgacat tcttggcaag     300
tacgtagact aa                                                        312

<210> SEQ ID NO 166
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y87K with residue
      Tyrosine (Y) 88 changed to Lysine (K) 88. This construct contains
      an extra N-terminal Alanine residue.

<400> SEQUENCE: 166

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Lys Phe Leu Phe Arg Asp Gly Asp Ile
                85                  90                  95

Leu Gly Lys Tyr Val Asp
            100

<210> SEQ ID NO 167
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Y87K

<400> SEQUENCE: 167
atggcagcag gacaagcgtt tagaaagttt cttccactct tgaccgagt attggttgaa       60 aggagtgctg ctgaaactgt aaccaaagga ggcattatgc ttccagaaaa atctcaagga     120

```
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagatgacaa ggataaattc ctatttagag atggtgacat tcttggaaag      300
tacgtagact ga                                                          312
```

<210> SEQ ID NO 168
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-Y87K
      (Gly, Arg and stop codons are optimized in the cDNA)

<400> SEQUENCE: 168

```
atggcagcag gccaagcgtt tcgcaagttt cttccactct tgaccgtgt attggttgaa       60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggataaattc ctatttcgtg atggtgacat tcttggcaag     300
tacgtagact aa                                                          312
```

<210> SEQ ID NO 169
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-F88K with residue
      Phenylalanine (F) 89 changed to Lysine (K) 89. This construct
      contains an extra N-terminal Alanine residue.

<400> SEQUENCE: 169

```
Ala Ala Gly Gln Ala Phe Arg Lys Phe Leu Pro Leu Phe Asp Arg Val
1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Lys Leu Phe Arg Asp Gly Asp Ile
                85                  90                  95

Leu Gly Lys Tyr Val Asp
            100
```

<210> SEQ ID NO 170
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

-continued

<223> OTHER INFORMATION: Native cDNA of Cpn10 variant Ala-Cpn10-F88K

<400> SEQUENCE: 170

```
atggcag

<210> SEQ ID NO 173
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-L89K

<400> SEQUENCE: 173

```
atggcagcag gacaagcgtt tagaaagttt cttccactct tgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc aaatttagag atggtgacat tcttggaaag    300
tacgtagact ga                                                       312
```

<210> SEQ ID NO 174
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-L89K (Gly, Arg and stop codons are optimized in the cDNA)

<400> SEQUENCE: 174

```
atggcagcag gccaagcgtt tcgcaagttt cttccactct tgaccgtgt attggttgaa      60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc aaatttcgtg atggtgacat tcttggcaag    300
tacgtagact aa                                                       312
```

<210> SEQ ID NO 175
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-D92K with residue Aspartic Acid (D) 93 changed to Lysine (K) 93. This construct contains an extra N-terminal Alanine residue.

<400> SEQUENCE: 175

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80
```

```
Val Val Leu Asp Asp Lys Asp Tyr Phe Leu Phe Arg Lys Gly Asp Ile
            85                  90                  95

Leu Gly Lys Tyr Val Asp
            100
```

<210> SEQ ID NO 176
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D92K

<400> SEQUENCE: 176

```
atggcagcag gacaagcgtt tagaaagttt cttccactct tgaccgagt  attggttgaa    60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagaa aggtgacat  tcttggaaag   300 tacgtagact ga                                                       312
```

<210> SEQ ID NO 177
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D92K
      (Gly, Arg and stop codons are optimized in the cDNA)

<400> SEQUENCE: 177

```
atggcagcag gccaagcgtt tcgcaagttt cttccactct tgaccgtgt  attggttgaa    60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgta aggtgacat  tcttggcaag   300 tacgtagact aa                                                       312
```

<210> SEQ ID NO 178
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-G93K with residue
      Glycine (G) 94 changed to Lysine (K) 94. This construct contains
      an extra N-terminal Alanine residue.

<400> SEQUENCE: 178

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30
```

```
Leu Pro Glu Lys Ser Gln Gly Lys Val Leu Gln Ala Thr Val Val Ala
         35                  40                  45

Val Gly Ser Gly Ser Lys Gly Lys Gly Gly Glu Ile Gln Pro Val Ser
 50                  55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Lys Asp Ile
                 85                  90                  95

Leu Gly Lys Tyr Val Asp
            100

<210> SEQ ID NO 179
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-G93K

<400> SEQUENCE: 179
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag ataaagacat tcttggaaag    300
tacgtagact ga                                                         312

<210> SEQ ID NO 180
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-G93K
      (Gly, Arg and stop codons are optimized in the cDNA)

<400> SEQUENCE: 180
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg ataaagacat tcttggcaag    300
tacgtagact aa                                                         312

<210> SEQ ID NO 181
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D94K with residue
      Aspartic Acid (D) 95 changed to Lysine (K) 95. This construct
      contains an extra N-terminal Alanine residue.
```

<400> SEQUENCE: 181

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Lys Leu
                85                  90                  95

Gly Lys Tyr Val Asp
            100

<210> SEQ ID NO 182
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Native cDNA of Cpn10 variant Ala-Cpn10-D94K

<400> SEQUENCE: 182
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtaaaat tcttggaaag    300
tacgtagact ga                                                       312

<210> SEQ ID NO 183
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Optimised cDNA of Cpn10 variant Ala-Cpn10-D94K
    (Gly, Arg and stop codons are optimized in the cDNA)

<400> SEQUENCE: 183
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtaaaat tcttggcaag    300
tacgtagact aa                                                       312

<210> SEQ ID NO 184
<211> LENGTH: 102
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D94R with residue
      Aspartic Acid (D) 95 changed to Arginine (R) 95. This construct
      contains an extra N-terminal Alanine residue.

<400> SEQUENCE: 184

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65              70                  75                  80

Val Val Leu Asp Asp Lys Asp Tyr Phe Leu Phe Arg Asp Gly Arg Ile
                85                  90                  95

Leu Gly Lys Tyr Val Asp
            100

<210> SEQ ID NO 185
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D94R

<400> SEQUENCE: 185
atggcagcag gacaagcgtt tagaaagttt cttccactct tgaccgagt attggttgaa        60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc     240
aaagtagttc tagatgacaa ggattatttc ctatttagag atggtcgcat tcttggaaag     300
tacgtagact ga                                                          312

<210> SEQ ID NO 186
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D94R
      (Gly, Arg and stop codons are optimized in the cDNA)

<400> SEQUENCE: 186
atggcagcag gccaagcgtt tcgcaagttt cttccactct tgaccgtgt attggttgaa         60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggattatttc ctatttcgtg atggtcgcat tcttggcaag     300
```
tacgtagact aa        312

<210> SEQ ID NO 187
<211> LENGTH: 102
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Human Cpn10 mutant Ala-Cpn10-L96K with residue
    Leucine (L) 97 changed to Lysine (K) 97. This construct contains
    an extra N-terminal Alanine residue.

<400> SEQUENCE: 187

Ala Ala Gly Gln Ala Phe Arg Lys Phe Leu Pro Leu Phe Asp Arg Val
1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Lys Gly Lys Tyr Val Asp
            100

<210> SEQ ID NO 188
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Native cDNA of Cpn10 variant Ala-Cpn10-L96K

<400> SEQUENCE: 188
atggcagcag gacaagcgtt tagaaagttt cttccactct tgaccgagt attggttgaa        60 aggagtgctg ctgaaactgt aaccaaagga ggcattatgc ttccagaaaa atctcaagga       120
aaagtattgc aagcaacagt agtcgctgtt ggatcgggtt ctaaaggaaa gggtggagag       180
attcaaccag ttagcgtgaa agttggagat aaagttcttc tcccagaata tggaggcacc       240
aaagtagttc tagatgacaa ggattatttc ctatttagag atggtgacat taaaggaaag       300
tacgtagact ga        312

<210> SEQ ID NO 189
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Optimised cDNA of Cpn10 variant Ala-Cpn10-L96K
    (Gly, Arg and stop codons are optimized in the cDNA)

<400> SEQUENCE: 189
atggcagcag gccaagcgtt tcgcaagttt cttccactct tgaccgtgt attggttgaa        60

```
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat taaaggcaag    300
tacgtagact aa                                                        312
```

<210> SEQ ID NO 190
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-V100K with residue
      Valine (V) 101 changed to Lysine (K) 101. This construct contains
      an extra N-terminal Alanine residue.

<400> SEQUENCE: 190

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Lys Asp
            100
```

<210> SEQ ID NO 191
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-V100K

<400> SEQUENCE: 191

```
atggcagcag gacaagcgtt tagaaagttt cttccactct tgaccgagt attggttgaa     60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacaaagact ga                                                        312
```

<210> SEQ ID NO 192
<211> LENGTH: 312
<212> TYPE: DNA
<213> ORGANISM: Artificial Sequence
<220> FEATURE:
<223> OTHER INFORMATION: Description of Artificial Sequence: Synthetic

```
                polynucleotide
<220> FEATURE:
<223> OTHER INFORMATION: Optimised cDNA of Cpn10 variant Ala-Cpn10-V100K
      (Gly, Arg and stop codons are optimized in the cDNA)

<400> SEQUENCE: 192
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc ccagaata tggtggcacc     240 aaagtagttc tagatgacaa ggattatttc ctatttcgtg atggtgacat tcttggcaag    300
tacaaagact aa                                                        312

<210> SEQ ID NO 193
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D101K with residue
      Aspartate (D) 102 changed to Lysine (K) 102. This construct
      contains an extra N-terminal Alanine residue.

<400> SEQUENCE: 193

Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Lys
            100

<210> SEQ ID NO 194
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D101K

<400> SEQUENCE: 194
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc ccagaata tggaggcacc     240 aaagtagttc tagatgacaa ggattatttc ctatttagag atggtgacat tcttggaaag    300
tacgtaaaat ga                                                        312
```

<210> SEQ ID NO 195
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-D101K (Gly, Arg and stop codons are optimized in the cDNA)

<400> SEQUENCE: 195

```
atggcagcag gccaagcgtt tcgcaagttt cttccactct tgaccgtgt attggttgaa        60 cgcagtgctg ctgaaactgt aaccaaaggt ggcattatgc ttccagaaaa atctcaaggc       120
aaagtattgc aagcaacagt agtcgctgtt ggctcgggtt ctaaaggtaa gggtggcgag       180
attcaaccag ttagcgtgaa agttggcgat aaagttcttc tcccagaata tggtggcacc       240
aaagtagttc tagatgacaa ggattatttc ctatttcgtg atggtgacat tcttggcaag       300
tacgtaaaat aa                                                          312
```

<210> SEQ ID NO 196
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-D101R with residue Aspartate (D) 102 changed to Arginine (R) 102. This construct contains an extra N-terminal Alanine residue.

<400> SEQUENCE: 196

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Arg
            100
```

<210> SEQ ID NO 197
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-D101R

<400> SEQUENCE: 197

```
atggcagcag gacaagcgtt tagaaagttt cttccactct tgaccgagt attggttgaa         60 aggagtgctg ctgaaactgt aaccaaagga ggcattatgc ttccagaaaa atctcaagga       120
```

-continued

```
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagatgacaa ggattatttc ctatttagag atggtgacat tcttggaaag      300
tacgtacgct ga                                                          312
```

<210> SEQ ID NO 198
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-D101R (Gly, Arg and stop codons are optimized in the cDNA)

<400> SEQUENCE: 198

```
atggcagcag gccaagcgtt tcgcaagttt cttccactct tgaccgtgt attggttgaa       60 cgcagtgctg ctgaaactgt aaccaaaggt ggcattatgc ttccagaaaa atctcaaggc      120
aaagtattgc aagcaacagt agtcgctgtt ggctcgggtt ctaaaggtaa gggtggcgag      180
attcaaccag ttagcgtgaa agttggcgat aaagttcttc tcccagaata tggtggcacc      240
aaagtagttc tagatgacaa ggattatttc ctatttcgtg atggtgacat tcttggcaag      300
tacgtacgct aa                                                          312
```

<210> SEQ ID NO 199
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-deltaE23 with residue Glutamic Acid (E) 24 removed. This construct contains an extra N-terminal Alanine residue.

<400> SEQUENCE: 199

```
Ala Ala Gly Gln Ala Phe Arg Lys Phe Leu Pro Leu Phe Asp Arg Val
1               5                   10                  15

Leu Val Glu Arg Ser Ala Ala Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Ser Gly Ser Lys Gly Lys Gly Gly Glu Ile Gln Pro Val Ser Val
    50                  55                  60

Lys Val Gly Asp Lys Val Leu Leu Pro Glu Tyr Gly Gly Thr Lys Val
65                  70                  75                  80

Val Leu Asp Asp Lys Asp Tyr Phe Leu Phe Arg Asp Gly Asp Ile Leu
                85                  90                  95

Gly Lys Tyr Val Asp
            100
```

<210> SEQ ID NO 200
<211> LENGTH: 309
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-deltaE23

<400> SEQUENCE: 200

```
atggcagcag acaagcgtt tagaaagttt cttccactct ttgaccgagt attggttgaa      60
aggagtgctg ctactgtaac caaaggaggc attatgcttc cagaaaaatc tcaaggaaaa    120
gtattgcaag caacagtagt cgctgttgga tcgggttcta aaggaaaggg tggagagatt    180
caaccagtta gcgtgaaagt tggagataaa gttcttctcc cagaatatgg aggcaccaaa    240
gtagttctag atgacaagga ttatttccta tttagagatg gtgacattct tggaaagtac    300
gtagactga                                                             309
```

<210> SEQ ID NO 201
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-deltaE23 (Gly, Arg and stop codons are optimized in the
      cDNA)

<400> SEQUENCE: 201

```
atggcagcag ccaagcgtt tcgcaagttt cttccactct ttgaccgtgt attggttgaa      60
cgcagtgctg ctactgtaac caaaggtggc attatgcttc cagaaaaatc tcaaggcaaa    120
gtattgcaag caacagtagt cgctgttggc tcgggttcta aaggtaaggg tggcgagatt    180
caaccagtta gcgtgaaagt tggcgataaa gttcttctcc cagaatatgg tggcaccaaa    240
gtagttctag atgacaagga ttatttccta tttcgtgatg gtgacattct tggcaagtac    300
gtagactaa                                                             309
```

<210> SEQ ID NO 202
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-deltaE34 with
      residue Glutamic Acid (E) 35 removed. This construct contains an
      extra N-terminal Alanine residue.

<400> SEQUENCE: 202

```
Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
                20                  25                  30
Leu Pro Lys Ser Gln Gly Lys Val Leu Gln Ala Thr Val Val Ala Val
            35                  40                  45
Gly Ser Gly Ser Lys Gly Lys Gly Gly Glu Ile Gln Pro Val Ser Val
        50                  55                  60
Lys Val Gly Asp Lys Val Leu Leu Pro Glu Tyr Gly Gly Thr Lys Val
65                  70                  75                  80
Val Leu Asp Asp Lys Asp Tyr Phe Leu Phe Arg Asp Gly Asp Ile Leu
                85                  90                  95
Gly Lys Tyr Val Asp
            100
```

<210> SEQ ID NO 203
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-deltaE34

<400> SEQUENCE: 203

```
atggcagcag acaagcgtt tagaaagttt cttccactct tgaccgagt attggttgaa      60
aggagtgctg ctgaaactgt aaccaaagga ggcattatgc ttccaaaatc tcaaggaaaa   120
gtattgcaag caacagtagt cgctgttgga tcgggttcta aaggaaaggg tggagagatt   180
caaccagtta gcgtgaaagt tggagataaa gttcttctcc cagaatatgg aggcaccaaa   240
gtagttctag atgacaagga ttatttccta tttagagatg gtgacattct tggaaagtac   300
gtagactga                                                           309
```

<210> SEQ ID NO 204
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-deltaE34 (Gly, Arg and stop codons are optimized in the
      cDNA)

<400> SEQUENCE: 204

```
atggcagcag gccaagcgtt tcgcaagttt cttccactct tgaccgtgt attggttgaa      60
cgcagtgctg ctgaaactgt aaccaaaggt ggcattatgc ttccaaaatc tcaaggcaaa   120
gtattgcaag caacagtagt cgctgttggc tcgggttcta aagtaagggg tggcgagatt   180
caaccagtta gcgtgaaagt tggcgataaa gttcttctcc cagaatatgg tggcaccaaa   240
gtagttctag atgacaagga ttatttccta tttcgtgatg gtgacattct tggcaagtac   300
gtagactaa                                                           309
```

<210> SEQ ID NO 205
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-deltaE58 with
      residue Glutamic Acid (E) 59 removed. This construct contains an
      extra N-terminal Alanine residue.

<400> SEQUENCE: 205

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Ile Gln Pro Val Ser Val
    50                  55                  60
```

Lys Val Gly Asp Lys Val Leu Leu Pro Glu Tyr Gly Thr Lys Val
65                  70                  75                  80

Val Leu Asp Asp Lys Asp Tyr Phe Leu Phe Arg Asp Gly Asp Ile Leu
                85                  90                  95

Gly Lys Tyr Val Asp
            100

<210> SEQ ID NO 206
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-deltaE58

<400> SEQUENCE: 206
atggcagcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggaatt    180
caaccagtta gcgtgaaagt tggagataaa gttcttctcc cagaatatgg aggcaccaaa   240
gtagttctag atgacaagga ttatttccta tttagagatg gtgacattct tggaaagtac    300
gtagactga                                                            309

<210> SEQ ID NO 207
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-deltaE58 (Gly, Arg and stop codons are optimized in the
      cDNA)

<400> SEQUENCE: 207
atggcagcag gccaagcgtt tcgcaagttt cttccactct tgaccgtgt attggttgaa     60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcatt   180
caaccagtta gcgtgaaagt tggcgataaa gttcttctcc cagaatatgg tggcaccaaa   240
gtagttctag atgacaagga ttatttccta tttcgtgatg gtgacattct tggcaagtac   300
gtagactaa                                                            309

<210> SEQ ID NO 208
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-deltaE74 with
      residue Glutamic Acid (E) 75 removed. This construct contains an
      extra N-terminal Alanine residue.

<400> SEQUENCE: 208

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Tyr Gly Gly Thr Lys Val
65                  70                  75                  80

Val Leu Asp Asp Lys Asp Tyr Phe Leu Phe Arg Asp Gly Asp Ile Leu
                85                  90                  95

Gly Lys Tyr Val Asp
            100

```
<210> SEQ ID NO 209
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-deltaE74

<400> SEQUENCE: 209
atggcagcag acaagcgtt tagaaagttt cttccactct tgaccgagt attggttgaa       60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag    180
attcaaccag ttagcgtgaa agttggagat aaagttcttc tcccatatgg aggcaccaaa    240
gtagttctag atgacaagga ttatttccta tttagagatg gtgacattct tggaaagtac    300
gtagactga                                                            309

<210> SEQ ID NO 210
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-deltaE74 (Gly, Arg and stop codons are optimized in the
      cDNA)

<400> SEQUENCE: 210
atggcagcag ccaagcgtt tcgcaagttt cttccactct tgaccgtgt attggttgaa       60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccatatgg tggcaccaaa    240
gtagttctag atgacaagga ttatttccta tttcgtgatg gtgacattct tggcaagtac    300
gtagactaa                                                            309

<210> SEQ ID NO 211
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: Human Cpn10 mutant Ala-Cpn10-deltaD84 with residue Aspartic Acid (D) 85 removed. This construct contains an extra N-terminal Alanine residue.

<400> SEQUENCE: 211

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Glu Tyr Gly Gly Thr Lys
65                  70                  75                  80

Val Val Leu Asp Lys Asp Tyr Phe Leu Phe Arg Asp Gly Asp Ile Leu
                85                  90                  95

Gly Lys Tyr Val Asp
            100

<210> SEQ ID NO 212
<211> LENGTH: 309
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-deltaD84

<400> SEQUENCE: 212
atggcagcag gacaagcgtt tagaaagttt cttccactct tgaccgagt attggttgaa        60 aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagataagga ttatttccta tttagagatg gtgacattct tggaaagtac      300
gtagactga                                                              309

<210> SEQ ID NO 213
<211> LENGTH: 309
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-deltaD84 (Gly, Arg and stop codons are optimized in the cDNA)

<400> SEQUENCE: 213
atggcagcag gccaagcgtt tcgcaagttt cttccactct tgaccgtgt attggttgaa        60 cgcagtgctg ctgaaactgt aaccaaaggt ggcattatgc ttccagaaaa atctcaaggc      120
aaagtattgc aagcaacagt agtcgctgtt ggctcgggtt ctaaaggtaa gggtggcgag      180
attcaaccag ttagcgtgaa agttggcgat aaagttcttc tcccagaata tggtggcacc      240
aaagtagttc tagataagga ttatttccta tttcgtgatg gtgacattct tggcaagtac      300
gtagactaa                                                              309

<210> SEQ ID NO 214
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-F12K,D92K with
      residue Phenylalanine (F) 13 changed to Lysine (K) 13 and residue
      Aspartate (D) 93 changed to Lysine (K) 93. This construct
      contains an extra N-terminal Alanine residue.

<400> SEQUENCE: 214

Ala Ala Gly Gln Ala Phe Arg Lys Phe Leu Pro Leu Lys Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Lys Gly Asp Ile
                85                  90                  95

Leu Gly Lys Tyr Val Asp
            100

<210> SEQ ID NO 215
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-F12K,D92K

<400> SEQUENCE: 215
atggcagcag gacaagcgtt tagaaagttt cttccactca agaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagaa aggtgacat tcttggaaag    300 tacgtagact ga                                                        312

<210> SEQ ID NO 216
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-F12K,D92K (Gly, Arg and stop codons are optimized in the
      cDNA)

<400> SEQUENCE: 216

```
atggcagcag gccaagcgtt tcgcaagttt cttccactca agaccgtgt attggttgaa    60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgta aaggtgacat tcttggcaag   300
tacgtagact aa                                                      312
```

```
<210> SEQ ID NO 217
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E18K,D101K with
      residue Glutamate (E) 19 changed to Lysine (K) 19 and residue
      Aspartate (D) 102 changed to Lysine (K) 102. This construct
      contains an extra N-terminal Alanine residue.

<400> SEQUENCE: 217
```

```
Ala Ala Gly Gln Ala Phe Arg Lys Phe Leu Pro Leu Phe Asp Arg Val
1               5                   10                  15

Leu Val Lys Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Lys
            100
```

```
<210> SEQ ID NO 218
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-E18K,D101K

<400> SEQUENCE: 218
```

```
atggcagcag gacaagcgtt tagaaagttt cttccactct tgaccgagt attggttaaa    60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtaaaat ga                                                      312
```

```
<210> SEQ ID NO 219
<211> LENGTH: 312
<212> TYPE: DNA
```

<210> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Optimised cDNA of Cpn10 variant
    Ala-Cpn10-E18K,D101K (Gly, Arg and stop codons are optimized in
    the cDNA)

<400> SEQUENCE: 219

```
atggcagcag gccaagcgtt tcgcaagttt cttccactct ttgaccgtgt attggttaaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggattatttc ctatttcgtg atggtgacat tcttggcaag     300
tacgtaaaat aa                                                         312
```

<210> SEQ ID NO 220
<211> LENGTH: 102
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Human Cpn10 mutant Ala-Cpn10-E34Q,Y75K with
    residue Glutamate (E) 35 changed to Glutamine (Q) 35 and residue
    Tyrosine (Y) 76 changed to Lysine (K) 76. This construct contains
    an extra N-terminal Alanine residue.

<400> SEQUENCE: 220

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Gln Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Lys Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 221
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Native cDNA of Cpn10 variant
    Ala-Cpn10-E34Q,Y75K

<400> SEQUENCE: 221

```
atggcagcag gacaagcgtt tagaaagttt cttccactct ttgaccgagt attggttgaa      60
aggagtgctg ctgaaactgt aaccaaagga ggcattatgc ttccacaaaa atctcaagga     120
aaagtattgc aagcaacagt agtcgctgtt ggatcgggtt ctaaaggaaa gggtggagag     180
```

```
attcaaccag ttagcgtgaa agttggagat aaagttcttc tcccagaaaa aggaggcacc    240
aaagtagttc tagatgacaa ggattatttc ctatttagag atggtgacat tcttggaaag    300
tacgtagact ga                                                         312

<210> SEQ ID NO 222
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-E34Q,Y75K (Gly, Arg and stop codons are optimized in the
      cDNA)

<400> SEQUENCE: 222
atggcagcag gccaagcgtt tcgcaagttt cttccactct tgaccgtgt attggttgaa      60 cgcagtgctg ctgaaactgt aaccaaaggt ggcattatgc ttccacaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaaaa aggtggcacc    240
aaagtagttc tagatgacaa ggattatttc ctatttcgtg atggtgacat tcttggcaag    300
tacgtagact aa                                                         312

<210> SEQ ID NO 223
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Q42K,D101K with
      residue Glutamine (Q) 43 changed to Lysine (K) 43 and residue
      Aspartate (D) 102 changed to Lysine (K) 102. This construct
      contains an extra N-terminal Alanine residue.

<400> SEQUENCE: 223

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Lys Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Lys
            100

<210> SEQ ID NO 224
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: Native cDNA of Cpn10 variant
      Ala-Cpn10-Q42K,D101K

<400> SEQUENCE: 224
atggcagcag gacaagcgtt tagaaagttt cttccactct tgaccgagt attggttgaa     60 aggagtgctg ctgaaactgt aaccaaagga ggcattatgc ttccagaaaa atctcaagga   120
aaagtattga agcaacagt agtcgctgtt ggatcgggtt ctaaaggaaa gggtggagag    180
attcaaccag ttagcgtgaa agttggagat aaagttcttc cccagaata tggaggcacc   240 aaagtagttc tagatgacaa ggattatttc ctatttagag atggtgacat tcttggaaag   300
tacgtaaaat ga                                                       312

<210> SEQ ID NO 225
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-Q42K,D101K (Gly, Arg and stop codons are optimized in
      the cDNA)

<400> SEQUENCE: 225
atggcagcag gccaagcgtt tcgcaagttt cttccactct tgaccgtgt attggttgaa     60 cgcagtgctg ctgaaactgt aaccaaaggt ggcattatgc ttccagaaaa atctcaaggc   120
aaagtattga agcaacagt agtcgctgtt ggctcgggtt ctaaaggtaa gggtggcgag    180
attcaaccag ttagcgtgaa agttggcgat aaagttcttc cccagaata tggtggcacc   240 aaagtagttc tagatgacaa ggattatttc ctatttcgtg atggtgacat tcttggcaag   300
tacgtaaaat aa                                                       312

<210> SEQ ID NO 226
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-T44K,D101K with
      residue Threonine (T) 45 changed to Lysine (K) 45 and residue
      Aspartate (D) 102 changed to Lysine (K) 102. This construct
      contains an extra N-terminal Alanine residue.

<400> SEQUENCE: 226

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Lys Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95
```

Leu Gly Lys Tyr Val Lys
            100

<210> SEQ ID NO 227
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-T44K,D101K

<400> SEQUENCE: 227
atggcagcag gacaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaaaagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtaaaat ga                                                        312

<210> SEQ ID NO 228
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-T44K,D101K (Gly, Arg and stop codons are optimized in
      the cDNA)

<400> SEQUENCE: 228
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc   120
aaagtattgc aagcaaaagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtaaaat aa                                                        312

<210> SEQ ID NO 229
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-S50K,D101K with
      residue Serine (S) 51 changed to Lysine (K) 51 and residue
      Aspartate (D) 102 changed to Lysine (K) 102. This construct
      contains an extra N-terminal Alanine residue.

<400> SEQUENCE: 229

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala

Val Gly Lys Gly Ser Lys Gly Lys Gly Gly Glu Ile Gln Pro Val Ser
            35                  40                  45
 50                  55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                    85                  90                  95

Leu Gly Lys Tyr Val Lys
            100

<210> SEQ ID NO 230
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-S50K,D101K

<400> SEQUENCE: 230
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggaaaaggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtaaaat ga                                                        312

<210> SEQ ID NO 231
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-S50K,D101K (Gly, Arg and stop codons are optimized in
      the cDNA)

<400> SEQUENCE: 231
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggcaaaggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtaaaat aa                                                        312

<210> SEQ ID NO 232
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Q60K,T78K with
      residue Glutamine (Q) 61 changed to Lysine (K) 61 and residue
      Threonine (T) 79 changed to Lysine (K) 79. This construct contains an extra N-terminal Alanine residue.

<400> SEQUENCE: 232

```
Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Gly Glu Ile Lys Pro Val Ser
50                  55                  60
Val Lys Val Gly Asp Lys Val Leu Leu Pro Glu Tyr Gly Gly Lys Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100
```

<210> SEQ ID NO 233
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-Q60K,T78K

<400> SEQUENCE: 233

```
atggcagcag gacaagcgtt tagaaagttt cttccactct tgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attaaaccag ttagcgtgaa agttggagat aaagttcttc tcccagaata tggaggcaag    240
aaagtagttc tagatgacaa ggattatttc ctatttagag atggtgacat tcttggaaag    300
tacgtagact ga                                                         312
```

<210> SEQ ID NO 234
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-Q60K,T78K (Gly, Arg and stop codons are optimized in the cDNA)

<400> SEQUENCE: 234

```
atggcagcag gccaagcgtt tcgcaagttt cttccactct tgaccgtgt attggttgaa      60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attaaaccag ttagcgtgaa agttggcgat aaagttcttc tcccagaata tggtggcaag    240
aaagtagttc tagatgacaa ggattatttc ctatttcgtg atggtgacat tcttggcaag    300
tacgtagact aa                                                         312
```

-continued

```
<210> SEQ ID NO 235
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E74K,Y75E with
      residue Glutamic Acid (E) 75 changed to Lysine (K) 75 and residue
      Tyrosine (Y) 76 changed to Glutamic Acid (E) 76. This construct
      contains an extra N-terminal Alanine residue.

<400> SEQUENCE: 235

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Lys Glu Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 236
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-E74K,Y75E

<400> SEQUENCE: 236
atggcagcag gacaagcgtt tagaaagttt cttccactct tgaccgagt attggttgaa        60 aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccaaaaga aggaggcacc      240
aaagtagttc tagatgacaa ggattatttc ctatttagag atggtgacat tcttggaaag      300
tacgtagact ga                                                           312

<210> SEQ ID NO 237
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-E74K,Y75E (Gly, Arg and stop codons are optimized in the
      cDNA)

<400> SEQUENCE: 237
atggcagcag gccaagcgtt tcgcaagttt cttccactct tgaccgtgt attggttgaa        60
```

```
cgcagtgctg ctgaaactgt aaccaaaggt ggcattatgc ttccagaaaa atctcaaggc      120
aaagtattgc aagcaacagt agtcgctgtt ggctcgggtt ctaaaggtaa gggtggcgag      180
attcaaccag ttagcgtgaa agttggcgat aaagttcttc tcccaaaaga aggtggcacc      240
aaagtagttc tagatgacaa ggattatttc ctatttcgtg atggtgacat tcttggcaag      300
tacgtagact aa                                                         312
```

<210> SEQ ID NO 238
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y75GK with residue
      Tyrosine (Y) 76 changed to Glycine_Lysine (GK) 76-77. This
      construct contains an extra N-terminal Alanine residue.

<400> SEQUENCE: 238

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Gly Lys Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 239
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-Y75GK

<400> SEQUENCE: 239

```
atggcagcag acaagcgtt tagaaagttt cttccactct ttgaccgagt attggttgaa      60
aggagtgctg ctgaaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaagg caaggaggc     240 accaaagtag ttctagatga caaggattat ttcctatttta gagatggtga cattcttgga   300
aagtacgtag actga                                                     315
```

<210> SEQ ID NO 240
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide -continued

```
<220> FEATURE:
<223> OTHER INFORMATION: Optimised cDNA of Cpn10 variant Ala-Cpn10-Y75GK
      (Gly, Arg and stop codons are optimized in the cDNA)

<400> SEQUENCE: 240
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaagg caaaggtggc    240
accaaagtag ttctagatga caaggattat ttcctatttc gtgatggtga cattcttggc    300
aagtacgtag actaa                                                      315

<210> SEQ ID NO 241
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y75G,G76K with
      residue Tyrosine (Y) 76 changed to Glycine (G) 76 and residue
      Glycine (G) 77 changed to Lysine (K) 77. This construct contains
      an extra N-terminal Alanine residue.

<400> SEQUENCE: 241

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Gly Lys Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 242
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-Y75G,G76K

<400> SEQUENCE: 242
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaagg taaaggcacc    240
aaagtagttc tagatgacaa ggattatttc ctatttagag atggtgacat tcttggaaag    300
```

```
tacgtagact ga                                                  312

<210> SEQ ID NO 243
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-Y75G,G76K (Gly, Arg and stop codons are optimized in the
      cDNA)

<400> SEQUENCE: 243
atggcagcag gccaagcgtt tcgcaagttt cttccactct ttgaccgtgt attggttgaa    60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc cccagaagg taaaggcacc    240 aaagtagttc tagatgacaa ggattatttc ctatttcgtg atggtgacat tcttggcaag   300
tacgtagact aa                                                      312

<210> SEQ ID NO 244
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y75K,D94K with
      residue Tyrosine (Y) 76 changed to Lysine (K) 76 and residue
      Aspartic Acid (D) 95 changed to Lysine (K) 95. This construct
      contains an extra N-terminal Alanine residue.

<400> SEQUENCE: 244

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Lys Gly Gly Thr Lys
65                  70                  75                  80

Val Val Leu Asp Asp Lys Asp Tyr Phe Leu Phe Arg Asp Gly Lys Ile
                85                  90                  95

Leu Gly Lys Tyr Val Asp
            100

<210> SEQ ID NO 245
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-Y75K,D94K

<400> SEQUENCE: 245
```

```
atggcagcag acaagcgtt tagaaagttt cttccactct tgaccgagt attggttgaa    60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc ccagaaaaa aggaggcacc   240 aaagtagttc tagatgacaa ggattatttc ctatttagag atggtaaaat tcttggaaag   300
tacgtagact ga                                                      312

<210> SEQ ID NO 246
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-Y75K,D94K (Gly, Arg and stop codons are optimized in the
      cDNA)

<400> SEQUENCE: 246
atggcagcag gccaagcgtt tcgcaagttt cttccactct tgaccgtgt attggttgaa    60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc cccagaaaaa aggtggcacc   240
aaagtagttc tagatgacaa ggattatttc ctatttcgtg atggtaaaat tcttggcaag   300
tacgtagact aa                                                      312

<210> SEQ ID NO 247
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-Y75K,D94N with
      residue Tyrosine (Y) 76 changed to Lysine (K) 76 and residue
      Aspartic Acid (D) 95 changed to Asparagine (N) 95. This construct
      contains an extra N-terminal Alanine residue.

<400> SEQUENCE: 247

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Lys Gly Gly Thr Lys
65                  70                  75                  80

Val Val Leu Asp Asp Lys Asp Tyr Phe Leu Phe Arg Asp Gly Asn Ile
                85                  90                  95

Leu Gly Lys Tyr Val Asp
            100

<210> SEQ ID NO 248
```

```
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant
      Ala-Cpn10-Y75K,D94N

<400> SEQUENCE: 248
atggcagcag gacaagcgtt tagaaagttt cttccactct tgaccgagt attggttgaa     60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaaaa aggaggcacc    240
aaagtagttc tagatgacaa ggattatttc ctatttagag atggtaacat tcttggaaag    300
tacgtagact ga                                                       312

<210> SEQ ID NO 249
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant
      Ala-Cpn10-Y75K,D94N (Gly, Arg and stop codons are optimized in the
      cDNA)

<400> SEQUENCE: 249
atggcagcag gccaagcgtt tcgcaagttt cttccactct tgaccgtgt attggttgaa     60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaaaa aggtggcacc    240
aaagtagttc tagatgacaa ggattatttc ctatttcgtg atggtaacat tcttggcaag    300
tacgtagact aa                                                       312

<210> SEQ ID NO 250
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D13N with residue
      Aspartic Acid (D) 14 changed to Asparagine (N) 14. This construct
      contains an extra N-terminal Alanine residue.

<400> SEQUENCE: 250

Ala Ala Gly Gln Ala Phe Arg Lys Phe Leu Pro Leu Phe Asn Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
```

```
                65                  70                  75                  80
Val Val Leu Asp Asp Lys Asp Tyr Phe Leu Phe Arg Asp Gly Asp Ile
                        85                  90                  95
Leu Gly Lys Tyr Val Asp
                100
```

<210> SEQ ID NO 251
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D13N

<400> SEQUENCE: 251

```
atggcagcag gacaagcgtt tagaaagttt cttccactct ttaaccgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc cccagaata tggaggcacc    240
aaagtagttc tagatgacaa ggattatttc ctatttagag atggtgacat tcttggaaag   300
tacgtagact ga                                                       312
```

<210> SEQ ID NO 252
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D13N
      (Gly, Arg and stop codons are optimized in the cDNA)

<400> SEQUENCE: 252

```
atggcagcag gccaagcgtt tcgcaagttt cttccactct ttaaccgtgt attggttgaa    60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc cccagaata tggtggcacc    240
aaagtagttc tagatgacaa ggattatttc ctatttcgtg atggtgacat tcttggcaag   300
tacgtagact aa                                                       312
```

<210> SEQ ID NO 253
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E18A with residue
      Glutamate (E) 19 changed to Alanine (A) 19. This construct
      contains an extra N-terminal Alanine residue.

<400> SEQUENCE: 253

```
Ala Ala Gly Gln Ala Phe Arg Lys Phe Leu Pro Leu Phe Asp Arg Val
1               5                   10                  15
Leu Val Ala Arg Ser Ala Ala Glu Thr Val Thr Lys Gly Gly Ile Met
            20                  25                  30
```

Leu Pro Glu Lys Ser Gln Gly Lys Val Leu Gln Ala Thr Val Val Ala
            35                  40                  45

Val Gly Ser Gly Ser Lys Gly Lys Gly Gly Glu Ile Gln Pro Val Ser
        50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 254
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E18A

<400> SEQUENCE: 254
atggcagcag gacaagcgtt tagaaagttt cttccactct tgaccgagt attggttgcg    60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                       312

<210> SEQ ID NO 255
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E18A
      (Gly, Arg and stop codons are optimized in the cDNA)

<400> SEQUENCE: 255
atggcagcag gccaagcgtt tcgcaagttt cttccactct tgaccgtgt attggttgcg    60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                       312

<210> SEQ ID NO 256
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E18M with residue
      Glutamate (E) 19 changed to Methionine (M) 19. This construct
      contains an extra N-terminal Alanine residue.

<400> SEQUENCE: 256

Ala Ala Gly Gln Ala Phe Arg Lys Phe Leu Pro Leu Phe Asp Arg Val
1               5                   10                  15

Leu Val Met Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 257
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E18M

<400> SEQUENCE: 257
atggcagcag gacaagcgtt tagaaagttt cttccactct tgaccgagt attggttatg    60 aggagtgctg ctgaaactgt aaccaaagga ggcattatgc ttccagaaaa atctcaagga  120
aaagtattgc aagcaacagt agtcgctgtt ggatcgggtt ctaaaggaaa gggtggagag  180
attcaaccag ttagcgtgaa agttggagat aaagttcttc tcccagaata tggaggcacc  240
aaagtagttc tagatgacaa ggattatttc ctatttagag atggtgacat tcttggaaag  300
tacgtagact ga                                                      312

<210> SEQ ID NO 258
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E18M
      (Gly, Arg and stop codons are optimized in the cDNA)

<400> SEQUENCE: 258
atggcagcag gccaagcgtt tcgcaagttt cttccactct tgaccgtgt attggttatg    60 cgcagtgctg ctgaaactgt aaccaaaggt ggcattatgc ttccagaaaa atctcaaggc  120
aaagtattgc aagcaacagt agtcgctgtt ggctcgggtt ctaaaggtaa gggtggcgag  180
attcaaccag ttagcgtgaa agttggcgat aaagttcttc tcccagaata tggtggcacc  240
aaagtagttc tagatgacaa ggattatttc ctatttcgtg atggtgacat tcttggcaag  300
tacgtagact aa                                                      312

<210> SEQ ID NO 259
<211> LENGTH: 102
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Human Cpn10 mutant Ala-Cpn10-E18Q with residue
Glutamate (E) 19 changed to Glutamine (Q) 19. This construct
contains an extra N-terminal Alanine residue.

<400> SEQUENCE: 259

Ala Ala Gly Gln Ala Phe Arg Lys Phe Leu Pro Leu Phe Asp Arg Val
1               5                   10                  15

Leu Val Gln Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 260
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Native cDNA of Cpn10 variant Ala-Cpn10-E18Q

<400> SEQUENCE: 260
atggcagcag gacaagcgtt tagaaagttt cttccactct tgaccgagt attggttcag      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                       312

<210> SEQ ID NO 261
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Optimised cDNA of Cpn10 variant Ala-Cpn10-E18Q
(Gly, Arg and stop codons are optimized in the cDNA)

<400> SEQUENCE: 261
atggcagcag gccaagcgtt tcgcaagttt cttccactct tgaccgtgt attggttcag      60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240

```
aaagtagttc tagatgacaa ggattatttc ctatttcgtg atggtgacat tcttggcaag    300
tacgtagact aa                                                        312
```

<210> SEQ ID NO 262
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E18S with residue
      Glutamate (E) 19 changed to Serine (S) 19. This construct contains
      an extra N-terminal Alanine residue.

<400> SEQUENCE: 262

```
Ala Ala Gly Gln Ala Phe Arg Lys Phe Leu Pro Leu Phe Asp Arg Val
1               5                   10                  15

Leu Val Ser Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 263
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E18S

<400> SEQUENCE: 263

```
atggcagcag gacaagcgtt tagaaagttt cttccactct tgaccgagt attggttagc     60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                        312
```

<210> SEQ ID NO 264
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E18S
      (Gly, Arg and stop codons are optimized in the cDNA)

<400> SEQUENCE: 264

```
atggcagcag gccaagcgtt tcgcaagttt cttccactct tgaccgtgt attggttagc      60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc ccagaata tggtggcacc      240 aaagtagttc tagatgacaa ggattatttc ctatttcgtg atggtgacat tcttggcaag     300
tacgtagact aa                                                         312
```

<210> SEQ ID NO 265
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-E23Q with residue Glutamate (E) 24 changed to Glutamine (Q) 24. This construct contains an extra N-terminal Alanine residue.

<400> SEQUENCE: 265

```
Ala Ala Gly Gln Ala Phe Arg Lys Phe Leu Pro Leu Phe Asp Arg Val
1               5                   10                  15

Leu Val Glu Arg Ser Ala Ala Gln Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 266
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-E23Q

<400> SEQUENCE: 266

```
atggcagcag gacaagcgtt tagaaagttt cttccactct tgaccgagt attggttgaa      60 aggagtgctg ctcagactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc ccagaata tggaggcacc      240 aaagtagttc tagatgacaa ggattatttc ctatttagag atggtgacat tcttggaaag     300
tacgtagact ga                                                         312
```

<210> SEQ ID NO 267
<211> LENGTH: 312
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: Optimised cDNA of Cpn10 variant Ala-Cpn10-E23Q
(Gly, Arg and stop codons are optimized in the cDNA)

<400> SEQUENCE: 267

```
atggcagcag gccaagcgtt tcgcaagttt cttccactct ttgaccgtgt attggttgaa      60
cgcagtgctg ctcagactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc cccagaata tggtggcacc      240 aaagtagttc tagatgacaa ggattatttc ctatttcgtg atggtgacat tcttggcaag     300
tacgtagact aa                                                         312
```

<210> SEQ ID NO 268
<211> LENGTH: 102
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Human Cpn10 mutant Ala-Cpn10-E34Q with residue
Glutamate (E) 35 changed to Glutamine (Q) 35. This construct
contains an extra N-terminal Alanine residue.

<400> SEQUENCE: 268

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Gln Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 269
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Native cDNA of Cpn10 variant Ala-Cpn10-E34Q

<400> SEQUENCE: 269

```
atggcagcag gacaagcgtt tagaaagttt cttccactct ttgaccgagt attggttgaa      60
aggagtgctg ctgaaactgt aaccaaagga ggcattatgc ttccacagaa atctcaagga     120
aaagtattgc aagcaacagt agtcgctgtt ggatcgggtt ctaaaggaaa gggtggagag     180
attcaaccag ttagcgtgaa agttggagat aaagttcttc cccagaata tggaggcacc      240 aaagtagttc tagatgacaa ggattatttc ctatttagag atggtgacat tcttggaaag     300
```

```
tacgtagact ga                                                          312

<210> SEQ ID NO 270
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E34Q
      (Gly, Arg and stop codons are optimized in the cDNA)

<400> SEQUENCE: 270
atggcagcag gccaagcgtt tcgcaagttt cttccactct ttgaccgtgt attggttgaa    60
cgcagtgctg ctgaaactgt aaccaaaggt ggcattatgc ttccacagaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                          312

<210> SEQ ID NO 271
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E58Q with residue
      Glutamate (E) 59 changed to Glutamine (Q) 59. This construct
      contains an extra N-terminal Alanine residue.

<400> SEQUENCE: 271

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Gln Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 272
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E58Q

<400> SEQUENCE: 272
atggcagcag gacaagcgtt tagaaagttt cttccactct ttgaccgagt attggttgaa    60
```

```
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggacag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 273
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E58Q
      (Gly, Arg and stop codons are optimized in the cDNA)

<400> SEQUENCE: 273

```
atggcagcag gccaagcgtt tcgcaagttt cttccactct tgaccgtgt attggttgaa     60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggccag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                       312
```

<210> SEQ ID NO 274
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D68N with residue
      Aspartate (D) 69 changed to Asparagine (N) 69. This construct
      contains an extra N-terminal Alanine residue.

<400> SEQUENCE: 274

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asn Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 275
<211> LENGTH: 312
<212> TYPE: DNA
<213> ORGANISM: Artificial Sequence
<220> FEATURE:
<223> OTHER INFORMATION: Description of Artificial Sequence: Synthetic

```
                                      polynucleotide
<220> FEATURE:
<223> OTHER INFORMATION: Native cDNA of Cpn10 variant Ala-Cpn10-D68N

<400> SEQUENCE: 275
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggaaac aaagttcttc tcccagaata tggaggcacc    240
aaagtagttc tagatgacaa ggattatttc ctatttagag atggtgacat tcttggaaag    300
tacgtagact ga                                                         312

<210> SEQ ID NO 276
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D68N
      (Gly, Arg and stop codons are optimized in the cDNA)

<400> SEQUENCE: 276
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcaac aaagttcttc tcccagaata tggtggcacc    240
aaagtagttc tagatgacaa ggattatttc ctatttcgtg atggtgacat tcttggcaag    300
tacgtagact aa                                                         312

<210> SEQ ID NO 277
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-E74Q with residue
      Glutamate (E) 75 changed to Glutamine (Q) 75. This construct
      contains an extra N-terminal Alanine residue.

<400> SEQUENCE: 277

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
                20                  25                  30

Leu Pro Glu Lys Ser Gln Gly Lys Val Leu Gln Ala Thr Val Val Ala
            35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Gln Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 278
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-E74Q

<400> SEQUENCE: 278
atggcagcag gacaagcgtt tagaaagttt cttccactct tgaccgagt attggttgaa        60 aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccacagta tggaggcacc      240
aaagtagttc tagatgacaa ggattatttc ctatttagag atggtgacat tcttggaaag      300
tacgtagact ga                                                          312

<210> SEQ ID NO 279
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-E74Q
      (Gly, Arg and stop codons are optimized in the cDNA)

<400> SEQUENCE: 279
atggcagcag gccaagcgtt tcgcaagttt cttccactct tgaccgtgt attggttgaa        60 cgcagtgctg ctgaaactgt aaccaaaggt ggcattatgc ttccagaaaa atctcaaggc      120
aaagtattgc aagcaacagt agtcgctgtt ggctcgggtt ctaaaggtaa gggtggcgag      180
attcaaccag ttagcgtgaa agttggcgat aaagttcttc tcccacagta tggtggcacc      240
aaagtagttc tagatgacaa ggattatttc ctatttcgtg atggtgacat tcttggcaag      300
tacgtagact aa                                                          312

<210> SEQ ID NO 280
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D83N with residue
      Aspartate (D) 84 changed to Asparagine (N) 84. This construct
      contains an extra N-terminal Alanine residue.

<400> SEQUENCE: 280

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

```
Val Lys Val Gly Asp Lys Val Leu Pro Glu Tyr Gly Gly Thr Lys
 65                  70                  75                  80

Val Val Leu Asn Asp Lys Asp Tyr Phe Leu Phe Arg Asp Gly Asp Ile
                 85                  90                  95

Leu Gly Lys Tyr Val Asp
            100
```

<210> SEQ ID NO 281
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D83N

<400> SEQUENCE: 281

```
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc cccagaata tggaggcacc     240 aaagtagttc taaacgacaa ggattatttc ctatttagag atggtgacat tcttggaaag    300
tacgtagact ga                                                         312
```

<210> SEQ ID NO 282
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D83N
      (Gly, Arg and stop codons are optimized in the cDNA)

<400> SEQUENCE: 282

```
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc cccagaata tggtggcacc     240 aaagtagttc taaacgacaa ggattatttc ctatttcgtg atggtgacat tcttggcaag    300
tacgtagact aa                                                         312
```

<210> SEQ ID NO 283
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D84N with residue
      Aspartate (D) 85 changed to Asparagine (N) 85. This construct
      contains an extra N-terminal Alanine residue.

<400> SEQUENCE: 283

```
Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
```

```
              20                  25                  30
Leu Pro Glu Lys Ser Gln Gly Lys Val Leu Gln Ala Thr Val Val Ala
             35                  40                  45

Val Gly Ser Gly Ser Lys Gly Lys Gly Gly Glu Ile Gln Pro Val Ser
         50                  55                  60

Val Lys Val Gly Asp Lys Val Leu Leu Pro Glu Tyr Gly Gly Thr Lys
 65                  70                  75                  80

Val Val Leu Asp Asn Lys Asp Tyr Phe Leu Phe Arg Asp Gly Asp Ile
                 85                  90                  95

Leu Gly Lys Tyr Val Asp
            100

<210> SEQ ID NO 284
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D84N

<400> SEQUENCE: 284
atggcagcag acaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagataacaa ggattatttc ctatttagag atggtgacat tcttggaaag   300
tacgtagact ga                                                       312

<210> SEQ ID NO 285
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D84N
      (Gly, Arg and stop codons are optimized in the cDNA)

<400> SEQUENCE: 285
atggcagcag ccaagcgtt tcgcaagttt cttccactct tgaccgtgt attggttgaa      60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagataacaa ggattatttc ctatttcgtg atggtgacat tcttggcaag   300
tacgtagact aa                                                       312

<210> SEQ ID NO 286
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D86N with residue
      Aspartate (D) 87 changed to Asparagine (N) 87. This construct
``` contains an extra N-terminal Alanine residue.

<400> SEQUENCE: 286

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asn Tyr Phe Leu Phe Arg Asp Gly Asp Ile
                85                  90                  95

Leu Gly Lys Tyr Val Asp
            100

<210> SEQ ID NO 287
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Native cDNA of Cpn10 variant Ala-Cpn10-D86N

<400> SEQUENCE: 287
atggcagcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa gaactatttc ctatttagag atggtgacat tcttggaaag    300
tacgtagact ga                                                        312

<210> SEQ ID NO 288
<211> LENGTH: 312
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Optimised cDNA of Cpn10 variant Ala-Cpn10-D86N
    (Gly, Arg and stop codons are optimized in the cDNA)

<400> SEQUENCE: 288
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa gaactatttc ctatttcgtg atggtgacat tcttggcaag    300
tacgtagact aa                                                        312

<210> SEQ ID NO 289
<211> LENGTH: 102

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D92N with residue
      Aspartate (D) 93 changed to Asparagine (N) 93. This construct
      contains an extra N-terminal Alanine residue.

<400> SEQUENCE: 289

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asn Gly Asp Ile
                85                  90                  95

Leu Gly Lys Tyr Val Asp
            100

<210> SEQ ID NO 290
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D92N

<400> SEQUENCE: 290
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagaa acggtgacat tcttggaaag    300
tacgtagact ga                                                        312

<210> SEQ ID NO 291
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D92N
      (Gly, Arg and stop codons are optimized in the cDNA)

<400> SEQUENCE: 291
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
```

```
aaagtagttc tagatgacaa ggattatttc ctatttcgta acggtgacat tcttggcaag    300
tacgtagact aa                                                        312
```

<210> SEQ ID NO 292
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D94A with residue
      Aspartate (D) 95 changed to Alanine (A) 95. This construct
      contains an extra N-terminal Alanine residue.

<400> SEQUENCE: 292

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Ala Ile
                85                  90                  95

Leu Gly Lys Tyr Val Asp
            100

<210> SEQ ID NO 293
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D94A

<400> SEQUENCE: 293

```
atggcagcag gacaagcgtt tagaaagttt cttccactct ttgaccgagt attggttgaa     60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgcgat tcttggaaag   300
tacgtagact ga                                                        312
```

<210> SEQ ID NO 294
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D94A
      (Gly, Arg and stop codons are optimized in the cDNA)

<400> SEQUENCE: 294

```
atggcagcag gccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc ccagaatat ggtggcacc      240 aaagtagttc tagatgacaa ggattatttc ctatttcgtg atggtgcgat tcttggcaag     300
tacgtagact aa                                                         312
```

<210> SEQ ID NO 295
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D94M with residue
      Aspartate (D) 95 changed to Methionine (M) 95. This construct
      contains an extra N-terminal Alanine residue.

<400> SEQUENCE: 295

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Met Ile
                85                  90                  95

Leu Gly Lys Tyr Val Asp
            100

<210> SEQ ID NO 296
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D94M

<400> SEQUENCE: 296

```
atggcagcag gacaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc ccagaatat ggaggcacc      240 aaagtagttc tagatgacaa ggattatttc ctatttagag atggtatgat tcttggaaag     300
tacgtagact ga                                                         312
```

<210> SEQ ID NO 297
<211> LENGTH: 312
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D94M
      (Gly, Arg and stop codons are optimized in the cDNA)

<400> SEQUENCE: 297
atggcagcag gccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc ccagaata tggtggcacc      240 aaagtagttc tagatgacaa ggattatttc ctatttcgtg atggtatgat tcttggcaag     300
tacgtagact aa                                                         312

<210> SEQ ID NO 298
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D94N with residue
      Aspartate (D) 95 changed to Asparagine (N) 95. This construct
      contains an extra N-terminal Alanine residue.

<400> SEQUENCE: 298

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asn Ile
                85                  90                  95

Leu Gly Lys Tyr Val Asp
            100

<210> SEQ ID NO 299
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D94N

<400> SEQUENCE: 299
atggcagcag gacaagcgtt tagaaagttt cttccactct ttgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc ccagaata tggaggcacc     240 aaagtagttc tagatgacaa ggattatttc ctatttagag atggtaacat tcttggaaag    300
```

```
tacgtagact ga                                                   312

<210> SEQ ID NO 300
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D94N
      (Gly, Arg and stop codons are optimized in the cDNA)

<400> SEQUENCE: 300
atggcagcag gccaagcgtt tcgcaagttt cttccactct ttgaccgtgt attggttgaa     60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtaacat tcttggcaag    300
tacgtagact aa                                                   312

<210> SEQ ID NO 301
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D94S with residue
      Aspartate (D) 95 changed to Serine (S) 95. This construct contains
      an extra N-terminal Alanine residue.

<400> SEQUENCE: 301

Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Ser Ile
                85                  90                  95

Leu Gly Lys Tyr Val Asp
            100

<210> SEQ ID NO 302
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-D94S

<400> SEQUENCE: 302
atggcagcag gacaagcgtt tagaaagttt cttccactct ttgaccgagt attggttgaa     60
```

```
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc ccagaata tggaggcacc     240 aaagtagttc tagatgacaa ggattatttc ctatttagag atggtagcat tcttggaaag    300
tacgtagact ga                                                        312
```

<210> SEQ ID NO 303
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-D94S
      (Gly, Arg and stop codons are optimized in the cDNA)

<400> SEQUENCE: 303

```
atggcagcag gccaagcgtt tcgcaagttt cttccactct tgaccgtgt attggttgaa     60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc ccagaata tggtggcacc    240 aaagtagttc tagatgacaa ggattatttc ctatttcgtg atggtagcat tcttggcaag   300
tacgtagact aa                                                       312
```

<210> SEQ ID NO 304
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-D101N with residue
      Aspartate (D) 102 changed to Asparagine (N) 102. This construct
      contains an extra N-terminal Alanine residue.

<400> SEQUENCE: 304

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asn
            100
```

<210> SEQ ID NO 305
<211> LENGTH: 312
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: Native cDNA of Cpn10 variant Ala-Cpn10-D101N

<400> SEQUENCE: 305

```
atggcagcag gacaagcgtt tagaaagttt cttccactct tgaccgagt attggttgaa        60
aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccagaata tggaggcacc      240
aaagtagttc tagatgacaa ggattatttc ctatttagag atggtgacat tcttggaaag      300
tacgtaaact ga                                                          312
```

<210> SEQ ID NO 306
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Optimised cDNA of Cpn10 variant Ala-Cpn10-D101N
(Gly, Arg and stop codons are optimized in the cDNA)

<400> SEQUENCE: 306

```
atggcagcag gccaagcgtt tcgcaagttt cttccactct tgaccgtgt attggttgaa        60
cgcagtgctg ctgaaactgt aaccaaaggt ggcattatgc ttccagaaaa atctcaaggc      120
aaagtattgc aagcaacagt agtcgctgtt ggctcgggtt ctaaaggtaa gggtggcgag      180
attcaaccag ttagcgtgaa agttggcgat aaagttcttc tcccagaata tggtggcacc      240
aaagtagttc tagatgacaa ggattatttc ctatttcgtg atggtgacat tcttggcaag      300
tacgtaaact aa                                                          312
```

<210> SEQ ID NO 307
<211> LENGTH: 103
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Human Cpn10 mutant MH-Cpn10 with an additional
Histidine (H) 2 residue. The initiation Methionine (M) 1 is not
removed from this protein

<400> SEQUENCE: 307

```
Met His Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
```

<210> SEQ ID NO 308
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant MH-Cpn10

<400> SEQUENCE: 308

```
atgcatgcag acaagcgtt tagaaagttt cttccactct tgaccgagt attggttgaa      60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                       312
```

<210> SEQ ID NO 309
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant MH-Cpn10 (Gly, Arg and stop codons are optimized in the cDNA)

<400> SEQUENCE: 309

```
atgcatgcag gccaagcgtt tcgcaagttt cttccactct tgaccgtgt attggttgaa      60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                       312
```

<210> SEQ ID NO 310
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant MR-Cpn10 with an additional Arginine (R) 2 residue. The initiation Methionine (M) 1 is not removed from this protein

<400> SEQUENCE: 310

```
Met Arg Ala Gly Gln Ala Phe Arg Lys Phe Leu Pro Leu Phe Asp Arg
1               5                   10                  15
Val Leu Val Glu Arg Ser Ala Ala Glu Thr Val Thr Lys Gly Gly Ile
                20                  25                  30
Met Leu Pro Glu Lys Ser Gln Gly Lys Val Leu Gln Ala Thr Val Val
            35                  40                  45
Ala Val Gly Ser Gly Ser Lys Gly Lys Gly Gly Glu Ile Gln Pro Val
        50                  55                  60
```

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 311
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant MR-Cpn10

<400> SEQUENCE: 311
atgcgcgcag acaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                        312

<210> SEQ ID NO 312
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant MR-Cpn10 (Gly,
      Arg and stop codons are optimized in the cDNA)

<400> SEQUENCE: 312
atgcgcgcag gccaagcgtt tcgcaagttt cttccactct tgaccgtgt attggttgaa      60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                        312

<210> SEQ ID NO 313
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant MK-Cpn10 with an additional
      Lysine (K) 2 residue. The initiation Methionine (M) 1 is not
      removed from this protein

<400> SEQUENCE: 313

Met Lys Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
             20                  25                  30

Met Leu Pro Glu Lys Ser Gln Gly Lys Val Leu Gln Ala Thr Val Val
         35                  40                  45

Ala Val Gly Ser Gly Ser Lys Gly Lys Gly Gly Glu Ile Gln Pro Val
 50                  55                  60

Ser Val Lys Val Gly Asp Lys Val Leu Leu Pro Glu Tyr Gly Gly Thr
 65                  70                  75                  80

Lys Val Val Leu Asp Asp Lys Asp Tyr Phe Leu Phe Arg Asp Gly Asp
                 85                  90                  95

Ile Leu Gly Lys Tyr Val Asp
            100

<210> SEQ ID NO 314
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant MK-Cpn10

<400> SEQUENCE: 314
atgaaagcag acaagcgtt tagaaagttt cttccactct tgaccgagt attggttgaa      60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 315
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant MK-Cpn10 (Gly,
      Arg and stop codons are optimized in the cDNA)

<400> SEQUENCE: 315
atgaaagcag ccaagcgtt tcgcaagttt cttccactct tgaccgtgt attggttgaa       60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 316
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant MKK-Cpn10 with two additional Lysine (K) 2-3 residues. The initiation Methionine (M) 1 is not removed from this protein

<400> SEQUENCE: 316

```
Met Lys Lys Ala Gly Gln Ala Phe Arg Lys Phe Leu Pro Leu Phe Asp
1               5                   10                  15
Arg Val Leu Val Glu Arg Ser Ala Ala Glu Thr Val Thr Lys Gly Gly
            20                  25                  30
Ile Met Leu Pro Glu Lys Ser Gln Gly Lys Val Leu Gln Ala Thr Val
        35                  40                  45
Val Ala Val Gly Ser Gly Ser Lys Gly Lys Gly Gly Glu Ile Gln Pro
50                  55                  60
Val Ser Val Lys Val Gly Asp Lys Val Leu Leu Pro Glu Tyr Gly Gly
65                  70                  75                  80
Thr Lys Val Val Leu Asp Asp Lys Asp Tyr Phe Leu Phe Arg Asp Gly
                85                  90                  95
Asp Ile Leu Gly Lys Tyr Val Asp
            100
```

<210> SEQ ID NO 317
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant MKK-Cpn10

<400> SEQUENCE: 317

```
atgaaaaaag caggacaagc gtttagaaag tttcttccac tctttgaccg agtattggtt      60
gaaaggagtg ctgctgaaac tgtaaccaaa ggaggcatta tgcttccaga aaaatctcaa     120
ggaaaagtat tgcaagcaac agtagtcgct gttggatcgg ttctaaagg aaagggtgga     180
gagattcaac cagttagcgt gaaagttgga gataaagttc ttctcccaga atatggaggc     240
accaaagtag ttctagatga caaggattat ttcctattta gagatggtga cattcttgga     300
aagtacgtag actga                                                      315
```

<210> SEQ ID NO 318
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant MKK-Cpn10 (Gly, Arg and stop codons are optimized in the cDNA)

<400> SEQUENCE: 318

```
atgaaaaaag caggccaagc gtttcgcaag tttcttccac tctttgaccg tgtattggtt      60
gaacgcagtg ctgctgaaac tgtaaccaaa ggtggcatta tgcttccaga aaaatctcaa     120
ggcaaagtat tgcaagcaac agtagtcgct gttggctcgg ttctaaagg taagggtggc     180
gagattcaac cagttagcgt gaaagttggc gataaagttc ttctcccaga atatggtggc     240
accaaagtag ttctagatga caaggattat ttcctatttc gtgatggtga cattcttggc     300
aagtacgtag actaa                                                      315
```

<210> SEQ ID NO 319

<211> LENGTH: 105
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant MKKK-Cpn10 with three additional Lysine (K) 2-4 residues. The initiation Methionine (M) 1 is not removed from this protein

<400> SEQUENCE: 319

```
Met Lys Lys Lys Ala Gly Gln Ala Phe Arg Lys Phe Leu Pro Leu Phe
1               5                   10                  15

Asp Arg Val Leu Val Glu Arg Ser Ala Ala Glu Thr Val Thr Lys Gly
            20                  25                  30

Gly Ile Met Leu Pro Glu Lys Ser Gln Gly Lys Val Leu Gln Ala Thr
        35                  40                  45

Val Val Ala Val Gly Ser Gly Ser Lys Gly Lys Gly Gly Glu Ile Gln
    50                  55                  60

Pro Val Ser Val Lys Val Gly Asp Lys Val Leu Leu Pro Glu Tyr Gly
65                  70                  75                  80

Gly Thr Lys Val Val Leu Asp Asp Lys Asp Tyr Phe Leu Phe Arg Asp
                85                  90                  95

Gly Asp Ile Leu Gly Lys Tyr Val Asp
            100                 105
```

<210> SEQ ID NO 320
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant MKKK-Cpn10

<400> SEQUENCE: 320

```
atgaaaaaga aagcaggaca agcgtttaga aagtttcttc cactctttga ccgagtattg      60
gttgaaagga gtgctgctga aactgtaacc aaaggaggca ttatgcttcc agaaaaatct     120
caaggaaaag tattgcaagc aacagtagtc gctgttggat cgggttctaa aggaaagggt     180
ggagagattc aaccagttag cgtgaaagtt ggagataaag ttcttctccc agaatatgga     240
ggcaccaaag tagttctaga tgacaaggat tatttcctat ttagagatgg tgacattctt     300
ggaaagtacg tagactga                                                    318
```

<210> SEQ ID NO 321
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant MKKK-Cpn10 (Gly, Arg and stop codons are optimized in the cDNA)

<400> SEQUENCE: 321

```
atgaaaaaga aagcaggcca agcgtttcgc aagtttcttc cactctttga ccgtgtattg      60
gttgaacgca gtgctgctga aactgtaacc aaaggtggca ttatgcttcc agaaaaatct     120
caaggcaaag tattgcaagc aacagtagtc gctgttggct cgggttctaa aggtaagggt     180
```

```
ggcgagattc aaccagttag cgtgaaagtt ggcgataaag ttcttctccc agaatatggt      240
ggcaccaaag tagttctaga tgacaaggat tatttcctat tcgtgatgg tgacattctt      300 ggcaagtacg tagactaa                                                    318
```

<210> SEQ ID NO 322
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K21 with an
      additional Lysine (K) inserted at position 22 (mobile loop). This
      construct contains an extra N-terminal Alanine residue.

<400> SEQUENCE: 322

```
Ala Ala Gly Gln Ala Phe Arg Lys Phe Leu Pro Leu Phe Asp Arg Val
1               5                  10                  15

Leu Val Glu Arg Ser Lys Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 323
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K21

<400> SEQUENCE: 323

```
atggcagcag acaagcgtt tagaaagttt cttccactct tgaccgagt attggttgaa       60 aggagtaaag ctgctgaaac tgtaaccaaa ggaggcatta tgcttccaga aaatctcaa     120 ggaaaagtat tgcaagcaac agtagtcgct gttggatcgg ttctaaagg aaagggtgga    180 gagattcaac cagttagcgt gaaagttgga gataaagttc ttctcccaga atatggaggc    240
accaaagtag ttctagatga caaggattat ttcctattta gagatggtga cattcttgga    300
aagtacgtag actga                                                     315
```

<210> SEQ ID NO 324
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K21
      (Gly, Arg and stop codons are optimized in the cDNA)

<400> SEQUENCE: 324

```
atggcagcag gccaagcgtt tcgcaagttt cttccactct ttgaccgtgt attggttgaa    60
cgcagtaaag ctgctgaaac tgtaaccaaa ggtggcatta tgcttccaga aaaatctcaa   120
ggcaaagtat tgcaagcaac agtagtcgct gttggctcgg ttctaaagg taagggtggc    180 gagattcaac cagttagcgt gaaagttggc gataaagttc ttctcccaga atatggtggc   240
accaaagtag ttctagatga caaggattat ttcctatttc gtgatggtga cattcttggc   300
aagtacgtag actaa                                                    315
```

<210> SEQ ID NO 325
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-KK21 with two
      additional Lysine (K) residues inserted at position 22-23 (mobile
      loop). This construct contains an extra N-terminal Alanine
      residue.

<400> SEQUENCE: 325

```
Ala Ala Gly Gln Ala Phe Arg Lys Phe Leu Pro Leu Phe Asp Arg Val
1               5                   10                  15

Leu Val Glu Arg Ser Lys Lys Ala Ala Glu Thr Val Thr Lys Gly Gly
            20                  25                  30

Ile Met Leu Pro Glu Lys Ser Gln Gly Lys Val Leu Gln Ala Thr Val
        35                  40                  45

Val Ala Val Gly Ser Gly Ser Lys Gly Lys Gly Gly Glu Ile Gln Pro
    50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
            100
```

<210> SEQ ID NO 326
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-KK21

<400> SEQUENCE: 326

```
atggcagcag gacaagcgtt tagaaagttt cttccactct ttgaccgagt attggttgaa    60
aggagtaaaa aagctgctga aactgtaacc aaaggaggca ttatgcttcc agaaaaatct   120
caaggaaaag tattgcaagc aacagtagtc gctgttggat cgggttctaa aggaaagggt   180
ggagagattc aaccagttag cgtgaaagtt ggagataaag ttcttctccc agaatatgga   240
ggcaccaaag tagttctaga tgacaaggat tatttcctat ttagagatgg tgacattctt   300
ggaaagtacg tagactga                                                 318
```

<210> SEQ ID NO 327
<211> LENGTH: 318

<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-KK21 (Gly, Arg and stop codons are optimized in the cDNA)

<400> SEQUENCE: 327

```
atggcagcag gccaagcgtt tcgcaagttt cttccactct tgaccgtgt attggttgaa      60
cgcagtaaaa aagctgctga aactgtaacc aaaggtggca ttatgcttcc agaaaaatct    120
caaggcaaag tattgcaagc aacagtagtc gctgttggct cgggttctaa aggtaagggt    180
ggcgagattc aaccagttag cgtgaaagtt ggcgataaag ttcttctccc agaatatggt    240
ggcaccaaag tagttctaga tgacaaggat tatttcctat tcgtgatgg tgacattctt     300
ggcaagtacg tagactaa                                                  318
```

<210> SEQ ID NO 328
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-K39 with an additional Lysine (K) inserted at position 40 (mobile loop). This construct contains an extra N-terminal Alanine residue.

<400> SEQUENCE: 328

```
Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Lys Val Leu Gln Ala Thr Val Val
        35                  40                  45
Ala Val Gly Ser Gly Ser Lys Gly Lys Gly Gly Glu Ile Gln Pro Val
    50                  55                  60
Ser Val Lys Val Gly Asp Lys Val Leu Leu Pro Glu Tyr Gly Gly Thr
65                  70                  75                  80
Lys Val Val Leu Asp Asp Lys Asp Tyr Phe Leu Phe Arg Asp Gly Asp
                85                  90                  95
Ile Leu Gly Lys Tyr Val Asp
            100
```

<210> SEQ ID NO 329
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Native cDNA of Cpn10 variant Ala-Cpn10-K39

<400> SEQUENCE: 329

```
atggcagcag gacaagcgtt tagaaagttt cttccactct tgaccgagt attggttgaa      60
aggagtgctg ctgaaactgt aaccaaagga ggcattatgc ttccagaaaa atctcaagga    120
aagaaagtat tgcaagcaac agtagtcgct gttggatcgg gttctaaagg aaagggtgga    180
gagattcaac cagttagcgt gaaagttgga gataaagttc ttctcccaga atatggaggc    240
```

```
accaaagtag ttctagatga caaggattat ttcctattta gagatggtga cattcttgga      300
aagtacgtag actga                                                       315
```

<210> SEQ ID NO 330
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K39
      (Gly, Arg and stop codons are optimized in the cDNA)

<400> SEQUENCE: 330

```
atggcagcag gccaagcgtt tcgcaagttt cttccactct tgaccgtgt attggttgaa       60 cgcagtgctg ctgaaactgt aaccaaaggt ggcattatgc ttccagaaaa atctcaaggc      120
aagaaagtat tgcaagcaac agtagtcgct gttggctcgg ttctaaagg taagggtggc      180 gagattcaac cagttagcgt gaaagttggc gataaagttc ttctcccaga atatggtggc     240
accaaagtag ttctagatga caaggattat ttcctatttc gtgatggtga cattcttggc     300
aagtacgtag actaa                                                      315
```

<210> SEQ ID NO 331
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-KK39 with two
      additional Lysine (K) residues inserted at position 40-41 (mobile
      loop). This construct contains an extra N-terminal Alanine
      residue.

<400> SEQUENCE: 331

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Lys Lys Val Leu Gln Ala Thr Val
        35                  40                  45

Val Ala Val Gly Ser Gly Ser Lys Gly Lys Gly Gly Glu Ile Gln Pro
    50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
            100
```

<210> SEQ ID NO 332
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-KK39

<400> SEQUENCE: 332

```
atggcagcag acaagcgtt  tagaaagttt cttccactct tgaccgagt  attggttgaa    60
aggagtgctg ctgaaactgt aaccaaagga ggcattatgc ttccagaaaa atctcaagga   120
aaaaagaaag tattgcaagc aacagtagtc gctgttggat cgggttctaa aggaaagggt   180
ggagagattc aaccagttag cgtgaaagtt ggagataaag ttcttctccc agaatatgga   240
ggcaccaaag tagttctaga tgacaaggat tatttcctat ttagagatgg tgacattctt   300
ggaaagtacg tagactga                                                 318
```

<210> SEQ ID NO 333
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-KK39 (Gly, Arg and stop codons are optimized in the cDNA)

<400> SEQUENCE: 333

```
atggcagcag gccaagcgtt tcgcaagttt cttccactct tgaccgtgt  attggttgaa    60
cgcagtgctg ctgaaactgt aaccaaaggt ggcattatgc ttccagaaaa atctcaaggc   120
aaaaagaaag tattgcaagc aacagtagtc gctgttggct cgggttctaa aggtaagggt   180
ggcgagattc aaccagttag cgtgaaagtt ggcgataaag ttcttctccc agaatatggt   240
ggcaccaaag tagttctaga tgacaaggat tatttcctat tcgtgatgg  tgacattctt   300
ggcaagtacg tagactaa                                                 318
```

<210> SEQ ID NO 334
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human Cpn10 mutant Ala-Cpn10-K57 with an additional Lysine (K) inserted at position 58 (roof loop). This construct contains an extra N-terminal Alanine residue.

<400> SEQUENCE: 334

```
Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Lys Gly Glu Ile Gln Pro Val
    50                  55                  60
Ser Val Lys Val Gly Asp Lys Val Leu Leu Pro Glu Tyr Gly Gly Thr
65                  70                  75                  80
Lys Val Val Leu Asp Asp Lys Asp Tyr Phe Leu Phe Arg Asp Gly Asp
                85                  90                  95
Ile Leu Gly Lys Tyr Val Asp
            100
```

<210> SEQ ID NO 335
<211> LENGTH: 315

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K59

<400> SEQUENCE: 335
atggcagcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtaaagga    180
gagattcaac cagttagcgt gaaagttgga gataaagttc ttctcccaga atatggaggc    240
accaaagtag ttctagatga caaggattat ttcctattta gagatggtga cattcttgga    300
aagtacgtag actga                                                    315

<210> SEQ ID NO 336
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K59
      (Gly, Arg and stop codons are optimized in the cDNA)

<400> SEQUENCE: 336
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtaaaggc    180
gagattcaac cagttagcgt gaaagttggc gataaagttc ttctcccaga atatggtggc    240
accaaagtag ttctagatga caaggattat ttcctatttc gtgatggtga cattcttggc    300
aagtacgtag actaa                                                    315

<210> SEQ ID NO 337
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-KK57 with two
      additional Lysine (K) residues inserted at position 58-59 (roof
      loop). This construct contains an extra N-terminal Alanine
      residue.

<400> SEQUENCE: 337

Ala Ala Gly Gln Ala Phe Arg Lys Phe Leu Pro Leu Phe Asp Arg Val
1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Lys Gly Glu Ile Gln Pro
    50                  55                  60

Val Ser Val Lys Val Gly Asp Lys Val Leu Leu Pro Glu Tyr Gly Gly
65                  70                  75                  80
```

Thr Lys Val Val Leu Asp Asp Lys Asp Tyr Phe Leu Phe Arg Asp Gly
                85                  90                  95

Asp Ile Leu Gly Lys Tyr Val Asp
            100

<210> SEQ ID NO 338
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-KK59

<400> SEQUENCE: 338
atggcagcag acaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtaagaaa   180
ggagagattc aaccagttag cgtgaaagtt ggagataaag ttcttctccc agaatatgga   240
ggcaccaaag tagttctaga tgacaaggat tatttcctat ttagagatgg tgacattctt   300
ggaaagtacg tagactga                                                 318

<210> SEQ ID NO 339
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-KK59
      (Gly, Arg and stop codons are optimized in the cDNA)

<400> SEQUENCE: 339
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtaagaaa   180
ggcgagattc aaccagttag cgtgaaagtt ggcgataaag ttcttctccc agaatatggt   240
ggcaccaaag tagttctaga tgacaaggat tatttcctat ttcgtgatgg tgacattctt   300
ggcaagtacg tagactaa                                                 318

<210> SEQ ID NO 340
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K76 with an
      additional Lysine (K) inserted at position 77 (L2 connection
      loop). This construct contains an extra N-terminal Alanine
      residue.

<400> SEQUENCE: 340

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

```
Leu Pro Glu Lys Ser Gln Gly Lys Val Leu Gln Ala Thr Val Val Ala
         35                  40                  45

Val Gly Ser Gly Ser Lys Gly Lys Gly Gly Ile Gln Pro Val Ser
 50                  55                  60

Val Lys Val Gly Asp Lys Val Leu Leu Pro Glu Tyr Lys Gly Thr
 65                  70                  75                  80

Lys Val Val Leu Asp Asp Lys Asp Tyr Phe Leu Phe Arg Asp Gly Asp
                 85                  90                  95

Ile Leu Gly Lys Tyr Val Asp
            100
```

```
<210> SEQ ID NO 341
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K76

<400> SEQUENCE: 341
atggcagcag gacaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata taaggaggc    240 accaaagtag ttctagatga caaggattat ttcctattta gagatggtga cattcttgga   300
aagtacgtag actga                                                    315

<210> SEQ ID NO 342
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K76
      (Gly, Arg and stop codons are optimized in the cDNA)

<400> SEQUENCE: 342
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata taaggtggc    240 accaaagtag ttctagatga caaggattat ttcctatttc gtgatggtga cattcttggc   300
aagtacgtag actaa                                                    315

<210> SEQ ID NO 343
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K85 with an
      additional Lysine (K) inserted at position 86 (L3 connection
      loop). This construct contains an extra N-terminal Alanine
      residue.
```

<400> SEQUENCE: 343

Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Lys Gly Gly Glu Ile Gln Pro Val Ser
50                  55                  60
Val Lys Val Gly Asp Lys Val Leu Leu Pro Glu Tyr Gly Gly Thr Lys
65                  70                  75                  80
Val Val Leu Asp Asp Lys Lys Asp Tyr Phe Leu Phe Arg Asp Gly Asp
                85                  90                  95
Ile Leu Gly Lys Tyr Val Asp
            100

<210> SEQ ID NO 344
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K85

<400> SEQUENCE: 344
atggcagcag gacaagcgtt tagaaagttt cttccactct tgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa aaaggattat ttcctattta gagatggtga cattcttgga    300
aagtacgtag actga                                                     315

<210> SEQ ID NO 345
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K85
      (Gly, Arg and stop codons are optimized in the cDNA)

<400> SEQUENCE: 345
atggcagcag gccaagcgtt tcgcaagttt cttccactct tgaccgtgt attggttgaa      60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa aaaggattat ttcctatttc gtgatggtga cattcttggc    300
aagtacgtag actaa                                                     315

<210> SEQ ID NO 346
<211> LENGTH: 104
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-KK85 with two
      additional Lysine (K) residues inserted at position 86-87 (L3
      connection loop). This construct contains an extra N-terminal
      Alanine residue.

<400> SEQUENCE: 346

Ala Ala Gly Gln Ala Phe Arg Lys Phe Leu Pro Leu Phe Asp Arg Val
1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Lys Lys Asp Tyr Phe Leu Phe Arg Asp Gly
                85                  90                  95

Asp Ile Leu Gly Lys Tyr Val Asp
            100

<210> SEQ ID NO 347
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-KK85

<400> SEQUENCE: 347
atggcagcag gacaagcgtt tagaaagttt cttccactct tgaccgagt attggttgaa       60 aggagtgctg ctgaaactgt aaccaaagga ggcattatgc ttccagaaaa atctcaagga      120
aaagtattgc aagcaacagt agtcgctgtt ggatcgggtt ctaaaggaaa gggtggagag      180
attcaaccag ttagcgtgaa agttggagat aaagttcttc tcccagaata tggaggcacc     240
aaagtagttc tagatgacaa gaaaaaggat tatttcctat ttagagatgg tgacattctt     300
ggaaagtacg tagactga                                                   318

<210> SEQ ID NO 348
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-KK85
      (Gly, Arg and stop codons are optimized in the cDNA)

<400> SEQUENCE: 348
atggcagcag gccaagcgtt tcgcaagttt cttccactct tgaccgtgt attggttgaa       60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240

```
aaagtagttc tagatgacaa gaaaaaggat tatttcctat ttcgtgatgg tgacattctt      300
ggcaagtacg tagactaa                                                    318
```

<210> SEQ ID NO 349
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-K102 with an
      additional Lysine (K) inserted at position 103 (the C-terminus).
      This construct contains an extra N-terminal Alanine residue.

<400> SEQUENCE: 349

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp Lys
            100
```

<210> SEQ ID NO 350
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-K102

<400> SEQUENCE: 350

```
atggcagcag gacaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc     240
aaagtagttc tagatgacaa ggattatttc ctatttagag atggtgacat tcttggaaag     300
tacgtagaca aatga                                                      315
```

<210> SEQ ID NO 351
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised cDNA of Cpn10 variant Ala-Cpn10-K102
      (Gly, Arg and stop codons are optimized in the cDNA)

<400> SEQUENCE: 351

```
atggcagcag gccaagcgtt tcgcaagttt cttccactct ttgaccgtgt attggttgaa    60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagaca aataa                                                    315
```

<210> SEQ ID NO 352
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Cpn10 mutant Ala-Cpn10-KK102 with two
      additional Lysine (K) residues inserted at position 103-104 (the
      C-terminus). This construct contains an extra N-terminal Alanine
      residue.

<400> SEQUENCE: 352

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp Lys Lys
            100

<210> SEQ ID NO 353
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Native cDNA of Cpn10 variant Ala-Cpn10-KK102

<400> SEQUENCE: 353

```
atggcagcag gacaagcgtt tagaaagttt cttccactct ttgaccgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagaca agaaatga                                                 318
```

<210> SEQ ID NO 354
<211> LENGTH: 318
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Optimised cDNA of Cpn10 variant Ala-Cpn10-KK102 (Gly, Arg and stop codons are optimized in the cDNA)

<400> SEQUENCE: 354

```
atggcagcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc cccagaata tggtggcacc     240 aaagtagttc tagatgacaa ggattatttc ctatttcgtg atggtgacat tcttggcaag    300
tacgtagaca agaaataa                                                   318
```

<210> SEQ ID NO 355
<211> LENGTH: 715
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Seven Cpn10 cDNA subunits joined through a Glycine (G) spacer. The 1st Cpn10 has the extra N-terminal alanine (A) however this extra alanine has been removed from the remaining six Cpn10 genes.
<220> FEATURE:
<223> OTHER INFORMATION: There is an extra isoleucine (I) residue on the final position 715

<400> SEQUENCE: 355

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp Gly Ala Gly Gln Ala Phe Arg Lys Phe Leu
            100                 105                 110

Pro Leu Phe Asp Arg Val Leu Val Glu Arg Ser Ala Ala Glu Thr Val
        115                 120                 125

Thr Lys Gly Gly Ile Met Leu Pro Glu Lys Ser Gln Gly Lys Val Leu
    130                 135                 140

Gln Ala Thr Val Val Ala Val Gly Ser Gly Ser Lys Gly Lys Gly Gly
145                 150                 155                 160

Glu Ile Gln Pro Val Ser Val Lys Val Gly Asp Lys Val Leu Leu Pro
                165                 170                 175

Glu Tyr Gly Gly Thr Lys Val Val Leu Asp Asp Lys Asp Tyr Phe Leu
            180                 185                 190

Phe Arg Asp Gly Asp Ile Leu Gly Lys Tyr Val Asp Gly Ala Gly Gln
        195                 200                 205
```

```
Ala Phe Arg Lys Phe Leu Pro Leu Phe Asp Arg Val Leu Val Glu Arg
    210                 215                 220

Ser Ala Ala Glu Thr Val Thr Lys Gly Gly Ile Met Leu Pro Glu Lys
225                 230                 235                 240

Ser Gln Gly Lys Val Leu Gln Ala Thr Val Ala Val Gly Ser Gly
            245                 250                 255

Ser Lys Gly Lys Gly Gly Glu Ile Gln Pro Val Ser Val Lys Val Gly
            260                 265                 270

Asp Lys Val Leu Leu Pro Glu Tyr Gly Gly Thr Lys Val Val Leu Asp
        275                 280                 285

Asp Lys Asp Tyr Phe Leu Phe Arg Asp Gly Asp Ile Leu Gly Lys Tyr
    290                 295                 300

Val Asp Gly Ala Gly Gln Ala Phe Arg Lys Phe Leu Pro Leu Phe Asp
305                 310                 315                 320

Arg Val Leu Val Glu Arg Ser Ala Ala Glu Thr Val Thr Lys Gly Gly
            325                 330                 335

Ile Met Leu Pro Glu Lys Ser Gln Gly Lys Val Leu Gln Ala Thr Val
            340                 345                 350

Val Ala Val Gly Ser Gly Ser Lys Gly Lys Gly Gly Glu Ile Gln Pro
        355                 360                 365

Val Ser Val Lys Val Gly Asp Lys Val Leu Leu Pro Glu Tyr Gly Gly
    370                 375                 380

Thr Lys Val Val Leu Asp Asp Lys Asp Tyr Phe Leu Phe Arg Asp Gly
385                 390                 395                 400

Asp Ile Leu Gly Lys Tyr Val Asp Gly Ala Gly Gln Ala Phe Arg Lys
            405                 410                 415

Phe Leu Pro Leu Phe Asp Arg Val Leu Val Glu Arg Ser Ala Ala Glu
            420                 425                 430

Thr Val Thr Lys Gly Gly Ile Met Leu Pro Glu Lys Ser Gln Gly Lys
        435                 440                 445

Val Leu Gln Ala Thr Val Val Ala Val Gly Ser Gly Ser Lys Gly Lys
    450                 455                 460

Gly Gly Glu Ile Gln Pro Val Ser Val Lys Val Gly Asp Lys Val Leu
465                 470                 475                 480

Leu Pro Glu Tyr Gly Gly Thr Lys Val Val Leu Asp Asp Lys Asp Tyr
            485                 490                 495

Phe Leu Phe Arg Asp Gly Asp Ile Leu Gly Lys Tyr Val Asp Gly Ala
            500                 505                 510

Gly Gln Ala Phe Arg Lys Phe Leu Pro Leu Phe Asp Arg Val Leu Val
        515                 520                 525

Glu Arg Ser Ala Ala Glu Thr Val Thr Lys Gly Gly Ile Met Leu Pro
    530                 535                 540

Glu Lys Ser Gln Gly Lys Val Leu Gln Ala Thr Val Val Ala Val Gly
545                 550                 555                 560

Ser Gly Ser Lys Gly Lys Gly Gly Glu Ile Gln Pro Val Ser Val Lys
            565                 570                 575

Val Gly Asp Lys Val Leu Leu Pro Glu Tyr Gly Gly Thr Lys Val Val
            580                 585                 590

Leu Asp Asp Lys Asp Tyr Phe Leu Phe Arg Asp Gly Asp Ile Leu Gly
        595                 600                 605

Lys Tyr Val Asp Gly Ala Gly Gln Ala Phe Arg Lys Phe Leu Pro Leu
    610                 615                 620
```

```
Phe Asp Arg Val Leu Val Glu Arg Ser Ala Ala Glu Thr Val Thr Lys
625                 630                 635                 640

Gly Gly Ile Met Leu Pro Glu Lys Ser Gln Gly Lys Val Leu Gln Ala
            645                 650                 655

Thr Val Ala Val Gly Ser Gly Ser Lys Gly Lys Gly Gly Glu Ile
        660                 665                 670

Gln Pro Val Ser Val Lys Val Gly Asp Lys Val Leu Leu Pro Glu Tyr
        675                 680                 685

Gly Gly Thr Lys Val Val Leu Asp Asp Lys Asp Tyr Phe Leu Phe Arg
    690                 695                 700

Asp Gly Asp Ile Leu Gly Lys Tyr Val Asp Ile
705                 710                 715

<210> SEQ ID NO 356
<211> LENGTH: 2151
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Covalent Cpn10. Seven Cpn10 cDNA
      subunits joined through a Glycine (G) spacer. The 1st Cpn10 has
      the extra N-terminal alanine (A) however this extra alanine has
      been removed from the remaining six Cpn10 genes. There is an extra
      isoleucine (I)

<400> SEQUENCE: 356
atggcagcag acaagcgtt tagaaagttt cttccactct tgaccgagt attggttgaa        60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagatg cgcaggaca agcgtttaga aagtttcttc actctttga ccgagtattg    360 gttgaaagga gtgctgctga aactgtaacc aaaggaggca ttatgcttcc agaaaaatct    420
caaggaaaag tattgcaagc aacagtagtc gctgttggat cgggttctaa aggaagggt    480 ggagagattc aaccagttag cgtgaaagtt ggagataaag ttcttctccc agaatatgga    540
ggcaccaaag tagttctaga tgacaaggat tatttcctat ttagagatgg tgacattctt    600
ggaaagtacg tagatggcgc aggacaagcg tttagaaagt tcttccact ctttgaccga    660 gtattggttg aaaggagtgc tgctgaaact gtaaccaaag gaggcattat gcttccagaa    720
aaatctcaag gaaaagtatt gcaagcaaca gtagtcgctg ttggatcggg ttctaaagga    780
aagggtggag agattcaacc agttagcgtg aaagttggag ataaagttct tctcccagaa    840
tatggaggca ccaaagtagt tctagatgac aaggattatt tcctatttag atggtgac    900 attcttggaa agtacgtaga tggcgcagga caagcgttta aagtttct tccactcttt    960 gaccgagtat tggttgaaag gagtgctgct gaaactgtaa ccaaggagg cattatgctt    1020 ccagaaaaat ctcaaggaaa agtattgcaa gcaacagtag tcgctgttgg atcgggttct    1080
aaaggaaagg gtggagagat tcaaccagtt agcgtgaaag ttggagataa agttcttctc    1140
ccagaatatg gaggcaccaa agtagttcta gatgacaagg attatttcct atttagagat    1200
ggtgacattc ttggaaagta cgtagatggc gcaggacaag cgtttagaaa gtttcttcca    1260
ctctttgacc gagtattggt tgaaaggagt gctgctgaaa ctgtaaccaa ggaggcatt    1320
```

```
atgcttccag aaaaatctca aggaaaagta ttgcaagcaa cagtagtcgc tgttggatcg    1380
ggttctaaag gaaagggtgg agagattcaa ccagttagcg tgaaagttgg agataaagtt    1440
cttctcccag aatatggagg caccaaagta gttctagatg acaaggatta tttcctattt    1500
agagatggtg acattcttgg aaagtacgta gatggcgcag acaagcgtt  tagaaagttt    1560 cttccactct ttgaccgagt attggttgaa aggagtgctg ctgaaactgt aaccaaagga    1620
ggcattatgc ttccagaaaa atctcaagga aaagtattgc aagcaacagt agtcgctgtt    1680
ggatcgggtt ctaaaggaaa gggtggagag attcaaccag ttagcgtgaa agttggagat    1740
aaagttcttc tcccagaata tggaggcacc aaagtagttc tagatgacaa ggattatttc    1800
ctatttagag atggtgacat tcttggaaag tacgtagatg gcgcaggaca agcgtttaga    1860
aagtttcttc cactctttga ccgagtattg gttgaaagga gtgctgctga aactgtaacc    1920
aaaggaggca ttatgcttcc agaaaatct  caaggaaaag tattgcaagc aacagtagtc    1980
gctgttggat cgggttctaa aggaaagggt ggagagattc aaccagttag cgtgaaagtt    2040
ggagataaag ttcttctccc agaatatgga ggcaccaaaa tagttctaga tgacaaggat    2100
tatttcctat ttagagatgg tgacattctt ggaaagtacg tagatatcta g             2151
```

<210> SEQ ID NO 357
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(4)
<223> OTHER INFORMATION: This region may encompass 0 to 4 residues
      selected from "Ala," "Met His," "Met Arg," "Met Lys,"
      "Met Lys Lys," "Met Lys Lys Lys" or is absent
<220> FEATURE:
<221> NAME/KEY: MOD_RES
<222> LOCATION: (5)..(5)
<223> OTHER INFORMATION: Ala or Lys
<220> FEATURE:
<221> NAME/KEY: MOD_RES
<222> LOCATION: (7)..(7)
<223> OTHER INFORMATION: Gln, Lys or Arg
<220> FEATURE:
<221> NAME/KEY: MOD_RES
<222> LOCATION: (9)..(9)
<223> OTHER INFORMATION: Phe or Lys
<220> FEATURE:
<221> NAME/KEY: MOD_RES
<222> LOCATION: (13)..(13)
<223> OTHER INFORMATION: Leu or Lys
<220> FEATURE:
<221> NAME/KEY: MOD_RES
<222> LOCATION: (16)..(16)
<223> OTHER INFORMATION: Phe or Lys
<220> FEATURE:
<221> NAME/KEY: MOD_RES
<222> LOCATION: (17)..(17)
<223> OTHER INFORMATION: Asp, Lys or Asn
<220> FEATURE:
<221> NAME/KEY: MOD_RES
<222> LOCATION: (22)..(22)
<223> OTHER INFORMATION: Glu, Ala, Met, Gln, Ser, Lys or Arg
<220> FEATURE:
<221> NAME/KEY: MOD_RES
<222> LOCATION: (24)..(24)
<223> OTHER INFORMATION: Ser or Lys
<220> FEATURE:
<221> NAME/KEY: MOD_RES
<222> LOCATION: (25)..(27)
<223> OTHER INFORMATION: This region may encompass 1 to 3 residues
      selected from "Ala," "Ala Lys" or "Ala Lys Lys"

-continued

```
<220> FEATURE:
<221> NAME/KEY: MOD_RES
<222> LOCATION: (28)..(28)
<223> OTHER INFORMATION: Ala or Lys
<220> FEATURE:
<221> NAME/KEY: MOD_RES
<222> LOCATION: (29)..(29)
<223> OTHER INFORMATION: Glu, Gln or absent
<220> FEATURE:
<221> NAME/KEY: MOD_RES
<222> LOCATION: (30)..(30)
<223> OTHER INFORMATION: Thr or Lys
<220> FEATURE:
<221> NAME/KEY: MOD_RES
<222> LOCATION: (35)..(35)
<223> OTHER INFORMATION: Gly or Lys
<220> FEATURE:
<221> NAME/KEY: MOD_RES
<222> LOCATION: (37)..(37)
<223> OTHER INFORMATION: Met or Lys
<220> FEATURE:
<221> NAME/KEY: MOD_RES
<222> LOCATION: (40)..(40)
<223> OTHER INFORMATION: Glu, Lys, Gln or absent
<220> FEATURE:
<221> NAME/KEY: MOD_RES
<222> LOCATION: (43)..(43)
<223> OTHER INFORMATION: Gln or Lys
<220> FEATURE:
<221> NAME/KEY: MOD_RES
<222> LOCATION: (44)..(46)
<223> OTHER INFORMATION: This region may encompass 1 to 3 residues
      selected from "Gly," "Gly Lys" or "Gly Lys Lys"
<220> FEATURE:
<221> NAME/KEY: MOD_RES
<222> LOCATION: (48)..(48)
<223> OTHER INFORMATION: Val or Lys
<220> FEATURE:
<221> NAME/KEY: MOD_RES
<222> LOCATION: (49)..(49)
<223> OTHER INFORMATION: Leu or Lys
<220> FEATURE:
<221> NAME/KEY: MOD_RES
<222> LOCATION: (50)..(50)
<223> OTHER INFORMATION: Gln or Lys
<220> FEATURE:
<221> NAME/KEY: MOD_RES
<222> LOCATION: (52)..(52)
<223> OTHER INFORMATION: Thr or Lys
<220> FEATURE:
<221> NAME/KEY: MOD_RES
<222> LOCATION: (58)..(58)
<223> OTHER INFORMATION: Ser, Lys or Arg
<220> FEATURE:
<221> NAME/KEY: MOD_RES
<222> LOCATION: (60)..(60)
<223> OTHER INFORMATION: Ser or Lys
<220> FEATURE:
<221> NAME/KEY: MOD_RES
<222> LOCATION: (62)..(62)
<223> OTHER INFORMATION: Gly or Lys
<220> FEATURE:
<221> NAME/KEY: MOD_RES
<222> LOCATION: (64)..(66)
<223> OTHER INFORMATION: This region may encompass 1 to 3 residues
      selected from "Gly," "Lys," "Gly Lys" or "Gly Lys Lys"
<220> FEATURE:
<221> NAME/KEY: MOD_RES
<222> LOCATION: (68)..(68)
<223> OTHER INFORMATION: Glu, Lys, Gln or absent
<220> FEATURE:
<221> NAME/KEY: MOD_RES
<222> LOCATION: (70)..(70)
<223> OTHER INFORMATION: Gln or Lys
<220> FEATURE:
<221> NAME/KEY: MOD_RES
<222> LOCATION: (71)..(71)
<223> OTHER INFORMATION: Pro or Lys
<220> FEATURE:
```

-continued

```
<221> NAME/KEY: MOD_RES
<222> LOCATION: (76)..(76)
<223> OTHER INFORMATION: Val or Lys
<220> FEATURE:
<221> NAME/KEY: MOD_RES
<222> LOCATION: (78)..(78)
<223> OTHER INFORMATION: Asp, Lys or Asn
<220> FEATURE:
<221> NAME/KEY: MOD_RES
<222> LOCATION: (83)..(83)
<223> OTHER INFORMATION: Pro or Lys
<220> FEATURE:
<221> NAME/KEY: MOD_RES
<222> LOCATION: (84)..(84)
<223> OTHER INFORMATION: Glu, Lys, Gln or absent
<220> FEATURE:
<221> NAME/KEY: MOD_RES
<222> LOCATION: (85)..(86)
<223> OTHER INFORMATION: This region may encompass 1 to 2 residues
      selected from "Tyr," "Lys," "His," "Arg," "Gly Lys," "Tyr Lys" or
      "Glu" when the residue at position 49 is Lys
<220> FEATURE:
<221> NAME/KEY: MOD_RES
<222> LOCATION: (87)..(88)
<223> OTHER INFORMATION: Gly or Lys
<220> FEATURE:
<221> NAME/KEY: MOD_RES
<222> LOCATION: (89)..(89)
<223> OTHER INFORMATION: Thr or Lys
<220> FEATURE:
<221> NAME/KEY: MOD_RES
<222> LOCATION: (92)..(92)
<223> OTHER INFORMATION: Val or Lys
<220> FEATURE:
<221> NAME/KEY: MOD_RES
<222> LOCATION: (94)..(94)
<223> OTHER INFORMATION: Asp, Lys or Asn
<220> FEATURE:
<221> NAME/KEY: MOD_RES
<222> LOCATION: (95)..(97)
<223> OTHER INFORMATION: This region may encompass 0 to 3 residues
      selected from "Asp," "Asp Lys," "Asp Lys Lys," "Lys," "Asn" or is
      absent
<220> FEATURE:
<221> NAME/KEY: MOD_RES
<222> LOCATION: (99)..(99)
<223> OTHER INFORMATION: Asp, Lys, Arg or Asn
<220> FEATURE:
<221> NAME/KEY: MOD_RES
<222> LOCATION: (100)..(100)
<223> OTHER INFORMATION: Tyr or Lys
<220> FEATURE:
<221> NAME/KEY: MOD_RES
<222> LOCATION: (101)..(101)
<223> OTHER INFORMATION: Phe or Lys
<220> FEATURE:
<221> NAME/KEY: MOD_RES
<222> LOCATION: (102)..(102)
<223> OTHER INFORMATION: Leu or Lys
<220> FEATURE:
<221> NAME/KEY: MOD_RES
<222> LOCATION: (105)..(105)
<223> OTHER INFORMATION: Asp, Lys or Asn
<220> FEATURE:
<221> NAME/KEY: MOD_RES
<222> LOCATION: (106)..(106)
<223> OTHER INFORMATION: Gly or Lys
<220> FEATURE:
<221> NAME/KEY: MOD_RES
<222> LOCATION: (107)..(107)
<223> OTHER INFORMATION: Asp, Lys, Arg, Ala, Met, Asn or Ser
<220> FEATURE:
<221> NAME/KEY: MOD_RES
<222> LOCATION: (109)..(109)
<223> OTHER INFORMATION: Leu or Lys
<220> FEATURE:
<221> NAME/KEY: MOD_RES
<222> LOCATION: (113)..(113)
<223> OTHER INFORMATION: Val or Lys
```

-continued

```
<220> FEATURE:
<221> NAME/KEY: MOD_RES
<222> LOCATION: (114)..(116)
<223> OTHER INFORMATION: This region may encompass 1 to 3 residues
      selected from "Asp," "Lys," "Arg," "Asn," "Asp Lys" or
      "Asp Lys Lys"

<400> SEQUENCE: 357

Xaa Xaa Xaa Xaa Xaa Gly Xaa Ala Xaa Arg Lys Phe Xaa Pro Leu Xaa
1               5                   10                  15

Xaa Arg Val Leu Val Xaa Arg Xaa Xaa Xaa Xaa Xaa Xaa Xaa Val Thr
            20                  25                  30

Lys Gly Xaa Ile Xaa Leu Pro Xaa Lys Ser Xaa Xaa Xaa Xaa Lys Xaa
            35                  40                  45

Xaa Xaa Ala Xaa Val Val Ala Val Gly Xaa Gly Xaa Lys Xaa Lys Xaa
        50                  55                  60

Xaa Xaa Gly Xaa Ile Xaa Xaa Val Ser Val Lys Xaa Gly Xaa Lys Val
65                  70                  75                  80

Leu Leu Xaa Xaa Xaa Xaa Xaa Xaa Xaa Lys Val Xaa Leu Xaa Xaa Xaa
                85                  90                  95

Xaa Lys Xaa Xaa Xaa Xaa Phe Arg Xaa Xaa Xaa Ile Xaa Gly Lys Tyr
            100                 105                 110

Xaa Xaa Xaa Xaa
            115

<210> SEQ ID NO 358
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Met Lys Lys Lys
1

<210> SEQ ID NO 359
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 359

His His His His His His
1               5

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ala Gly Gln Ala Phe Arg Lys Phe Leu
1               5

<210> SEQ ID NO 361
<211> LENGTH: 4
<212> TYPE: PRT
```

<210> SEQ ID NO 361
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Met Ala Gly Gln
1

<210> SEQ ID NO 362
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ala Ala Gly Gln
1

<210> SEQ ID NO 363
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ala Gly Gln Ala Phe Arg Lys
1               5

<210> SEQ ID NO 364
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Glu Arg Ser Ala Ala Glu Thr Val Thr Arg Gly Gly Ile Met Leu Pro
1               5                   10                  15

Glu Lys Ser Gln Gly Lys Val Leu Gln
            20                  25

<210> SEQ ID NO 365
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ser Lys Gly Lys Gly Gly Glu Ile Gln Pro Val Ser
1               5                   10

<210> SEQ ID NO 366
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Lys Val Gly Asp Lys
1               5

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Pro Glu Tyr Gly Gly Thr Lys
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Asp Asp Lys Asp Tyr Phe Leu
1               5

<210> SEQ ID NO 369
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Arg Asp Gly Asp
1

<210> SEQ ID NO 370
<211> LENGTH: 97
<212> TYPE: PRT
<213> ORGANISM: Escherichia coli

<400> SEQUENCE: 370

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
                85                  90                  95

Ala

<210> SEQ ID NO 371
<211> LENGTH: 101
<212> TYPE: PRT
<213> ORGANISM: Mus musculus

<400> SEQUENCE: 371

```
Ala Gly Gln Ala Phe Arg Lys Phe Leu Pro Leu Phe Asp Arg Val Leu
1               5                   10                  15

Val Glu Arg Ser Ala Ala Glu Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Ser Gly Gly Lys Gly Ser Gly Glu Ile Glu Pro Val Ser Val
50                  55                  60

Lys Val Gly Asp Lys Val Leu Leu Pro Glu Tyr Gly Gly Thr Lys Val
65                  70                  75                  80

Val Leu Asp Asp Lys Asp Tyr Phe Leu Phe Arg Asp Ser Asp Ile Leu
                85                  90                  95

Gly Lys Tyr Val Asp
            100
```

<210> SEQ ID NO 372
<211> LENGTH: 101
<212> TYPE: PRT
<213> ORGANISM: Gallus gallus

<400> SEQUENCE: 372

```
Ala Gly Lys Ala Phe Arg Lys Phe Leu Pro Leu Phe Asp Arg Val Leu
1               5                   10                  15

Val Glu Arg Cys Ala Ala Glu Thr Val Thr Lys Gly Gly Ile Met Ile
            20                  25                  30

Pro Glu Lys Ala Gln Gly Lys Val Leu Gln Ala Thr Val Val Ala Val
        35                  40                  45

Gly Ser Gly Ala Arg Gly Lys Asp Gly Glu Ile His Pro Val Ser Val
50                  55                  60

Lys Val Gly Glu Lys Val Leu Leu Pro Glu Tyr Gly Gly Thr Lys Ile
65                  70                  75                  80

Val Leu Glu Asp Lys Asp Tyr Tyr Leu Phe Arg Asp Gly Asp Ile Leu
                85                  90                  95

Gly Lys Tyr Leu Asp
            100
```

<210> SEQ ID NO 373
<211> LENGTH: 101
<212> TYPE: PRT
<213> ORGANISM: Xenopus tropicalis

<400> SEQUENCE: 373

```
Ala Val Arg Ala Phe Lys Lys Phe Val Pro Leu Phe Asp Arg Val Leu
1               5                   10                  15

Val Glu Arg Leu Ala Ala Glu Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Asp Gly Ser Arg Gly Lys Thr Gly Asp Ile Gln Pro Val Ser Val
50                  55                  60

Lys Val Gly Glu Lys Ile Leu Leu Pro Glu Tyr Gly Gly Thr Lys Val
65                  70                  75                  80

Val Leu Asp Asp Lys Glu Tyr Phe Leu Phe Arg Asp Gly Asp Ile Leu
                85                  90                  95
```

```
Gly Lys Tyr Ile Asp
            100

<210> SEQ ID NO 374
<211> LENGTH: 100
<212> TYPE: PRT
<213> ORGANISM: Danio rerio

<400> SEQUENCE: 374

Met Gln Ala Phe Arg Lys Phe Leu Pro Met Phe Asp Arg Val Leu Val
1               5                   10                  15

Glu Arg Leu Ala Ala Glu Thr Val Ser Arg Gly Gly Ile Met Ile Pro
            20                  25                  30

Glu Lys Ser Gln Ala Lys Val Leu Gln Ala Thr Val Ala Val Gly
        35                  40                  45

Pro Gly Ser Thr Asn Lys Asp Gly Lys Val Ile Pro Val Cys Val Lys
    50                  55                  60

Val Gly Asp Lys Val Leu Leu Pro Glu Tyr Gly Gly Thr Lys Val Met
65                  70                  75                  80

Leu Glu Asp Lys Asp Tyr Phe Leu Phe Arg Asp Ala Asp Ile Leu Gly
                85                  90                  95

Lys Tyr Val Asp
            100

<210> SEQ ID NO 375
<211> LENGTH: 101
<212> TYPE: PRT
<213> ORGANISM: Ciona savignyi

<400> SEQUENCE: 375

Ala Gly Lys Ile Phe Lys Asn Phe Met Pro Leu Phe Asp Arg Val Leu
1               5                   10                  15

Val Gln Arg Phe Ala Ala Glu Thr Thr Thr Lys Gly Gly Ile Val Leu
            20                  25                  30

Pro Glu Lys Thr Ser Gly Lys Val Leu Arg Ala Thr Val Val Ala Thr
        35                  40                  45

Gly Pro Gly Val Glu Gly Lys Asp Gly Asn Ile Lys Pro Leu Ser Ile
    50                  55                  60

Asn Pro Gly Asp Glu Val Leu Leu Pro Glu Tyr Gly Gly Thr Lys Val
65                  70                  75                  80

Thr Leu Asp Asp Glu Glu Phe His Leu Phe Arg Asp Gly Asp Ile Leu
                85                  90                  95

Gly Lys Phe Ser Lys
            100

<210> SEQ ID NO 376
<211> LENGTH: 102
<212> TYPE: PRT
<213> ORGANISM: Schistosoma japonicum

<400> SEQUENCE: 376

Met Ser Ala Arg Ala Phe Arg Lys Phe Ala Pro Leu Phe Asp Arg Val
1               5                   10                  15

Leu Val Gln Arg Phe Glu Ala Glu Thr Lys Ser Lys Gly Gly Ile Met
            20                  25                  30

Leu Pro Glu Lys Ala Lys Gly Lys Val Leu Glu Ala Thr Val Val Ala
        35                  40                  45

His Gly Pro Gly Val Lys Asn Glu Lys Gly Glu Val Val Pro Val Cys
```

```
              50                  55                  60
Val Thr Val Gly Asp Lys Val Phe Leu Pro Glu Tyr Gly Gly Thr Lys
 65                  70                  75                  80

Val Val Leu Glu Asp Thr Glu Tyr Phe Leu Phe Arg Glu Ser Asp Ile
                 85                  90                  95

Leu Ala Lys Phe Glu Lys
                100

<210> SEQ ID NO 377
<211> LENGTH: 101
<212> TYPE: PRT
<213> ORGANISM: Anopheles gambiae

<400> SEQUENCE: 377

Met Ser Ala Val Lys Arg Leu Leu Pro Leu Leu Asp Arg Val Leu Ile
  1               5                  10                  15

Gln Arg Ala Glu Ala Leu Thr Lys Thr Lys Gly Gly Ile Val Ile Pro
                 20                  25                  30

Glu Lys Ala Gln Ser Lys Val Leu Glu Gly Thr Val Ala Val Gly
             35                  40                  45

Pro Gly Ala Arg His Ala Gln Thr Gly Glu His Val Pro Leu Ser Val
         50                  55                  60

Lys Val Gly Glu Lys Val Leu Leu Pro Glu Tyr Gly Gly Thr Lys Val
 65                  70                  75                  80

Asp Leu Gly Asp Ser Lys Glu Tyr His Leu Phe Arg Glu Ala Asp Ile
                 85                  90                  95

Leu Ala Lys Met Glu
                100

<210> SEQ ID NO 378
<211> LENGTH: 102
<212> TYPE: PRT
<213> ORGANISM: Drosophila melanogaster

<400> SEQUENCE: 378

Ala Ala Ala Ile Lys Lys Ile Ile Pro Met Leu Asp Arg Ile Leu Ile
  1               5                  10                  15

Gln Arg Ala Glu Ala Leu Thr Lys Thr Lys Gly Gly Ile Val Leu Pro
                 20                  25                  30

Glu Lys Ala Val Gly Lys Val Leu Glu Gly Thr Val Leu Ala Val Gly
             35                  40                  45

Pro Gly Thr Arg Asn Ala Ser Thr Gly Asn His Ile Pro Ile Gly Val
         50                  55                  60

Lys Glu Gly Asp Arg Val Leu Leu Pro Glu Phe Gly Gly Thr Lys Val
 65                  70                  75                  80

Asn Leu Glu Gly Asp Gln Lys Glu Leu Phe Leu Phe Arg Glu Ser Asp
                 85                  90                  95

Ile Leu Ala Lys Leu Glu
                100

<210> SEQ ID NO 379
<211> LENGTH: 98
<212> TYPE: PRT
<213> ORGANISM: Arabidopsis thaliana

<400> SEQUENCE: 379

Met Met Lys Arg Leu Ile Pro Thr Phe Asn Arg Ile Leu Val Gln Arg
  1               5                  10                  15
```

```
Val Ile Gln Pro Ala Lys Thr Glu Ser Gly Ile Leu Pro Glu Lys
            20                  25                  30

Ser Ser Lys Leu Asn Ser Gly Lys Val Ile Ala Val Gly Pro Gly Ser
        35                  40                  45

Arg Asp Lys Asp Gly Lys Leu Ile Pro Val Ser Val Lys Glu Gly Asp
 50                  55                  60

Thr Val Leu Leu Pro Glu Tyr Gly Gly Thr Gln Val Lys Leu Gly Glu
 65                  70                  75                  80

Asn Glu Tyr His Leu Phe Arg Asp Glu Asp Val Leu Gly Thr Leu His
                 85                  90                  95

Glu Asp

<210> SEQ ID NO 380
<211> LENGTH: 106
<212> TYPE: PRT
<213> ORGANISM: Saccharomyces cerevisiae

<400> SEQUENCE: 380

Met Ser Thr Leu Leu Lys Ser Ala Lys Ser Ile Val Pro Leu Met Asp
 1               5                  10                  15

Arg Val Leu Val Gln Arg Ile Lys Ala Gln Ala Lys Thr Ala Ser Gly
            20                  25                  30

Leu Tyr Leu Pro Glu Lys Asn Val Glu Lys Leu Asn Gln Ala Glu Val
        35                  40                  45

Val Ala Val Gly Pro Gly Phe Thr Asp Ala Asn Gly Asn Lys Val Val
 50                  55                  60

Pro Gln Val Lys Val Gly Asp Gln Val Leu Ile Pro Gln Phe Gly Gly
 65                  70                  75                  80

Ser Thr Ile Lys Leu Gly Asn Asp Asp Glu Val Ile Leu Phe Arg Asp
                 85                  90                  95

Ala Glu Ile Leu Ala Lys Ile Ala Lys Asp
            100                 105

<210> SEQ ID NO 381
<211> LENGTH: 103
<212> TYPE: PRT
<213> ORGANISM: Plasmodium falciparum

<400> SEQUENCE: 381

Met Ser Ser Thr Ile Thr Arg Lys Phe Ile Pro Leu Met Asp Arg Ile
 1               5                  10                  15

Leu Ile Ser Lys Ile Val Pro Lys Thr Thr Thr Lys Ser Gly Leu Phe
            20                  25                  30

Leu Pro Glu Ser Ala Thr Glu Pro Ser Tyr Thr Gly Lys Val Leu Ala
        35                  40                  45

Val Gly Pro Gly Arg Val Thr Ser Asn Gly Thr Lys Ile Ser Pro Ser
 50                  55                  60

Val Lys Glu Gly Asp Val Val Leu Pro Glu Tyr Gly Gly Ser Ser
 65                  70                  75                  80

Leu Lys Ile Asp Gly Glu Glu Phe Phe Val Tyr Arg Asp Asp Asp Ile
                 85                  90                  95

Ile Gly Ile Ile Lys Asp Glu
            100

<210> SEQ ID NO 382
<211> LENGTH: 99
```

```
<212> TYPE: PRT
<213> ORGANISM: Mycobacterium tuberculosis

<400> SEQUENCE: 382

Ala Lys Val Asn Ile Lys Pro Leu Glu Asp Lys Ile Leu Val Gln Ala
1               5                   10                  15

Asn Glu Ala Glu Thr Thr Thr Ala Ser Gly Leu Val Ile Pro Asp Thr
            20                  25                  30

Ala Lys Glu Lys Pro Gln Glu Gly Thr Val Val Ala Val Gly Pro Gly
        35                  40                  45

Arg Trp Asp Glu Asp Gly Glu Lys Arg Ile Pro Leu Asp Val Ala Glu
    50                  55                  60

Gly Asp Thr Val Ile Tyr Ser Lys Tyr Gly Gly Thr Glu Ile Lys Tyr
65                  70                  75                  80

Asn Gly Glu Glu Tyr Leu Ile Leu Ser Ala Arg Asp Val Leu Ala Val
                85                  90                  95

Val Ser Lys

<210> SEQ ID NO 383
<211> LENGTH: 92
<212> TYPE: PRT
<213> ORGANISM: Methanosarcina mazei

<400> SEQUENCE: 383

Met Ile Val Lys Pro Ile Gly Glu Arg Val Leu Leu Lys His Gln Lys
1               5                   10                  15

Lys Glu Glu Val Thr Lys Gly Gly Ile Tyr Ile Pro Glu Ser Ala Arg
            20                  25                  30

Gln Glu Lys Lys Glu Gly Ile Val Val Ala Val Gly Thr Phe Glu Asp
        35                  40                  45

Gly Lys Glu Leu Pro Leu Lys Lys Asp Asp His Val Ile Tyr Gly Gly
    50                  55                  60

Tyr Gln Ala Asp Glu Ile Glu Ile Asp Asp Glu Lys Tyr Ile Phe Val
65                  70                  75                  80

Asp Phe Lys Asp Ile Leu Ala Thr Val Val Glu Glu
                85                  90

<210> SEQ ID NO 384
<211> LENGTH: 111
<212> TYPE: PRT
<213> ORGANISM: Enterobacteria phage
<220> FEATURE:
<223> OTHER INFORMATION: Bacteriophage T4

<400> SEQUENCE: 384

Met Ser Glu Val Gln Gln Leu Pro Ile Arg Ala Val Gly Glu Tyr Val
1               5                   10                  15

Ile Leu Val Ser Glu Pro Ala Gln Ala Gly Asp Glu Glu Val Thr Glu
            20                  25                  30

Ser Gly Leu Ile Ile Gly Lys Arg Val Gln Gly Glu Val Pro Glu Leu
        35                  40                  45

Cys Val Val His Ser Val Gly Pro Asp Val Pro Glu Gly Phe Cys Glu
    50                  55                  60

Val Gly Asp Leu Thr Ser Leu Pro Val Gly Gln Ile Arg Asn Val Pro
65                  70                  75                  80

His Pro Phe Val Ala Leu Gly Leu Lys Gln Pro Lys Glu Ile Lys Gln
                85                  90                  95
```

-continued

```
Lys Phe Val Thr Cys His Tyr Lys Ala Ile Pro Cys Leu Tyr Lys
            100                 105                 110
```